US012774331B2

(12) United States Patent
Niwa et al.

(10) Patent No.: US 12,774,331 B2
(45) Date of Patent: Oct. 27, 2026

(54) BISPECIFIC ANTIBODY BINDING TO CD3

(71) Applicant: Kyowa Kirin Co., Ltd., Tokyo (JP)

(72) Inventors: Rinpei Niwa, Tokyo (JP); Shinya Ogawa, Tokyo (JP); Mami Wajima, Tokyo (JP); Tsuguo Kubota, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 784 days.

(21) Appl. No.: 17/799,425

(22) PCT Filed: Feb. 12, 2021

(86) PCT No.: PCT/JP2021/005276

§ 371 (c)(1),
(2) Date: Aug. 12, 2022

(87) PCT Pub. No.: WO2021/162098

PCT Pub. Date: Aug. 19, 2021

(65) Prior Publication Data

US 2023/0406926 A1 Dec. 21, 2023

(30) Foreign Application Priority Data

Feb. 14, 2020 (JP) ................................ 2020-023855

(51) Int. Cl.
*C07K 16/28* (2006.01)
*C07K 16/32* (2006.01)

(52) U.S. Cl.
CPC .......... *C07K 16/2809* (2013.01); *C07K 16/32* (2013.01); *C07K 2317/24* (2013.01); *C07K 2317/31* (2013.01); *C07K 2317/35* (2013.01); *C07K 2317/41* (2013.01); *C07K 2317/52* (2013.01); *C07K 2317/526* (2013.01); *C07K 2317/565* (2013.01); *C07K 2317/622* (2013.01); *C07K 2317/71* (2013.01); *C07K 2317/732* (2013.01); *C07K 2317/92* (2013.01)

(58) Field of Classification Search
CPC ................ C07K 16/2809; C07K 16/32; C07K 2317/24; C07K 2317/31; C07K 2317/35; C07K 2317/41; C07K 2317/52; C07K 2317/526; C07K 2317/565; C07K 2317/622; C07K 2317/71; C07K 2317/732; C07K 2317/92; C07K 16/2866; C07K 16/3084; C07K 2317/14; C07K 2317/21; C07K 2317/34; C07K 2317/515; C07K 2317/524; C07K 2317/53; C07K 2317/55; C07K 2317/567; C07K 2317/624; C07K 2317/64; C07K 16/2803; C07K 2317/73; G01N 33/57492; G01N 2333/7051; G01N 33/574; A61P 35/00; A61K 2039/505
See application file for complete search history.

(56) References Cited

U.S. PATENT DOCUMENTS

| | | | |
|---|---|---|---|
| 9,714,291 B2 * | 7/2017 | Niwa ..................... | C07K 16/32 |
| 2013/0195849 A1 | 8/2013 | Spreter Von Kreudenstein et al. | |
| 2014/0066378 A1 | 3/2014 | Dixit et al. | |
| 2014/0120581 A1 | 5/2014 | Niwa et al. | |
| 2014/0154253 A1 | 6/2014 | Ng et al. | |
| 2015/0125449 A1 | 5/2015 | Ng et al. | |
| 2015/0284470 A1 | 10/2015 | Spreter Von Kreudenstein et al. | |
| 2016/0039934 A1 | 2/2016 | Zhukovsky et al. | |
| 2016/0152728 A1 | 6/2016 | Ellwanger et al. | |
| 2016/0207979 A1 | 7/2016 | Dixit et al. | |
| 2016/0326249 A1 | 11/2016 | Ng et al. | |
| 2016/0355588 A1 | 12/2016 | Ng et al. | |
| 2017/0174783 A1 | 6/2017 | Ng et al. | |
| 2017/0362323 A1 | 12/2017 | Niwa et al. | |
| 2018/0016346 A1 | 1/2018 | Takahashi et al. | |
| 2018/0016347 A1 | 1/2018 | Spreter Von Kreudenstein et al. | |
| 2018/0030150 A1 | 2/2018 | Spreter Von Kreudenstein et al. | |

(Continued)

FOREIGN PATENT DOCUMENTS

| | | |
|---|---|---|
| CN | 107001468 | 8/2017 |
| CN | 107207600 | 9/2017 |

(Continued)

OTHER PUBLICATIONS

Baeuerle et al. Br J Cancer 96, 417-423 (2007). (Year: 2007).*

(Continued)

*Primary Examiner* — Sean E Aeder
*Assistant Examiner* — Yie Chia Lee
(74) *Attorney, Agent, or Firm* — Wenderoth, Lind & Ponack, L.L.P.

(57) ABSTRACT

An object of the present invention is to provide a bispecific antibody that binds to CD3 or a bispecific antibody fragment thereof. The present invention relates to a bispecific antibody that binds to CD3 or a bispecific antibody fragment thereof, a DNA encoding the bispecific antibody or the bispecific antibody fragment thereof, a vector containing the DNA, a hybridoma and a transformant that produce the bispecific antibody or the bispecific antibody fragment thereof, a method for producing the bispecific antibody or the bispecific antibody fragment thereof, therapeutic and diagnostic agents containing the bispecific antibody or the bispecific antibody fragment thereof, therapeutic and diagnostic methods using the bispecific antibody or the bispecific antibody fragment thereof, and a reagent for detection or measurement containing the bispecific antibody or the bispecific antibody fragment thereof.

21 Claims, 56 Drawing Sheets

Specification includes a Sequence Listing.

(56) References Cited

U.S. PATENT DOCUMENTS

| | | | |
|---|---|---|---|
| 2018/0371089 A1 | 12/2018 | Wu et al. |
| 2019/0248897 A1 | 8/2019 | Ng et al. |
| 2019/0375823 A1 | 12/2019 | Dixit et al. |
| 2020/0087414 A1 | 3/2020 | Spreter Von Kreudenstein et al. |
| 2021/0317212 A1 | 10/2021 | Ng et al. |
| 2024/0343802 A1 | 10/2024 | Ng et al. |

FOREIGN PATENT DOCUMENTS

| | | | |
|---|---|---|---|
| KR | 10-2012-0129834 | 11/2012 | |
| KR | 10-2015-0036606 | 4/2015 | |
| TW | 201904998 | 2/2019 | |
| WO | 2004/069876 | 8/2004 | |
| WO | 2010/088522 | 8/2010 | |
| WO | 2011/028952 | 3/2011 | |
| WO | 2014/054804 | 4/2014 | |
| WO | 2014/151910 | 9/2014 | |
| WO | 2015/048272 | 4/2015 | |
| WO | WO-2015095392 A1 * | 6/2015 | ................ A61P 9/00 |
| WO | 2016/014974 | 1/2016 | |
| WO | WO-2017079272 A2 * | 5/2017 | ......... A61K 47/6849 |
| WO | WO-2018237364 A1 * | 12/2018 | .............. A61P 35/00 |

OTHER PUBLICATIONS

Wagh et al. PLoS pathogens 14, No. 3 (2018) (Year: 2018).*
Yang et al. Vaccine. May 27, 2019;37(24):3142-3145. (Year: 2019).*
Keller et al. Cell Stress, vol. 3, No. 6, pp. 165-180, 2019. (Year: 2019).*
Harris Biotechnology, vol. 11, p. 1293-1297, 1993 (Year: 1993).*
Bortoletto et al. Eur. J. Immunol. 2002. 32: 3102-3107 (Year: 2002).*
Rudikoff et al. Proc. Natl. Acad. Sci. USA, 79(6):1979-1983, Mar. 1982 (Year: 1982).*
Colman Research in Immunology, 145:33-36, 1994 (Year: 1994).*
Deyev and Lebedenko BioEssays 30(9):904-918, 2008 (Year: 2008).*
Carter P., "Improving The Efficacy of Antibody-Based Cancer Therapies", Nat Rev Cancer. 1: 118-129, 2001.
Cartron G, Dacheux L, Salles G, et al., "Therapeutic activity of humanized anti-CD20 monoclonal antibody and polymorphism in IgG Fc receptor FcγRIIIa gene", Blood. 99: 754-758, 2002.
Weng WK, Levy R., "Two Immunoglobulin G Fragment C Receptor Polymorphisms Independently Predict Response to Rituximab in Patients With Follicular Lymphoma", J Clin Oncol. 21: 3940-3947, 2003.
Shinkawa T, Nakamura K, Yamane N, et al., "The Absence of Fucose but Not the Presence of Galactose or Bisecting *N*-Acetylglucosamine of Human IgG1 Complex-type Oligosaccharides Shows the Critical Role of Enhancing Antibody-dependent Cellular Cytotoxicity", J Biol Chem. 278: 3466-3473, 2003.
Beck A, Reichert J.M., "Marketing approval of mogamulizumab, A triumph for glyco-engineering", MAbs. 4: 419-425, 2012.
Gagez AL, Cartron G., "Obinutuzumab: a new class of anti-CD20 monoclonal antibody", Curr Opin Oncol. 26: 484-491, 2014.
Carter P.J., Lazar G.A., "Next generation antibody drugs: pursuit of the 'high-hanging fruit'", Nat Rev Drug Disc. 17: 197-223, 2018.
Bokemeyer C., "Catumaxomab-trifunctional anti-EpCAM antibody used to treat malignant ascites", Expert Opin Biol Ther. 10: 1259-1269, 2010.
Nagorsen D, Kufer P, Baeuerle PA, Bargou R., "Blinatumomab: A historical perspective", Pharmacol Ther. 136: 334-342, 2012.
Lehmann S, et al., "In Vivo Fluorescence, Imaging of the Activity of CEA TCB, a Novel T-Cell Bispecific Antibody, Reveals Highly Specific Tumor Targeting and Fast Induction of T-Cell-Mediated Tumor Killing", Clin Cancer Res. 22: 4417-4427, 2016.
Bergman I, Basse P, Barmada M, Griffin J, Cheung N., "Comparison of in vitro antibody-targeted cytotoxicity using mouse, rat and human effectors", Cancer Immunol Immunother. 49: 259-266, 2000.
Ceuppens J.L., Bloemmen F.J., Van Wauwe J.P., "T cell unresponsiveness to the mitogenic activity of OKT3 antibody results from a deficiency of monocyte Fc gamma receptors for murine IgG2a and inability to cross-link the T3-Ti complex.", J Immunol. 135: 3882-3886, 1985.
Borlak J, Länger F, Spanel R., Schöndorfer G., Dittrich C., "Immune-mediated liver injury of the cancer therapeutic antibody catumaxomab targeting EpCAM, CD3 and Fcγ receptors", Oncotarget. 7: 28059-28074, 2016.
Bacac M, Klein C., Umana P., "CEA TCB: A novel head-to-tail 2:1 T cell bispecific antibody for treatment of CEA-positive solid tumors", Oncoimmunology. 5(8):e1203498, 2016.
Bacac M, Fauti T, Sam J, et al., "A Novel Carcinoembryonic Antigen T-Cell Bispecific Antibody (CEA TCB) for the Treatment of Solid Tumors", Clin Cancer Res. 22(13), 3286-3297, 2016.
Extended European Search Report issued Feb. 12, 2024 in corresponding European Patent Application No. 21753218.3.
Moore, G.L. et al., "Tuning T Cell Affinity Improves Efficacy and Safety of Anti-CD38 x Anti-CD3 Bispecific Antibodies in Monkeys—a Potential Therapy for Multiple Myeloma", Blood, 2015, 126(23): 1798.
Leong, S.R. et al., "An anti-CD3/anti-CLL-1 bispecific antibody for the treatment of acute myeloid leukemia", Blood, 2017, 129(5): 609-618.
Huang, L. et al., "Tailoring Cytolytic Activity, Proliferation and Cytokine Release via CD3 Engineering of DART Molecules for Redirected T-cell Killing", presented at 2018 Keystone Symposium "Antibodies as Drugs: Translating Molecules into Treatments", Mar. 1, 2018, Whistler, British Columbia, Canada.
Trinklein, N.D. et al., "Efficient tumor killing and minimal cytokine release with novel T-cell agonist bispecific antibodies", MABS, 2019, 11(4): 639-652.
Bortoletto, N. et al., "Optimizing anti-CD3 affinity for effective T cell targeting against tumor cells", European Journal of Immunology, 2002, 32(11): 3102-3107.
Office Action issued Mar. 30, 2026 in corresponding Korean Patent Application No. 10-2022-7027592, with English translation.
Christina L. Zuch De Zafra et al., "Targeting Multiple Myeloma with AMG 424, a Novel Anti-CD38/CD3 Bispecific T-cell-recruiting Antibody Optimized for Cytotoxicity and Cytokine Release", Clin Cancer Res; vol. 25, No. 13 (Jul. 1, 2019), pp. 3921-3933.

* cited by examiner

[FIG. 1]
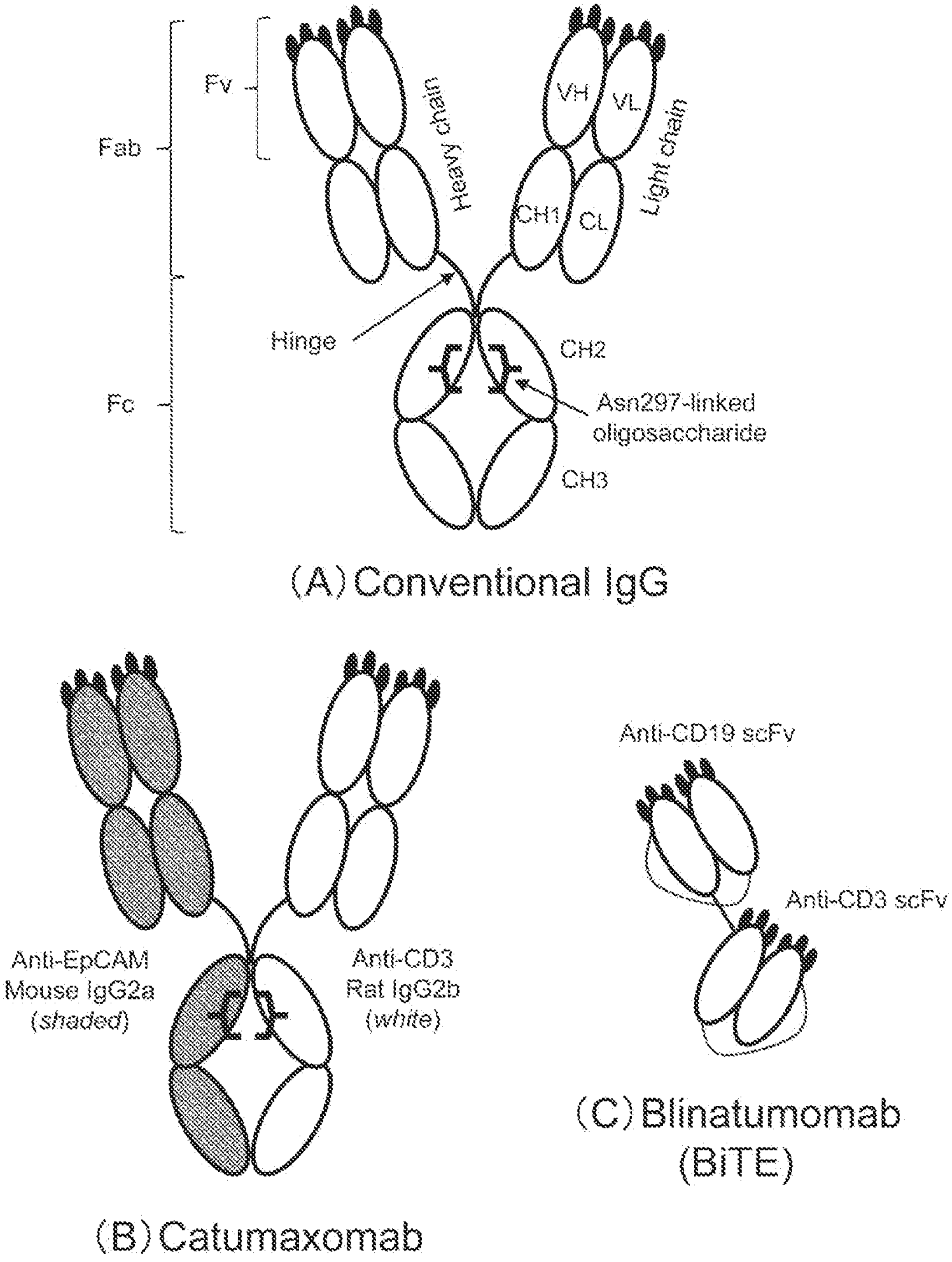

[FIG. 2]
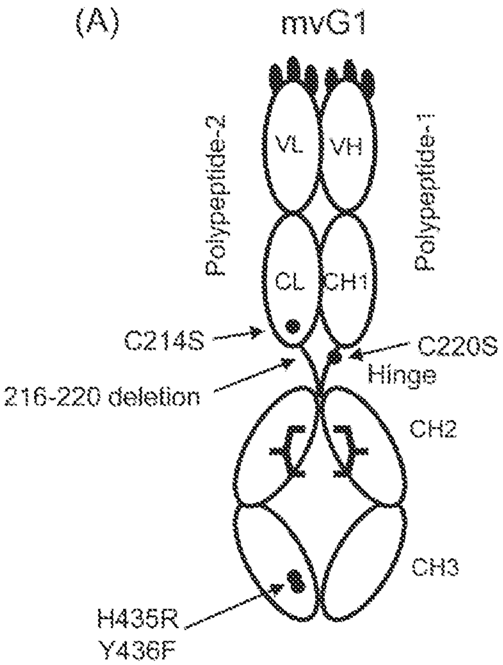
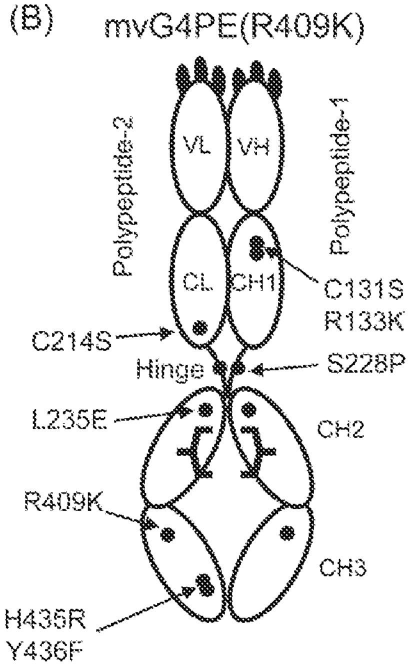
[FIG. 3]
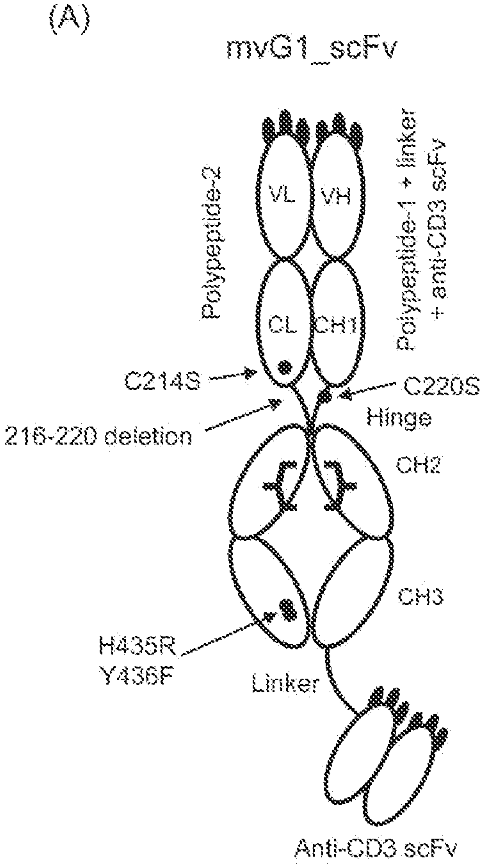
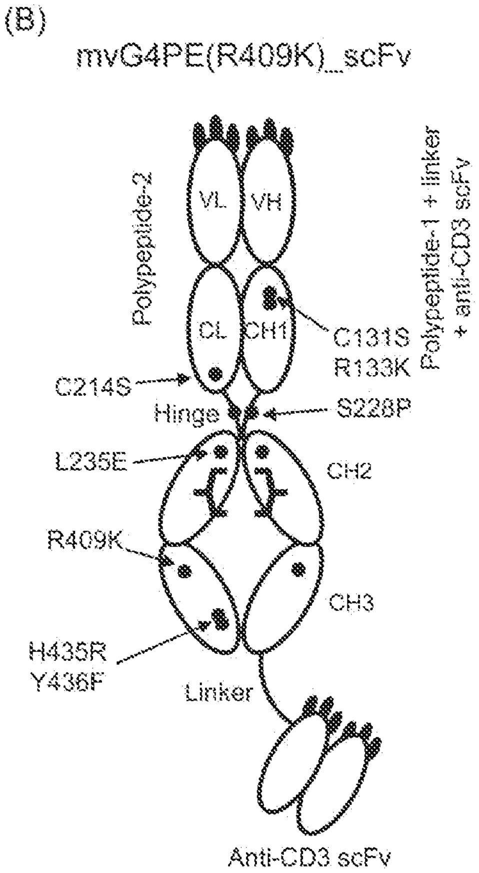

[FIG. 4]
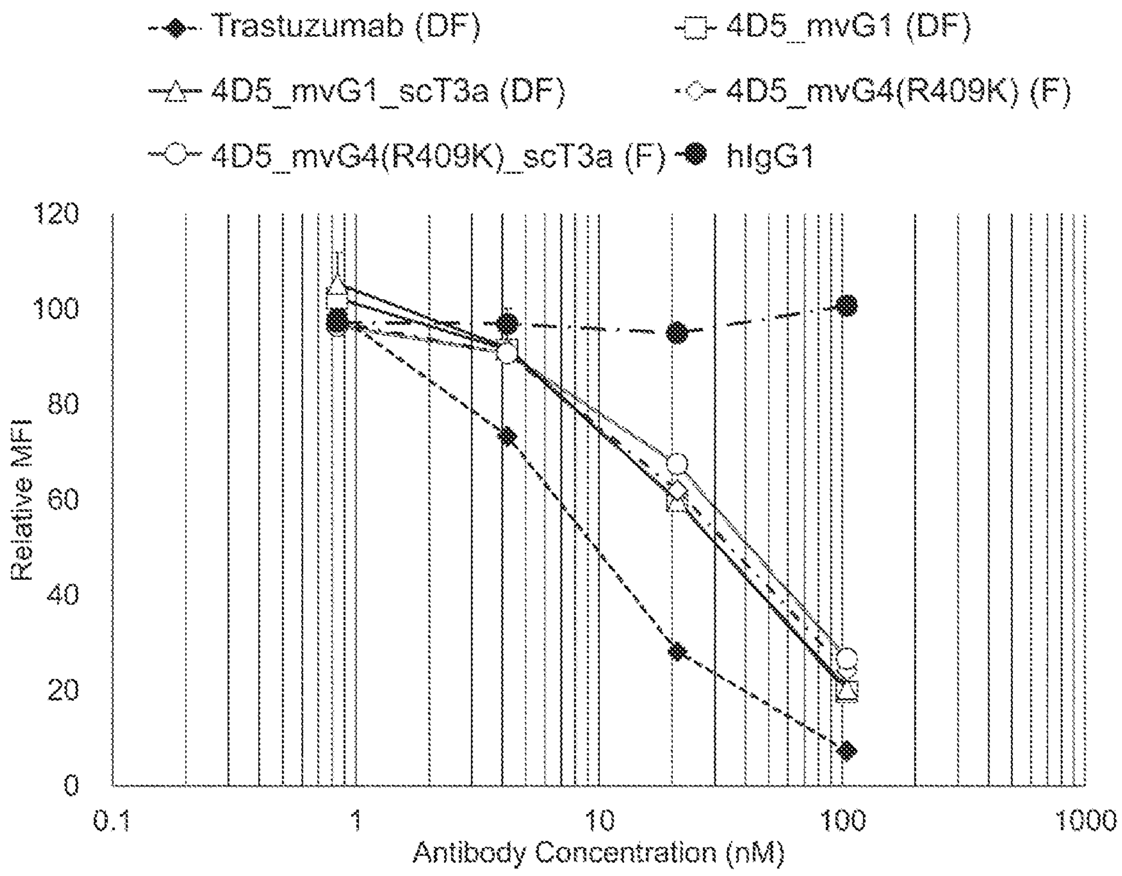
MFI : Mean fluorecent intensity

[FIG. 5]
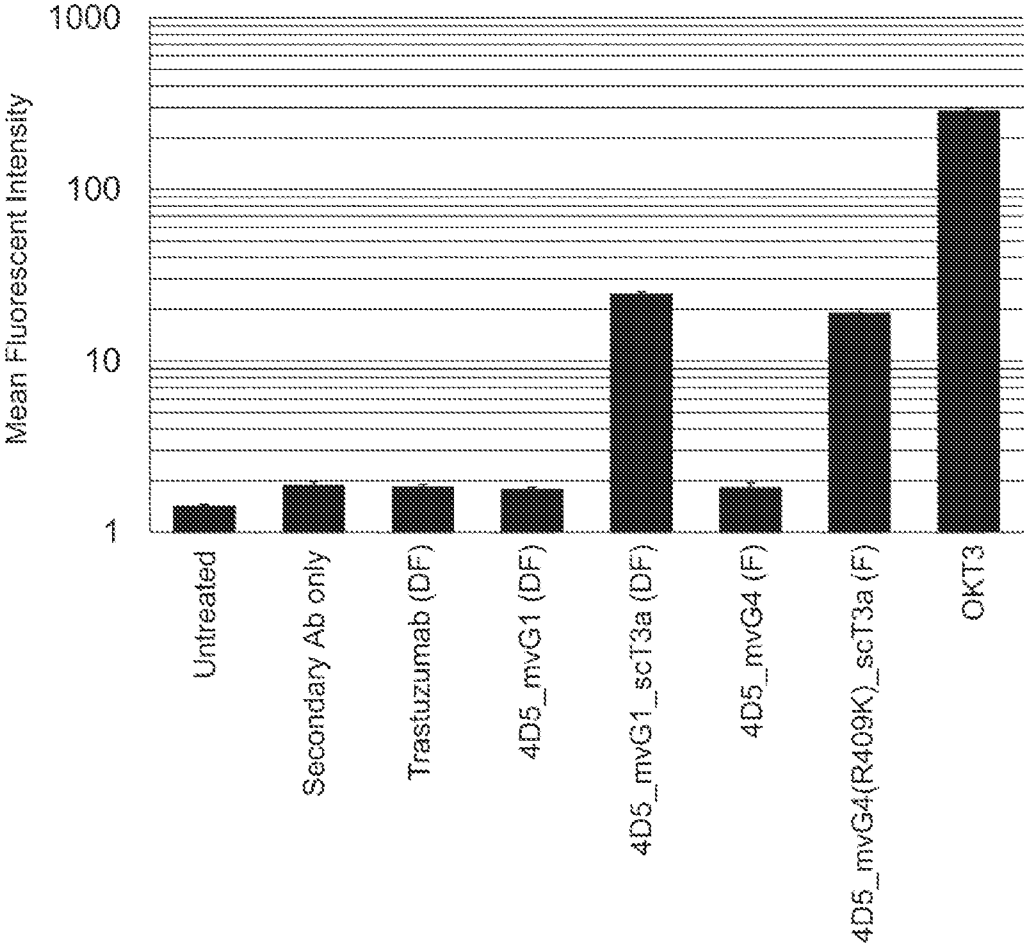

[FIG. 6]
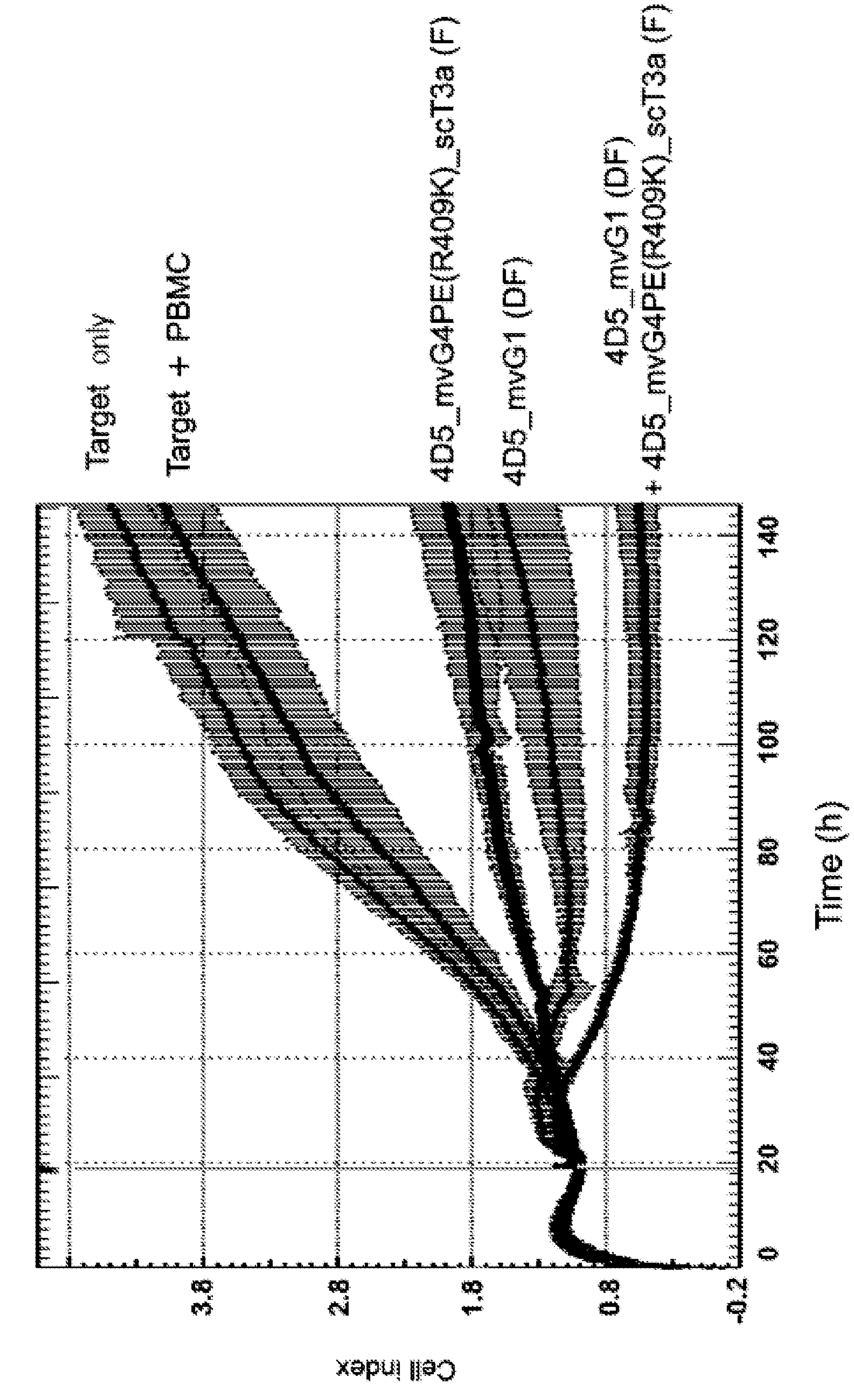

[FIG. 7]
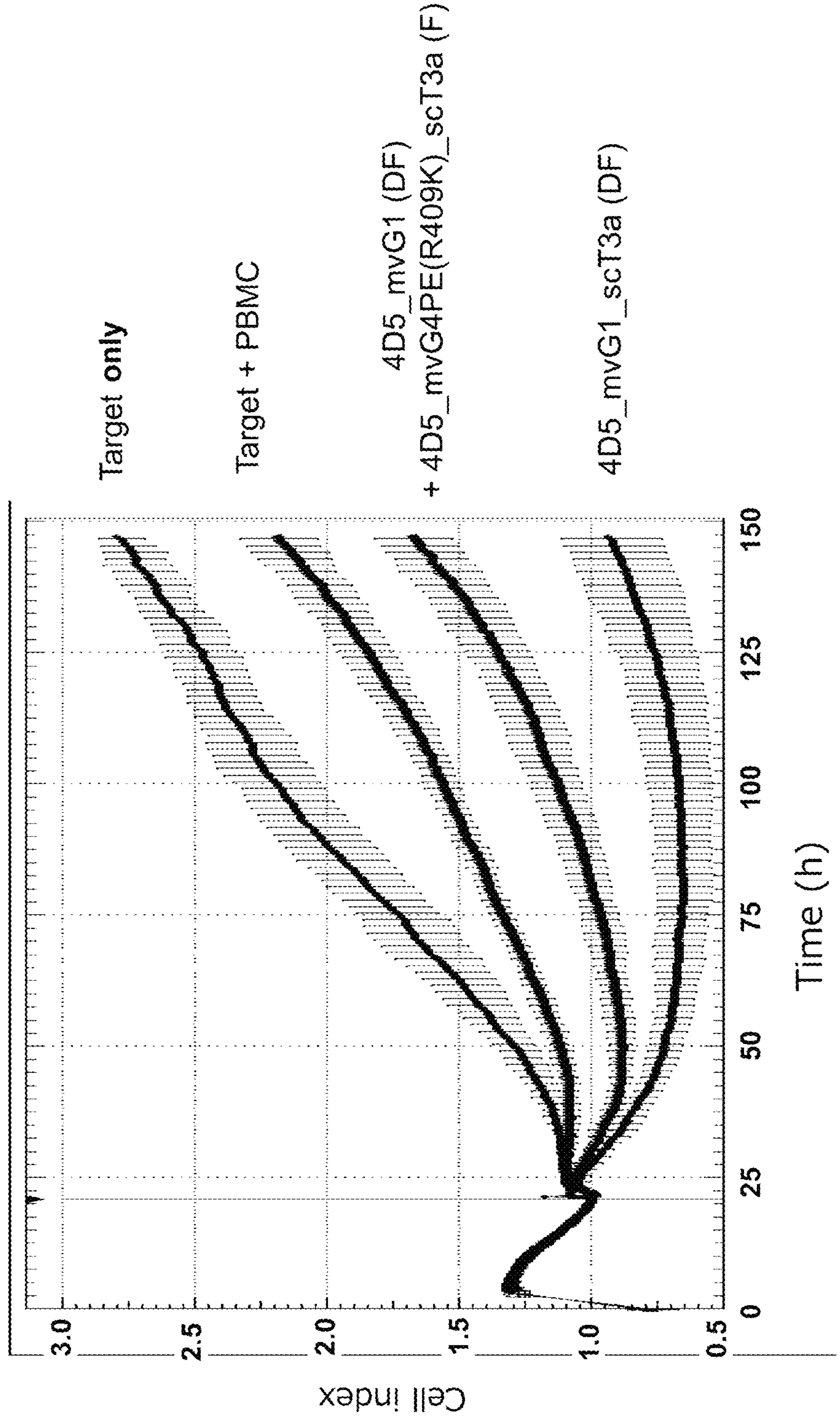

[FIG. 8]
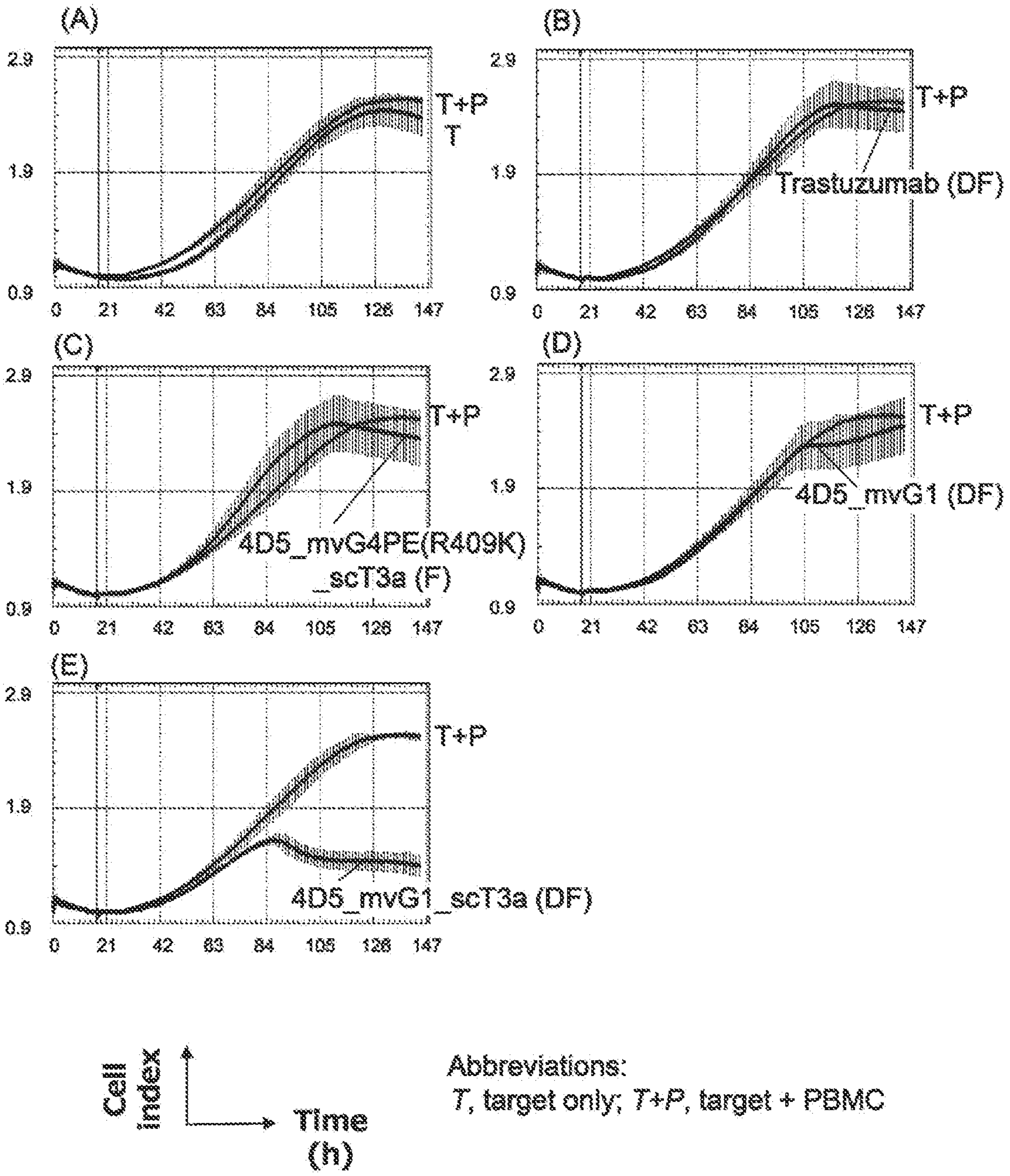

[FIG. 9]
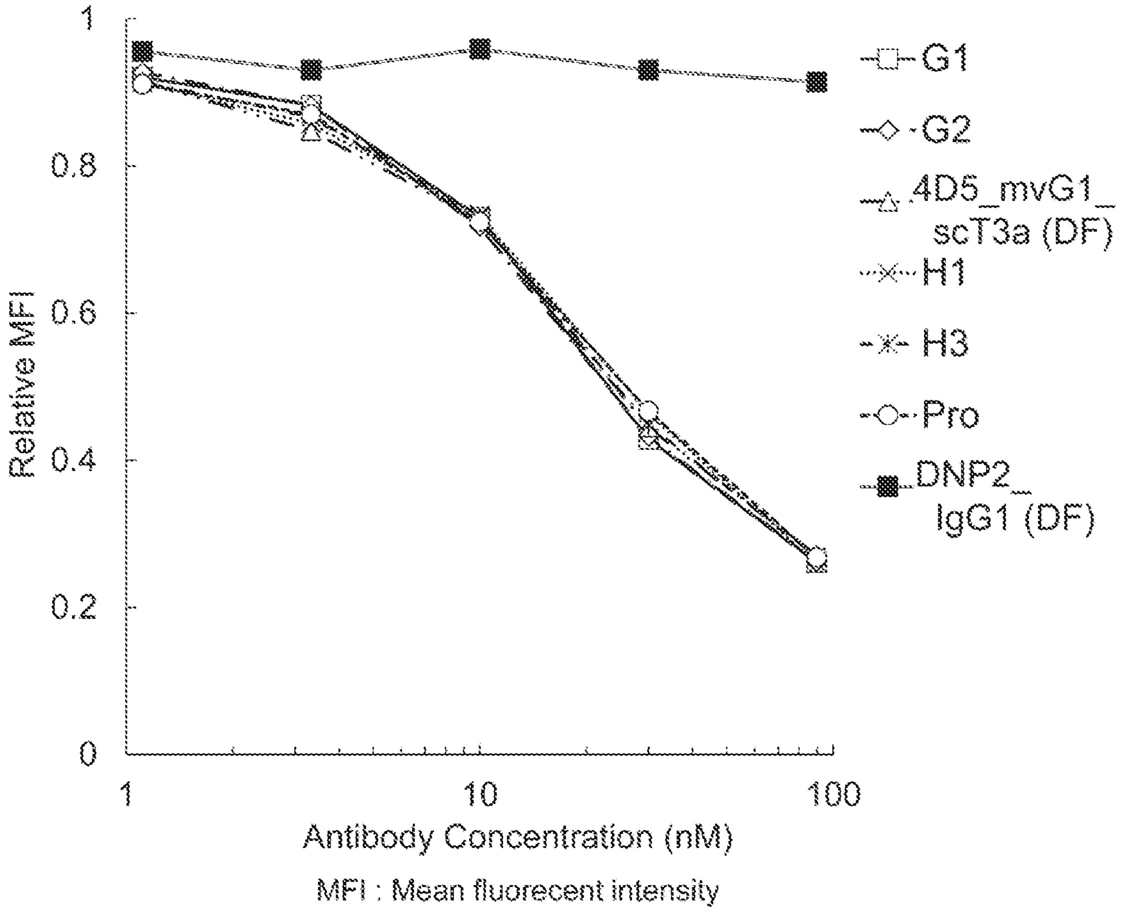
MFI : Mean fluorecent intensity

[FIG. 10]
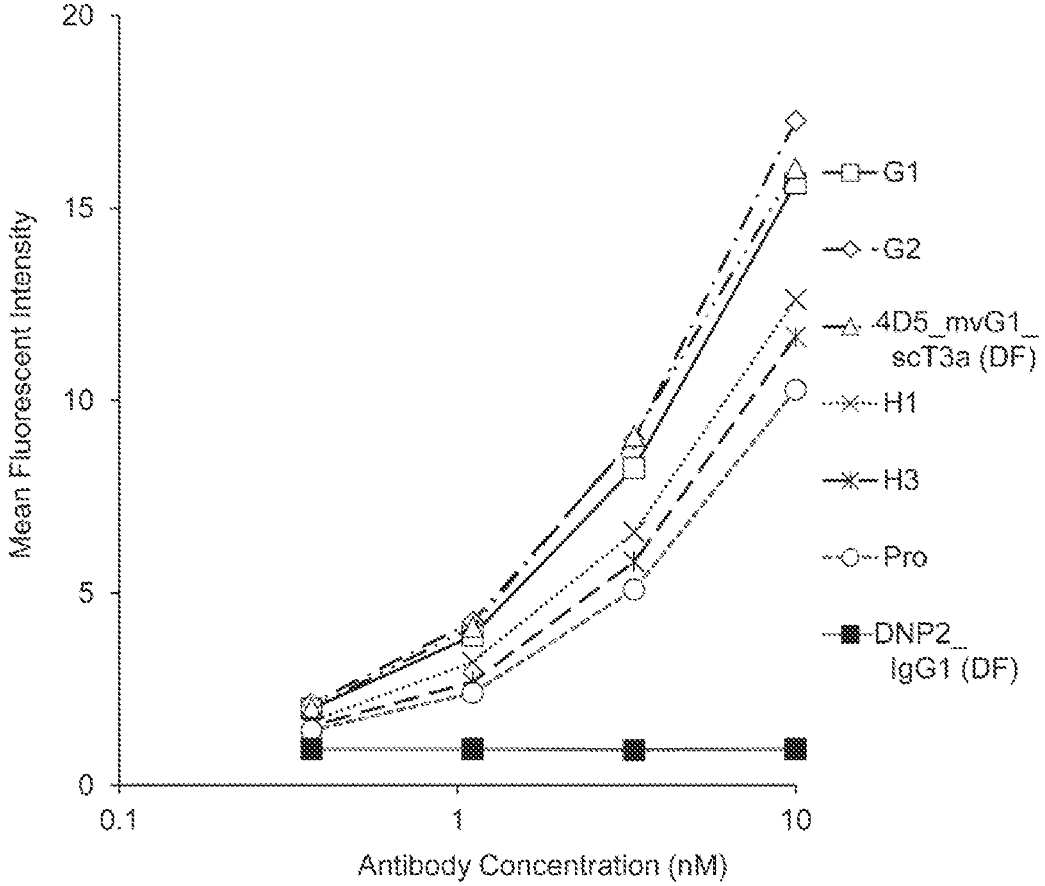

[FIG. 11]
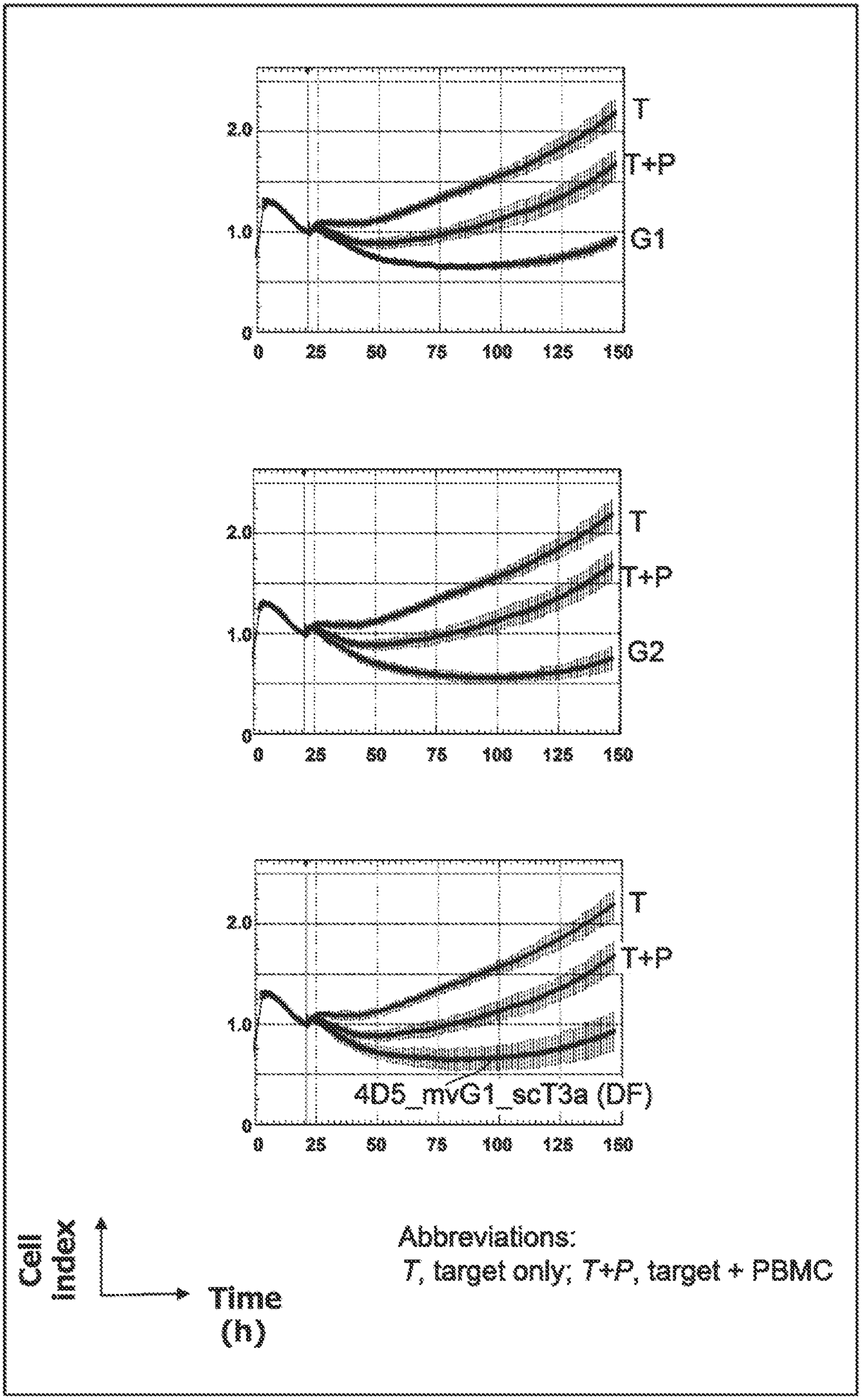

[FIG. 12]
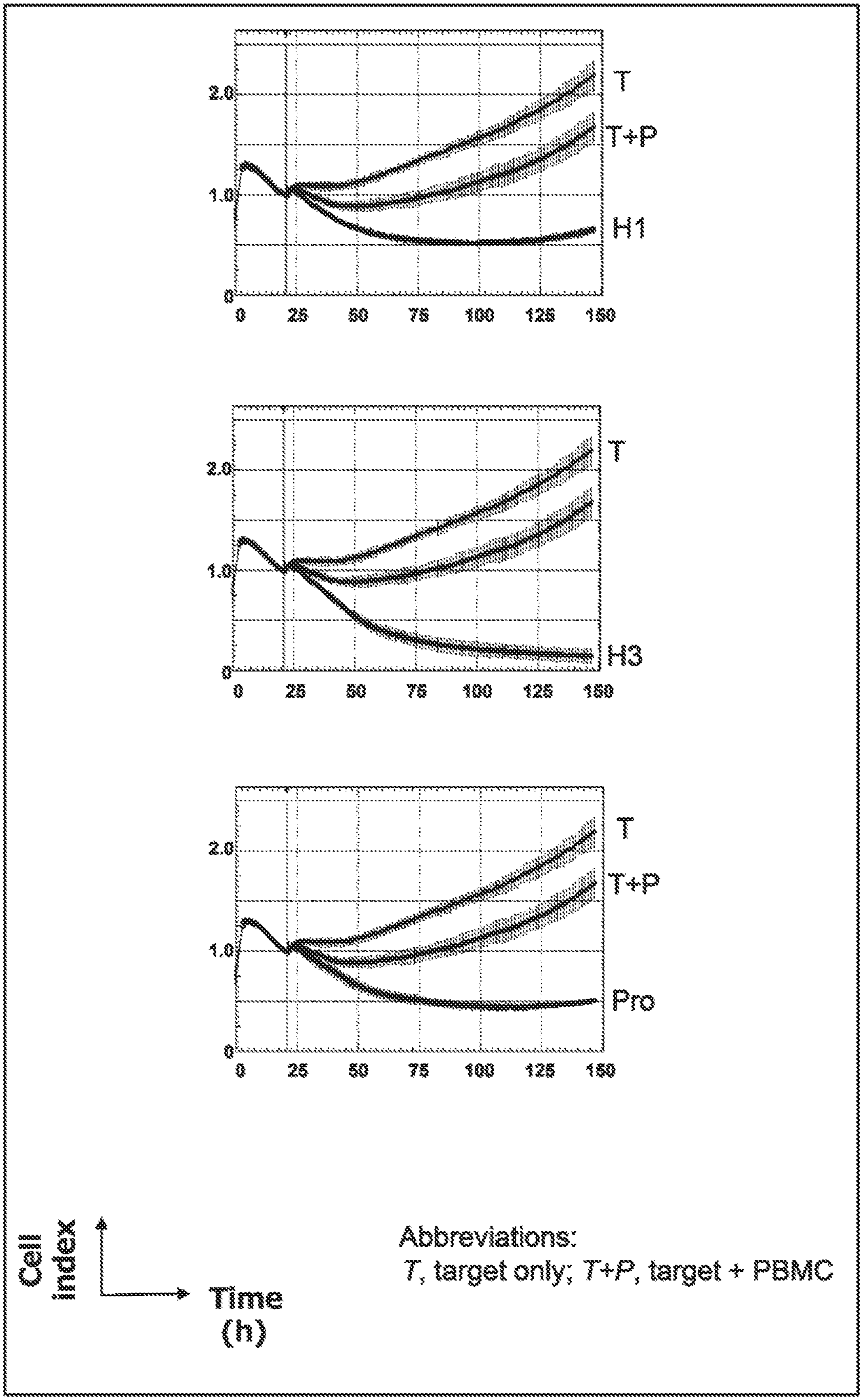

[FIG. 13]
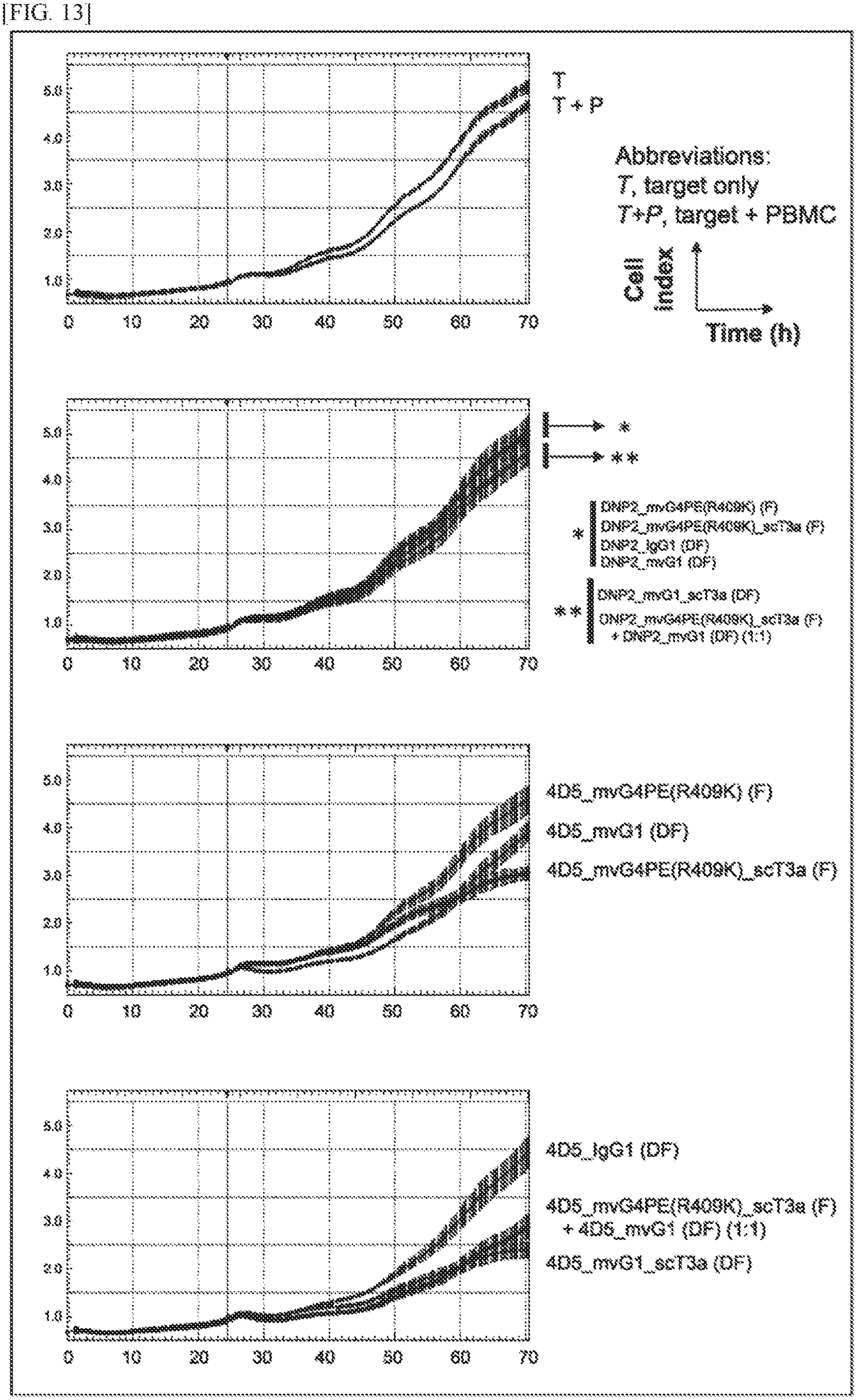

[FIG. 14]
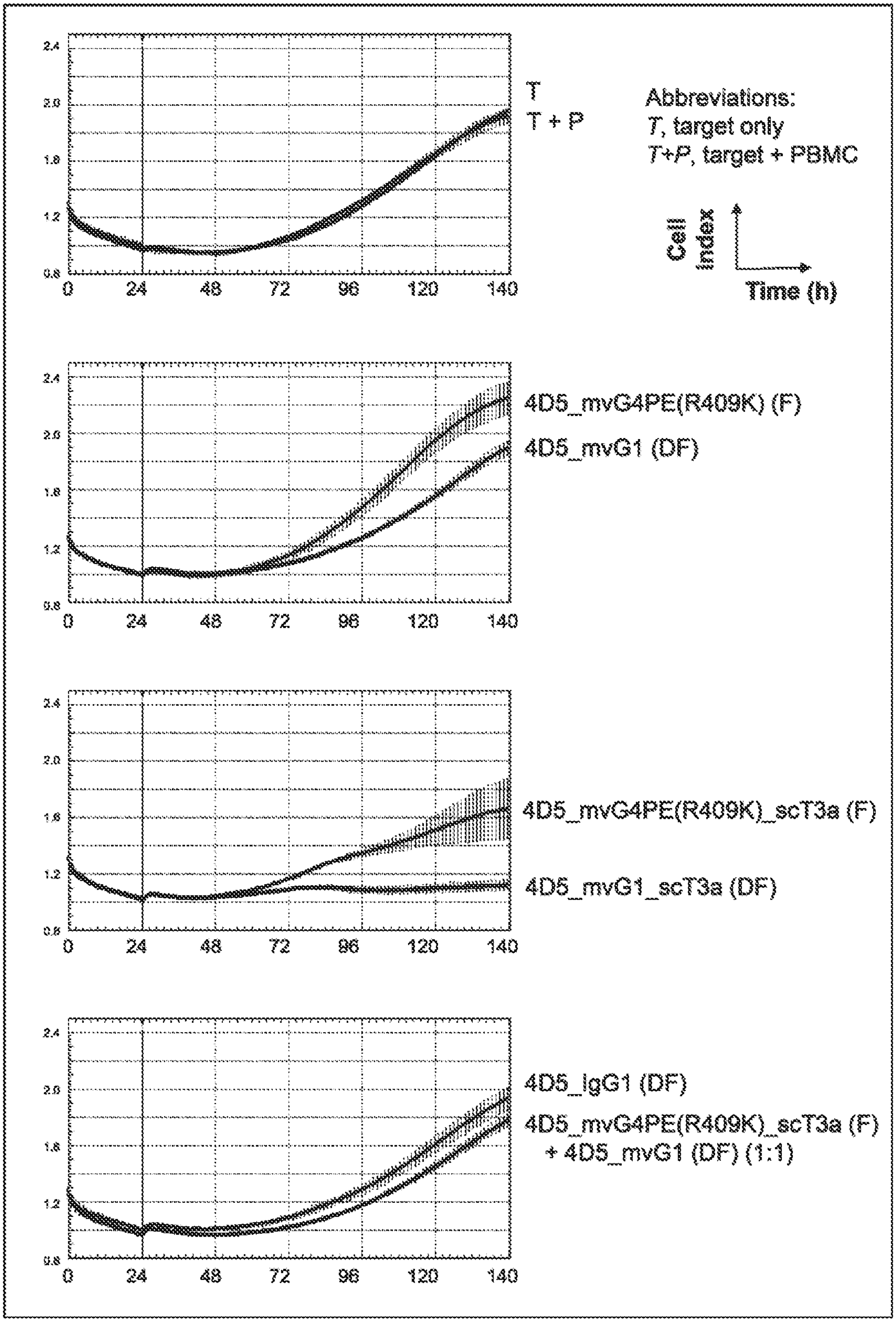

[FIG. 15]
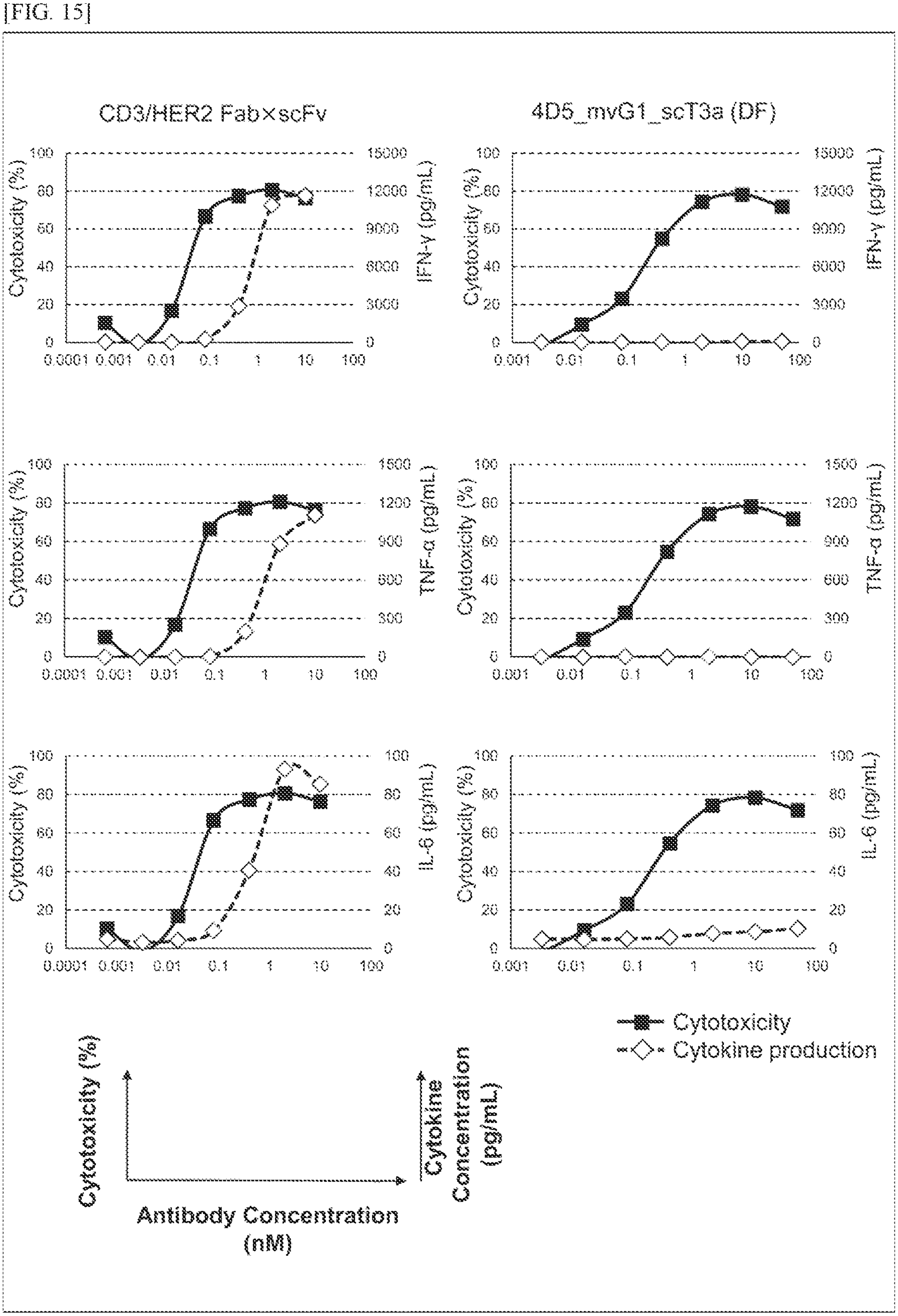

[FIG. 16]
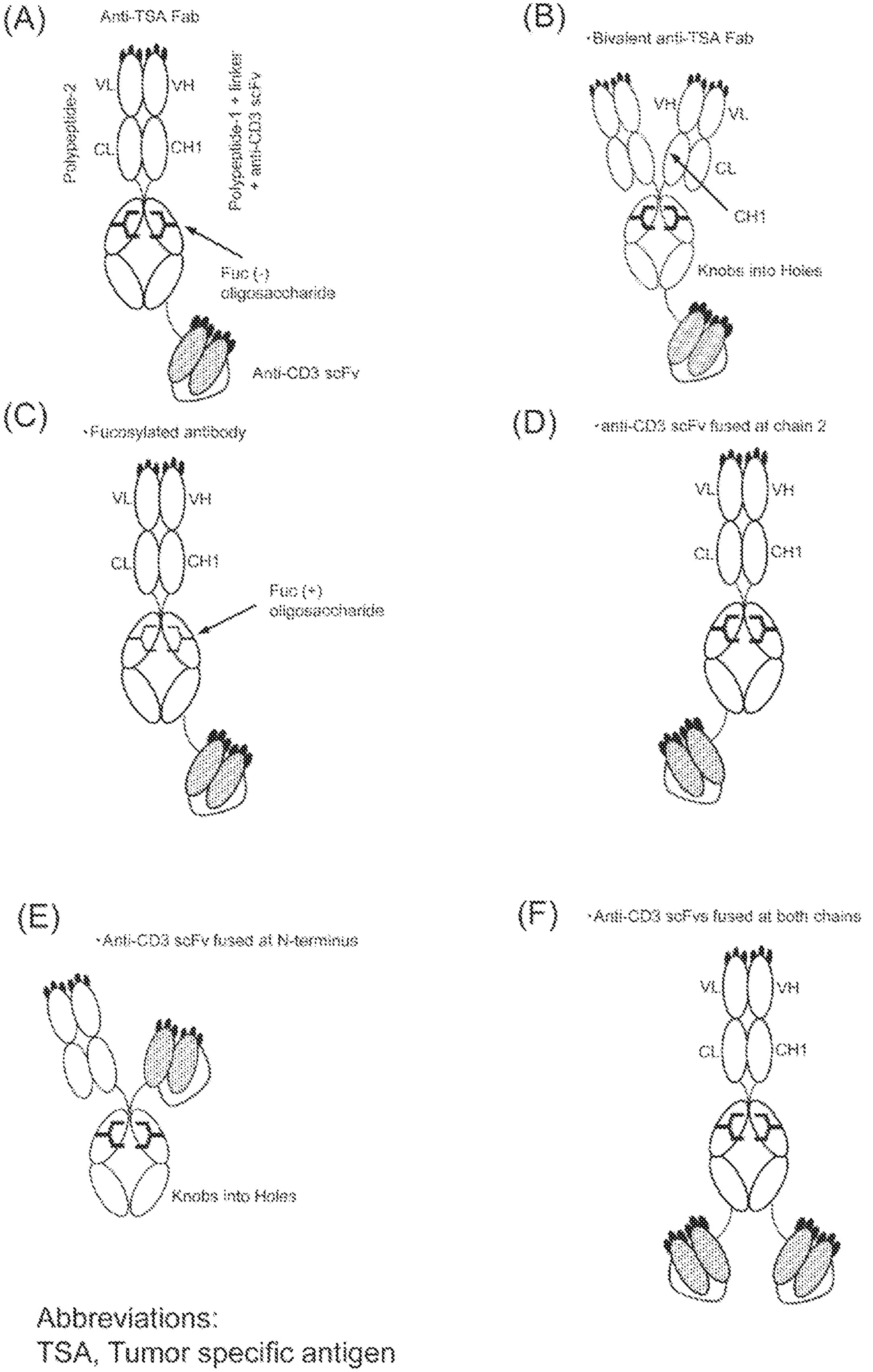
Abbreviations:
TSA, Tumor specific antigen

[FIG. 17]
(A)
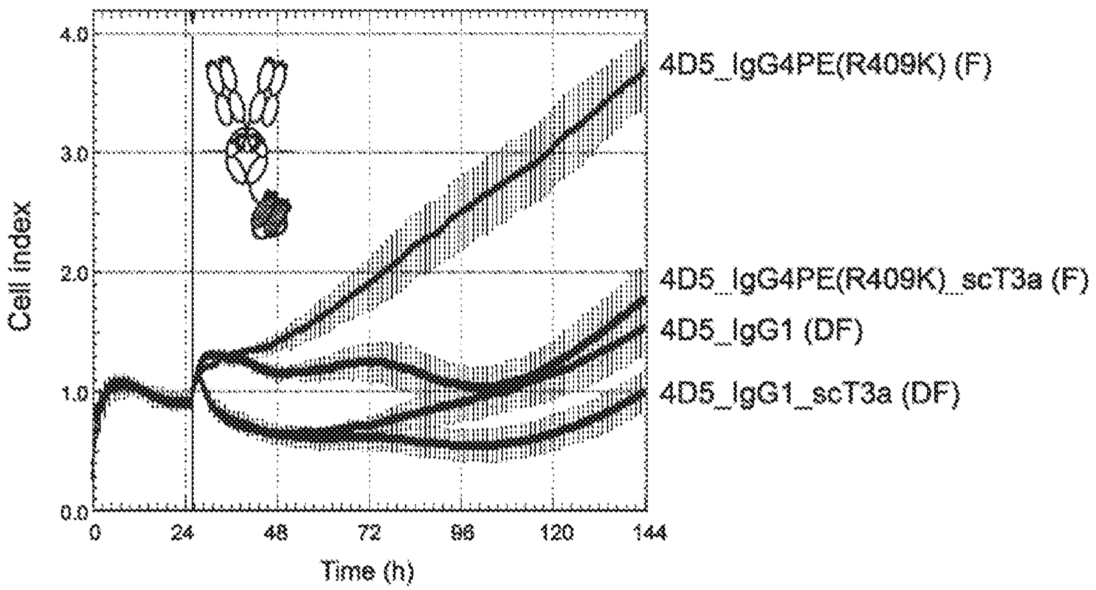
(B)
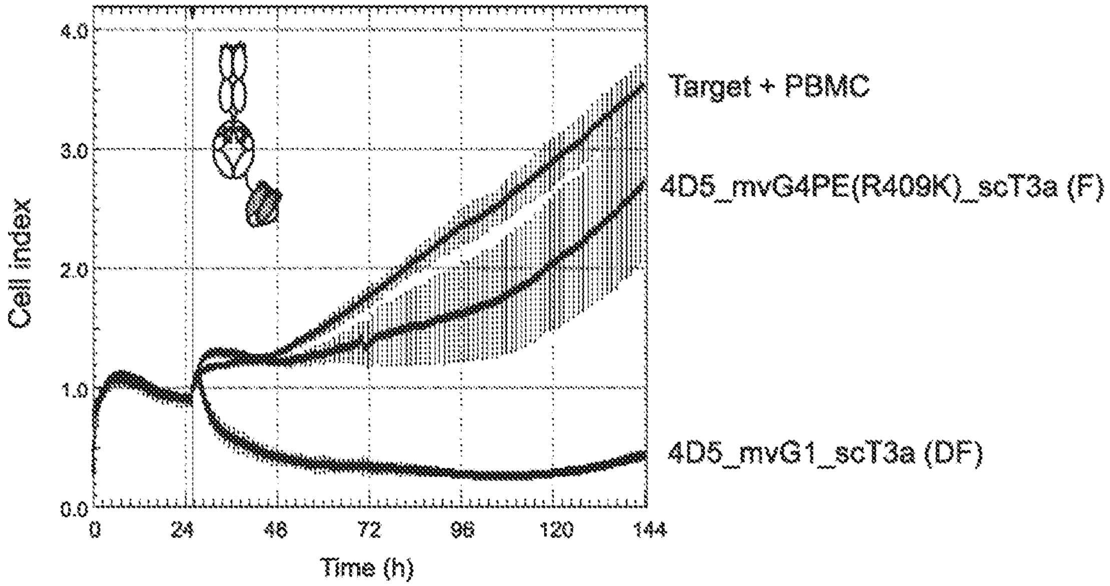

[FIG. 18]
(A)
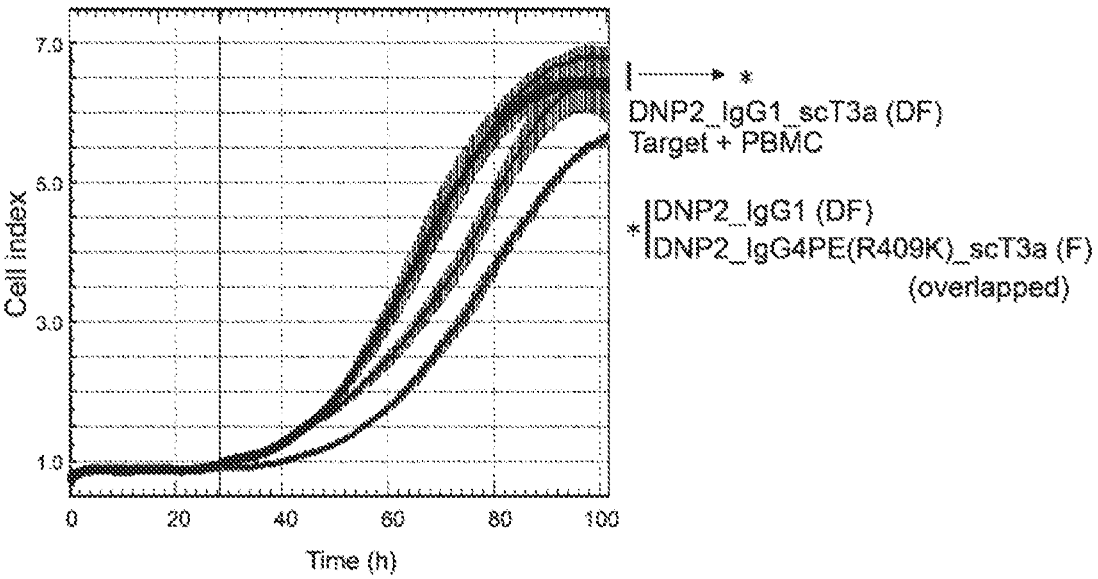
(B)
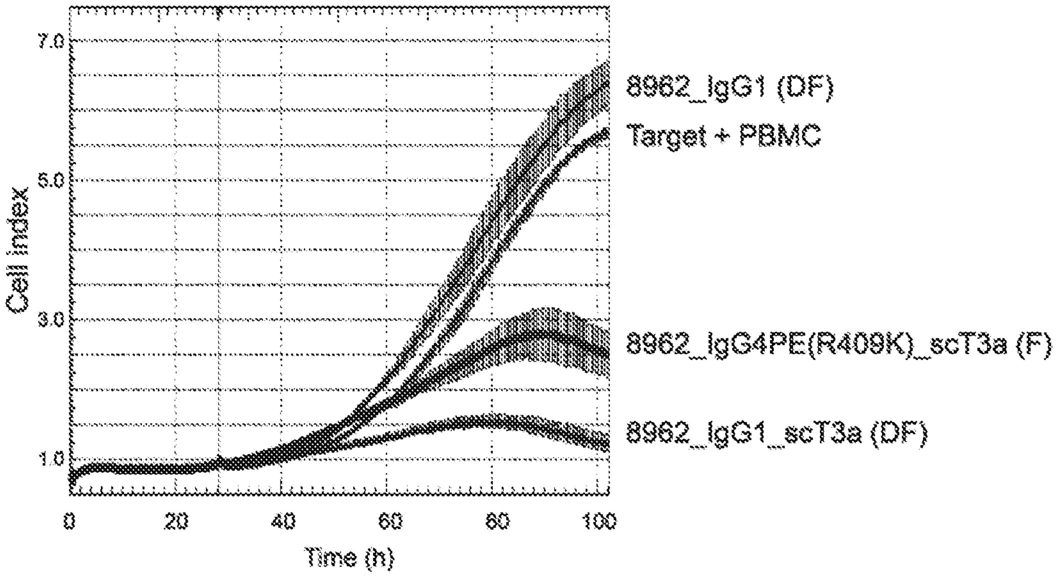

[FIG. 19]
(A)
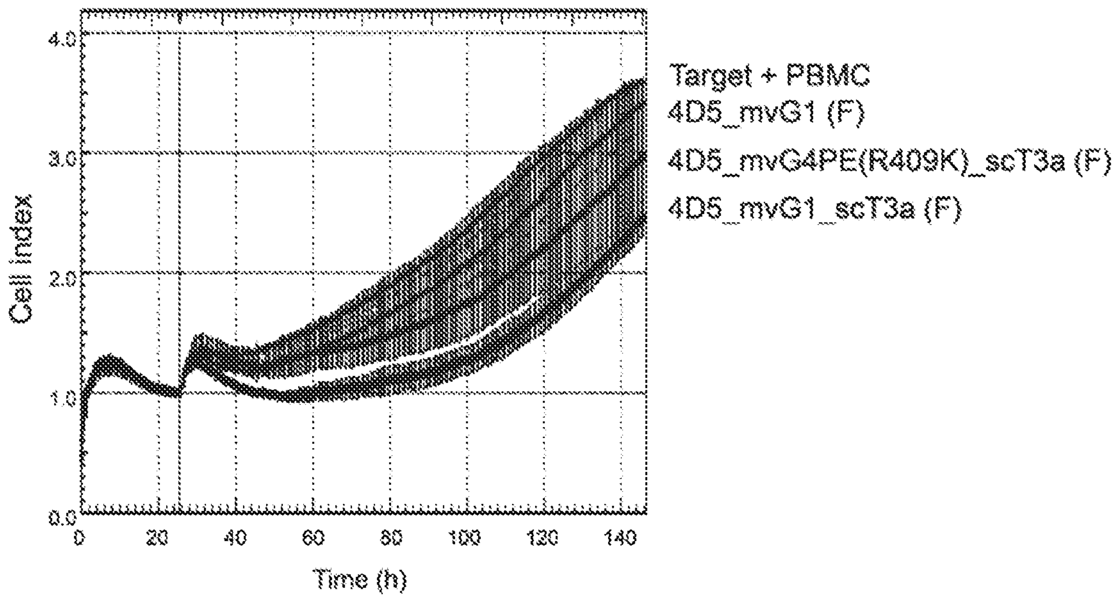
(B)
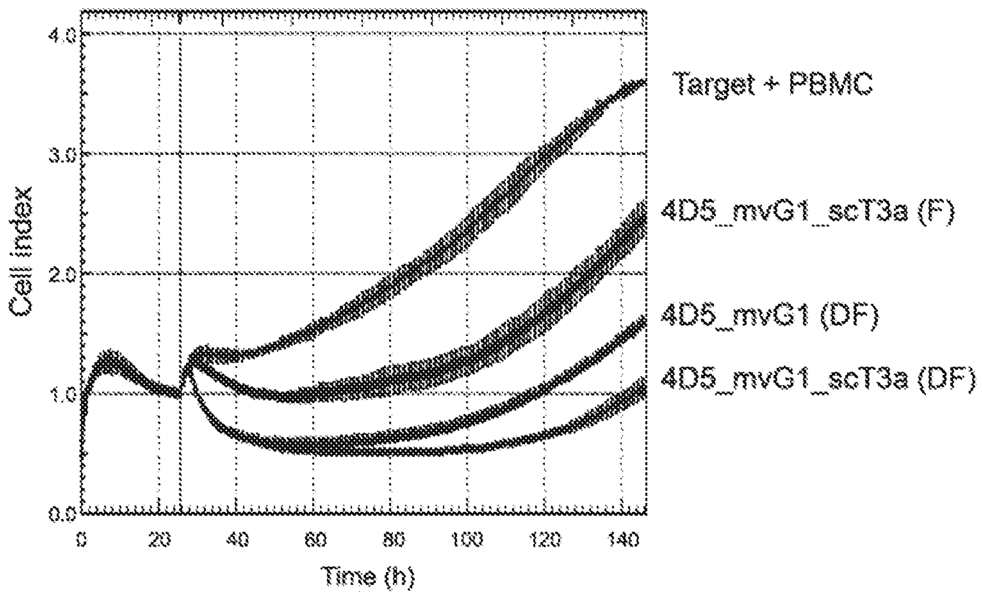

[FIG. 20]
(A)
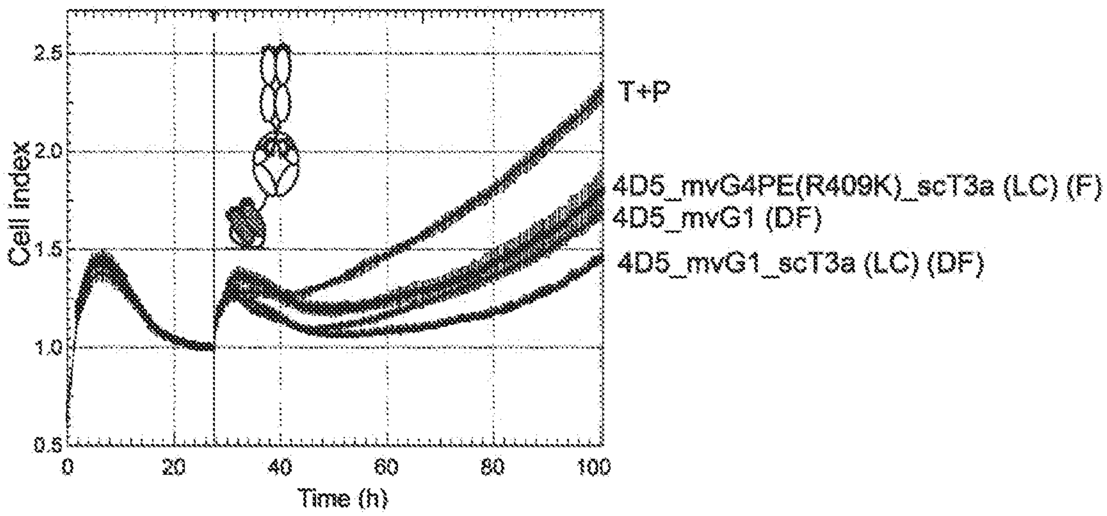
(B)
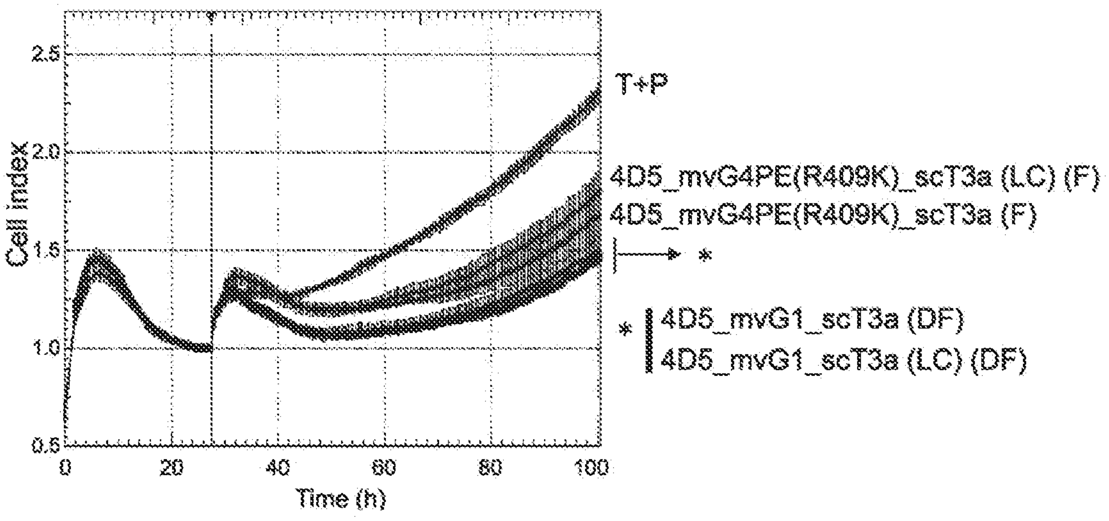

[FIG. 21]
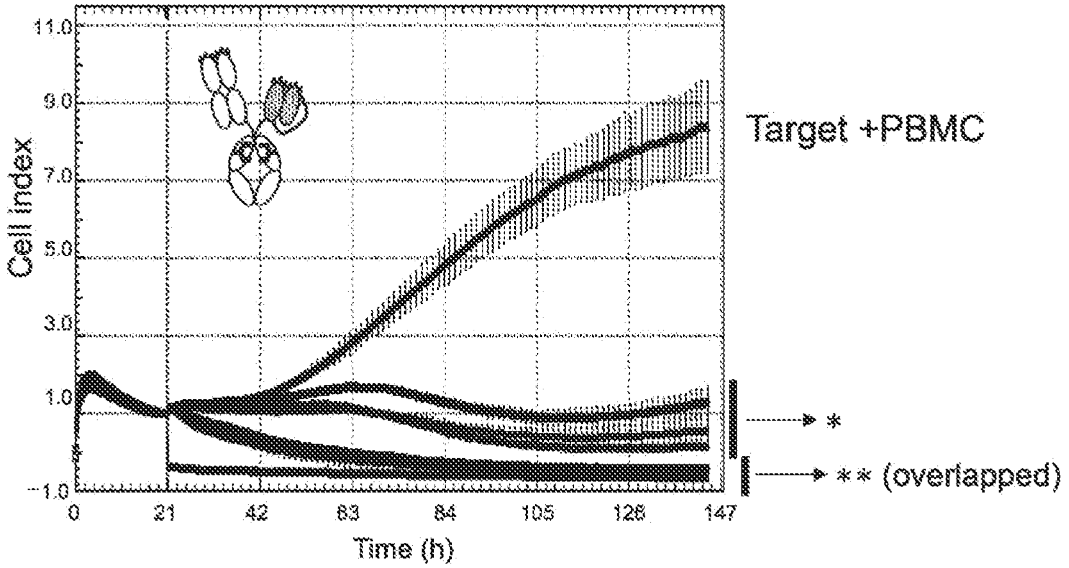
| | | |
|---|---|---|
| * | | 4D5mut_scT3a_IgG1 (DF) (0.5 nM) |
| | | 4D5mut_scT3a_IgG1 (DF) (50 nM) |
| | | 4D5mut_scT3a_IgG1 (DF) (5 nM) |
| ** | | 4D5_scT3a_IgG1 (DF) (0.5 nM) |
| | | 4D5_scT3a_IgG1 (DF) (50 nM) |
| | | 4D5_scT3a_IgG1 (DF) (5 nM) |
| | | 0.5% Triton X-100 |

[FIG. 22A]
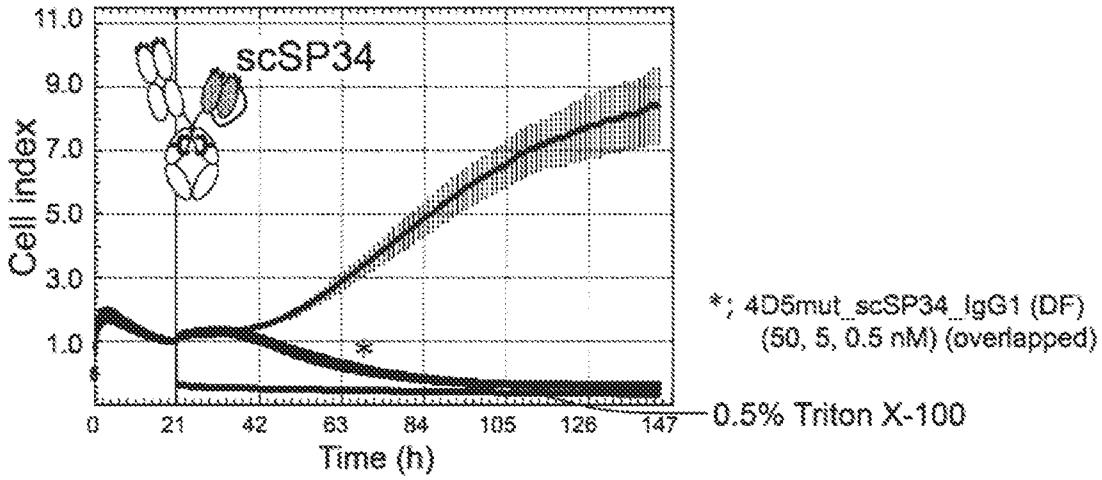
[FIG. 22B]
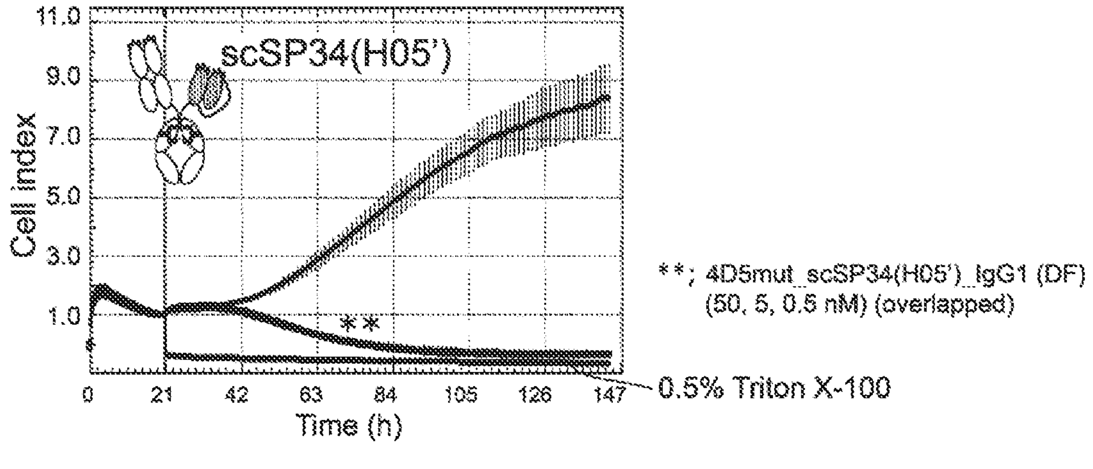

[FIG. 22C]
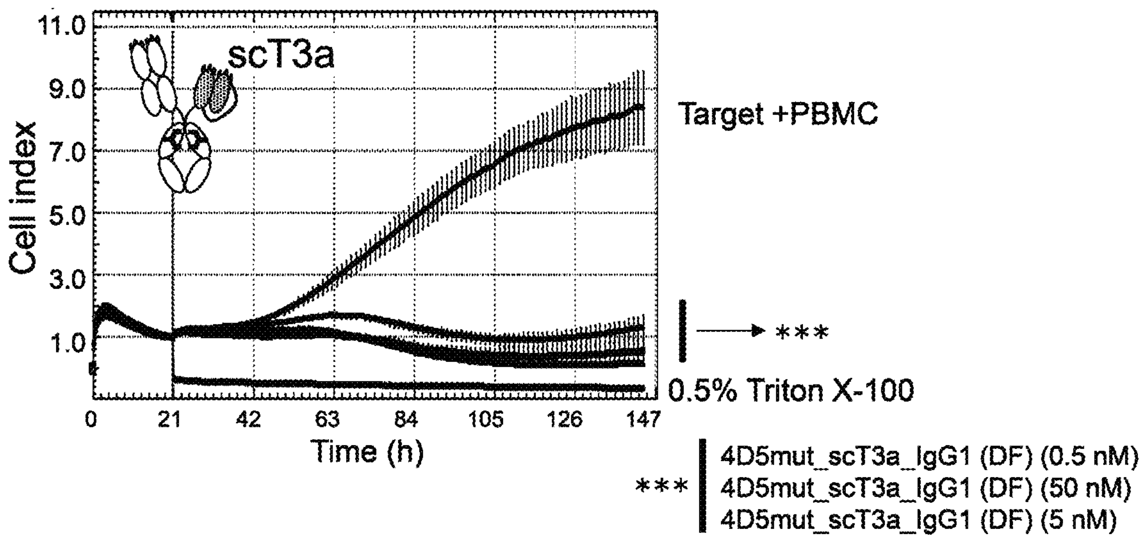
[FIG. 22D]
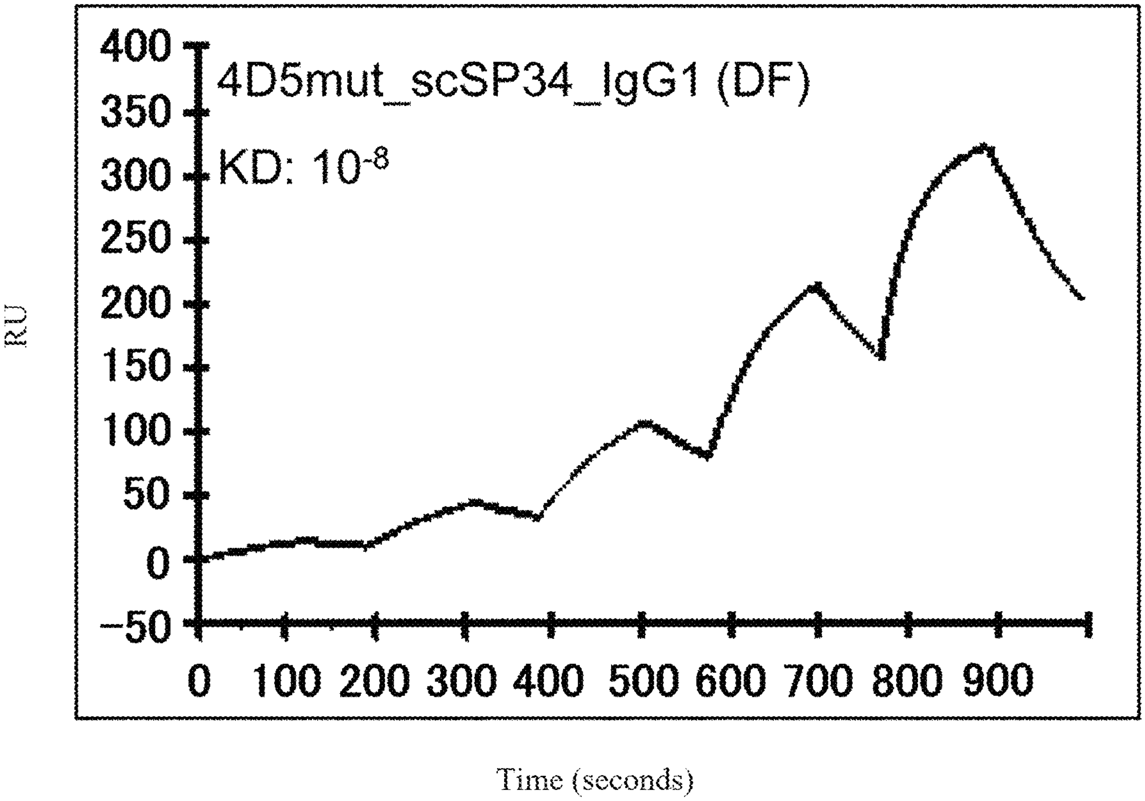

[FIG. 22E]
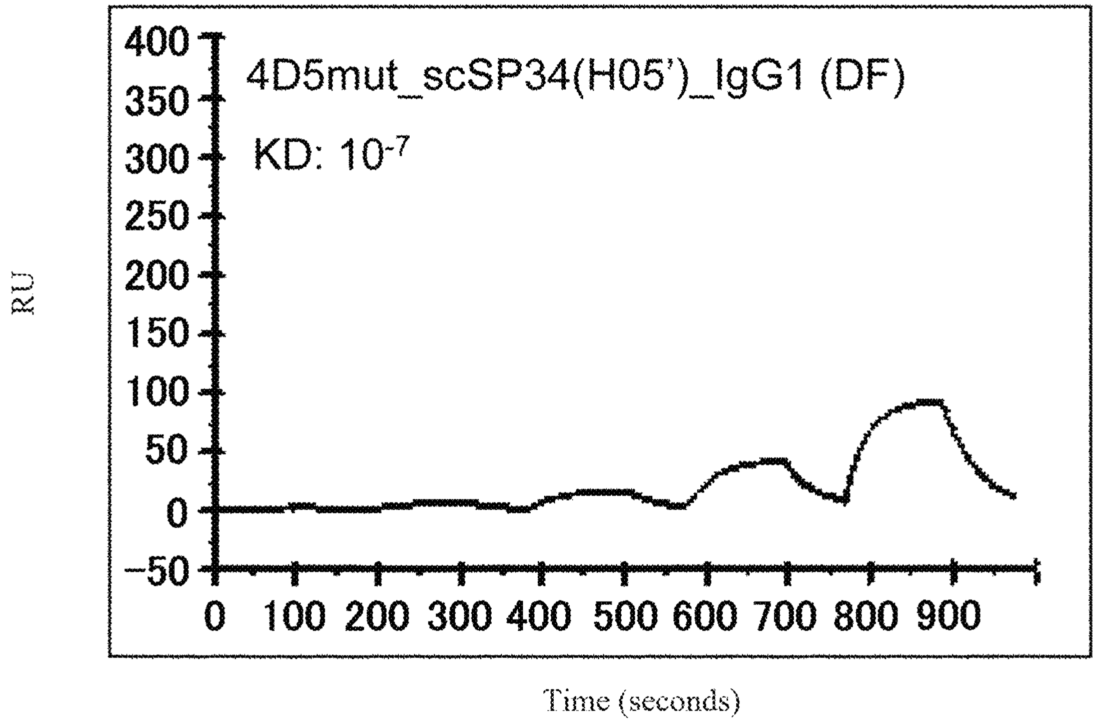
[FIG. 22F]
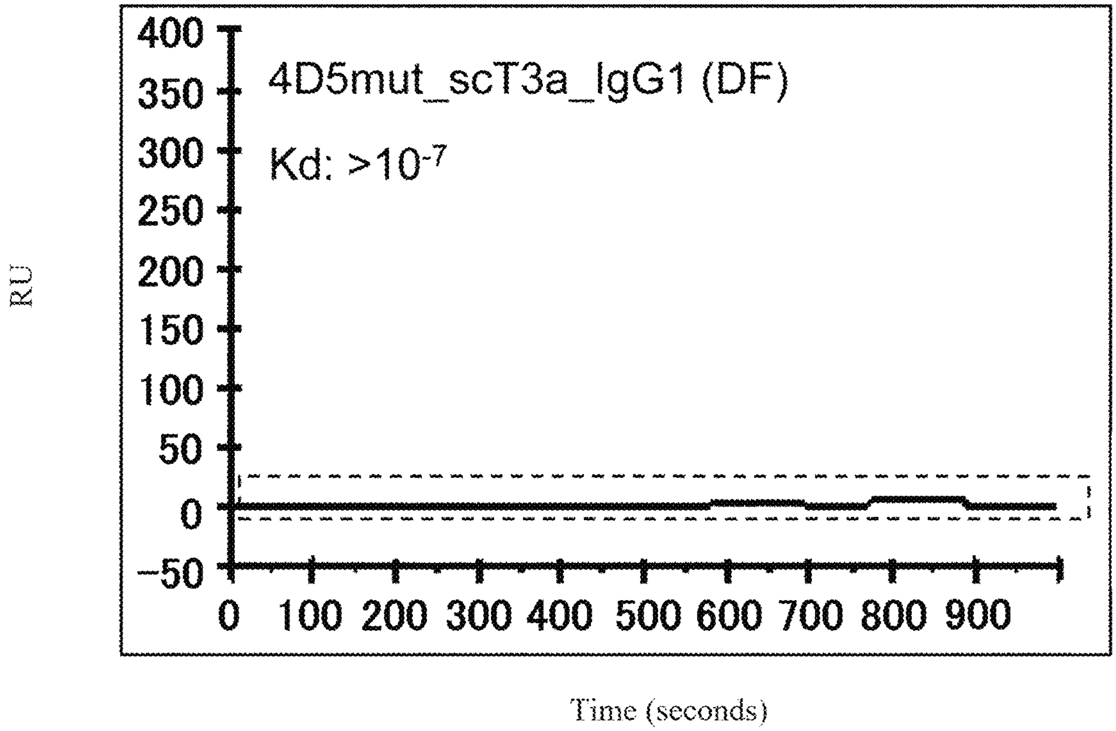

[FIG. 22G]
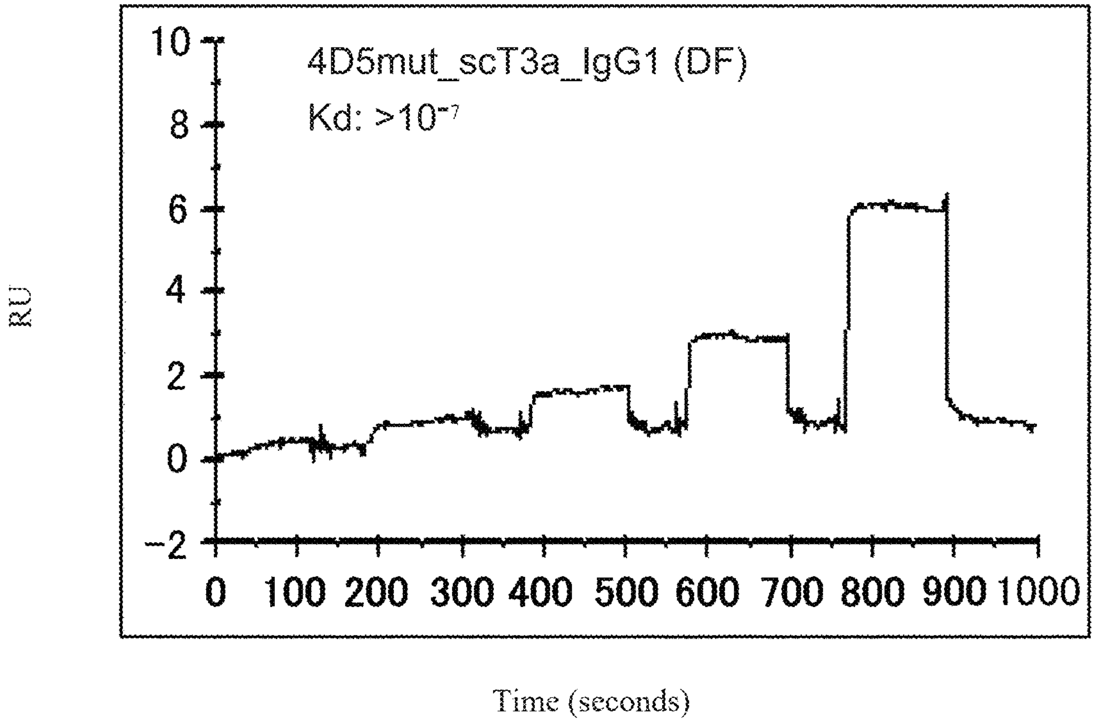

[FIG. 23]
(A)
4D5mut_mvG1_scT3a (DF)
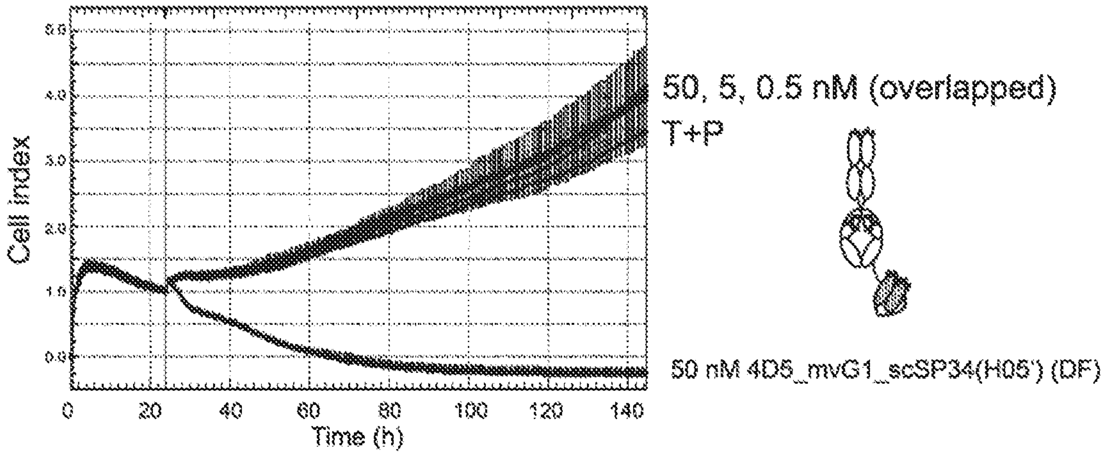
(B)
DNP2_mvG1_(scT3a)$_2$ (DF)
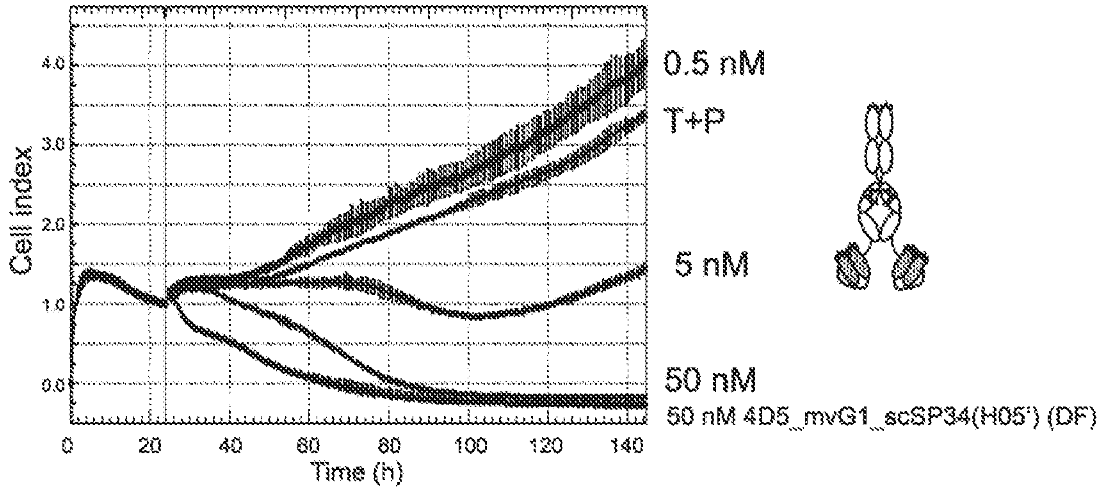

[FIG. 24A]
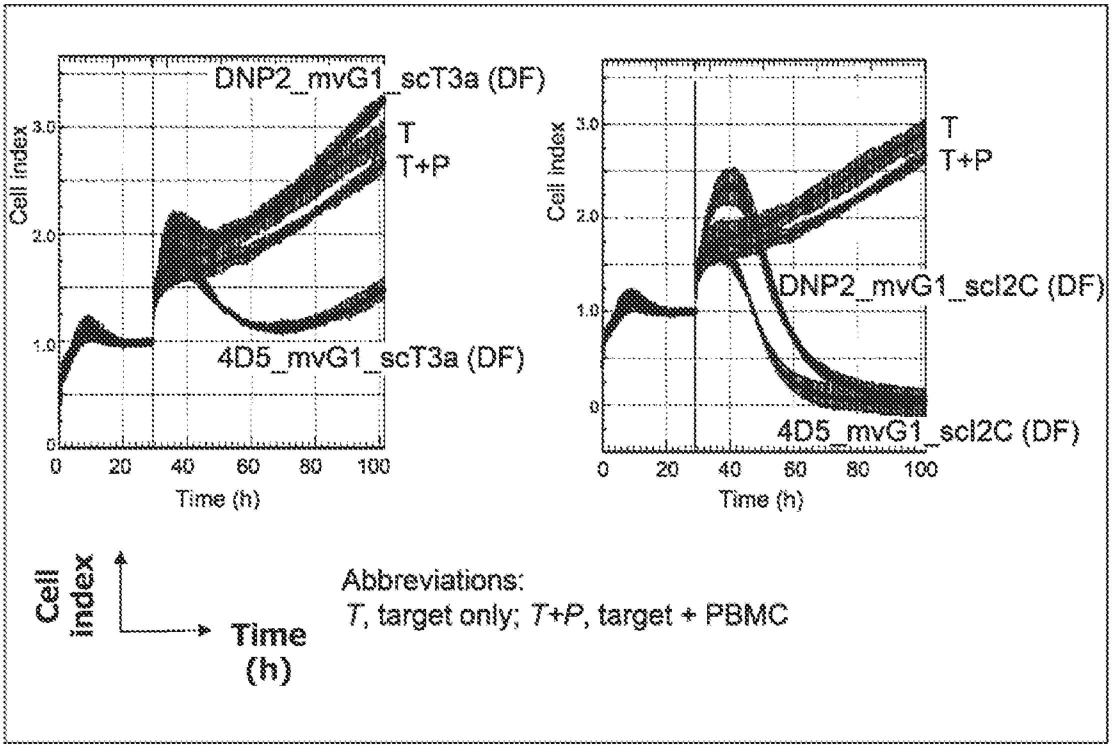

[FIG. 24B]
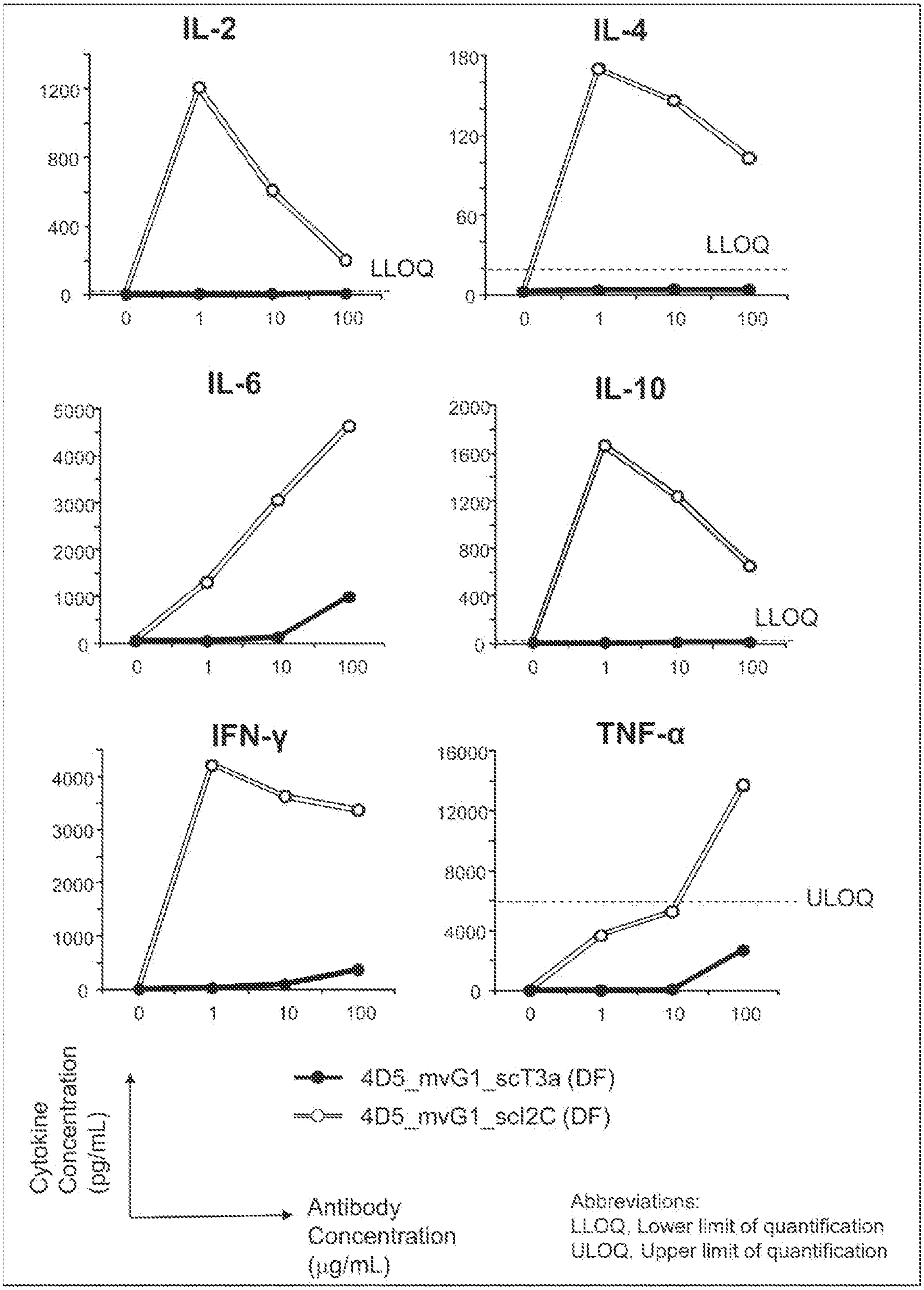

[FIG. 25]

(A)

| | | CDRL1 | CDRL2 | CDRL3 |
|---|---|---|---|---|
| SP_34VL | | RSSTGAVTTSNYAN | GTNKRAP | ALWYSNLWV |
| L01 | L32-YA | RSSTGAVTTSN**A**AN | GTNKRAP | ALWYSNLWV |
| L02 | L50-GP | RSSTGAVTTSNYAN | **P**TNKRAP | ALWYSNLWV |
| L03 | L53-KA | RSSTGAVTTSNYAN | GTN**A**RAP | ALWYSNLWV |
| L04 | L53-KI | RSSTGAVTTSNYAN | GTN**I**RAP | ALWYSNLWV |
| L05 | L53-KS | RSSTGAVTTSNYAN | GTN**S**RAP | ALWYSNLWV |
| L06 | L56-PG | RSSTGAVTTSNYAN | GTNKRA**G** | ALWYSNLWV |
| L07 | L92-YA | RSSTGAVTTSNYAN | GTNKRAP | ALW**A**SNLWV |
| L08 | L92-YR | RSSTGAVTTSNYAN | GTNKRAP | ALW**R**SNLWV |
| L09 | L92-YT | RSSTGAVTTSNYAN | GTNKRAP | ALW**T**SNLWV |
| L10 | L93-SE | RSSTGAVTTSNYAN | GTNKRAP | ALWY**E**NLWV |
| L11 | L96-WD | RSSTGAVTTSNYAN | GTNKRAP | ALWYSNL**D**V |

| | | CDRH1 | CDRH2 | CDRH3 |
|---|---|---|---|---|
| SP34 VH | | TYAMN | RIRSKYNNYATYYADSVKD | HGNFGNSYVSWFAY |
| H01 | H32-YA | T**A**AMN | RIRSKYNNYATYYADSVKD | HGNFGNSYVSWFAY |
| H02 | H98-FA | TYAMN | RIRSKYNNYATYYADSVKD | HGN**A**GNSYVSWFAY |
| H03 | H98-FY | TYAMN | RIRSKYNNYATYYADSVKD | HGN**Y**GNSYVSWFAY |
| H04 | H100A-SE | TYAMN | RIRSKYNNYATYYADSVKD | HGNFGN**E**YVSWFAY |
| H05 | H100B-YD | TYAMN | RIRSKYNNYATYYADSVKD | HGNFGNS**D**VSWFAY |
| H06 | H100B-YE | TYAMN | RIRSKYNNYATYYADSVKD | HGNFGNS**E**VSWFAY |
| H07 | H100B-YR | TYAMN | RIRSKYNNYATYYADSVKD | HGNFGNS**R**VSWFAY |

(B)

| No. | VL mutation | | | VH mutation |
|---|---|---|---|---|
| 2-01 | L32-YA | L93-SE | | |
| 2-02 | L32-YA | L53-KA | L93-SE | |
| 2-03 | L32-YF | | | H98-FY |
| 2-04 | L32-YF | | | H100A-SE |
| 2-05 | L32-YF | | | H100B-YD |
| 2-06 | L32-YF | | | H100B-YE |
| 2-07 | L32-YF | L93-SE | | H98-FY |
| 2-08 | L32-YF | L93-SE | | H100A-SE |
| 2-09 | L32-YF | L93-SE | | H100B-YD |
| 2-10 | L32-YF | L93-SE | | H100B-YE |
| 2-11 | L53-KA | L93-SE | | H98-FY |
| 2-12 | L53-KA | L93-SE | | H100A-SE |
| 2-13 | L92-YA | L93-SE | | |
| 2-14 | L92-YT | L93-SE | | H98-FY |
| 2-15 | L92-YT | L93-SE | | H100A-SE |

| No. | VL mutation | | VH mutation | |
|---|---|---|---|---|
| 2-16 | L92-YT | L93-SE | H100B-YD | |
| 2-17 | L92-YT | L93-SE | H100B-YE | |
| 2-18 | | L93-SE | H98-FY | H100A-SE |
| 2-19 | | L93-SE | H98-FY | H100B-YD |
| 2-20 | | L93-SE | H98-FY | H100B-YE |
| 2-21 | L32-YA | L93-SE | H100B-YR | |
| 2-22 | L53KA | L53-SE | H100B-YR | |
| 2-23 | L92-YT | L93-SE | H100B-YR | |
| 2-24 | | L93-SE | H100B-YA | |
| 2-25 | | L93-SE | H100B-YL | |
| 2-26 | | L93-SE | H100B-YM | |
| 2-27 | | L93-SE | H100B-YN | |
| 2-28 | | L93-SE | H100B-YS | |

[FIG. 26]

(A)

| | FR L1 | | FR L2 | | FR L3 | | FR L4 |
|---|---|---|---|---|---|---|---|
| SP34 VL | XXXXXXXXXXXXXXXXXXXXXX | CDR L1 | XXXXXXXXXXXXXXX | CDR L2 | XXXXXXXXXXXXXXXXXXXXXXXXXXXXXXXX | CDR L3 | XXXXXXXXXX |
| LV0 | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV4a | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV4b | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV5 | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV8a | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV8b | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV13 | XXXXXXXXXXXXXXXXXXXXXX | | XXXXXXXXXXXXXXX | | XXXXXXXXXXXXXXXXXXXXXXXXXXXXXXXX | | XXXXXXXXXX |

(B)

| | FR H1 | | FR H2 | | FR H3 | | FR H4 |
|---|---|---|---|---|---|---|---|
| SP34 VH | XXXXXXXXXXXXXXXXXXXXXXXXXXXXXX | CDR H1 | XXXXXXXXXXXXXX | CDR H2 | XXXXXXXXXXXXXXXXXXXXXXXXXXXXXXXX | CDR H3 | XXXXXXXXXXX |
| HV0 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV1 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV2a | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV2b | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV2c | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV3 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV5 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |

(C)

| | FR L1 | | FR L2 | | FR L3 | | FR L4 |
|---|---|---|---|---|---|---|---|
| SP34 VL | XXXXXXXXXXXXXXXXXXXXXX | CDR L1 | XXXXXXXXXXXXXXX | CDR L2 | XXXXXXXXXXXXXXXXXXXXXXXXXXXXXXXX | CDR L3 | XXXXXXXXXX |
| LV0 | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV3 | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV4 | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV5 | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV8a | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV8b | XXXXXXXXXXXXXXXXXXXXXX | | XXXXXXXXXXXXXXX | | XXXXXXXXXXXXXXXXXXXXXXXXXXXXXXXX | | XXXXXXXXXX |
| LV12 | XXXXXXXXXXXXXXXXXXXXXX | | XXXXXXXXXXXXXXX | | XXXXXXXXXXXXXXXXXXXXXXXXXXXXXXXX | | XXXXXXXXXX |

(D)

| | FR H1 | | FR H2 | | FR H3 | | FR H4 |
|---|---|---|---|---|---|---|---|
| SP34 VH | XXXXXXXXXXXXXXXXXXXXXXXXXXXXXX | CDR H1 | XXXXXXXXXXXXXX | CDR H2 | XXXXXXXXXXXXXXXXXXXXXXXXXXXXXXXX | CDR H3 | XXXXXXXXXXX |
| HV0 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV1 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV2a | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV2b | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV2c | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV3 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |
| HV5 | XXXXXXXXXXXXXXXXXXXXXXXXXXXXXX | | XXXXXXXXXXXXXX | | XXXXXXXXXXXXXXXXXXXXXXXXXXXXXXXX | | XXXXXXXXXXX |

[FIG. 27]

| antibody | mutation | Cycle | ka (1/Ms) | kd (1/s) | KD (M) |
|---|---|---|---|---|---|
| 01. 4D5_mvG1_scSP34(L03) | L53-KA | Cycle: 13 | 2.24E+5 | 7.34E-3 | 3.28E-8 |
| 02. 4D5_mvG1_scSP34(L04) | L53-KI | Cycle: 16 | 2.85E+5 | 3.77E-3 | 1.32E-8 |
| 03. 4D5_mvG1_scSP34(L08) | L92-YR | Cycle: 19 | 3.04E+5 | 8.00E-3 | 2.63E-8 |
| 04. 4D5_mvG1_scSP34(L09) | L92-YT | Cycle: 22 | 4.89E+5 | 26.81E-3 | 5.48E-8 |
| 05. 4D5_mvG1_scSP34(H03) | H98-FY | Cycle: 25 | 4.62E+5 | 36.71E-3 | 7.95E-8 |
| 06. 4D5_mvG1_scSP34(H04) | H100A-SE | Cycle: 28 | 5.88E+5 | 44.69E-3 | 7.60E-8 |
| 07. 4D5_mvG1_scSP34(H05) | H100B-YD | Cycle: 31 | 5.50E+5 | 45.91E-3 | 8.35E-8 |
| 08. 4D5_mvG1_scSP34(H06) | H100B-YE | Cycle: 34 | 3.29E+5 | 25.01E-3 | 7.61E-8 |
| 09. 4D5_mvG1_scSP34(L03') | L53-KA, L93-SE | Cycle: 37 | 2.59E+5 | 6.85E-3 | 2.65E-8 |
| 10. 4D5_mvG1_scSP34(L04') | L53-KI, L93-SE | Cycle: 40 | 1.89E+5 | 3.10E-3 | 1.64E-8 |
| 11. 4D5_mvG1_scSP34(L08') | L92-YR, L93-SE | Protein not obtained | | | |
| 12. 4D5_mvG1_scSP34(L09') | L92-YT, L93-SE | Cycle: 43 | 2.96E+5 | 15.09E-3 | 5.10E-8 |
| 13. 4D5_mvG1_scSP34(H03') | H98-FY, L93-SE | Cycle: 46 | 2.46E+5 | 35.10E-3 | 14.25E-8 |
| 14. 4D5_mvG1_scSP34(H04') | H100A-SE, L93-SE | Cycle: 49 | 7.10E+5 | 48.56E-3 | 6.84E-8 |
| 15. 4D5_mvG1_scSP34(H05') | H100B-YD, L93-SE | Cycle: 52 | 3.06E+5 | 30.96E-3 | 10.12E-8 |
| 16. 4D5_mvG1_scSP34(H06') | H100B-YE, L93-SE | Cycle: 55 | 2.18E+5 | 18.70E-3 | 8.57E-8 |
| 17. 4D5_mvG1_scSP34 | - | Cycle: 7 | 3.86E+5 | 3.50E-3 | 0.91E-8 |
| 18. 4D5_mvG1_scSP34 | - | Cycle: 58 | 3.96E+5 | 3.59E-3 | 0.91E-8 |

[FIG. 28]
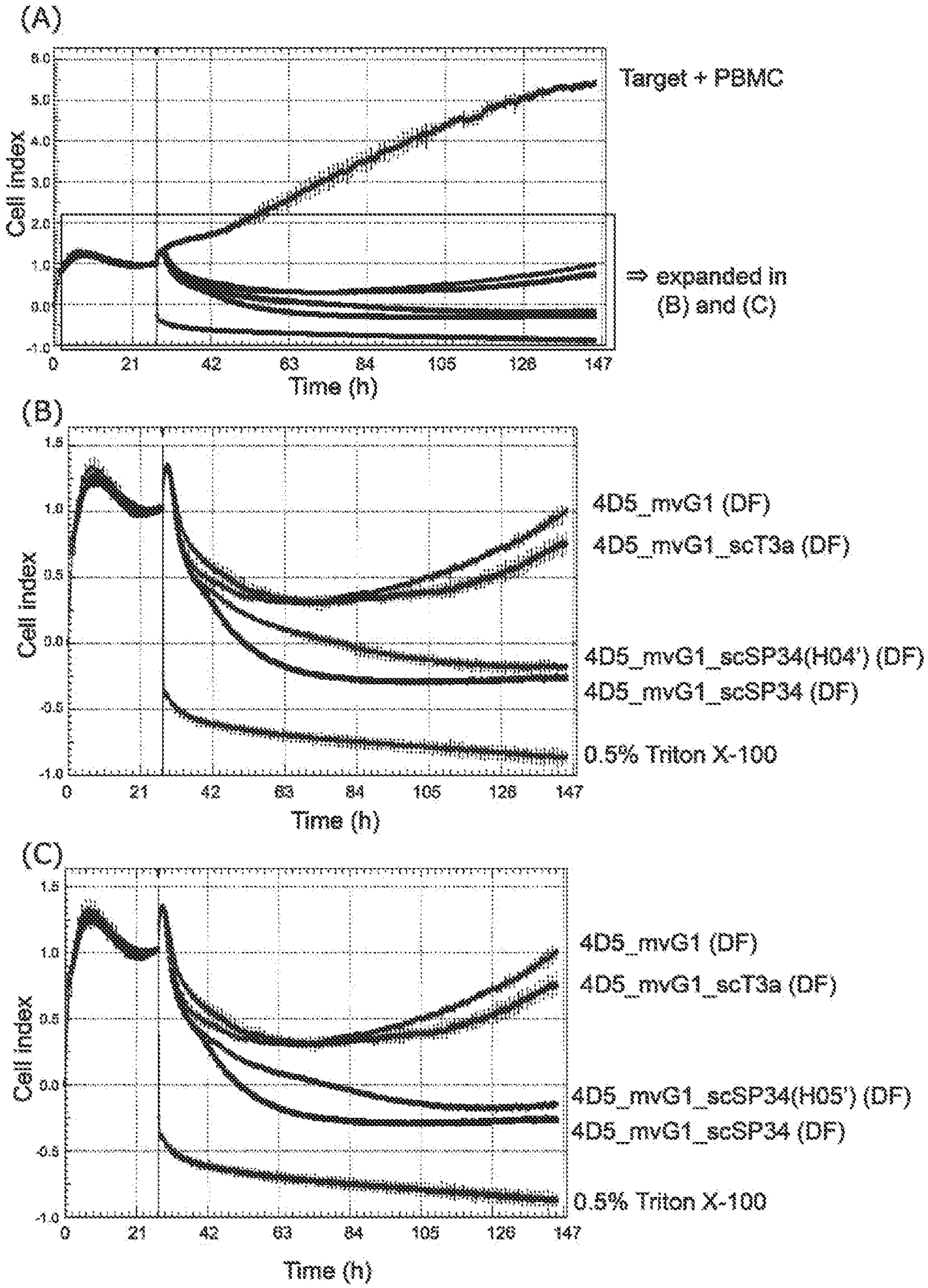

[FIG. 29]
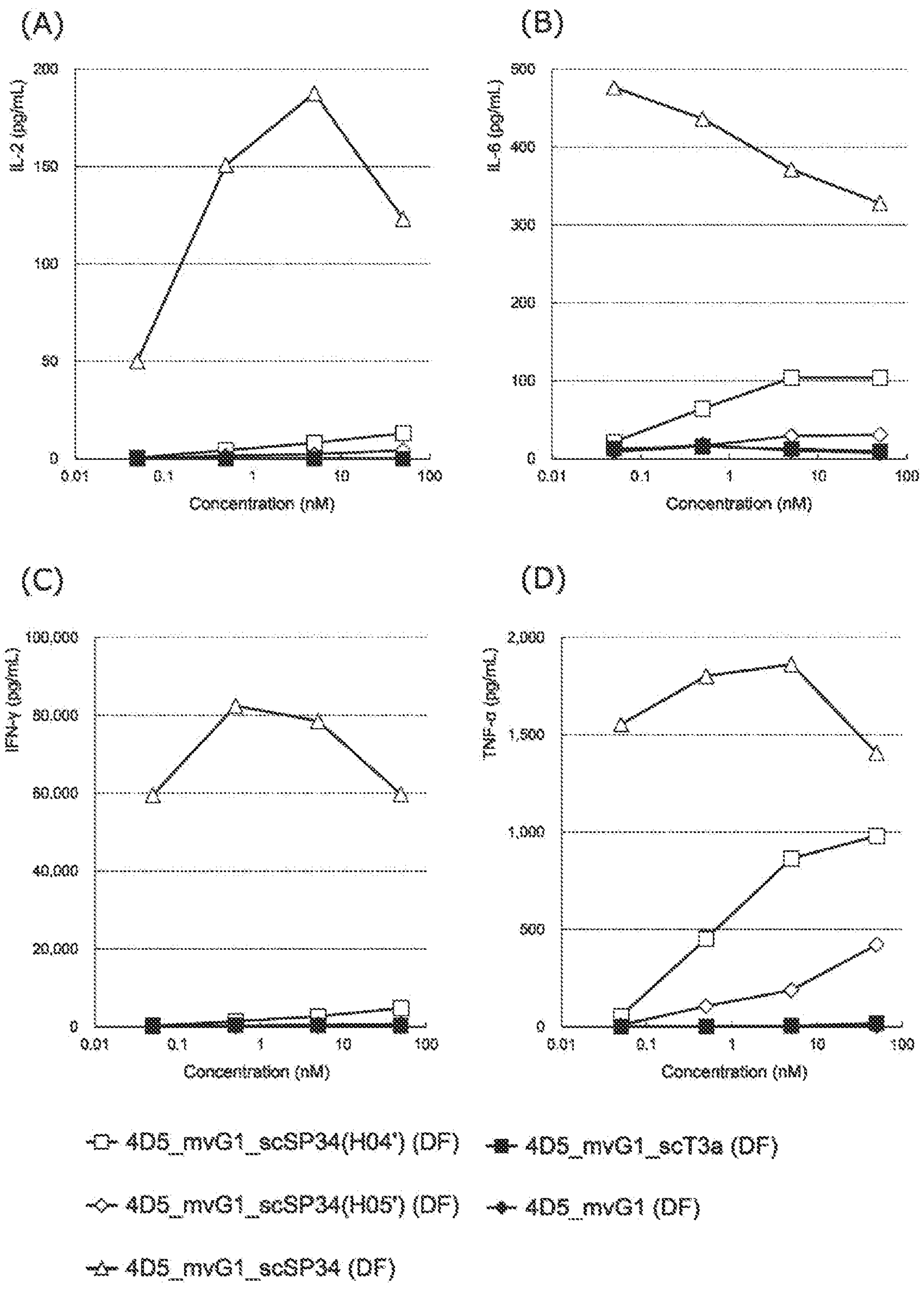

[FIG. 30]
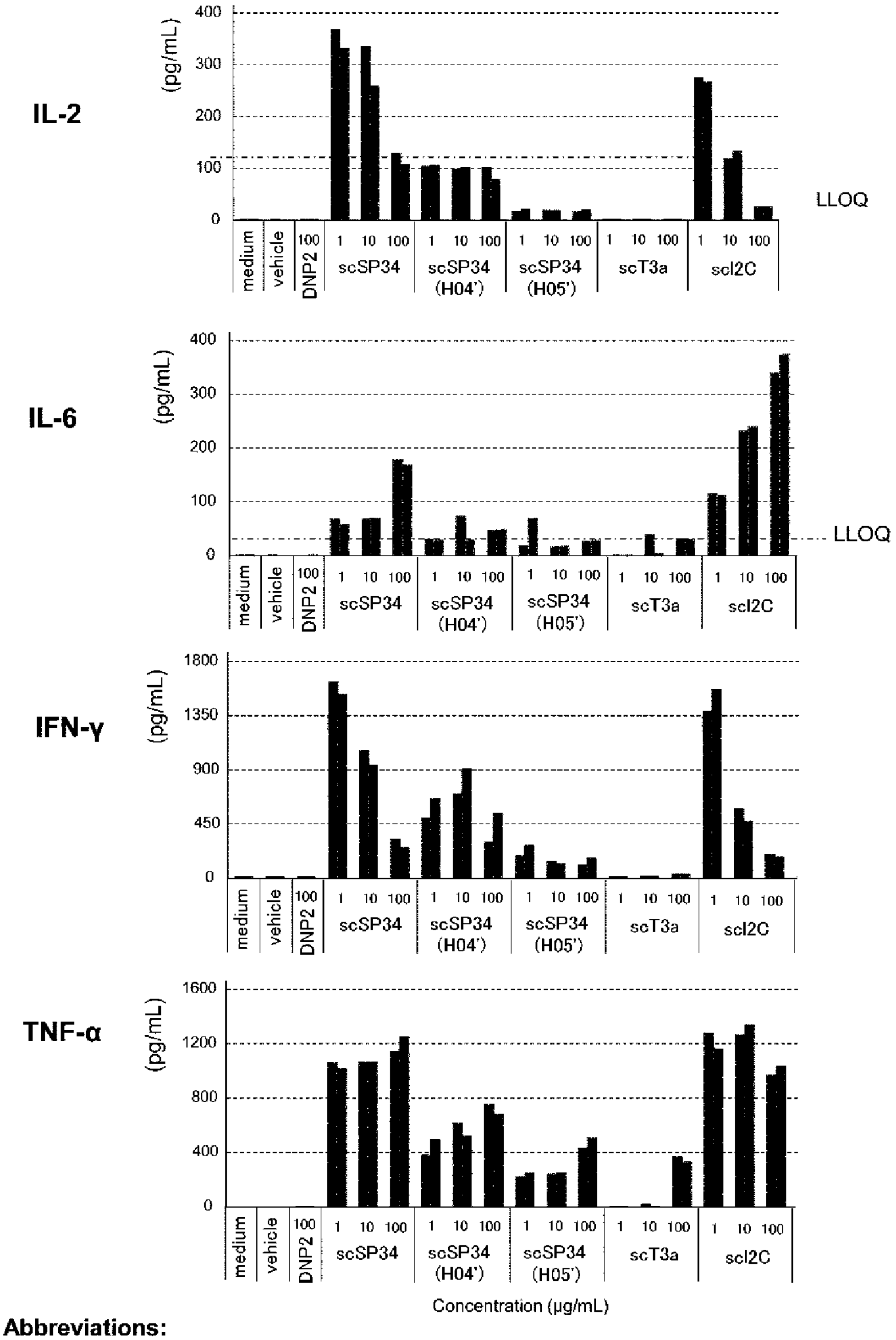
Abbreviations:
LLOQ, Lower limit of quantification
DNP2: DNP2_IgG1 (DF),
scSP34: 4D5_mvG1_scSP34 (DF)
scSP34(H04'): 4D5_mvG1_scSP34(H04') (DF)
scSP34(H05'): 4D5_mvG1_scSP34(H05') (DF)
scT3a: 4D5_mvG1_scT3a (DF)
scI2C: 4D5_mvG1_scI2C (DF)

[FIG. 31]

| | | CDRL1 | CDRL2 | CDRL3 |
|---|---|---|---|---|
| KM14 VL | | RASQGISSALA | DASSLES | QQFNSYPRT |
| mut1-01 | L29-IK | RASQGKSSALA | DASSLES | QQFNSYPRT |
| mut1-02 | L29-IE | RASQGESSALA | DASSLES | QQFNSYPRT |
| mut1-03 | L29-IR | RASQGRSSALA | DASSLES | QQFNSYPRT |
| mut1-04 | L29-IQ | RASQGQSSALA | DASSLES | QQFNSYPRT |
| mut1-05 | L54-LH | RASQGISSALA | DASSHES | QQFNSYPRT |
| mut1-06 | L91-FA | RASQGISSALA | DASSLES | QQANSYPRT |
| mut1-07 | L91-FD | RASQGISSALA | DASSLES | QQDNSYPRT |
| mut1-08 | L94-YA | RASQGISSALA | DASSLES | QQFNSAPRT |
| mut1-09 | L94-YD | RASQGISSALA | DASSLES | QQFNSDPRT |
| mut1-10 | L94-YE | RASQGISSALA | DASSLES | QQFNSEPRT |
| mut1-11 | L94-YN | RASQGISSALA | DASSLES | QQFNSNPRT |

| | | CDRH1 | CDRH2 | CDRH3 |
|---|---|---|---|---|
| KM14 VH | | SHGMH | SIWYDGSKKYYADSVKG | TLYYYGSERAHGLDV |
| mut1-12 | H31-SW | WHGMH | SIWYDGSKKYYADSVKG | TLYYYGSERAHGLDV |
| mut1-13 | H31-SY | YHGMH | SIWYDGSKKYYADSVKG | TLYYYGSERAHGLDV |
| mut1-14 | H52-WS | SHGMH | SISYDGSKKYYADSVKG | TLYYYGSERAHGLDV |
| mut1-15 | H52-WD | SHGMH | SIDYDGSKKYYADSVKG | TLYYYGSERAHGLDV |
| mut1-16 | H52-WE | SHGMH | SIEYDGSKKYYADSVKG | TLYYYGSERAHGLDV |
| mut1-17 | H53-DA | SHGMH | SIWYAGSKKYYADSVKG | TLYYYGSERAHGLDV |
| mut1-18 | H53-DE | SHGMH | SIWYEGSKKYYADSVKG | TLYYYGSERAHGLDV |
| mut1-19 | H56-KA | SHGMH | SIWYDGSAKYYADSVKG | TLYYYGSERAHGLDV |
| mut1-20 | H56-KD | SHGMH | SIWYDGSDKYYADSVKG | TLYYYGSERAHGLDV |
| mut1-21 | H56-KE | SHGMH | SIWYDGSEKYYADSVKG | TLYYYGSERAHGLDV |
| mut1-22 | H56-KV | SHGMH | SIWYDGSVKYYADSVKG | TLYYYGSERAHGLDV |
| mut1-23 | H56-KW | SHGMH | SIWYDGSWKYYADSVKG | TLYYYGSERAHGLDV |
| mut1-24 | H58-YA | SHGMH | SIWYDGSKKAYADSVKG | TLYYYGSERAHGLDV |
| mut1-25 | H58-YD | SHGMH | SIWYDGSKKDYADSVKG | TLYYYGSERAHGLDV |
| mut1-26 | H58-YS | SHGMH | SIWYDGSKKSYADSVKG | TLYYYGSERAHGLDV |
| mut1-27 | H58-YT | SHGMH | SIWYDGSKKTYADSVKG | TLYYYGSERAHGLDV |
| mut1-28 | H61-DS | SHGMH | SIWYDGSKKYYASSVKG | TLYYYGSERAHGLDV |
| mut1-29 | H97-YA | SHGMH | SIWYDGSKKYYADSVKG | TLAYYGSERAHGLDV |
| mut1-30 | H97-YD | SHGMH | SIWYDGSKKYYADSVKG | TLDYYGSERAHGLDV |
| mut1-31 | H97-YE | SHGMH | SIWYDGSKKYYADSVKG | TLEYYGSERAHGLDV |
| mut1-32 | H98-YA | SHGMH | SIWYDGSKKYYADSVKG | TLYAYGSERAHGLDV |
| mut1-33 | H98-YD | SHGMH | SIWYDGSKKYYADSVKG | TLYDYGSERAHGLDV |
| mut1-34 | H98-YE | SHGMH | SIWYDGSKKYYADSVKG | TLYEYGSERAHGLDV |
| mut1-35 | H99-YA | SHGMH | SIWYDGSKKYYADSVKG | TLYYAGSERAHGLDV |
| mut1-36 | H99-YD | SHGMH | SIWYDGSKKYYADSVKG | TLYYDGSERAHGLDV |
| mut1-37 | H99-YE | SHGMH | SIWYDGSKKYYADSVKG | TLYYEGSERAHGLDV |
| mut1-38 | H100B-EA | SHGMH | SIWYDGSKKYYADSVKG | TLYYYGSARAHGLDV |
| mut1-39 | H100B-ET | SHGMH | SIWYDGSKKYYADSVKG | TLYYYGSTRAHGLDV |
| mut1-40 | H100C-RK | SHGMH | SIWYDGSKKYYADSVKG | TLYYYGSEKAHGLDV |
| mut1-41 | H100C-RS | SHGMH | SIWYDGSKKYYADSVKG | TLYYYGSESAHGLDV |
| mut1-42 | H100C-RY | SHGMH | SIWYDGSKKYYADSVKG | TLYYYGSEYAHGLDV |
| mut1-43 | H100E-HA | SHGMH | SIWYDGSKKYYADSVKG | TLYYYGSERAAGLDV |

[FIG. 32]

| scFv | KD (M) (Biacore) | Specific cytotoxicity |
|---|---|---|
| KM14 | 5.78E-8 | +++ |
| mut1-01 | 8.08E-8 | not tested |
| mut1-03 | 9.80E-8 | ++ |
| mut1-04 | 24.77E-8 | ++ |
| mut1-05 | 6.33E-8 | +++ |
| mut1-12 | 4.34E-8 | +++ |
| mut1-13 | 7.19E-8 | not tested |
| mut1-18 | 22.10E-8 | ++ |
| mut1-19 | 11.94E-8 | not tested |
| mut1-22 | 42.60E-8 | ++ |
| mut1-23 | 9.15E-8 | not tested |
| mut1-24 | 10.34E-8 | not tested |
| mut1-25 | 46.90E-8 | + |
| mut1-26 | 13.55E-8 | ++ |
| mut1-27 | 9.70E-8 | not tested |
| mut1-28 | 6.36E-8 | not tested |
| mut1-35 | 8.22E-8 | +++ |
| mut1-37 | 26.81E-8 | not tested |
| mut1-38 | 8.33E-8 | not tested |
| mut1-39 | 7.48E-8 | +++ |
| mut1-40 | 6.79E-8 | +++ |
| mut1-42 | 91.57E-8 | not tested |

[FIG. 33]
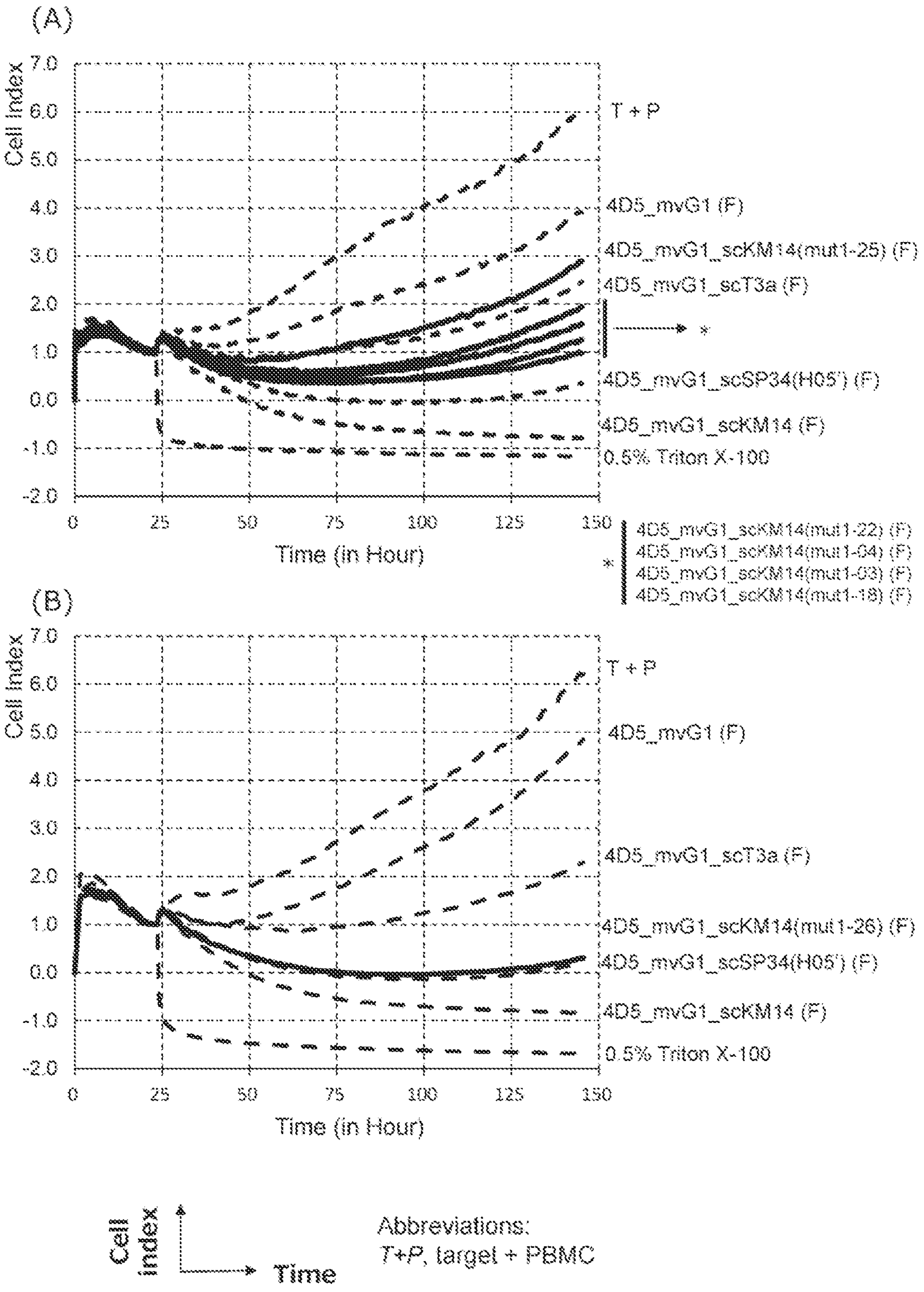

[FIG. 34]
(A)
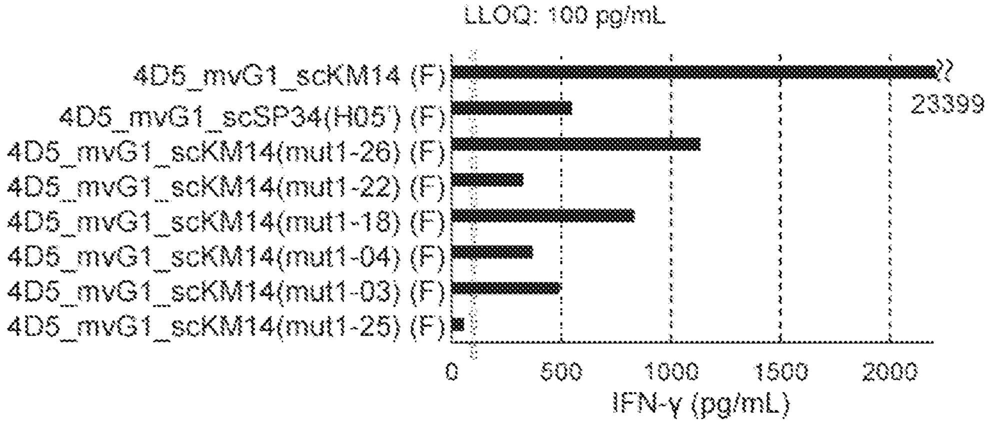
(B)
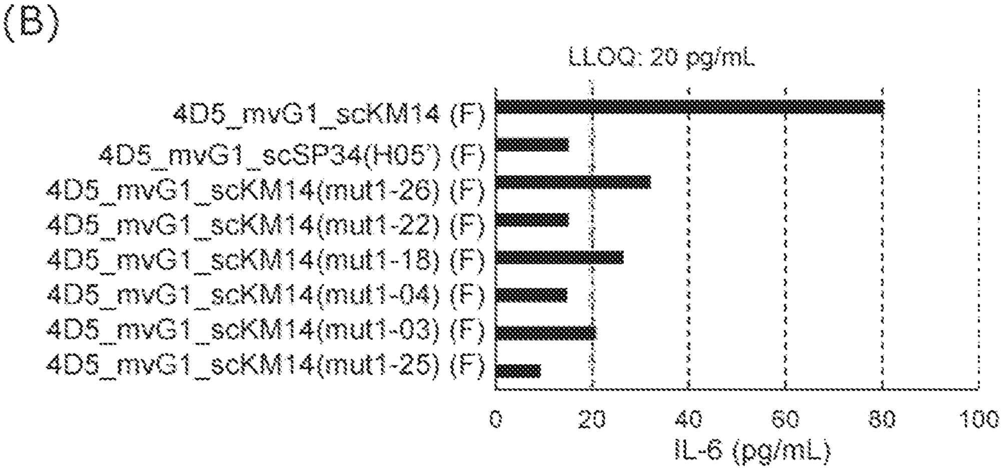
LLOQ: Lower limit of quantification

[FIG. 35]
(A)
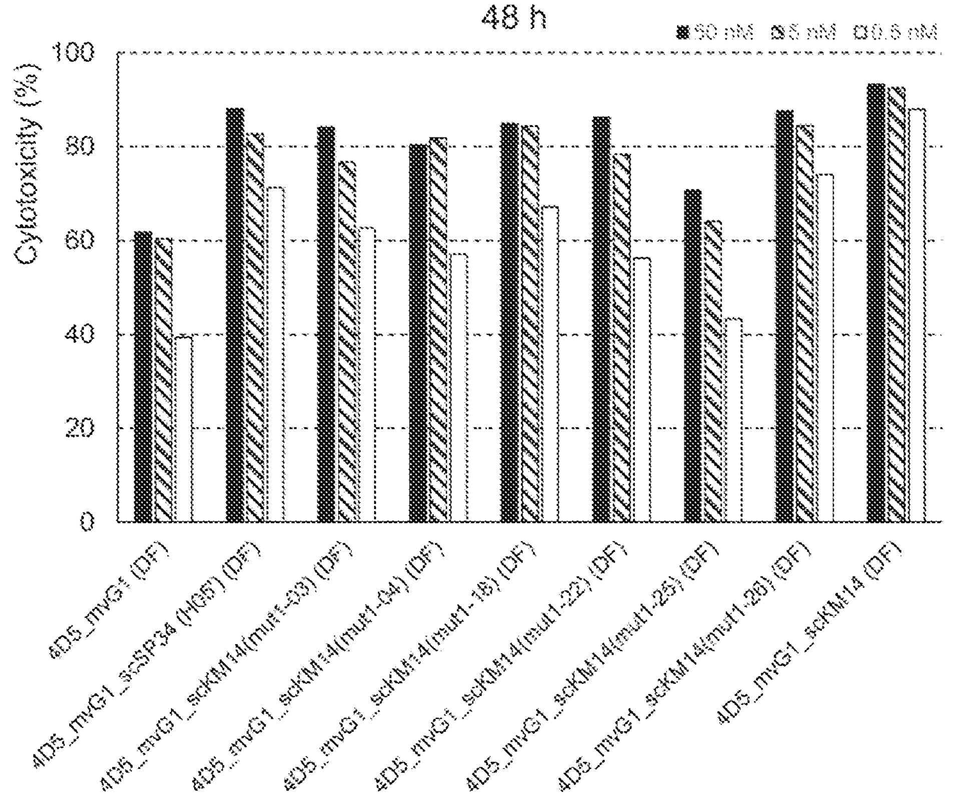
(B)
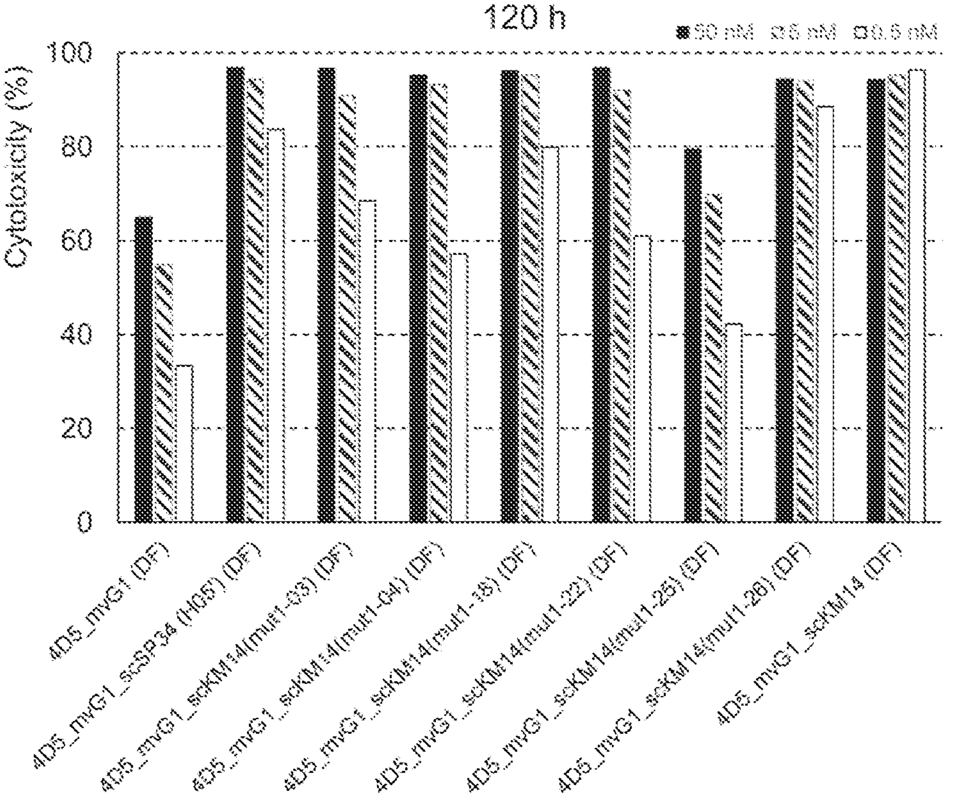

[FIG. 36]
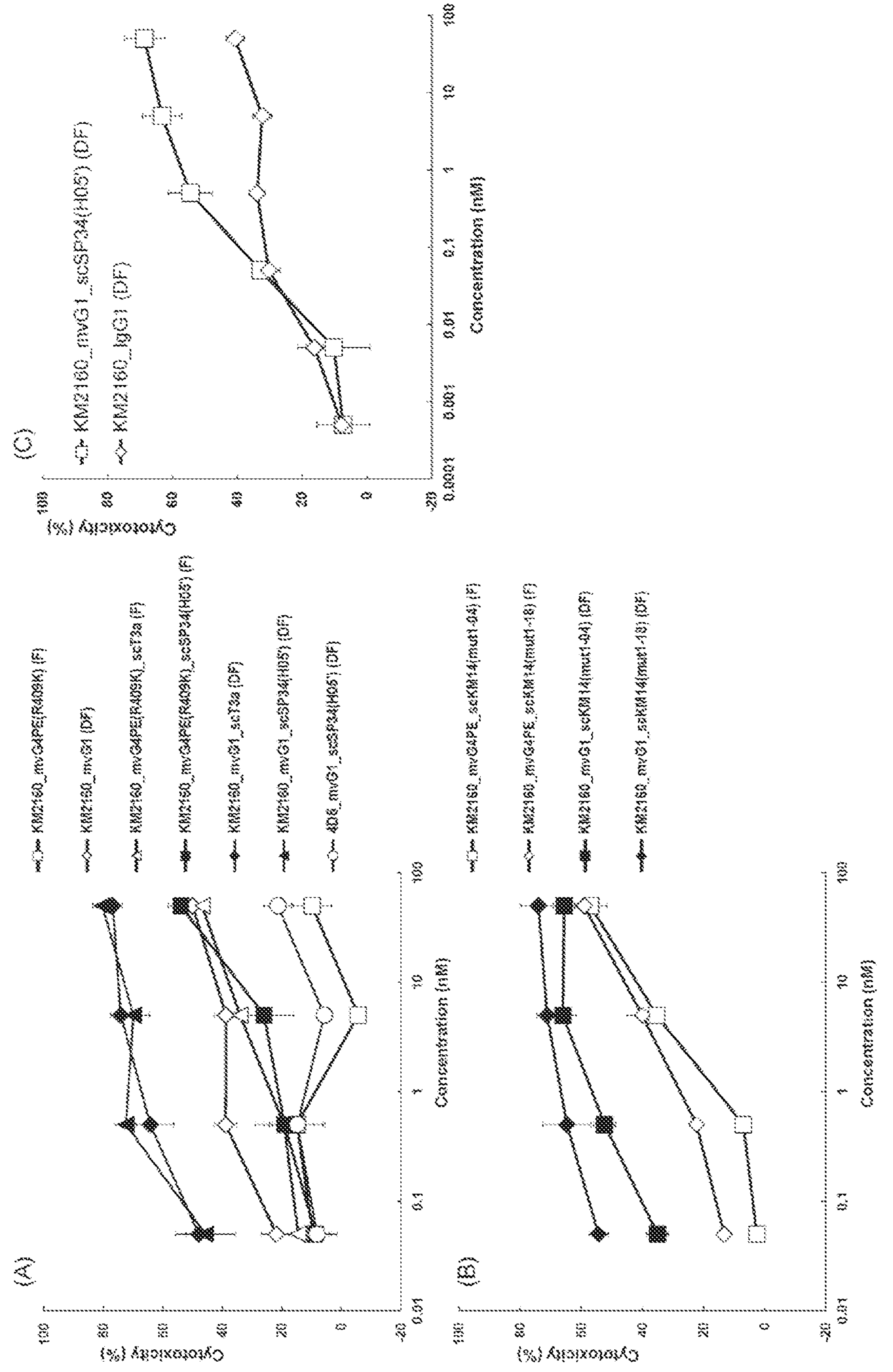

[FIG. 37]
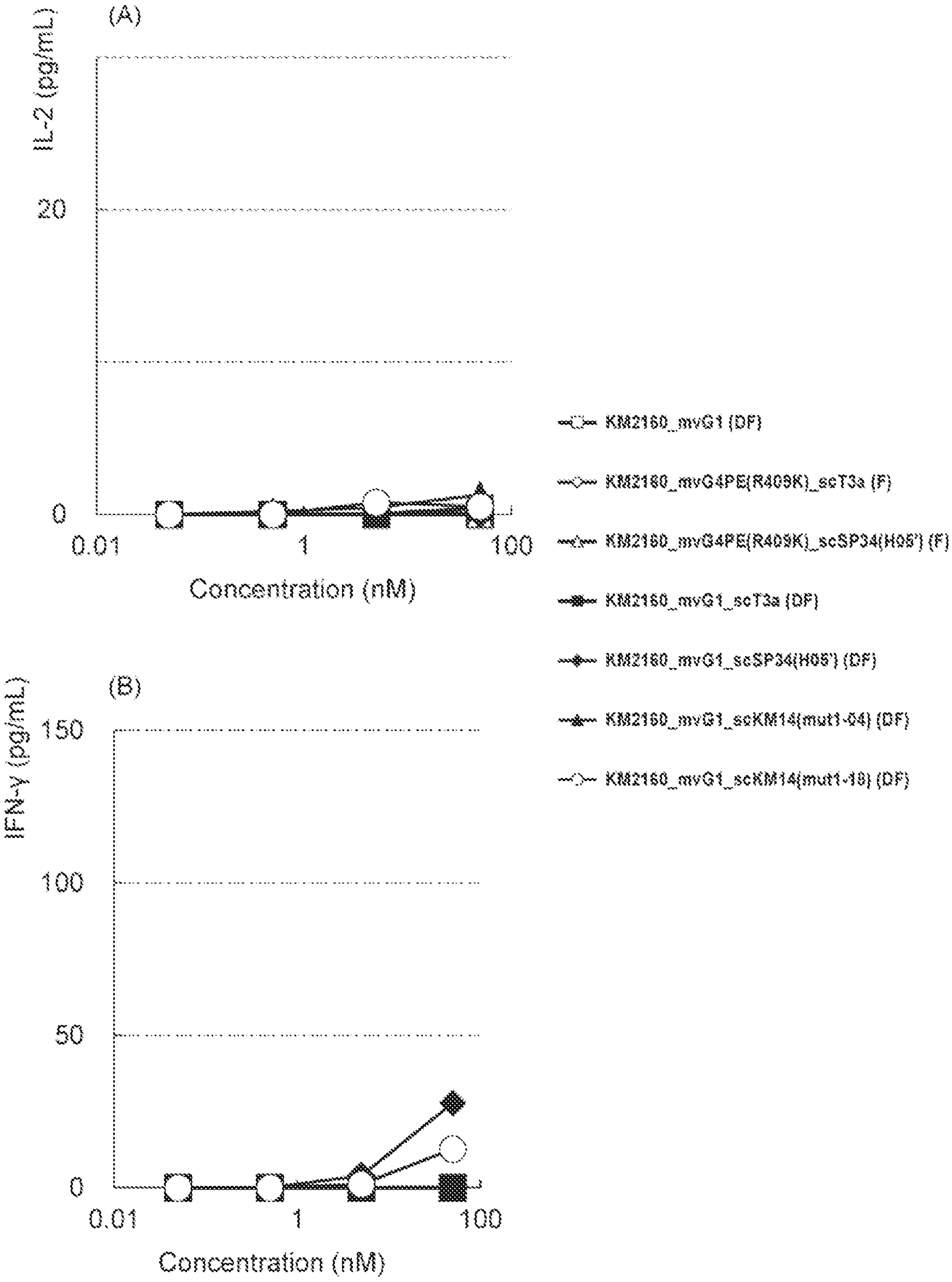

[FIG. 38]
(A)
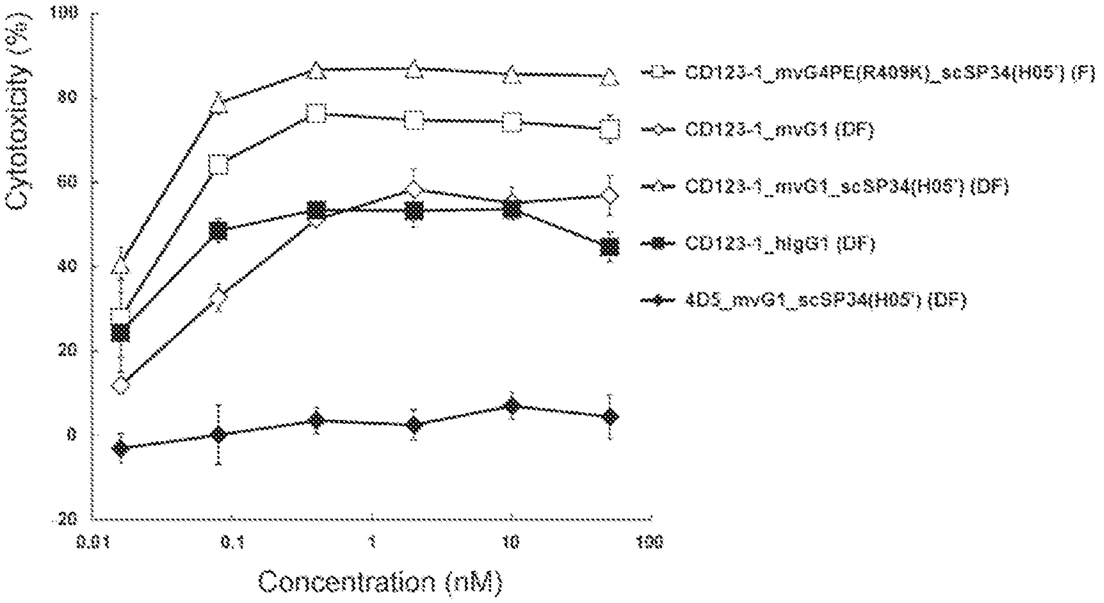
(B)
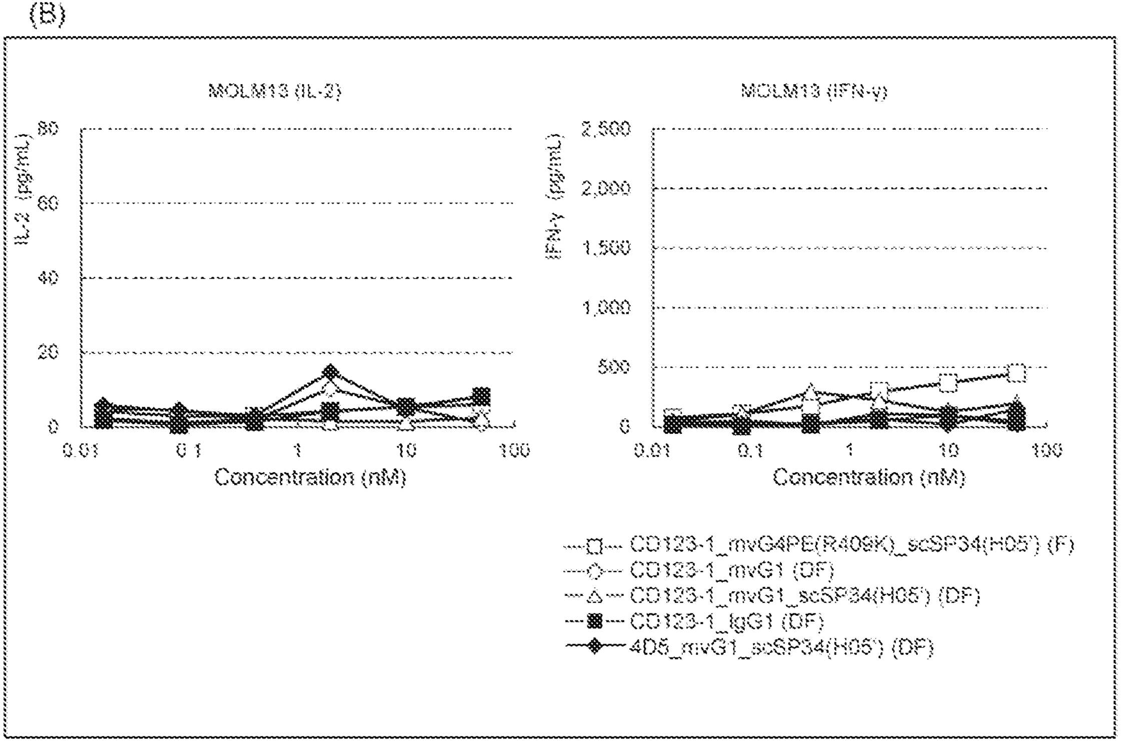

[FIG. 39]
(A)
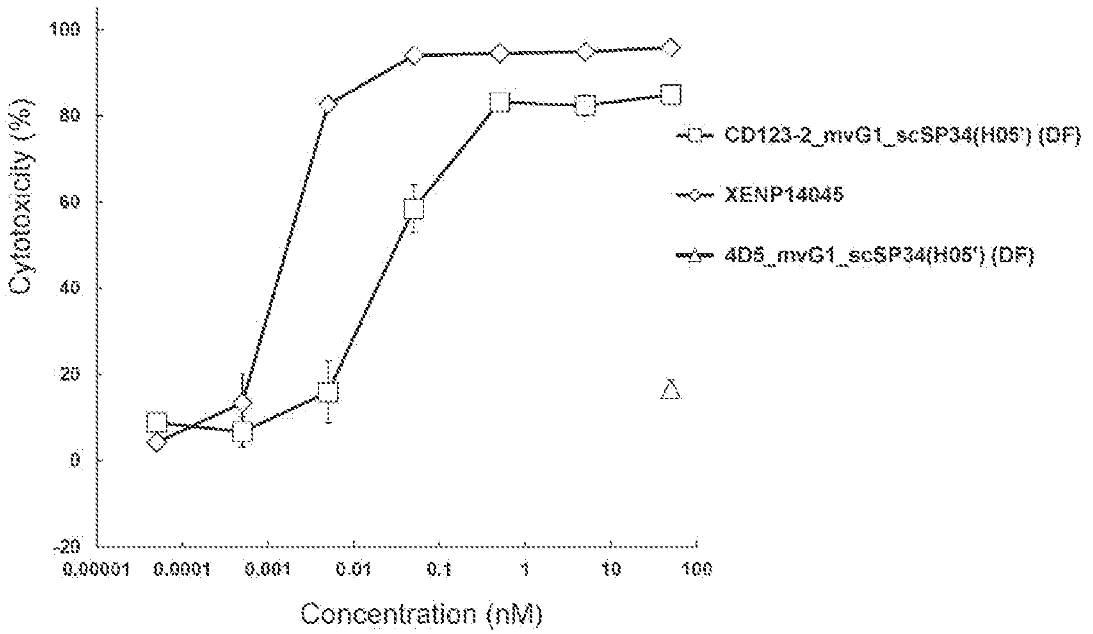
(B)
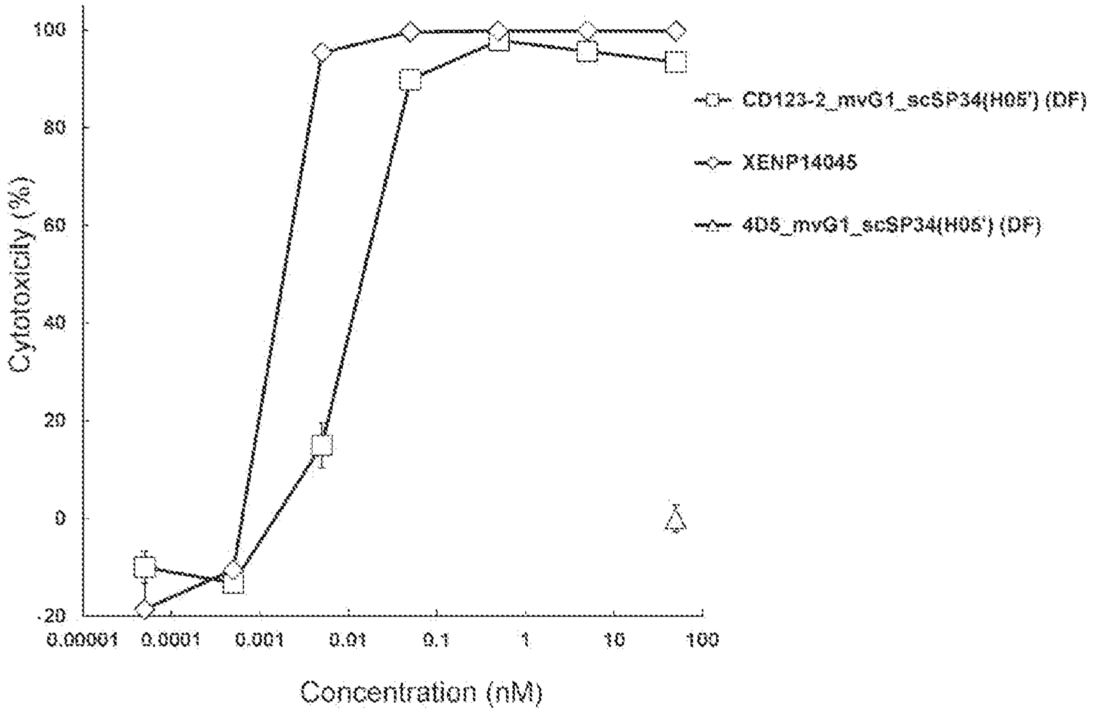

[FIG. 40]
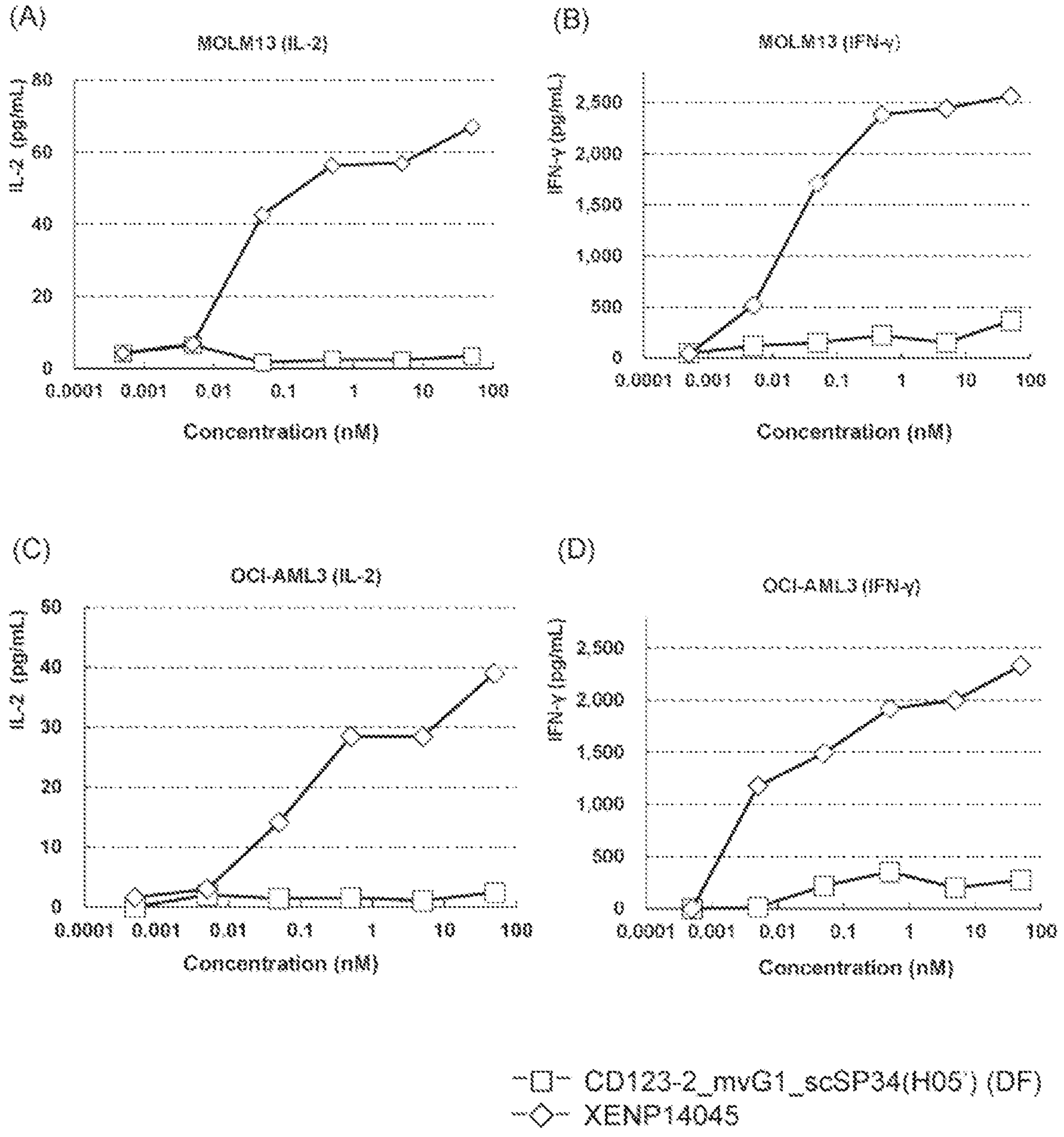

[FIG. 41]
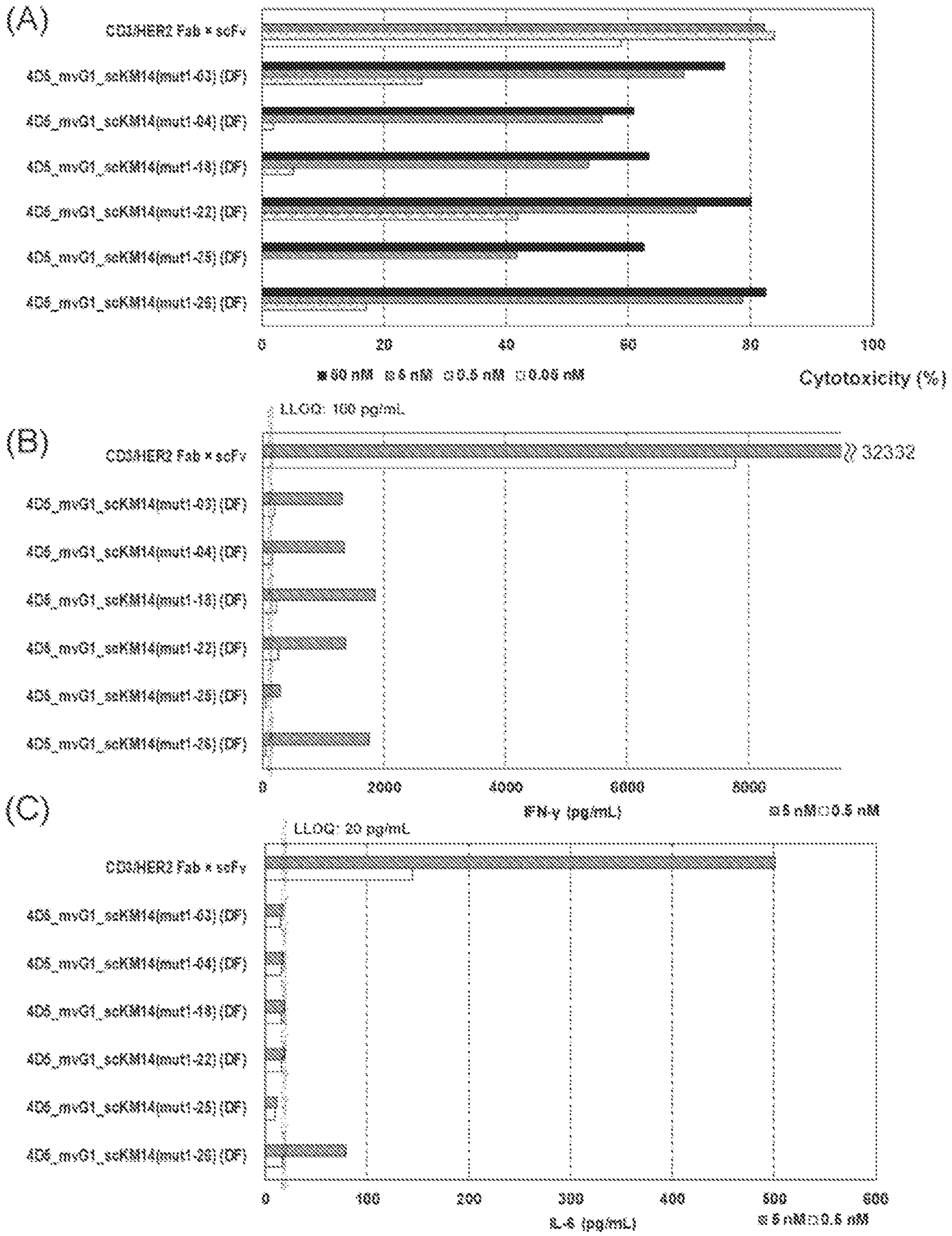

[FIG. 42]
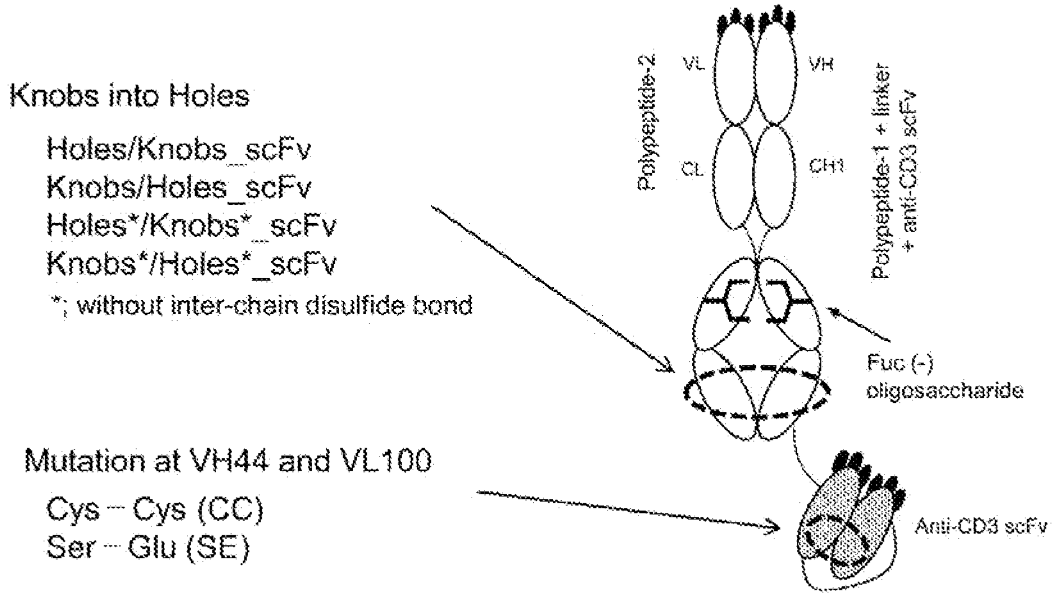
[FIG. 43]
| CH3 (polypeptide-1) / CH3 (polypeptide-2) | Anti-CD3 scFv | scFv type | scFv mutation (VH44 -- VL100) |
|---|---|---|---|
| KIH-1:<br>Knobs_scFv / Holes<br>KIH-2:<br>Holes_scFv / Knobs<br>KIH-3:<br>Knobs*_scFv / Holes*<br>KIH-4:<br>Holes*_scFv / Knobs* | scSP34(H05')<br>scKM14(mut1-03)<br>scKM14(mut1-04)<br>scKM14(mut1-18)<br>scKM14(mut1-22)<br>scKM14(mut1-25)<br>scKM14(mut1-26) | VH-linker-VL<br>VL-linker-VH | Cys -- Cys (CC)<br>Ser -- Glu (SE) |
*; without inter-chain disulfide bond

[FIG. 44]

| antibody | $K_D$ (M) (Biacore) |
|---|---|
| 4D5_mvG1_scSP34(H05') (DF) -1 | 1.63E-7 |
| 4D5_mvG1_scSP34(H05') (DF) -2 | 1.60E-7 |
| 4D5_mvG1_scSP34(H05')(LH) (DF) | 2.54E-7 |
| 4D5_mvG1_scSP34(H05')(CC) (DF) | 7.07E-7 |
| 4D5_mvG1_scSP34(H05')(SE) (DF) | 7.49E-7 |
| | |
| 4D5_mvG1(KIH-1)_scSP34(H05') (DF) | 1.41E-7 |
| 4D5_mvG1(KIH-2)_scSP34(H05') (DF) | 1.43E-7 |
| 4D5_mvG1(KIH-3)_scSP34(H05') (DF) | 1.39E-7 |
| 4D5_mvG1(KIH-4)_scSP34(H05') (DF) | 1.41E-7 |
| | |
| 4D5_mvG1(KIH-1)_scSP34(H05'_HV3LV8a)(CC) (DF) | 3.44E-7 |
| 4D5_mvG1(KIH-1)_scSP34(H05'_HV5LV8a)(CC) (DF) | 3.57E-7 |
| 4D5_mvG1(KIH-1)_scSP34(H05'_HV3LV8a)(SE) (DF) | 7.53E-7 |
| 4D5_mvG1(KIH-1)_scSP34(H05'_HV5LV8a)(SE) (DF) | 6.42E-7 |
| 4D5_mvG1(KIH-1)_scSP34(H05')(CC) (DF) | 7.29E-7 |
| 4D5_mvG1(KIH-1)_scSP34(H05')(SE) (DF) | 7.25E-7 |
| | |
| 4D5_mvG1(KIH-1)_scSP34(H05'_HV3LV8a)(CC)(LH) (DF) | 8.42E-7 |
| 4D5_mvG1(KIH-1)_scSP34(H05'_HV3LV8a)(LH) (DF) | 2.70E-7 |
| 4D5_mvG1(KIH-1)_scSP34(H05'_HV5LV8a)(CC)(LH) (DF) | 8.33E-7 |
| 4D5_mvG1(KIH-1)_scSP34(H05'_HV5LV8a)(LH) (DF) | 2.20E-7 |
| 4D5_mvG1(KIH-1)_scSP34(H05')(CC)(LH) (DF) | 1.86E-6 |

| antibody | $K_D$ (M) (Biacore) |
|---|---|
| 4D5_mvG1_scKM14(mut1-03) (DF) | 1.72E-7 |
| 4D5_mvG1_scKM14(mut1-04) (DF) | 1.44E-7 |
| 4D5_mvG1_scKM14(mut1-18) (DF) | 8.16E-8 |
| 4D5_mvG1_scKM14(mut1-22) (DF) | 1.15E-7 |
| 4D5_mvG1_scKM14(mut1-25) (DF) | 1.18E-7 |
| 4D5_mvG1_scKM14(mut1-26) (DF) | 8.06E-8 |
| | |
| 4D5_mvG1(KIH-1)_scKM14(mut1-03)(LH) (DF) | 1.93E-7 |
| 4D5_mvG1(KIH-1)_scKM14(mut1-04)(LH) (DF) | 2.63E-7 |
| 4D5_mvG1(KIH-1)_scKM14(mut1-18)(LH) (DF) | 9.43E-8 |
| 4D5_mvG1(KIH-1)_scKM14(mut1-22)(LH) (DF) | 1.09E-7 |
| 4D5_mvG1(KIH-1)_scKM14(mut1-25)(LH) (DF) | 1.12E-7 |
| 4D5_mvG1(KIH-1)_scKM14(mut1-26)(LH) (DF) | 2.72E-7 |
| | |
| 4D5_mvG1(KIH-1)_scKM14(mut1-04)(CC) (DF) | 2.45E-7 |
| 4D5_mvG1(KIH-1)_scKM14(mut1-18)(CC) (DF) | 1.55E-7 |
| 4D5_mvG1(KIH-1)_scKM14(mut1-22)(CC) (DF) | 1.74E-7 |
| 4D5_mvG1(KIH-1)_scKM14(mut1-25)(CC) (DF) | 2.77E-7 |
| 4D5_mvG1(KIH-1)_scKM14(mut1-26)(CC) (DF) | 2.74E-7 |
| 4D5_mvG1(KIH-1)_scKM14(mut1-18)(SE) (DF) | 2.04E-7 |
| 4D5_mvG1(KIH-1)_scKM14(mut1-22)(SE) (DF) | 1.06E-7 |
| 4D5_mvG1(KIH-1)_scKM14(mut1-25)(SE) (DF) | 2.23E-7 |
| 4D5_mvG1(KIH-1)_scKM14(mut1-26)(SE) (DF) | 2.98E-7 |

[FIG. 45A]
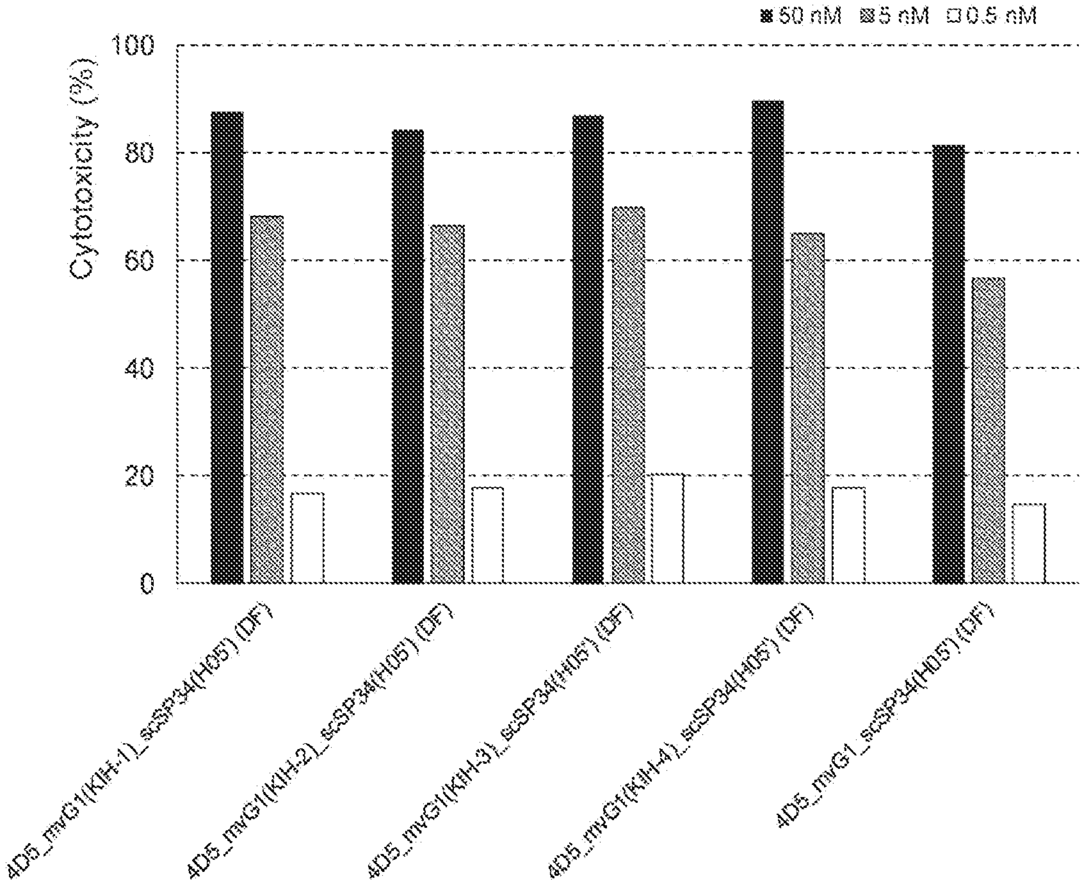

[FIG. 45B]
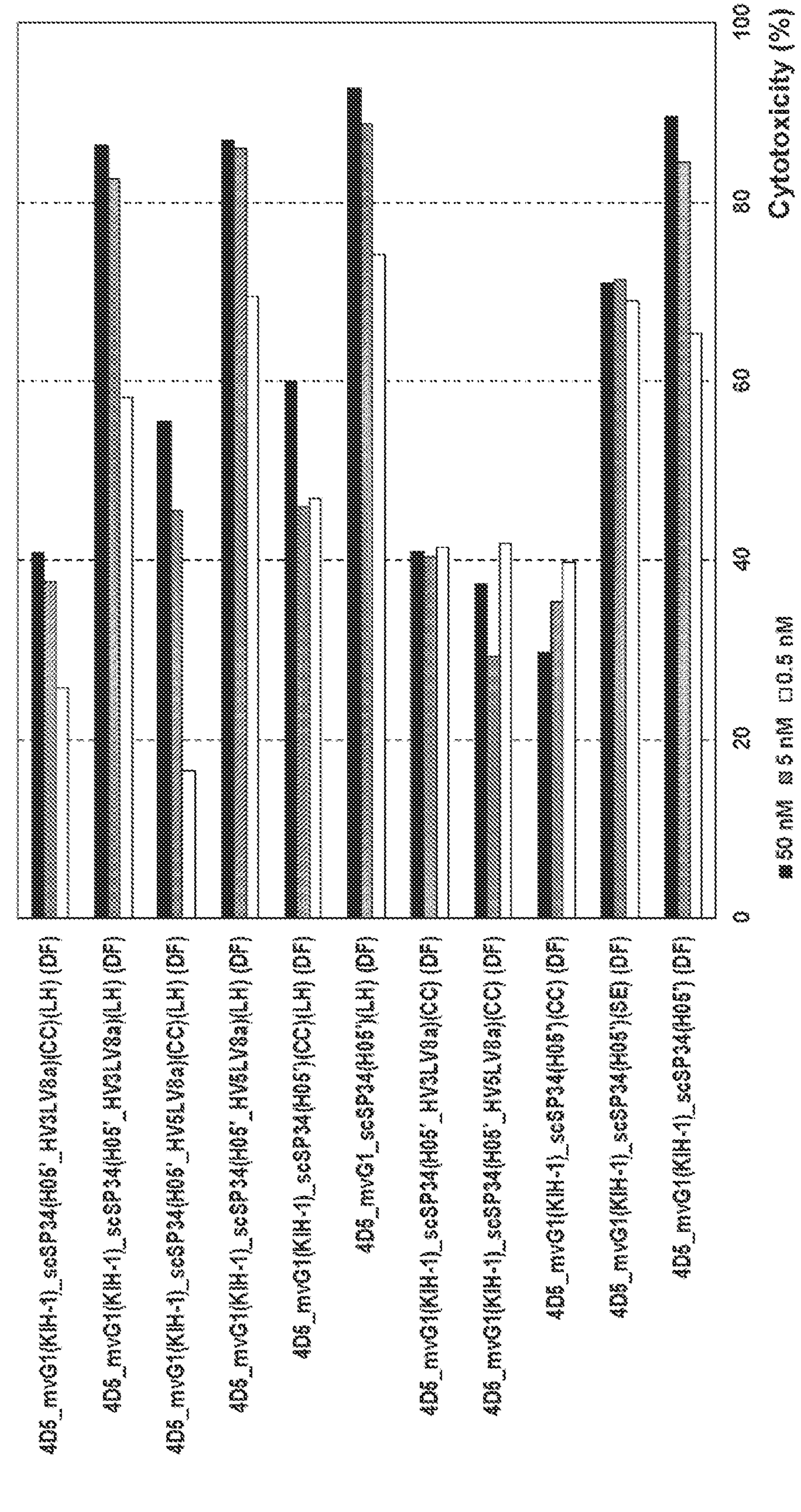

[FIG. 45C]
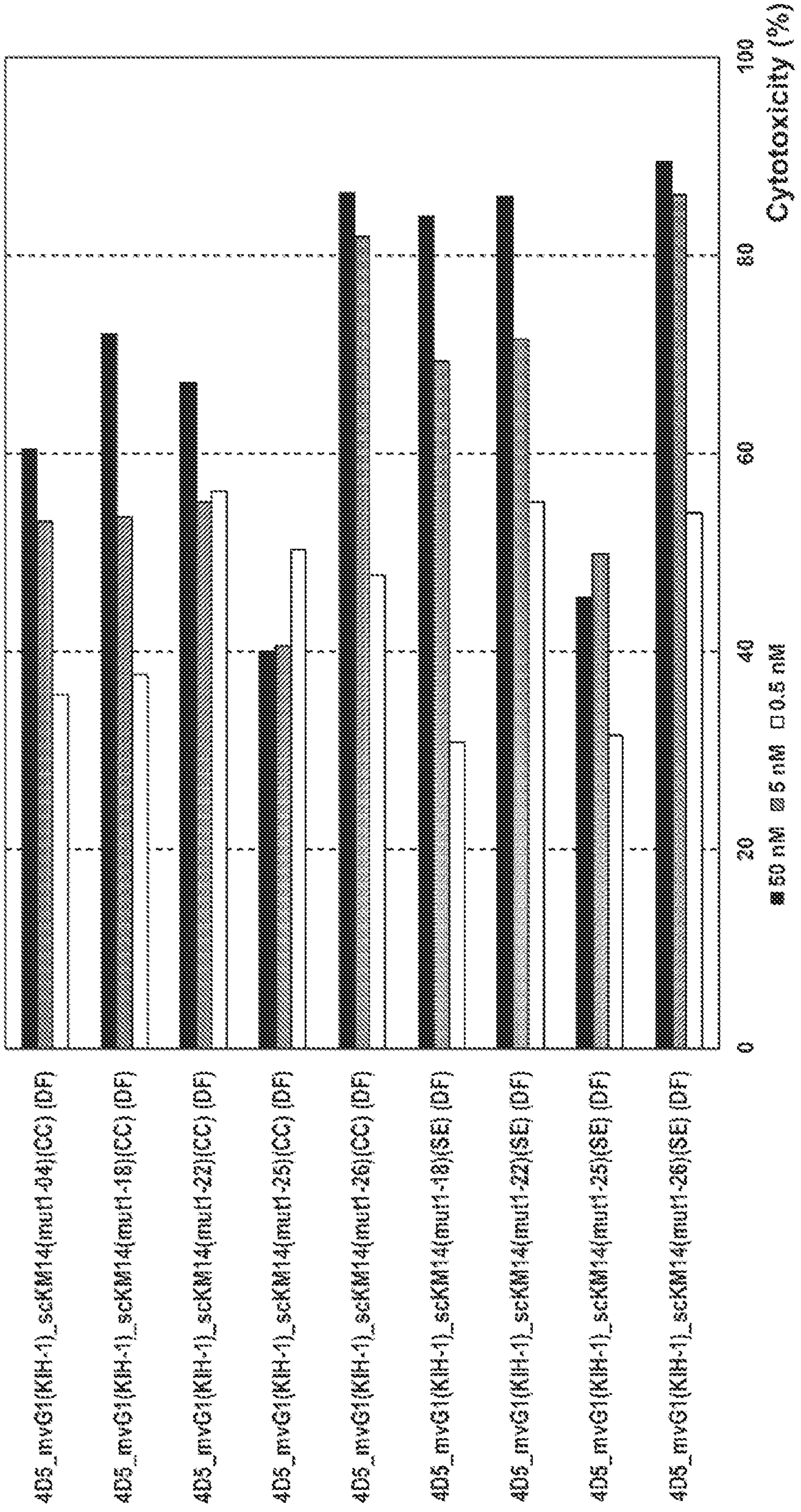

[FIG. 45D]
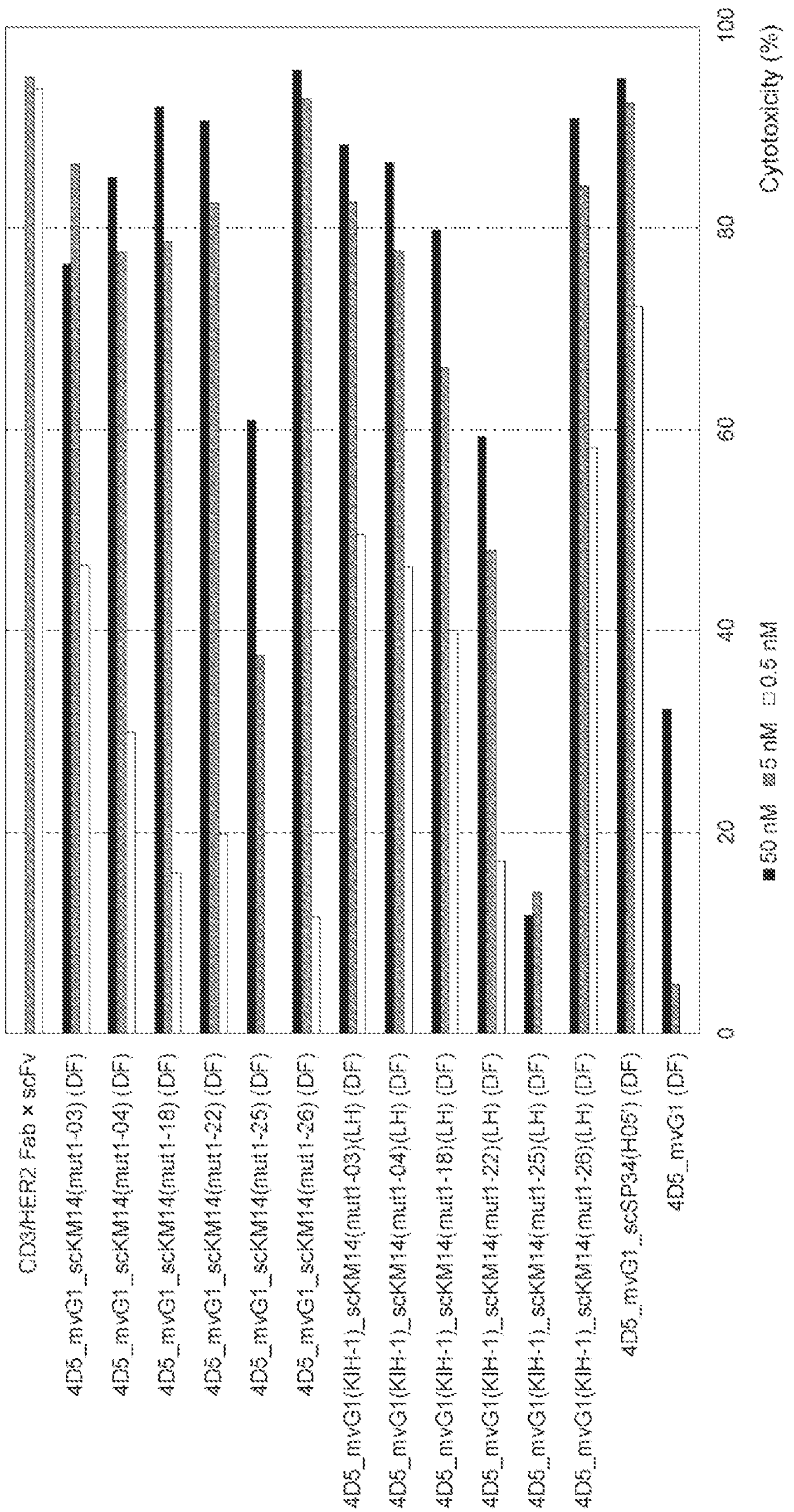

[FIG. 46A]
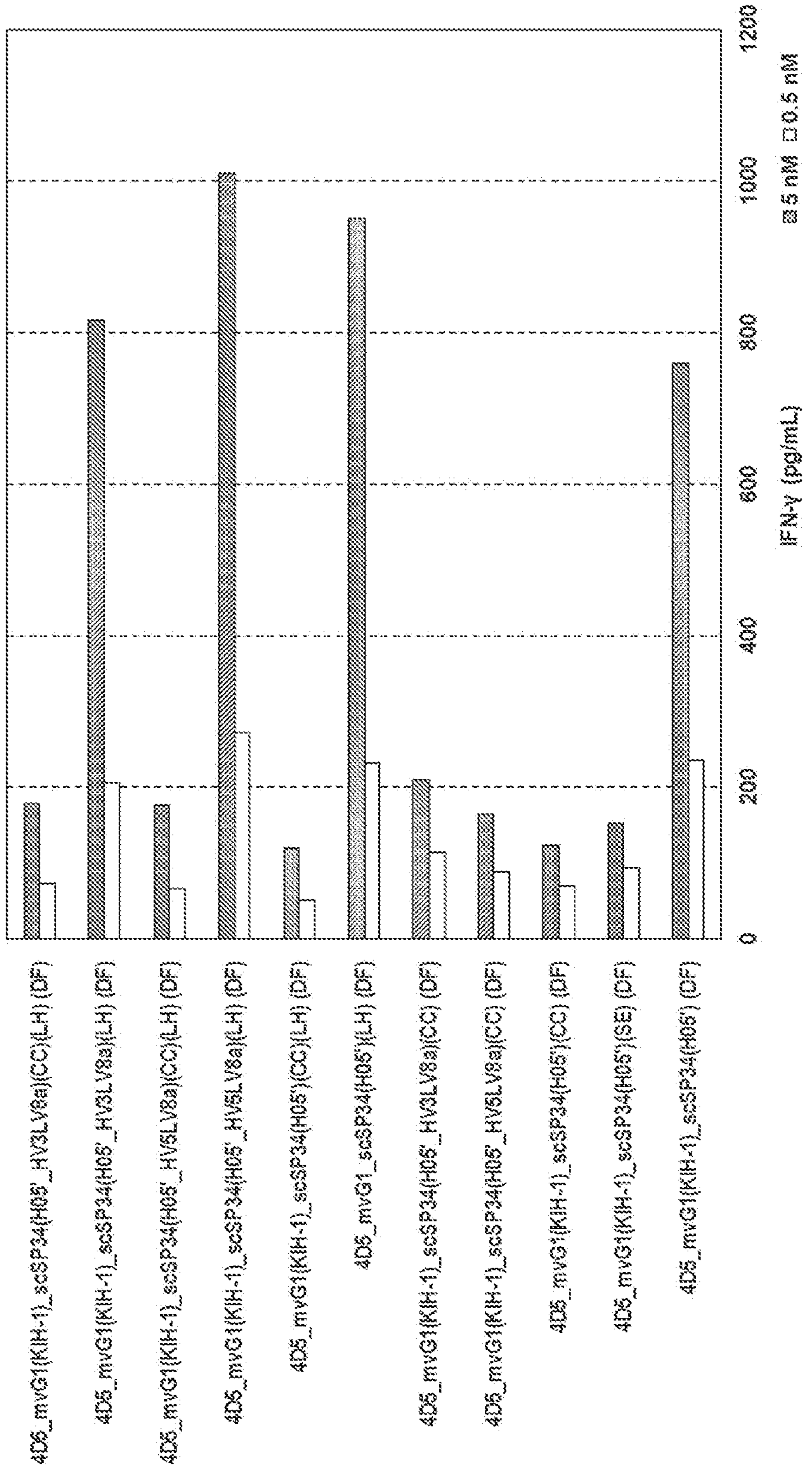

[FIG. 46B]
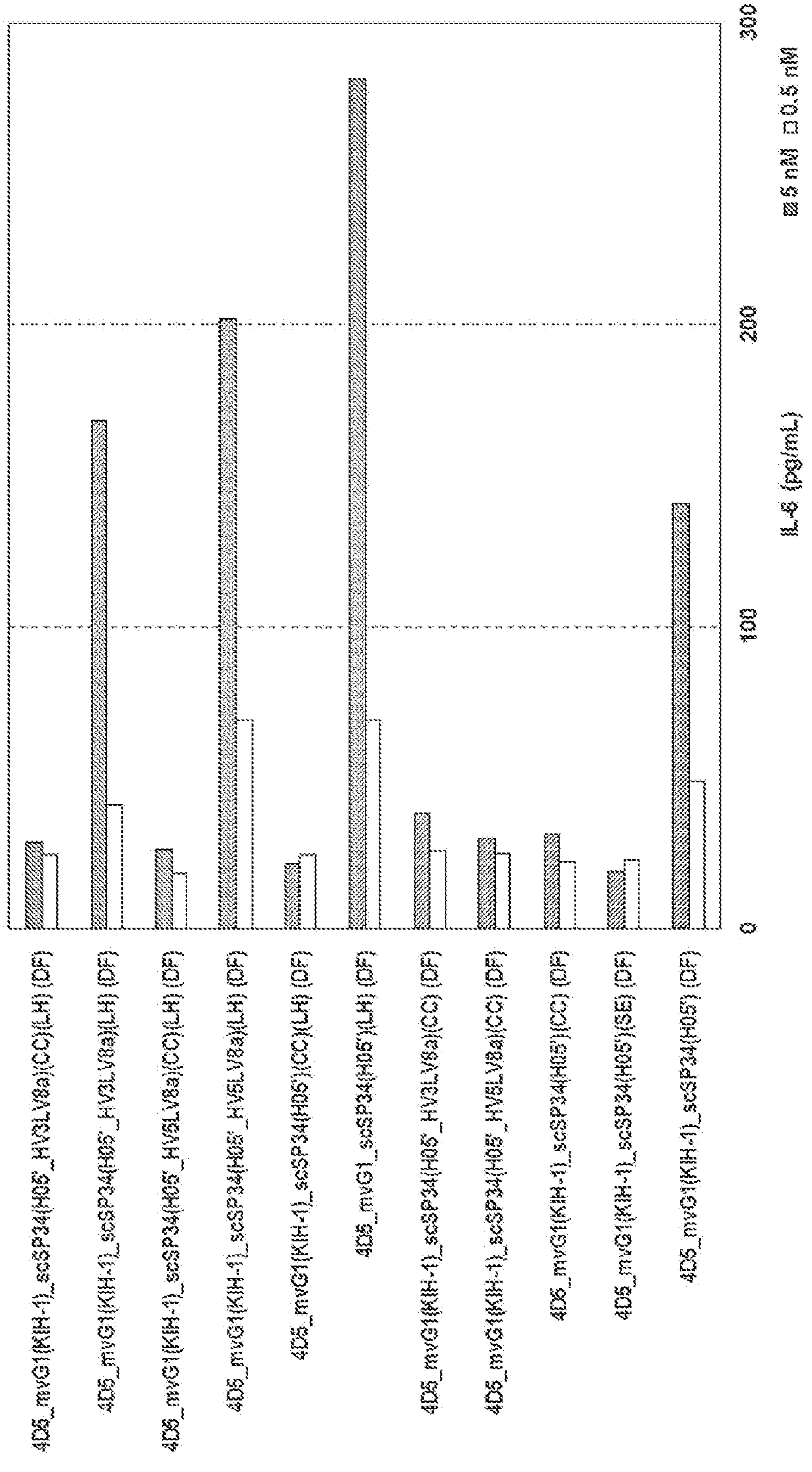

[FIG. 46C]
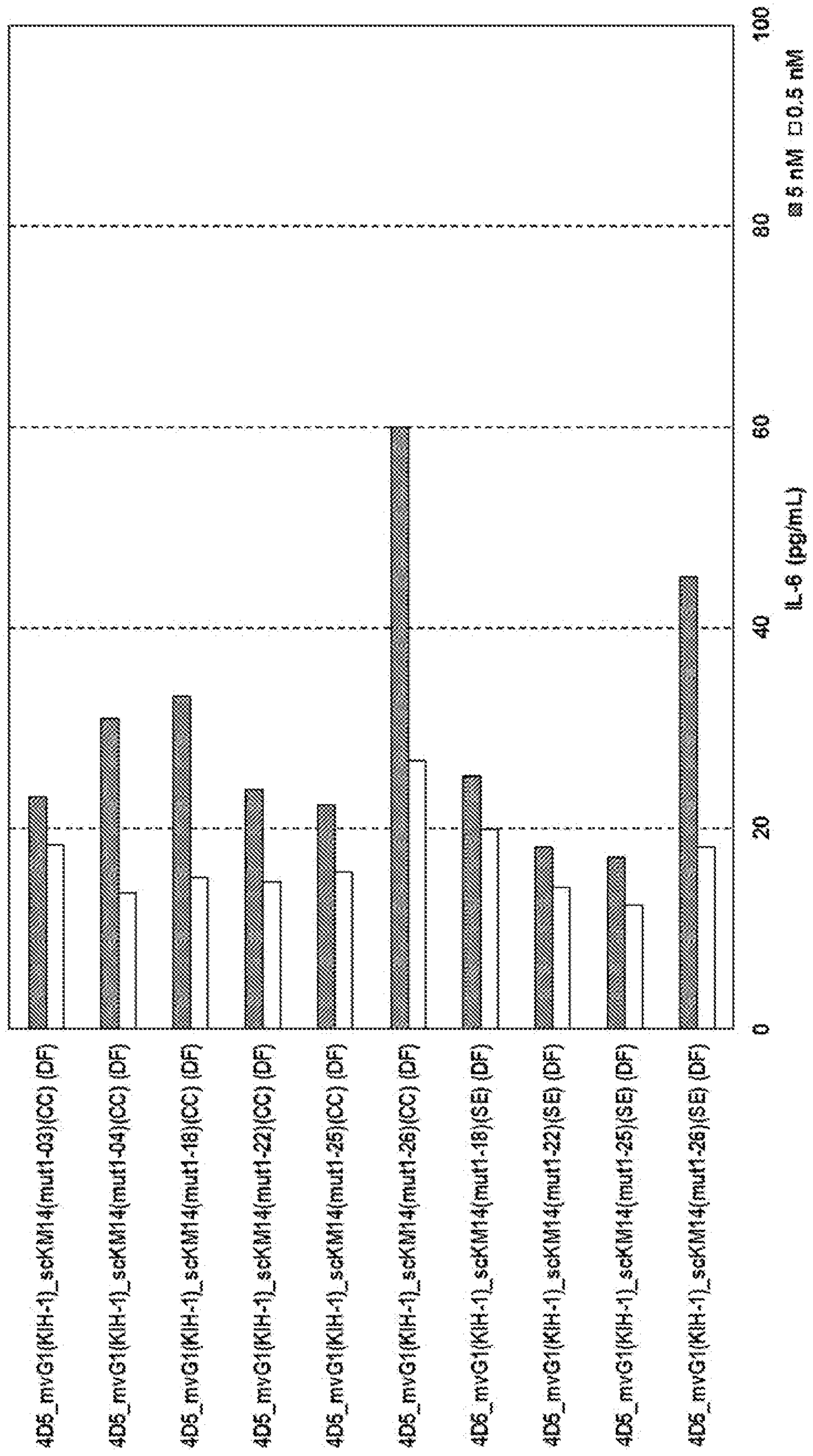

[FIG. 46D]
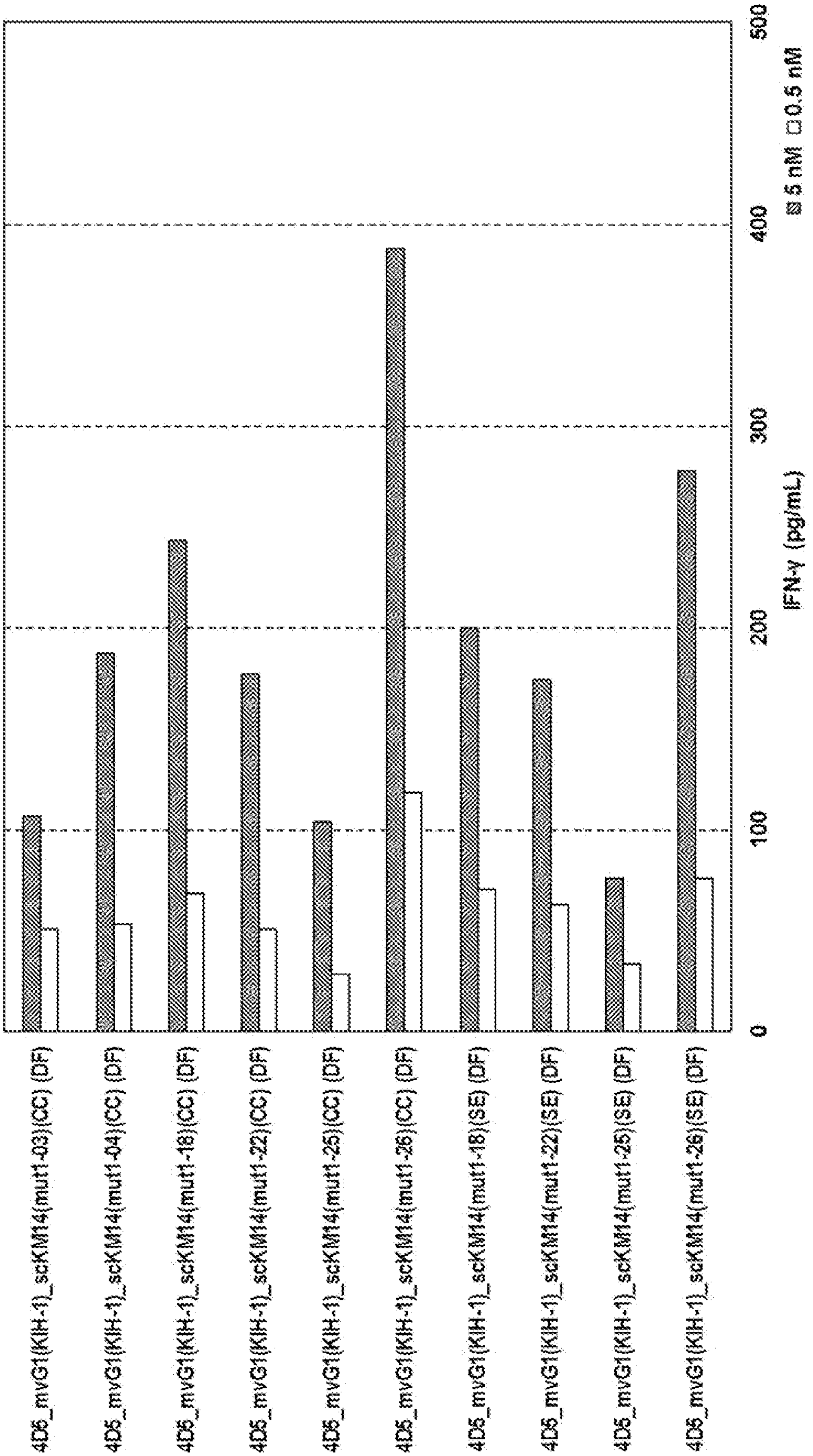

[FIG. 46E]
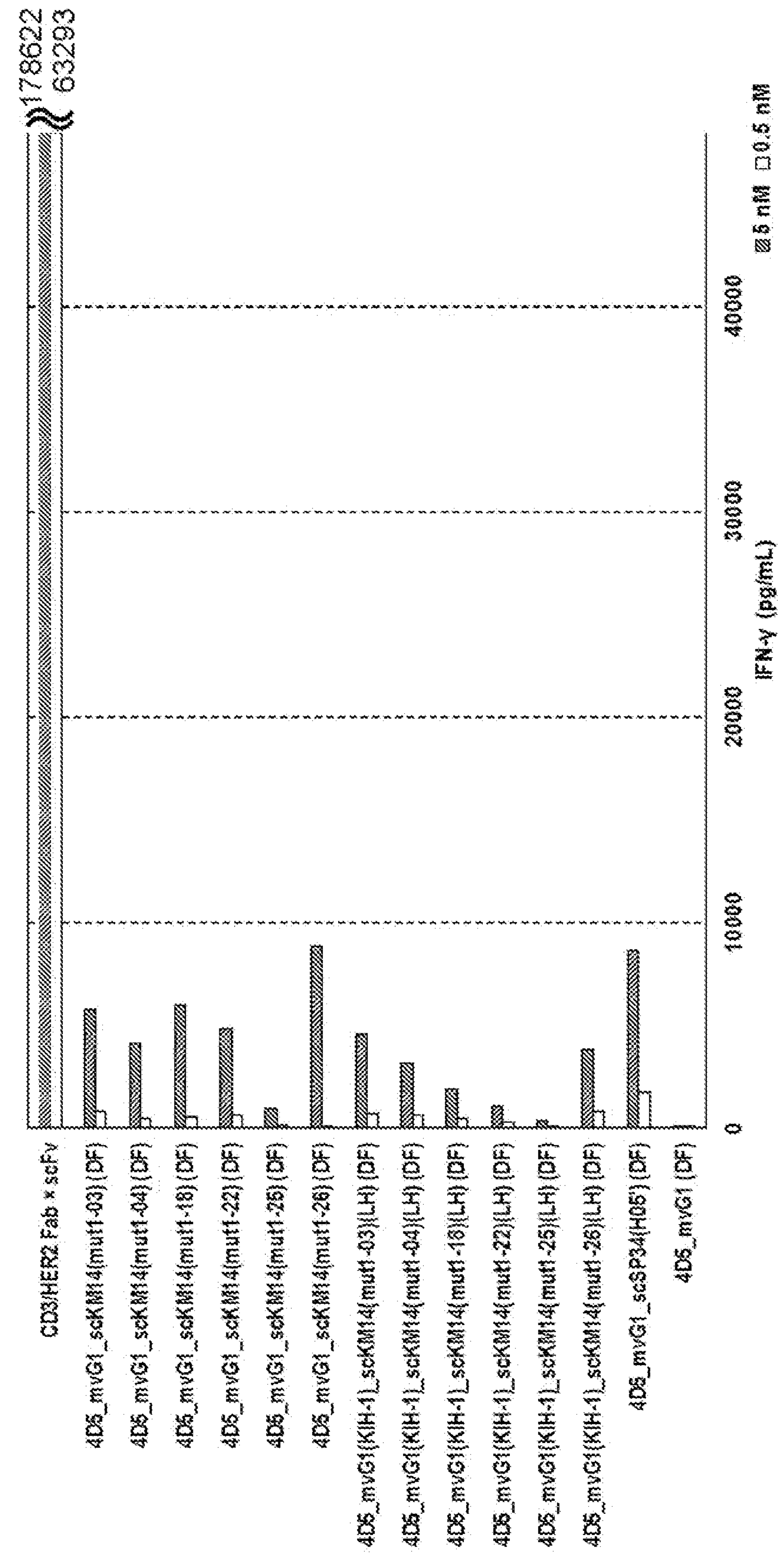

[FIG. 46F]
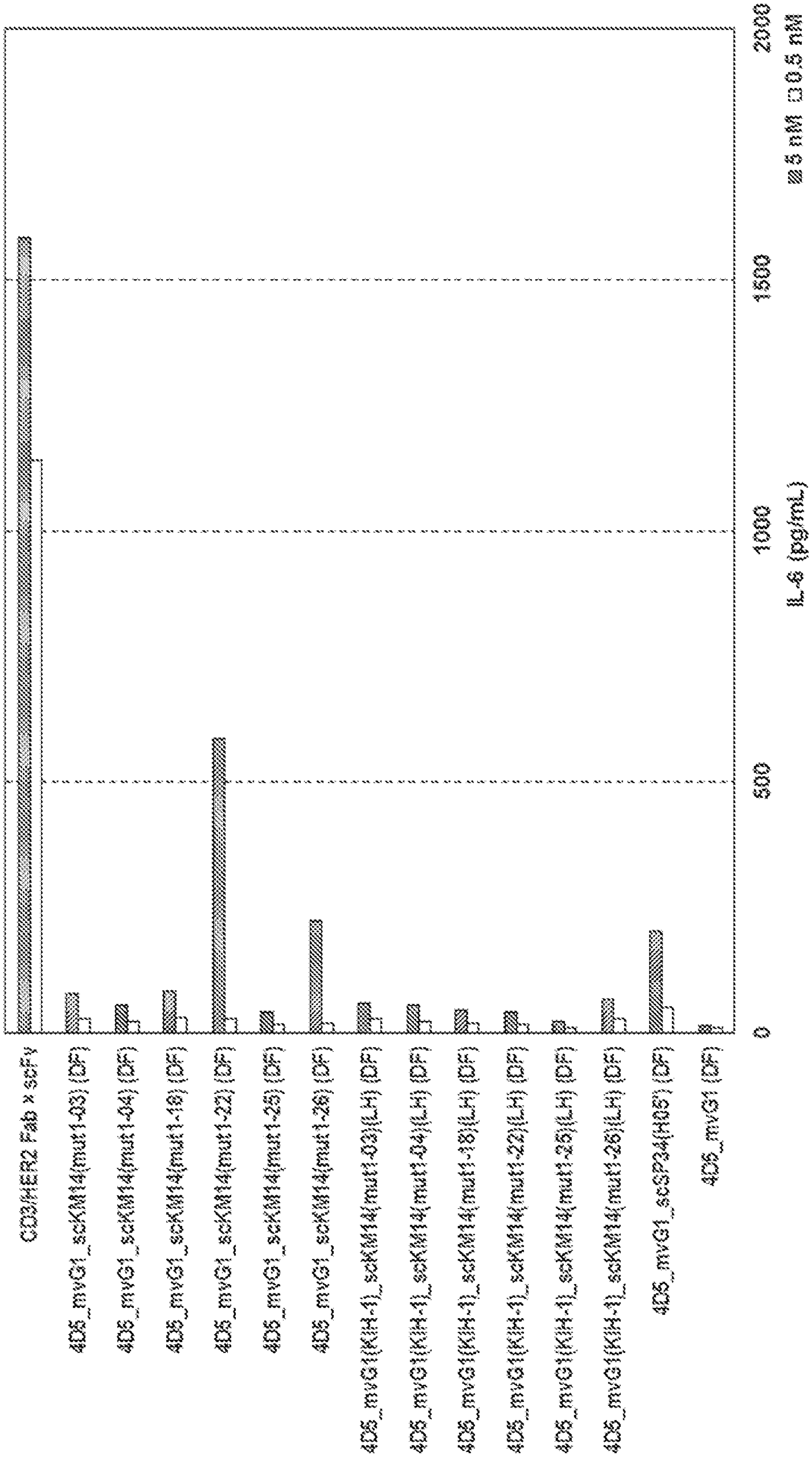

BISPECIFIC ANTIBODY BINDING TO CD3

SEQUENCE LISTING

A sequence listing in electronic (ASCII text file) format is filed with this application and incorporated herein by reference. The name of the ASCII text file is "Revised-Sequence-Listing-1489A.txt"; the file was created on May 15, 2026; the size of the file is 480,195 bytes.

TECHNICAL FIELD

The present invention relates to a bispecific antibody that binds to CD3 or a bispecific antibody fragment thereof, a DNA encoding the bispecific antibody or the bispecific antibody fragment thereof, a vector comprising the DNA, a hybridoma and a transformant that produce the bispecific antibody or the bispecific antibody fragment thereof, a method for producing the bispecific antibody or the bispecific antibody fragment thereof, a therapeutic and/or diagnostic agent comprising the bispecific antibody or the bispecific antibody fragment thereof, a therapeutic and/or diagnostic method using the bispecific antibody or the bispecific antibody fragment thereof, and a reagent for detection or measurement comprising the bispecific antibody or the bispecific antibody fragment thereof.

BACKGROUND ART

It is known that antibody drugs for cancer that have been approved so far have various mechanisms of action (NPL 1). Representative examples are effector functions possessed by IgG-type antibody molecules such as a neutralization activity of inhibiting the binding of a ligand such as a growth factor to a receptor, an agonistic activity of activating a bound receptor, and antibody-dependent cellular cytotoxicity (hereinafter, ADCC activity), complement-dependent cytotoxicity (hereinafter, CDC activity), and the like. Among these, a biomarker analysis of a clinical trial of rituximab and trastuzumab suggests that the ADCC activity is an important mechanism in clinical practice of antibody drugs (NPLs 2 and 3).

The ADCC activity is a cytotoxic mechanism caused by recognizing Fc of an IgG-type antibody bound to a membrane-associated antigen on a cancer cell surface by a natural killer cell (hereinafter referred to as NK cell) or the like through one type of Fc receptor, FcγRIIIA (CD16a) (NPL 1).

In humans, it is the IgG1 subclass that can strongly bind to an Fc receptor and induce an ADCC activity, and in mice, it is the IgG2a subclass. Therefore, the ADCC activity can be enhanced by artificially modifying the human IgG1-type Fc of an antibody drug to increase the binding ability to FcγRIIIA.

In fact, it is known that the ADCC activity can be enhanced by modifying an amino acid of Fc or modifying a sugar chain of an N-linked complex sugar chain that binds to Fc (NPL 4), and particularly a technique for enhancing the ADCC activity by a sugar chain modification is applied to approved antibody drugs such as mogamulizumab (NPL 5) and obinutuzumab (NPL 6).

A bispecific antibody is an artificially modified antibody molecule that is enabled to bind to two different types of antigens unlike a natural antibody, and many molecular forms have been reported (NPL 7). Examples of its application to medicine include a technique for damaging a cancer cell by binding to an antigen on the cancer cell and CD3 on the surface of a T cell and crosslinking them.

The T cell-mediated cellular cytotoxicity caused by binding of a CD3/cancer antigen bispecific antibody to CD3 on a T cell is described here as an ADTC activity (Antibody-dependent T-cell-mediated cytotoxicity).

Examples of the CD3/cancer antigen bispecific antibody include an IgG-type bispecific antibody catumaxomab which is against CD3 and a cancer antigen EpCAM (NPL 8), a bispecific T-cell engager [BiTE (registered trademark)] (NPL 9), an IgG-type bispecific antibody RG7802 which is against CD3 and a cancer antigen CEA, and the like.

Although there are many other molecular forms (NPL 7), these anti-CD3 bispecific antibodies generally have a structure having only an ADTC activity and no ADCC activity or a suppressed ADCC activity.

For example, BiTE (registered trademark) is configured to bind two different types of antibody fragments called single chain Fv (scFv) that bind to CD3 and a cancer antigen through a peptide linker, and does not contain Fc so that it has no mechanism of action through Fc such as an ADCC activity [FIG. 1 (C)]. Further, although RG7802 has Fc, the binding ability to an Fc receptor is removed by introducing a mutation of P329G into Fc, and it also does not exhibit an ADCC activity (NPL 10).

The exception is catumaxomab, and it is known that this anti-CD3 bispecific antibody has a hybrid Fc of mouse IgG2a/rat IgG2b that binds to an Fc receptor, thereby inducing an ADCC activity (NPL 8). However, rodent-derived Fc has a lower ability to induce an ADCC activity as compared with human-derived Fc used in an ordinary antibody drug (NPL 11).

It is considered that the reason why an examination that an anti-CD3 bispecific antibody is combined with Fc having a strong Fc receptor binding ability has not been performed is that T cell activation is caused by Fc receptor-mediated clustering (aggregation on the cell membrane) of CD3, and there is a concern about a side effect accompanying it.

For example, an anti-CD3 antibody OKT3 which is used to suppress rejection during organ transplantation causes a side effect of cytokine release syndrome, which is considered to be caused by clustering of CD3 by leukocytes having an Fc receptor through the mouse IgG2a-type Fc of OKT3 (NPL 12).

It is presumed that a serious side effect accompanied by cytokine release syndrome after administration of catumaxomab, which is a bispecific antibody of CD3 and EpCAM and has a binding ability to an Fc receptor, is caused by activation of T cells via Kupffer cells in the liver having an Fc receptor (NPL 13).

In addition, as a format of a bispecific antibody having Fc, a heterodimer-type structure for having a CD3 binding site in a monovalent manner is generally used in order to avoid a concern about a side effect due to non-specific activation of CD3. (PTLs 1 to 4).

An anti-CD3 bispecific antibody using an anti-CD3 antibody with low affinity for CD3 has also been produced. As an example of such bispecific antibody, RG7802 having an affinity for CD3: $K_D$=1.0×$10^{-7}$ has been clinically developed (NPLs 14 and 15). RG7802 has an Fc region that does not have a binding ability to an Fc receptor, and does not have an effector activity including an ADCC activity (NPL 15).

CITATION LIST

Patent Literature

PTL 1: WO 2011/028952
PTL 2: WO 2014/151910

PTL 3: WO 2015/048272
PTL 4: WO 2014/054804

Non Patent Literature

NPL 1: Carter P. Nat Rev Cancer. 1: 118-129, 2001
NPL 2: Cartron G, Dacheux L, Salles G, et al. Blood. 99: 754-758, 2002
NPL 3: Weng W K, Levy R. J Clin Oncol. 21: 3940-3947, 2003
NPL 4: Shinkawa T, Nakamura K, Yamane N, et al. J Biol Chem. 278: 3466-3473, 2003
NPL 5: Beck A, Reichert J M. MAbs. 4: 419-425, 2012
NPL 6: Gagez A L, Cartron G. Curr Opin Oncol. 26: 484-491, 2014
NPL 7: Carter P J, Lazar G A. Nat Rev Drug Disc. 17: 197-223, 2018
NPL 8: Bokemeyer C. Expert Opin Biol Ther. 10: 1259-1269, 2010
NPL 9: Nagorsen D, Kufer P, Baeuerle P A, Bargou R. Pharmacol Ther. 136: 334-342, 2012
NPL 10: Lehmann S, et al. Clin Cancer Res. 22: 4417-4427, 2016
NPL 11: Bergman I, Basse P, Barmada M, Griffin J, Cheung N. Cancer Immunol Immunother. 49: 259-266, 2010
NPL 12: Ceuppens J L, Bloemmen F J, Van Wauwe J P. J Immunol. 135: 3882-3886, 1985
NPL 13: Borlak J, Langer F, Spanel R., Schondorfer G., Dittrich C. Oncotarget. 7: 28059-28074, 2016
NPL 14: Bacac M, Klein C., Umana P Oncoimmunology. 5(8): e1203498, 2016
NPL 15: Bacac M, Fauti T, Sam J, et al. Clin Cancer Res. 22(13): 3286-97, 2016

SUMMARY OF INVENTION

Technical Problem

Various anti-CD3 bispecific antibodies that bind to CD3 and a specific antigen have been known so far, but a sufficient drug efficacy has not yet been obtained, and also, a problem of a serious side effect due to an excessive immune reaction such as cytokine release syndrome still remains.

Further, a heterodimeric CD3/cancer antigen bispecific antibody that exhibits an ADCC activity or a high ADCC activity and its cellular cytotoxicity have not yet been studied in detail, and an anti-CD3 bispecific antibody, which has high cellular cytotoxicity, and whose induction of excessive cytokine production is suppressed, has not been known.

On the other hand, although it has been known that an antibody containing an Fc region whose affinity for an Fc receptor is enhanced by amino acid residue-modified Fc or sugar chain-modified Fc contributes to the high ADCC activity of a monoclonal antibody, there is no motivation to purposefully enhance the immune reaction by a bispecific antibody by enhancing the ADCC activity using an Fc region with enhanced affinity for an Fc receptor by the amino acid residue-modified Fc or the sugar chain-modified Fc in an anti-CD3 bispecific antibody in which a problem of a serious side effect remains.

An object of the present invention is to provide an anti-CD3 bispecific antibody whose induction of cytokine production is suppressed, and a bispecific antibody that specifically binds to CD3 and a disease-related antigen. In addition, an object is to provide a bispecific antibody comprising an antigen binding domain that binds to CD3 and an antigen binding domain that binds to a disease-related antigen, a bispecific antibody fragment thereof, a DNA encoding the bispecific antibody or the bispecific antibody fragment thereof, a vector comprising the DNA, a hybridoma and a transformant that produce the bispecific antibody or the bispecific antibody fragment thereof, a method for producing the bispecific antibody or the bispecific antibody fragment thereof, a therapeutic agent and diagnostic agent comprising the bispecific antibody or the bispecific antibody fragment thereof, a therapeutic method and diagnostic method using the bispecific antibody or the bispecific antibody fragment thereof, and a reagent for detection or measurement comprising the bispecific antibody or the bispecific antibody fragment thereof, a CD3 binding domain with reduced affinity for CD3 for producing an anti-CD3 bispecific antibody, and a CD3 binding domain with reduced affinity for CD3 for suppressing the induction of cytokine production by an anti-CD3 bispecific antibody.

Solution to Problem

The present invention relates to the following.

1. An anti-CD3 bispecific antibody or a bispecific antibody fragment thereof, containing an Fc region having a binding ability to an Fc receptor, and one CD3 binding domain with reduced affinity for CD3 bound to the C-terminal side of the Fc region, and further containing a disease-related antigen binding domain.
2. An anti-CD3 bispecific antibody or a bispecific antibody fragment thereof, containing an Fc region having a binding ability to an Fc receptor, and one CD3 binding domain bound to the C-terminal side of the Fc region, and further containing a disease-related antigen binding domain, wherein in the presence of CD3-positive T cells and disease-related antigen-positive cells, an ability to induce cytokine production is reduced as compared with an anti-CD3 bispecific antibody using an anti-CD3 monoclonal antibody SP34.
3. The anti-CD3 bispecific antibody or the bispecific antibody fragment thereof according to the above 1 or 2, wherein the dissociation constant ($K_D$) of the CD3 binding domain for CD3 is $6\times10^{-8}$ or more.
4. The anti-CD3 bispecific antibody or the bispecific antibody fragment thereof according to any one of the above 1 to 3, wherein the dissociation constant of the CD3 binding domain for CD3 is larger than that of an anti-CD3 monoclonal antibody SP34 or KM14 serving as a comparison control.
5. The anti-CD3 bispecific antibody or the bispecific antibody fragment thereof according to any one of the above 1 to 4, wherein the amino acid sequence of the CD3 binding domain has 90% or more homology with the amino acid sequence of the CD3 binding domain of an anti-CD3 monoclonal antibody SP34 or KM14 serving as a comparison control, and the affinity for CD3 is reduced by 10% or more as compared with that of the anti-CD3 monoclonal antibody SP34 or KM14.
6. The anti-CD3 bispecific antibody or the bispecific antibody fragment thereof according to any one of the above 1 to 5, which comprises one or two disease-related antigen binding domains.
7. The anti-CD3 bispecific antibody or the bispecific antibody fragment thereof according to any one of the above 1 to 6, wherein each of the CD3 binding domain and the disease-related antigen binding domain is any one selected from scFv, Fab, and VHH.

8. The anti-CD3 bispecific antibody or the bispecific antibody fragment thereof according to any one of the above 1 to 7, wherein the CD3 binding domain and/or the disease-related antigen binding domain is bound to the Fc region through a linker.
9. The anti-CD3 bispecific antibody or the bispecific antibody fragment thereof according to any one of the above 1 to 8, wherein the CD3 binding domain comprises a heavy chain variable region (abbreviated as VH) comprising complementarity determining regions (abbreviated as CDRs) 1 to 3 of an antibody heavy chain and a light chain variable region (abbreviated as VL) comprising CDRs 1 to 3 of an antibody light chain.
10. The anti-CD3 bispecific antibody or the bispecific antibody fragment thereof according to any one of the above 1 to 9, wherein the CD3 binding domain is scFv.
11. The anti-CD3 bispecific antibody or the bispecific antibody fragment thereof according to any one of the above 1 to 10, wherein the amino acid sequences of CDRs 1 to 3 of VH (HCDRs 1 to 3) and CDRs 1 to 3 of VL (LCDRs 1 to 3) of the CD3 binding domain have 90% or more homology with the amino acid sequences of HCDRs 1 to 3 and LCDRs 1 to 3, respectively, of any one selected from the following (a) to (h):
(a) HCDRs 1 to 3 comprising the amino acid sequences represented by SEQ ID NOS: 118 to 120, respectively, and LCDRs 1 to 3 comprising the amino acid sequences represented by SEQ ID NOS: 121 to 123, respectively;
(b) HCDRs 1 to 3 comprising the amino acid sequences represented by SEQ ID NOS: 83 to 85, respectively, and LCDRs 1 to 3 comprising the amino acid sequences represented by SEQ ID NOS: 86 to 88, respectively;
(c) HCDRs 1 to 3 comprising the amino acid sequences represented by SEQ ID NOS: 98 to 100, respectively, and LCDRs 1 to 3 comprising the amino acid sequences represented by SEQ ID NOS: 132, 96, and 97, respectively;
(d) HCDRs 1 to 3 comprising the amino acid sequences represented by SEQ ID NOS: 98 to 100, respectively, and LCDRs 1 to 3 comprising the amino acid sequences represented by SEQ ID NOS: 133, 96, and 97, respectively;
(e) HCDRs 1 to 3 comprising the amino acid sequences represented by SEQ ID NOS: 98, 134, and 100, respectively, and LCDRs 1 to 3 comprising the amino acid sequences represented by SEQ ID NOS: 95 to 97, respectively;
(f) HCDRs 1 to 3 comprising the amino acid sequences represented by SEQ ID NOS: 98, 135, and 100, respectively, and LCDRs 1 to 3 comprising the amino acid sequences represented by SEQ ID NOS: 95 to 97, respectively;
(g) HCDRs 1 to 3 comprising the amino acid sequences represented by SEQ ID NOS: 98, 136, and 100, respectively, and LCDRs 1 to 3 comprising the amino acid sequences represented by SEQ ID NOS: 95 to 97, respectively; and
(h) HCDRs 1 to 3 comprising the amino acid sequences represented by SEQ ID NOS: 98, 137, and 100, respectively, and LCDRs 1 to 3 comprising the amino acid sequences represented by SEQ ID NOS: 95 to 97, respectively.
12. The anti-CD3 bispecific antibody or the bispecific antibody fragment thereof according to any one of the above 1 to 11, wherein the amino acid sequences of VH and VL of the CD3 binding domain have 80% or more homology with the amino acid sequences of VH and VL, respectively, of any one selected from the following (aa) to (rr):
(aa) VH comprising the amino acid sequence represented by SEQ ID NO: 124 and VL comprising the amino acid sequence represented by SEQ ID NO: 125;
(bb) VH comprising the amino acid sequence represented by SEQ ID NO: 115 and VL comprising the amino acid sequence represented by SEQ ID NO: 116;
(cc) VH comprising the amino acid sequence represented by SEQ ID NO: 94 and VL comprising the amino acid sequence represented by SEQ ID NO: 126;
(dd) VH comprising the amino acid sequence represented by SEQ ID NO: 94 and VL comprising the amino acid sequence represented by SEQ ID NO: 127;
(ee) VH comprising the amino acid sequence represented by SEQ ID NO: 128 and VL comprising the amino acid sequence represented by SEQ ID NO: 93;
(ff) VH comprising the amino acid sequence represented by SEQ ID NO: 129 and VL comprising the amino acid sequence represented by SEQ ID NO: 93;
(gg) VH comprising the amino acid sequence represented by SEQ ID NO: 130 and VL comprising the amino acid sequence represented by SEQ ID NO: 93;
(hh) VH comprising the amino acid sequence represented by SEQ ID NO: 131 and VL comprising the amino acid sequence represented by SEQ ID NO: 93;
(ii) VH comprising the amino acid sequence represented by SEQ ID NO: 159 and VL comprising the amino acid sequence represented by SEQ ID NO: 165;
(j) VH comprising the amino acid sequence represented by SEQ ID NO: 160 and VL comprising the amino acid sequence represented by SEQ ID NO: 165;
(kk) VH comprising the amino acid sequence represented by SEQ ID NO: 161 and VL comprising the amino acid sequence represented by SEQ ID NO: 166;
(ll) VH comprising the amino acid sequence represented by SEQ ID NO: 162 and VL comprising the amino acid sequence represented by SEQ ID NO: 166;
(mm) VH comprising the amino acid sequence represented by SEQ ID NO: 168 and VL comprising the amino acid sequence represented by SEQ ID NO: 180;
(nn) VH comprising the amino acid sequence represented by SEQ ID NO: 169 and VL comprising the amino acid sequence represented by SEQ ID NO: 181;
(oo) VH comprising the amino acid sequence represented by SEQ ID NO: 170 and VL comprising the amino acid sequence represented by SEQ ID NO: 182;
(pp) VH comprising the amino acid sequence represented by SEQ ID NO: 171 and VL comprising the amino acid sequence represented by SEQ ID NO: 183;
(qq) VH comprising the amino acid sequence represented by SEQ ID NO: 172 and VL comprising the amino acid sequence represented by SEQ ID NO: 184; and
(rr) VH comprising the amino acid sequence represented by SEQ ID NO: 173 and VL comprising the amino acid sequence represented by SEQ ID NO: 185.
13. The anti-CD3 bispecific antibody or the bispecific antibody fragment thereof according to any one of the above 1 to 12, wherein the amino acid sequences of HCDRs 1 to 3 and LCDRs 1 to 3 of the CD3 binding domain are any one selected from the following (a) to (h):
(a) HCDRs 1 to 3 comprising the amino acid sequences represented by SEQ ID NOS: 118 to 120, respectively, and LCDRs 1 to 3 comprising the amino acid sequences represented by SEQ ID NOS: 121 to 123, respectively;

(b) HCDRs 1 to 3 comprising the amino acid sequences represented by SEQ ID NOS: 83 to 85, respectively, and LCDRs 1 to 3 comprising the amino acid sequences represented by SEQ ID NOS: 86 to 88, respectively;

(c) HCDRs 1 to 3 comprising the amino acid sequences represented by SEQ ID NOS: 98 to 100, respectively, and LCDRs 1 to 3 comprising the amino acid sequences represented by SEQ ID NOS: 132, 96, and 97, respectively;

(d) HCDRs 1 to 3 comprising the amino acid sequences represented by SEQ ID NOS: 98 to 100, respectively, and LCDRs 1 to 3 comprising the amino acid sequences represented by SEQ ID NOS: 133, 96, and 97, respectively;

(e) HCDRs 1 to 3 comprising the amino acid sequences represented by SEQ ID NOS: 98, 134, and 100, respectively, and LCDRs 1 to 3 comprising the amino acid sequences represented by SEQ ID NOS: 95 to 97, respectively;

(f) HCDRs 1 to 3 comprising the amino acid sequences represented by SEQ ID NOS: 98, 135, and 100, respectively, and LCDRs 1 to 3 comprising the amino acid sequences represented by SEQ ID NOS: 95 to 97, respectively;

(g) HCDRs 1 to 3 comprising the amino acid sequences represented by SEQ ID NOS: 98, 136, and 100, respectively, and LCDRs 1 to 3 comprising the amino acid sequences represented by SEQ ID NOS: 95 to 97, respectively; and (h) HCDRs 1 to 3 comprising the amino acid sequences represented by SEQ ID NOS: 98, 137, and 100, respectively, and LCDRs 1 to 3 comprising the amino acid sequences represented by SEQ ID NOS: 95 to 97, respectively.

14. The anti-CD3 bispecific antibody or the bispecific antibody fragment thereof according to any one of the above 1 to 13, wherein the amino acid sequences of VH and VL of the CD3 binding domain are any one selected from the following (aa) to (rr):

(aa) VH comprising the amino acid sequence represented by SEQ ID NO: 124 and VL comprising the amino acid sequence represented by SEQ ID NO: 125;

(bb) VH comprising the amino acid sequence represented by SEQ ID NO: 115 and VL comprising the amino acid sequence represented by SEQ ID NO: 116;

(cc) VH comprising the amino acid sequence represented by SEQ ID NO: 94 and VL comprising the amino acid sequence represented by SEQ ID NO: 126;

(dd) VH comprising the amino acid sequence represented by SEQ ID NO: 94 and VL comprising the amino acid sequence represented by SEQ ID NO: 127;

(ee) VH comprising the amino acid sequence represented by SEQ ID NO: 128 and VL comprising the amino acid sequence represented by SEQ ID NO: 93;

(ff) VH comprising the amino acid sequence represented by SEQ ID NO: 129 and VL comprising the amino acid sequence represented by SEQ ID NO: 93;

(gg) VH comprising the amino acid sequence represented by SEQ ID NO: 130 and VL comprising the amino acid sequence represented by SEQ ID NO: 93;

(hh) VH comprising the amino acid sequence represented by SEQ ID NO: 131 and VL comprising the amino acid sequence represented by SEQ ID NO: 93;

(ii) VH comprising the amino acid sequence represented by SEQ ID NO: 159 and VL comprising the amino acid sequence represented by SEQ ID NO: 165;

(jj) VH comprising the amino acid sequence represented by SEQ ID NO: 160 and VL comprising the amino acid sequence represented by SEQ ID NO: 165;

(kk) VH comprising the amino acid sequence represented by SEQ ID NO: 161 and VL comprising the amino acid sequence represented by SEQ ID NO: 166;

(ll) VH comprising the amino acid sequence represented by SEQ ID NO: 162 and VL comprising the amino acid sequence represented by SEQ ID NO: 166;

(mm) VH comprising the amino acid sequence represented by SEQ ID NO: 168 and VL comprising the amino acid sequence represented by SEQ ID NO: 180;

(nn) VH comprising the amino acid sequence represented by SEQ ID NO: 169 and VL comprising the amino acid sequence represented by SEQ ID NO: 181;

(oo) VH comprising the amino acid sequence represented by SEQ ID NO: 170 and VL comprising the amino acid sequence represented by SEQ ID NO: 182;

(pp) VH comprising the amino acid sequence represented by SEQ ID NO: 171 and VL comprising the amino acid sequence represented by SEQ ID NO: 183;

(qq) VH comprising the amino acid sequence represented by SEQ ID NO: 172 and VL comprising the amino acid sequence represented by SEQ ID NO: 184; and (rr) VH comprising the amino acid sequence represented by SEQ ID NO: 173 and VL comprising the amino acid sequence represented by SEQ ID NO: 185.

15. The anti-CD3 bispecific antibody or the bispecific antibody fragment thereof according to any one of the above 1 to 14, wherein the Fc region is an Fc region having an enhanced binding activity to an Fc receptor.

16. The anti-CD3 bispecific antibody or the bispecific antibody fragment thereof according to the above 15, wherein the Fc region having an enhanced binding activity to an Fc receptor is an Fc region comprising an amino acid residue modification and/or a sugar chain modification.

17. The anti-CD3 bispecific antibody or the bispecific antibody fragment thereof according to the above 15 or 16, wherein the Fc region having an enhanced binding activity to an Fc receptor is an Fc region comprising both an amino acid residue modification and a sugar chain modification.

18. The anti-CD3 bispecific antibody or the bispecific antibody fragment thereof according to the above 16 or 17, wherein the amino acid residue modification is an amino acid residue modification including at least one amino acid residue modification for enhancing the binding activity to an Fc receptor.

19. The anti-CD3 bispecific antibody or the bispecific antibody fragment thereof according to the above 16 or 17, wherein the sugar chain modification is a sugar chain modification in which fucose that is α-1,6-linked to N-acetylglucosamine at the reducing end of an N-linked sugar chain that binds to Asn at position 297 according to EU numbering of the Fc region is deleted.

20. The anti-CD3 bispecific antibody or the bispecific antibody fragment thereof according to any one of the above 1 to 19, wherein two Fabs are included as the disease-related antigen binding domains, and the C terminus of the heavy chain (VH-CH1) of each of the Fabs is bound to the Fc region directly or through a linker.

21. The anti-CD3 bispecific antibody or the bispecific antibody fragment thereof according to any one of the above 1 to 19, wherein one Fab is included as the disease-related antigen binding domain, and the C termini of the heavy chain (VH-CH1) and the light chain (VL-CL) of the Fab are bound to the Fc region directly or through a linker.
22. The anti-CD3 bispecific antibody or the bispecific antibody fragment thereof according to any one of the above 1 to 19 or 21, wherein one Fab is included as the disease-related antigen binding domain, and the CD3 binding domain is bound to an Fc chain at a side bound to the heavy chain (VH-CH1) of the Fab directly or through a linker.
23. The anti-CD3 bispecific antibody or the bispecific antibody fragment thereof according to any one of the above 1 to 19 or 21, wherein one Fab is included as the disease-related antigen binding domain, and the CD3 binding domain is bound to an Fc chain at a side bound to the light chain (VL-CL) of the Fab directly or through a linker.
24. The anti-CD3 bispecific antibody or the bispecific antibody fragment thereof according to any one of the above 20 to 23, wherein the linker is a hinge or a variant thereof.
25. A DNA encoding the anti-CD3 bispecific antibody or the bispecific antibody fragment thereof according to any one of the above 1 to 24.
26. A recombinant vector comprising the DNA according to the above 25.
27. A transformant, obtained by introducing the recombinant vector according to the above 26 into a host cell.
28. A method for producing the anti-CD3 bispecific antibody or the bispecific antibody fragment thereof according to any one of the above 1 to 24, comprising culturing the transformant according to the above 27 in a culture medium, allowing the transformant to produce and accumulate the anti-CD3 bispecific antibody or the bispecific antibody fragment thereof according to any one of the above 1 to 24 in a culture, and collecting the anti-CD3 bispecific antibody or the bispecific antibody fragment thereof from the culture.
29. A therapeutic and/or diagnostic agent for a disease associated with at least one of CD3 and the disease-related antigen, comprising the anti-CD3 bispecific antibody or the bispecific antibody fragment thereof according to any one of the above 1 to 24 as an active ingredient.
30. The therapeutic and/or diagnostic agent according to the above 29, wherein the disease associated with at least one of CD3 and the disease-related antigen is a cancer.
31. A therapeutic and/or diagnostic method for a disease associated with at least one of CD3 and the disease-related antigen, using the anti-CD3 bispecific antibody or the bispecific antibody fragment thereof according to any one of the above 1 to 24.
32. The therapeutic and/or diagnostic method according to the above 31, wherein the disease associated with at least one of CD3 and the disease-related antigen is a cancer.
33. The anti-CD3 bispecific antibody or the bispecific antibody fragment thereof according to any one of the above 1 to 24 for use in therapy and/or diagnosis for a disease associated with at least one of CD3 and the disease-related antigen.
34. The anti-CD3 bispecific antibody or the bispecific antibody fragment thereof according to the above 33, wherein the disease associated with at least one of CD3 and the disease-related antigen is a cancer.
35. Use of the anti-CD3 bispecific antibody or the bispecific antibody fragment thereof according to any one of the above 1 to 24 for producing a therapeutic and/or diagnostic agent for a disease associated with at least one of CD3 and the disease-related antigen.
36. The use according to the above 35, wherein the disease associated with at least one of CD3 and the disease-related antigen is a cancer.
37. A reagent for detecting or measuring at least one of CD3 and the disease-related antigen, comprising the anti-CD3 bispecific antibody or the bispecific antibody fragment thereof according to any one of the above 1 to 24.
38. A method for producing an anti-CD3 bispecific antibody or a bispecific antibody fragment thereof which comprises an Fc region having a binding ability to an Fc receptor, and a disease-related antigen binding domain, wherein a CD3 binding domain with reduced affinity for CD3 is bound to the Fc region.
39. A method for suppressing the induction of cytokine production of an anti-CD3 bispecific antibody or a bispecific antibody fragment thereof which comprises an Fc region having a binding ability to an Fc receptor, and a disease-related antigen binding domain, wherein a CD3 binding domain with reduced affinity for CD3 is used.
40. The method according to the above 38 or 39, wherein the dissociation constant ($K_D$) of the CD3 binding domain for CD3 is $6\times10^{-8}$ or more.
41. The method according to any one of the above 38 to 40, wherein the dissociation constant of the CD3 binding domain for CD3 is larger than that of an anti-CD3 monoclonal antibody SP34 or KM14 serving as a comparison control.
42. The method according to any one of the above 38 to 41, wherein the amino acid sequence of the CD3 binding domain has 90% or more homology with the amino acid sequence of the CD3 binding domain of an anti-CD3 monoclonal antibody SP34 or KM14 serving as a comparison control, and the affinity is reduced by 10% or more as compared with that of the anti-CD3 antibody SP34 or KM14.
43. The method according to any one of the above 38 to 42, wherein the anti-CD3 bispecific antibody or the bispecific antibody fragment thereof comprises one or two disease-related antigen binding domains.
44. The method according to any one of the above 38 to 43, wherein each of the CD3 binding domain and the disease-related antigen binding domain is any one selected from scFv, Fab, and VHH.
45. The method according to any one of the above 38 to 44, wherein the CD3 binding domain and/or the disease-related antigen binding domain is bound to the Fc region through a linker.
46. The method according to any one of the above 38 to 45, wherein the CD3 binding domain includes VH having CDRs 1 to 3 of an antibody heavy chain and VL having CDRs 1 to 3 of an antibody light chain.
47. The method according to any one of the above 38 to 46, wherein the CD3 binding domain is scFv.
48. The method according to any one of the above 38 to 47, wherein the amino acid sequences of CDRs 1 to 3 of VH (HCDRs 1 to 3) and CDRs 1 to 3 of VL (LCDRs 1 to 3) of the CD3 binding domain have 90% or more homology with the amino acid sequences of HCDRs 1 to 3 and LCDRs 1 to 3, respectively, of any one selected from the following (a) to (h):

(a) HCDRs 1 to 3 comprising the amino acid sequences represented by SEQ ID NOS: 118 to 120, respectively, and LCDRs 1 to 3 comprising the amino acid sequences represented by SEQ ID NOS: 121 to 123, respectively;

(b) HCDRs 1 to 3 comprising the amino acid sequences represented by SEQ ID NOS: 83 to 85, respectively, and LCDRs 1 to 3 comprising the amino acid sequences represented by SEQ ID NOS: 86 to 88, respectively;

(c) HCDRs 1 to 3 comprising the amino acid sequences represented by SEQ ID NOS: 98 to 100, respectively, and LCDRs 1 to 3 comprising the amino acid sequences represented by SEQ ID NOS: 132, 96, and 97, respectively;

(d) HCDRs 1 to 3 comprising the amino acid sequences represented by SEQ ID NOS: 98 to 100, respectively, and LCDRs 1 to 3 comprising the amino acid sequences represented by SEQ ID NOS: 133, 96, and 97, respectively;

(e) HCDRs 1 to 3 comprising the amino acid sequences represented by SEQ ID NOS: 98, 134, and 100, respectively, and LCDRs 1 to 3 comprising the amino acid sequences represented by SEQ ID NOS: 95 to 97, respectively;

(f) HCDRs 1 to 3 comprising the amino acid sequences represented by SEQ ID NOS: 98, 135, and 100, respectively, and LCDRs 1 to 3 comprising the amino acid sequences represented by SEQ ID NOS: 95 to 97, respectively;

(g) HCDRs 1 to 3 comprising the amino acid sequences represented by SEQ ID NOS: 98, 136, and 100, respectively, and LCDRs 1 to 3 comprising the amino acid sequences represented by SEQ ID NOS: 95 to 97, respectively; and (h) HCDRs 1 to 3 comprising the amino acid sequences represented by SEQ ID NOS: 98, 137, and 100, respectively, and LCDRs 1 to 3 comprising the amino acid sequences represented by SEQ ID NOS: 95 to 97, respectively.

49. The method according to any one of the above 38 to 48, wherein the amino acid sequences of VH and VL of the CD3 binding domain have 80% or more homology with the amino acid sequences of VH and VL, respectively, of any one selected from the following (aa) to (rr):

(aa) VH comprising the amino acid sequence represented by SEQ ID NO: 124 and VL comprising the amino acid sequence represented by SEQ ID NO: 125;

(bb) VH comprising the amino acid sequence represented by SEQ ID NO: 115 and VL comprising the amino acid sequence represented by SEQ ID NO: 116;

(cc) VH comprising the amino acid sequence represented by SEQ ID NO: 94 and VL comprising the amino acid sequence represented by SEQ ID NO: 126;

(dd) VH comprising the amino acid sequence represented by SEQ ID NO: 94 and VL comprising the amino acid sequence represented by SEQ ID NO: 127;

(ee) VH comprising the amino acid sequence represented by SEQ ID NO: 128 and VL comprising the amino acid sequence represented by SEQ ID NO: 93;

(ff) VH comprising the amino acid sequence represented by SEQ ID NO: 129 and VL comprising the amino acid sequence represented by SEQ ID NO: 93;

(gg) VH comprising the amino acid sequence represented by SEQ ID NO: 130 and VL comprising the amino acid sequence represented by SEQ ID NO: 93;

(hh) VH comprising the amino acid sequence represented by SEQ ID NO: 131 and VL comprising the amino acid sequence represented by SEQ ID NO: 93;

(ii) VH comprising the amino acid sequence represented by SEQ ID NO: 159 and VL comprising the amino acid sequence represented by SEQ ID NO: 165;

(j) VH comprising the amino acid sequence represented by SEQ ID NO: 160 and VL comprising the amino acid sequence represented by SEQ ID NO: 165;

(kk) VH comprising the amino acid sequence represented by SEQ ID NO: 161 and VL comprising the amino acid sequence represented by SEQ ID NO: 166;

(ll) VH comprising the amino acid sequence represented by SEQ ID NO: 162 and VL comprising the amino acid sequence represented by SEQ ID NO: 166;

(mm) VH comprising the amino acid sequence represented by SEQ ID NO: 168 and VL comprising the amino acid sequence represented by SEQ ID NO: 180;

(nn) VH comprising the amino acid sequence represented by SEQ ID NO: 169 and VL comprising the amino acid sequence represented by SEQ ID NO: 181;

(oo) VH comprising the amino acid sequence represented by SEQ ID NO: 170 and VL comprising the amino acid sequence represented by SEQ ID NO: 182;

(pp) VH comprising the amino acid sequence represented by SEQ ID NO: 171 and VL comprising the amino acid sequence represented by SEQ ID NO: 183;

(qq) VH comprising the amino acid sequence represented by SEQ ID NO: 172 and VL comprising the amino acid sequence represented by SEQ ID NO: 184; and (rr) VH comprising the amino acid sequence represented by SEQ ID NO: 173 and VL comprising the amino acid sequence represented by SEQ ID NO: 185.

50. The method according to any one of the above 38 to 49, wherein the amino acid sequences of HCDRs 1 to 3 and LCDRs 1 to 3 of the CD3 binding domain are any one selected from the following (a) to (h):

(a) HCDRs 1 to 3 comprising the amino acid sequences represented by SEQ ID NOS: 118 to 120, respectively, and LCDRs 1 to 3 comprising the amino acid sequences represented by SEQ ID NOS: 121 to 123, respectively;

(b) HCDRs 1 to 3 comprising the amino acid sequences represented by SEQ ID NOS: 83 to 85, respectively, and LCDRs 1 to 3 comprising the amino acid sequences represented by SEQ ID NOS: 86 to 88, respectively;

(c) HCDRs 1 to 3 comprising the amino acid sequences represented by SEQ ID NOS: 98 to 100, respectively, and LCDRs 1 to 3 comprising the amino acid sequences represented by SEQ ID NOS: 132, 96, and 97, respectively;

(d) HCDRs 1 to 3 comprising the amino acid sequences represented by SEQ ID NOS: 98 to 100, respectively, and LCDRs 1 to 3 comprising the amino acid sequences represented by SEQ ID NOS: 133, 96, and 97, respectively;

(e) HCDRs 1 to 3 comprising the amino acid sequences represented by SEQ ID NOS: 98, 134, and 100, respectively, and LCDRs 1 to 3 comprising the amino acid sequences represented by SEQ ID NOS: 95 to 97, respectively;

(f) HCDRs 1 to 3 comprising the amino acid sequences represented by SEQ ID NOS: 98, 135, and 100, respectively, and LCDRs 1 to 3 comprising the amino acid sequences represented by SEQ ID NOS: 95 to 97, respectively;

(g) HCDRs 1 to 3 comprising the amino acid sequences represented by SEQ ID NOS: 98, 136, and 100, respectively, and LCDRs 1 to 3 comprising the amino acid sequences represented by SEQ ID NOS: 95 to 97, respectively; and (h) HCDRs 1 to 3 comprising the amino acid sequences represented by SEQ ID NOS: 98, 137, and 100, respectively, and LCDRs 1 to 3 comprising the amino acid sequences represented by SEQ ID NOS: 95 to 97, respectively.

51. The method according to any one of the above 38 to 50, wherein the amino acid sequences of VH and VL of the CD3 binding domain are any one selected from the following (aa) to (rr):

(aa) VH comprising the amino acid sequence represented by SEQ ID NO: 124 and VL comprising the amino acid sequence represented by SEQ ID NO: 125;

(bb) VH comprising the amino acid sequence represented by SEQ ID NO: 115 and VL comprising the amino acid sequence represented by SEQ ID NO: 116;

(cc) VH comprising the amino acid sequence represented by SEQ ID NO: 94 and VL comprising the amino acid sequence represented by SEQ ID NO: 126;

(dd) VH comprising the amino acid sequence represented by SEQ ID NO: 94 and VL comprising the amino acid sequence represented by SEQ ID NO: 127;

(ee) VH comprising the amino acid sequence represented by SEQ ID NO: 128 and VL comprising the amino acid sequence represented by SEQ ID NO: 93;

(ff) VH comprising the amino acid sequence represented by SEQ ID NO: 129 and VL comprising the amino acid sequence represented by SEQ ID NO: 93;

(gg) VH comprising the amino acid sequence represented by SEQ ID NO: 130 and VL comprising the amino acid sequence represented by SEQ ID NO: 93;

(hh) VH comprising the amino acid sequence represented by SEQ ID NO: 131 and VL comprising the amino acid sequence represented by SEQ ID NO: 93;

(ii) VH comprising the amino acid sequence represented by SEQ ID NO: 159 and VL comprising the amino acid sequence represented by SEQ ID NO: 165;

(j) VH comprising the amino acid sequence represented by SEQ ID NO: 160 and VL comprising the amino acid sequence represented by SEQ ID NO: 165;

(kk) VH comprising the amino acid sequence represented by SEQ ID NO: 161 and VL comprising the amino acid sequence represented by SEQ ID NO: 166;

(ll) VH comprising the amino acid sequence represented by SEQ ID NO: 162 and VL comprising the amino acid sequence represented by SEQ ID NO: 166;

(mm) VH comprising the amino acid sequence represented by SEQ ID NO: 168 and VL comprising the amino acid sequence represented by SEQ ID NO: 180;

(nn) VH comprising the amino acid sequence represented by SEQ ID NO: 169 and VL comprising the amino acid sequence represented by SEQ ID NO: 181;

(oo) VH comprising the amino acid sequence represented by SEQ ID NO: 170 and VL comprising the amino acid sequence represented by SEQ ID NO: 182;

(pp) VH comprising the amino acid sequence represented by SEQ ID NO: 171 and VL comprising the amino acid sequence represented by SEQ ID NO: 183;

(qq) VH comprising the amino acid sequence represented by SEQ ID NO: 172 and VL comprising the amino acid sequence represented by SEQ ID NO: 184; and (rr) VH comprising the amino acid sequence represented by SEQ ID NO: 173 and VL comprising the amino acid sequence represented by SEQ ID NO: 185.

52. The method according to any one of the above 38 to 51, wherein the Fc region is an Fc region having an enhanced binding activity to an Fc receptor.

53. A CD3 binding domain with reduced affinity for CD3 for producing an anti-CD3 bispecific antibody or a bispecific antibody fragment thereof which comprises an Fc region and a disease-related antigen binding domain.

54. A CD3 binding domain with reduced affinity for CD3 for suppressing the induction of cytokine production of an anti-CD3 bispecific antibody or a bispecific antibody fragment thereof which comprises an Fc region and a disease-related antigen binding domain.

55. Use of a CD3 binding domain with reduced affinity for CD3 for producing an anti-CD3 bispecific antibody or a bispecific antibody fragment thereof which comprises an Fc region and a disease-related antigen binding domain.

Advantageous Effects of Invention

The present invention can provide a bispecific antibody comprising an antigen binding domain that binds to CD3 and an antigen binding domain that binds to a disease-related antigen, a bispecific antibody fragment thereof, a DNA encoding the bispecific antibody or the bispecific antibody fragment thereof, a vector comprising the DNA, a hybridoma and a transformant that produce the bispecific antibody or the bispecific antibody fragment thereof, a method for producing the bispecific antibody or the bispecific antibody fragment thereof, a therapeutic or a diagnostic agent comprising the bispecific antibody or the bispecific antibody fragment thereof, a therapeutic or a diagnostic method using the bispecific antibody or the bispecific antibody fragment thereof, a reagent for detection or measurement comprising the bispecific antibody or the bispecific antibody fragment thereof, a CD3 binding domain with reduced affinity for CD3 for producing an anti-CD3 bispecific antibody, and a CD3 binding domain with reduced affinity for CD3 for suppressing the cytokine release by an anti-CD3 bispecific antibody.

The bispecific antibody or the bispecific antibody fragment thereof of the present invention comprises an Fc region having a binding ability to an Fc receptor, one CD3 binding domain with reduced affinity for CD3 bound to the C-terminal side of the Fc region, and further comprises a disease-related antigen binding domain, and therefore has disease-related antigen specific cellular cytotoxicity due to an ADCC activity and an ADTC activity (antibody-dependent T-cell-mediated cytotoxicity). Therefore, the composition of the present invention targets an antigen expressed by a cell related to any of various diseases, and can be used for a treatment of the disease.

BRIEF DESCRIPTION OF DRAWINGS

FIGS. 1(A) to 1(C) show schematic views of the molecular types of antibody drug products. FIG. 1(A) is a general IgG antibody, FIG. 1(B) is Catumaxomab which is a CD3/EpCAM bispecific antibody, and FIG. 1(C) is Blinatumomab which is a bispecific T-cell engager [BiTE (registered trademark)].

FIGS. 2(A) and 2(B) show schematic views of the molecular types of an IgG1-type monovalent antibody (FIG. 2(A)) and an IgG4PE(R409K)-type monovalent antibody (FIG. 2(B)), and amino acid modification sites contained in each molecular type. In each monovalent antibody, the H chain is referred to as the first polypeptide and the light chain-Fc fusion protein is referred to as the second polypeptide.

FIGS. 3(A) and 3(B) show schematic views of the bispecific antibody molecules to which anti-CD3 scFv is added to the C terminus of the Fc region at the first polypeptide (H chain, VH-CH1-hinge-Fc) side of an IgG1-type monovalent antibody (FIG. 3(A)) and an IgG4PE(R409K)-type monovalent antibody (FIG. 3(B)), and amino acid modification sites.

FIG. 4 shows the results of measuring the binding of an IgG antibody, a monovalent antibody, and a bispecific antibody molecule to HER2 on the surface of the cell membrane using the inhibition of binding of fluorescently labeled Trastuzumab as index. The horizontal axis represents the concentration of the test antibody molecules, and the vertical axis represents the relative value (%) of the mean fluorescent intensity of cells. The higher the binding of the molecule to HER2 is, the more the binding of the fluorescently labeled Trastuzumab is inhibited so that the value of the vertical axis becomes smaller in a concentration dependent manner.

FIG. 5 shows the results of measuring the binding of an IgG antibody, a monovalent antibody, and a bispecific antibody molecule to CD3 on the surface of the membrane using a fluorescently labeled secondary antibody. The vertical axis represents the relative value of the mean fluorescent intensity of cells (the reference value is set to 1) on the logarithmic axis. It is shown that the molecules with anti-CD3 scFv are bound to T cells.

FIG. 6 shows the results of measuring the cellular cytotoxicity against BT-20 cells by a real-time cell analyzer. The horizontal axis represents the time (h) after the start of measurement, and the vertical axis represents the cell index value of the wells to which the test antibodies were added. The lower the cell index value is, the smaller number of cells adhering to the well is, that is, the higher the cellular cytotoxicity is. It is shown that as compared with the antibody having only ADCC activity and the antibody having only ADTC activity, the cellular cytotoxicity becomes higher when a half amount of each of these antibodies is mixed with each other.

FIG. 7 shows the results of measuring the cellular cytotoxicity against BT-20 cells by a real-time cell analyzer. The horizontal axis represents the time (h) after the start of measurement, and the vertical axis represents the cell index value of the wells to which the test antibodies were added. The lower the cell index value is, the higher the cellular cytotoxicity is. It is shown that as compared with the case where a half amount of the antibody having only ADCC activity and a half amount of the antibody having only ADTC activity are mixed, the cellular cytotoxicity becomes higher in the case of the antibody having both ADCC and ADTC activities in one molecule.

FIGS. 8(A) to 8(E) show the results of measuring the cellular cytotoxicity against MCF-7 cells by a real-time cell analyzer. The horizontal axis represents the time (h) after the start of measurement, and the vertical axis represents the cell index value of the wells to which the test antibodies were added. The lower the cell index value is, the higher the cellular cytotoxicity is. Under the conditions that the antibody having only ADCC activity and the antibody having only ADTC activity exhibit little cellular cytotoxicity, the antibody having both ADCC and ADTC activities in one molecule exhibits high cellular cytotoxicity.

FIG. 9 shows the results of measuring the binding of the CD3/HER2 bispecific antibody molecules to HER2 on the surface of the cell membrane using the inhibition of binding of fluorescently labeled Trastuzumab as the index. The horizontal axis represents the concentration of the test antibody molecules, and the vertical axis represents the relative value (the reference value is set to 1) of the mean fluorescent intensity of cells. The higher the binding of the molecule to HER2 is, the more the binding of the fluorescently labeled Trastuzumab is inhibited so that the value of the vertical axis becomes smaller in a concentration dependent manner. It is shown that in the test molecules, the linker moiety that binds the C-terminal side of an Fc region and the N-terminal side of anti-CD3 scFv is different, but the binding activity to HER2 does not change.

FIG. 10 shows the results of measuring the binding of the IgG antibody, the monovalent antibody, and the bispecific antibody molecules to CD3 on the surface of the membrane using a fluorescently labeled secondary antibody. The vertical axis represents the relative value of the mean fluorescent intensity of cells (the reference value is set to 1) on the logarithmic axis. It is shown that in the test molecules, a linker moiety that binds the C-terminal side of an Fc region and the N-terminal side of anti-CD3 scFv is different, but the binding activity to CD3 does not change significantly.

FIG. 11 shows the results of measuring the cellular cytotoxicity against BT-20 cells by a real-time cell analyzer. The horizontal axis represents the time (h) after the start of measurement, and the vertical axis represents the cell index value of the wells to which the test antibodies were added. The lower the cell index value is, the higher the cellular cytotoxicity is. It is shown that in the test molecules, the linker moiety that binds the C-terminal side of an Fc region and the N-terminal side of anti-CD3 scFv is different, but the test molecules have substantially the same cellular cytotoxicity.

FIG. 12 shows the results of measuring the cellular cytotoxicity against BT-20 cells by a real-time cell analyzer. The horizontal axis represents the time (h) after the start of measurement, and the vertical axis represents the cell index value of the wells to which the test antibodies were added. The lower the cell index value is, the higher the cellular cytotoxicity is. It is shown that in the test molecules, the linker moiety that binds the C-terminal side of an Fc region and the N-terminal side of anti-CD3 scFv is different, but the test molecule has substantially the same cellular cytotoxicity.

FIG. 13 shows the results of measuring the cellular cytotoxicity against MKN-7 cells by a real-time cell analyzer. The horizontal axis represents the time after the start of measurement, and the vertical axis represents the cell index value of the wells to which the test antibodies were added. The lower the cell index value is, the higher the cellular cytotoxicity is.

FIG. 14 shows the results of measuring the cellular cytotoxicity against MKN-45 cells by a real-time cell analyzer. The horizontal axis represents the time (h) after the start of measurement, and the vertical axis represents the cell index value of the wells to which the test antibodies were added. The lower the cell index value is, the higher the cellular cytotoxicity is.

FIG. 15 is a view showing the results of measuring the cellular cytotoxicity against BT-20 cells of the control antibody (left graphs) and 4D5_mvG1_scT3a (DF) (right graphs) when a known anti-CD3 bispecific antibody was used as the control antibody, and the concentration of the cytokines in the culture supernatant plotted on the same graph. In each graph, the horizontal axis represents the concentration of the test substance, the left vertical axis represents the cellular cytotoxicity (%), and the right vertical axis represents the concentration of each cytokine (pg/mL). The cellular cytotoxicity is indicated by black squares (■) and a solid line, and the cytokine concentration is indicated by ◇ and a dotted line.

FIGS. 16(A) to 16(F) are views showing molecular types designed for verifying a synergistic increase in cellular cytotoxicity by combining ADCC activity and ADTC activity. FIG. 16(A) shows a molecular type in which anti-CD3 scFv is bound to the C terminus of the Fc region of the first polypeptide (H chain) of a monovalent antibody, FIG. 16(B) shows a molecular type in which anti-CD3 scFv is bound to the C terminus of one heavy chain of a bivalent antibody, FIG. 16(C) shows a molecular type which is the same molecular type as that in FIG. 16(A), but has sugar chains to which α1,6-fucose is added, FIG. 16(D) shows a molecular type in which anti-CD3 scFv is bound to the C terminus of the Fc region of the second polypeptide (light chain-Fc fusion protein or VL-CL-hinge-Fc) of a monovalent antibody, FIG. 16(E) shows a molecular type in which both of Fab against the cancer antigen and anti-CD3 scFv are located at the N-terminal side of the Fc region, and FIG. 16(F) shows a molecular type in which anti-CD3 scFvs are bound one by one to the C terminus of each of the first and second polypeptides of a monovalent antibody.

FIGS. 17(A) and 17(B) show the results of measuring the cellular cytotoxicity against BT-20 cells of CD3/HER2 bispecific antibodies that is bivalent [FIG. 17(A)] or monovalent [FIG. 17(B)] against the cancer antigen by a real-time cell analyzer for the purpose of verification of the molecular type. The horizontal axis represents the time (h) after the start of measurement, and the vertical axis represents the cell index value of the wells to which the test antibodies were added. The lower the cell index value is, the higher the cellular cytotoxicity is.

FIGS. 18(A) and 18(B) show the results of measuring the cellular cytotoxicity against SBC-3 cells of CD3/GM2 bispecific antibodies that is bivalent against the cancer antigen by a real-time cell analyzer for the purpose of verification of the molecular type. FIG. 18(A) is the result of the negative control molecules using an anti-DNP antibody in the variable region at the cancer antigen side, and FIG. 18(B) is that of the molecules using an anti-GM2 antibody. The horizontal axis represents the time (h) after the start of measurement, and the vertical axis represents the cell index value of the wells to which the test antibodies were added. The lower the cell index value is, the higher the cellular cytotoxicity is.

FIG. 19(A) is a view showing the results of measuring the cellular cytotoxicity against BT-20 cells of CD3/HER2 bispecific antibodies having α1,6-fucose, or the like by a real-time cell analyzer for the purpose of verification of the molecular type. FIG. 19(B) is a view showing the results of comparing the cellular cytotoxicity against BT-20 cells of an anti-CD3/HER2 bispecific antibody with α1,6-fucose with that of a CD3/HER2 bispecific antibody without α1,6-fucose. The horizontal axis represents the time (h) after the start of measurement, and the vertical axis represents the cell index value of the wells to which the test antibodies were added. The lower the cell index value is, the higher the cellular cytotoxicity is.

FIG. 20(A) is a view showing the results of measuring the cellular cytotoxicity against BT-20 cells of the molecules in which anti-CD3 scFv is bound to the C terminus of the second polypeptide (light chain-Fc fusion protein or VL-CL-hinge-Fc) of a monovalent antibody, or the like by a real-time cell analyzer for the purpose of verification of the molecular type. FIG. 20(B) is a view showing the results of comparing the cellular cytotoxicity against BT-20 cells of the molecules in which anti-CD3 scFv is bound to the C terminus of the second polypeptide, or the like with that of the molecules in which anti-CD3 scFv is bound to the C terminus of the first polypeptide (VH-CHT-hinge-Fc) of a monovalent antibody. The horizontal axis represents the time (h) after the start of measurement, and the vertical axis represents the cell index value of the wells to which the test antibodies were added. That the lower the cell index value is, the higher the cellular cytotoxicity is.

FIG. 21 is a view showing the results of measuring the cellular cytotoxicity against BT-20 cells of anti-CD3 bispecific antibodies which do not bind to HER2 and serves as the negative control, and HER2/CD3 bispecific antibodies by a real-time cell analyzer for the purpose of verification of the molecular type. The horizontal axis represents the time (h) after the start of measurement, and the vertical axis represents the cell index value of the wells to which the test antibodies were added. The lower the cell index value is, the higher the cellular cytotoxicity is. "Target+PBMC" indicates no test substance, and "0.5% Triton X-100" indicates 100% cytotoxicity. The measurement of the test substance was performed at three points where the final concentration was 50 nM, 5 nM, and 0.5 nM. Since the measured values are close to each other, * and ** indicate the respective test substances in the lower part.

FIG. 22A is a view showing the results of measuring the cellular cytotoxicity against BT-20 cells of an anti-CD3 bispecific antibody which does not bind to HER2 by a real-time cell analyzer for the purpose of verification of the molecular type. The horizontal axis represents the time (h) after the start of measurement, and the vertical axis represents the cell index value of the wells to which the test antibodies were added. The lower the cell index value is, the higher the cellular cytotoxicity is. "Target+PBMC" indicates no test substance, and "0.5% Triton X-100" indicates 100% cytotoxicity. A variable region of 4D5mut does not bind to HER2, and therefore, the cellular cytotoxicity observed in this measurement is non-specific activity.

FIG. 22B is a view showing the results of measuring the cellular cytotoxicity against BT-20 cells of an anti-CD3 bispecific antibody which does not bind to HER2 by a real-time cell analyzer for the purpose of verification of the molecular type. The horizontal axis represents the time (h) after the start of measurement, and the vertical axis represents the cell index value of the wells to which the test antibodies were added. The lower the cell index value is, the higher the cellular cytotoxicity is. "Target+PBMC" indicates no test substance, and "0.5% Triton X-100" indicates 100% cytotoxicity. A variable region of 4D5mut does not bind to HER2, and therefore, the cellular cytotoxicity observed in this measurement is non-specific activity.

FIG. 22C is a view showing the results of measuring the cellular cytotoxicity against BT-20 cells of an anti-CD3 bispecific antibody which does not bind to HER2 by a real-time cell analyzer for the purpose of verification of the molecular type. The horizontal axis represents the time (h)

after the start of measurement, and the vertical axis represents the cell index value of the wells to which the test antibodies were added. The lower the cell index value is, the higher the cellular cytotoxicity is. "Target+PBMC" indicates no test substance, and "0.5% Triton X-100" indicates 100% cytotoxicity. A variable region of 4D5mut does not bind to HER2, and therefore, the cellular cytotoxicity observed in this measurement is non-specific activity.

FIG. 22D shows a sensorgram obtained by measuring the binding activity of an anti-CD3 bispecific antibody to the human CD3D&E protein by surface plasmon resonance (SPR) method. The name of the test antibody and approximate $K_D$ value are shown in the drawing.

FIG. 22E shows a sensorgram obtained by measuring the binding activity of an anti-CD3 bispecific antibody to the human CD3D&E protein by surface plasmon resonance (SPR) method. The name of the test antibody and approximate $K_D$ value are shown in the drawing.

FIG. 22F shows a sensorgram obtained by measuring the binding activity of an anti-CD3 bispecific antibody to the human CD3D&E protein by surface plasmon resonance (SPR) method. The name of the test antibody and approximate $K_D$ value are shown in the drawing.

FIG. 22G is an expanded view of the dotted line portion of FIG. 22F.

FIGS. 23(A) and 23(B) are views showing the results of measuring the cellular cytotoxicity against BT-20 cells of two types of anti-CD3 bispecific antibodies which do not bind to HER2 by a real-time cell analyzer for the purpose of verification of the molecular type. The horizontal axis represents the time (h) after the start of measurement, and the vertical axis represents the cell index value of the wells to which the test antibodies were added. The lower the cell index value is, the higher the cellular cytotoxicity is. Both variable regions of 4D5mut and DNP2 do not bind to HER2, and therefore, the cellular cytotoxicity observed in this measurement is a non-specific activity.

FIG. 24A is a view obtained by measuring the cellular cytotoxicity of an anti-CD3/HER2 bispecific antibody using a high affinity anti-CD3 scFv or a negative control bispecific antibody. The cellular cytotoxicity against BT-20 cells was measured by a real-time cell analyzer. The horizontal axis represents the time (h) after the start of measurement, and the vertical axis represents the cell index value of the wells to which the test antibodies were added. The lower the cell index value is, the higher the cellular cytotoxicity is.

FIG. 24B is a view obtained by measuring the non-specific cytokine production of anti-CD3/HER2 using anti-CD3 scFv with high affinity or a negative control bispecific antibody. The cytokine production when human PBMC and the test antibody were mixed was measured. The horizontal axis represents the concentration of the test antibody, and the vertical axis represents the concentration of the cytokine in a culture supernatant. Legends and abbreviations are shown in the lower part of the drawing.

FIGS. 25(A) and 25(B) show the design examples of amino acid modification to be introduced into the CDRs of an anti-CD3 monoclonal antibody clone SP34. FIG. 25(A) shows a design to introduce a modification of one amino acid into VL CDRs or VH CDRs of an anti-CD3 monoclonal antibody clone SP34. The leftmost column of the table shows the serial number of the modification, and the second column from the left shows the amino acid residue number according to Kabat numbering of the modified residue and the amino acid residues before and after the amino acid residue modification in one letter. The amino acid residue that is underlined in the amino acid sequence of each CDR in the table indicates the amino acid residue after modification. In FIG. 25(A), the amino acid sequence of CDRL1 of SP34 VL, L02, L03, L04, L05, L06, L07, L08, L09, L10 and L11 is the amino acid sequence represented by SEQ ID NO: 79, and the amino acid sequence of CDRL1 of L01 is the amino acid sequence represented by SEQ ID NO: 218. The amino acid sequence of CDRL2 of SP34 VL, L01, L07, L08, L09, L10 and L11 is the amino acid sequence represented by SEQ ID NO: 80, the amino acid sequence of CDRL2 of L02 is the amino acid sequence represented by SEQ ID NO: 219, the amino acid sequence of CDRL2 of L03 is the amino acid sequence represented by SEQ ID NO: 220, the amino acid sequence of CDRL2 of L04 is the amino acid sequence represented by SEQ ID NO: 221, the amino acid sequence of CDRL2 of L05 is the amino acid sequence represented by SEQ ID NO: 222, and the amino acid sequence of CDRL2 of L06 is the amino acid sequence represented by SEQ ID NO: 223. The amino acid sequence of CDRL3 of SP34 VL, L01, L02, L03, L04, L05, and L06 is the amino acid sequence represented by SEQ ID NO: 81, the amino acid sequence of CDRL3 of L07 is the amino acid sequence represented by SEQ ID NO: 224, the amino acid sequence of CDRL3 of L08 is the amino acid sequence represented by SEQ ID NO: 225, the amino acid sequence of CDRL3 of L09 is the amino acid sequence represented by SEQ ID NO: 226, the amino acid sequence of CDRL3 of L10 is the amino acid sequence represented by SEQ ID NO: 88, and the amino acid sequence of CDRL3 of L11 is the amino acid sequence represented by SEQ ID NO: 227. The amino acid sequence of CDRH1 of SP34 VH, H02, H03, H04, H05, H06, and H07 is the amino acid sequence represented by SEQ ID NO: 76, and the amino acid sequence of CDRH1 of HO1 is the amino acid sequence represented by SEQ ID NO: 228. The amino acid sequence of CDRH2 of SP34 VH, HO1, H02, H03, H04, H05, H06, and H07 is the amino acid sequence represented by SEQ ID NO: 77. The amino acid sequence of CDRH1 of SP34 VH, and HO1 is the amino acid sequence represented by SEQ ID NO: 78, the amino acid sequence of CDRH1 of H02 is the amino acid sequence represented by SEQ ID NO: 229, the amino acid sequence of CDRH1 of H03 is the amino acid sequence represented by SEQ ID NO: 230, the amino acid sequence of CDRH1 of H is the amino acid sequence represented by SEQ ID NO: 231, the amino acid sequence of CDRH1 of H05 is the amino acid sequence represented by SEQ ID NO: 85, the amino acid sequence of CDRH1 of H06 is the amino acid sequence represented by SEQ ID NO: 232, and the amino acid sequence of CDRH1 of H07 is the amino acid sequence represented by SEQ ID NO: 233. FIG. 25(B) shows the examples of combinations of two or more CDR-modified residues in the CDRs of an anti-CD3 monoclonal antibody clone SP34.

FIGS. 26(A) and 26(C) show the design examples of the VL FR sequence of a humanized antibody using a modified CDRs of an anti-CD3 monoclonal antibody clone SP34. FIGS. 26(B) and 26(D) show the design examples of the VH FR sequence of a humanized antibody using a modified CDRs of an anti-CD3 monoclonal antibody clone SP34. X shows an amino acid residue.

FIG. 27 is a view showing the results of measuring the binding activity of the CD3/HER2 bispecific antibodies using CDR variants of an anti-CD3 monoclonal antibody clone SP34 by surface plasmon resonance (SPR) method. From the left column, the name of the test bispecific antibodies, the mutation introduction site, the number of cycles in the measurement, ka ($M^{-1}s^{-1}$), kd ($s^{-1}$), and $K_D$ (M) are shown. "–" in the mutation column indicates that no mutation was introduced, and "Protein not obtained" indicates that the test bispecific antibody could not be obtained as a purified protein.

FIGS. 28(A) to 28(C) are views showing the results of measuring the cellular cytotoxicity against BT-20 cells of the CD3/HER2 bispecific antibodies using CDR variants of an anti-CD3 monoclonal antibody clone SP34 by a real-time cell analyzer. The horizontal axis represents the time (h) after the start of measurement, and the vertical axis represents the cell index value of the wells to which the test antibodies were added. The lower the cell index value is, the higher the cellular cytotoxicity is. "Target+PBMC" indicates no test substance, and "0.5% Triton X-100" indicates 100% cytotoxicity. FIGS. 28(B) and 28(C) are expanded views of a portion surrounded by a rectangular frame in FIG. 28(A), and in FIG. 28(B), the activity of 4D5_mvG1_scSP34(H04') (DF) and in FIG. 28(C), the activity of 4D5_mvG1_scSP34 (H05') (DF) are shown in comparison with other antibody groups in the drawings.

FIGS. 29(A) to 29(D) are views showing the results of measuring the cytokine production of the CD3/HER2 bispecific antibodies using CDR variants of an anti-CD3 monoclonal antibody clone SP34 during cytotoxic assay against BT-20 cells. The results of measuring the concentration of the cytokines (IL-2, IL-6, IFN-γ, or TNF-α) in the culture supernatant by flow cytometry are shown. The vertical axis represents the cytokine concentration (pg/mL), and the horizontal axis represents the antibody concentration (nM).

FIG. 30 is a view showing the results of measuring the non-specific cytokine production (IL-2, IL-6, IFN-γ, or TNF-α) of CD3/HER2 bispecific antibodies using CDR variants of an anti-CD3 monoclonal antibody clone SP34. "medium" indicates only PBMC and the culture medium, and "vehicle" indicates one obtained by adding an equal amount of the buffer (citrate buffer) in which the test substance was dissolved. The vertical axis represents the cytokine concentration (pg/mL), and the horizontal axis represents the name and concentration (μg/mL) of the antibodies. The names of the test substance in the drawing are denoted by abbreviations, and the correspondence is shown in the lower part.

FIG. 31 shows design examples of amino acid modification to be introduced into the CDRs of an anti-CD3 monoclonal antibody clone KM14. The upper part of the drawing shows the modification to be introduced into the CDRs of VL, and the lower part shows the modification to be introduced into the CDRs of VH. The left side of the table shows the serial number of the modification, and the right side thereof shows the amino acid residue number according to Kabat numbering of the modified residue. A residue that is underlined indicates a residue resulting from the modification. In FIG. 31, the amino acid sequence of CDRL1 of KM14 VL, mut1-05, mut1-06, mut1-07, mut1-08, mut1-09, mut1-10 and mut1-11 is the amino acid sequence represented by SEQ ID NO: 95, the amino acid sequence of CDRL1 of mut1-01 is the amino acid sequence represented by SEQ ID NO: 234, the amino acid sequence of CDRL1 of mut1-02 is the amino acid sequence represented by SEQ ID NO: 235, the amino acid sequence of CDRL1 of mut1-03 is the amino acid sequence represented by SEQ ID NO: 132, and the amino acid sequence of CDRL1 of mut1-04 is the amino acid sequence represented by SEQ ID NO: 133. The amino acid sequence of CDRL2 of KM14 VL, mut1-01, mut1-02, mut1-03, mut1-04, mut1-06, mut1-07, mut1-08, mut1-09, mut1-10 and mut1-11 is the amino acid sequence represented by SEQ ID NO: 96, and the amino acid sequence of CDRL2 of mut1-05 is the amino acid sequence represented by SEQ ID NO: 236. The amino acid sequence of CDRL3 of KM14 VL, mut1-01, mut1-02, mut1-03, mut1-04, and mut1-05 is the amino acid sequence represented by SEQ ID NO: 97, the amino acid sequence of CDRL3 of mut1-06 is the amino acid sequence represented by SEQ ID NO: 237, the amino acid sequence of CDRL3 of mut1-07 is the amino acid sequence represented by SEQ ID NO: 238, the amino acid sequence of CDRL3 of mut1-08 is the amino acid sequence represented by SEQ ID NO: 239, the amino acid sequence of CDRL3 of mut1-09 is the amino acid sequence represented by SEQ ID NO: 240, the amino acid sequence of CDRL3 of mut1-10 is the amino acid sequence represented by SEQ ID NO: 241, and the amino acid sequence of CDRL3 of mut1-11 is the amino acid sequence represented by SEQ ID NO: 242. The amino acid sequence of CDRH1 of KM14-VH, mut1-14, mut1-15, mut1-16, mut1-17, mut1-18, mut1-19, mut1-20, mut1-21, mut1-22, mut1-23, mut1-24, mut1-25, mut1-26, mut1-27, mut1-28, mut1-29, mut1-30, mut1-31, mut1-32, mut1-33, mut1-34, mut1-35, mut1-36, mut1-37, mut1-38, mut1-39, mut1-40, mut1-41, mut1-42 and mut1-43 is the amino acid sequence represented by SEQ ID NO: 98, the amino acid sequence of CDRH1 of mut1-12 is the amino acid sequence represented by SEQ ID NO: 243 and the amino acid sequence of CDRH1 of mut1-13 is the amino acid sequence represented by SEQ ID NO: 244. The amino acid sequence of CDRH2 of KM14-VH, mut1-12, mut1-13, mut1-29, mut1-30, mut1-31, mut1-32, mut1-33, mut1-34, mut1-35, mut1-36, mut1-37, mut1-38, mut1-39, mut1-40, mut1-41, mut1-42 and mut1-43 is the amino acid sequence represented by SEQ ID NO: 99, the amino acid sequence of CDRH2 of mut1-14 is the amino acid sequence represented by SEQ ID NO: 245, the amino acid sequence of CDRH2 of mut1-15 is the amino acid sequence represented by SEQ ID NO: 246, the amino acid sequence of CDRH2 of mut1-16 is the amino acid sequence represented by SEQ ID NO: 247, the amino acid sequence of CDRH2 of mut1-17 is the amino acid sequence represented by SEQ ID NO: 248, the amino acid sequence of CDRH2 of mut1-18 is the amino acid sequence represented by SEQ ID NO: 134, the amino acid sequence of CDRH2 of mut1-19 is the amino acid sequence represented by SEQ ID NO: 249, the amino acid sequence of CDRH2 of mut1-20 is the amino acid sequence represented by SEQ ID NO: 250, the amino acid sequence of CDRH2 of mut1-21 is the amino acid sequence represented by SEQ ID NO: 251, the amino acid sequence of CDRH2 of mut1-22 is the amino acid sequence represented by SEQ ID NO: 135, the amino acid sequence of CDRH2 of mut1-23 is the amino acid sequence represented by SEQ ID NO: 252, the amino acid sequence of CDRH2 of mut1-24 is the amino acid sequence represented by SEQ ID NO: 253, the amino acid sequence of CDRH2 of mut1-25 is the amino acid sequence represented by SEQ ID NO: 136, the amino acid sequence of CDRH2 of mut1-26 is the amino acid sequence represented by SEQ ID NO: 137, the amino acid sequence of CDRH2 of mut1-27 is the amino acid sequence represented by SEQ ID NO: 254, and the amino acid sequence of CDRH2 of mut1-28 is the amino acid sequence represented by SEQ ID NO: 255. The amino acid sequence of CDRH3 of KM14-VH, mut1-12, mut1-13, mut1-14, mut1-15, mut1-16, mut1-17, mut1-18, mut1-19, mut1-20, mut1-21, mut1-22, mut1-23, mut1-24, mut1-25, mut1-26, mut1-27, and mut1-28 is the amino acid sequence represented by SEQ ID NO: 100, the amino acid sequence of CDRH3 of mut1-29 is the amino acid sequence represented by SEQ ID NO: 256, the amino acid sequence of CDRH3 of mut1-30 is the amino acid sequence represented by SEQ ID NO: 257, the amino acid sequence of CDRH3 of mut1-31 is the amino acid sequence represented by SEQ ID NO: 258, the amino acid sequence of CDRH3 of mut1-32 is the amino acid sequence represented by SEQ ID NO: 259, the amino acid sequence of CDRH3 of mut1-33 is the amino acid sequence represented by SEQ ID NO: 260, the amino acid sequence of CDRH3 of mut1-34 is the amino acid sequence represented by SEQ ID NO: 261, the amino acid sequence of CDRH3 of mut1-35 is the amino acid sequence represented by SEQ ID NO: 262, the amino acid sequence of CDRH3 of mut1-36 is the amino acid sequence represented by SEQ ID NO: 263, the amino acid sequence of CDRH3 of mut1-37 is the amino acid sequence represented by SEQ ID NO: 264, the amino acid sequence of CDRH3 of mut1-38 is the amino acid sequence represented by SEQ ID NO: 265, the amino acid sequence of CDRH3 of mut1-39 is the amino acid sequence represented by SEQ ID NO: 266, the amino acid sequence of CDRH3 of mut1-40 is the amino acid sequence represented by SEQ ID NO: 267, the amino acid sequence of CDRH3 of mut1-41 is the amino acid sequence represented by SEQ ID NO: 268, the amino acid sequence of CDRH3 of mut1-42 is the amino acid sequence represented by SEQ ID NO: 269, and the amino acid sequence of CDRH3 of mut1-43 is the amino acid sequence represented by SEQ ID NO: 270.

FIG. 32 shows the results of measuring the binding activity to the human CD3 protein of the bispecific antibodies having an anti-CD3 scFv with a modified sequence of the anti-CD3 monoclonal antibody clone KM14 by using Biacore (KD (M) Biacore) and the results of measuring the cellular cytotoxicity thereof against BT-20 cells by a real-time cell analyzer (Specific cytotoxicity). The number of "+" symbols for the cellular cytotoxicity indicates the strength of the activity.

FIGS. 33(A) and 33(B) show the results of measuring the cellular cytotoxicity against BT-20 cells of the bispecific antibodies having an anti-CD3 scFv with a modified sequence of the anti-CD3 monoclonal antibody clone KM14 by a real-time cell analyzer. The horizontal axis represents the time (h) after the start of measurement, and the vertical axis represents the cell index value of the wells to which the test antibodies were added. The lower the cell index value is, the higher the cellular cytotoxicity is. "T+P" indicates no test substance, and "0.5% Triton X-100" is the line indicating 100% cytotoxicity. FIGS. 33(A) and 33(B) show the results obtained by performing experiments under the same conditions but performing measurement on different plates.

FIGS. 34(A) and 34(B) show the results of measuring the cytokine production of the bispecific antibodies having an anti-CD3 scFv with a modified sequence of the anti-CD3 monoclonal antibody clone KM14 during cytotoxic assay against BT-20 cells by flow cytometry. The concentration of the test substance is 10 nM, and FIG. 34(A) shows the concentration of INF-γ in the culture supernatant and FIG. 34(B) shows the concentration of IL-6 in the culture supernatant. "LLOQ" indicates the lower limit of quantification specified in the kit.

FIGS. 35(A) and 35(B) show the results of measuring the cellular cytotoxicity against BT-20 cells of the bispecific antibodies having an anti-CD3 scFv with a modified sequence of the clone KM14 by a real-time cell analyzer. The cell index value of the well to which the test substance was not added is taken as 0%, and the cell index value of the wells to which 0.5% Triton X-100 was added is taken as 100%, and the cellular cytotoxicity at the specific time is calculated and shown. FIGS. 35(A) and 35(B) show the cellular cytotoxicity at 48 and 120 hours after the addition of the test substance, respectively. The vertical axis represents the cellular cytotoxicity (%) and the horizontal axis represents the names of each antibody.

FIGS. 36(A) to 36(C) are views showing the concentration-dependent cellular cytotoxicity of the CD3/CCR4 bispecific antibodies or the like against PEER cells. The vertical axis represents the cellular cytotoxicity (%), and the horizontal axis represents the antibody concentration (nM).

FIGS. 37(A) and 37(B) are views showing the concentration-dependent production of cytokines (IL-2 and IFN-γ) in the culture supernatant during cytotoxic assay of the CD3/CCR4 bispecific antibodies or the like against PEER cells. The vertical axis represents the cytokine concentration (pg/mL), and the horizontal axis represents the antibody concentration (nM).

FIGS. 38(A) and 38(B) are a view (FIG. 38(A)) showing the concentration-dependent cellular cytotoxicity of the CD3/CD123 bispecific antibodies against MOLM13 cells, and a view (FIG. 38(B)) showing the concentration of a cytokine in the culture supernatant at the time. The vertical axis represents the cellular cytotoxicity (%), and the horizontal axis represents the antibody concentration (nM).

FIGS. 39(A) and 39(B) are views showing the concentration-dependent cellular cytotoxicity of the CD3/CD123 bispecific antibodies, and the concentration of a cytokine in the culture supernatant at the time. FIG. 39(A) shows the cellular cytotoxicity against MOLM13 cells, and FIG. 39(B) shows the cellular cytotoxicity against OCI-AML3 cells of the same antibodies. In each view, the vertical axis represents the cellular cytotoxicity (%), and the horizontal axis represents the antibody concentration (nM).

FIGS. 40(A) to 40(D) are views showing the concentration-dependent production of cytokines in the culture supernatant during cell injury of the CD3/CD123 bispecific antibodies. FIG. 40(A) shows the concentration of IL-2 in the culture supernatant during cytotoxic assay against MOLM13 cells, and FIG. 40(B) shows the concentration of IFN-γ. FIG. 40(C) shows the concentration of IL-2 in the culture supernatant during cytotoxic assay against OCI-AML3 cells of the same antibodies, and FIG. 40(D) shows the concentration of IFN-γ. In each view, the vertical axis represents the cytokine concentration (pg/mL), and the horizontal axis represents the antibody concentration (nM).

FIGS. 41(A) to 41(C) show the results of measuring the cellular cytotoxicity against BT-20 cells of the bispecific antibodies having an anti-CD3 scFv with a modified sequence of the anti-CD3 monoclonal antibody clone KM14 [FIG. 41(A)], and the cytokine production during cytotoxic assay measured by flow cytometry [FIGS. 41(B) and 41(C)]. The vertical axis of FIG. 41(A) represents the name of the bispecific antibodies, and the horizontal axis represents the cellular cytotoxicity (%). The vertical axis of FIGS. 41(B) and 41(C) represents the name of the bispecific antibodies, and the horizontal axis represents the cytokine concentration (pg/mL). FIG. 41(B) shows the concentration of INF-γ in the culture supernatant, and FIG. 41(C) shows the concentration of IL-6 in a culture supernatant. "LLOQ" indicates the lower limit of quantification specified in the kit which used.

FIG. 42 illustrates the design examples and the structural position of amino acid modification to be introduced into CH3 region and anti-CD3 scFv for the purpose of improving the productivity and physicochemical stability of the bispecific antibodies.

FIG. 43 is a view listing a modification of the CH3 moiety, scFv clones, the order of VH and VL of scFv, and the amino acid modification to be introduced into scFv for each element, introduced into the anti-CD3 bispecific antibodies designed for the purpose of improving the productivity and physicochemical stability.

FIG. 44 shows the results of measuring the binding activity to soluble CD3 of the bispecific antibodies in which the modifications were introduced into the Fc (CH3), the bispecific antibodies in which the anti-CD3 scFv was changed to VL-Linker-VH type, and the bispecific antibodies in which the modifications were introduced into the anti-CD3 scFv by surface plasmon resonance (SPR) method. From the left column, the name of the test bispecific antibodies, and KD (M) are shown.

FIG. 45A is a view showing the results of measuring the cellular cytotoxicity against BT-20 of the bispecific antibodies in which the modifications were introduced into the Fc (CH3), the bispecific antibodies in which the anti-CD3 scFv was changed to VL-Linker-VH type, and the bispecific antibodies in which the modifications were introduced into the anti-CD3 scFv. The activity value of the wells to which no test substance was added is taken as 0%, and that of the wells to which 0.5% Triton X-100 was added is taken as 100%, and the cellular cytotoxicity at 48 hours is shown. The vertical axis represents the cellular cytotoxicity (%), and the horizontal axis represents the respective bispecific antibodies.

FIG. 45B is a view showing the results of measuring the cellular cytotoxicity against BT-20 of the bispecific antibodies in which the modifications were introduced into the Fc (CH3), the bispecific antibodies in which the anti-CD3 scFv was changed to VL-Linker-VH type, and the bispecific antibodies in which the modifications were introduced into the anti-CD3 scFv. The activity value of the wells to which no test substance was added is taken as 0%, and that of the wells to which 0.5% Triton X-100 was added is taken as 100%, and the cellular cytotoxicity at 48 hours is shown. The vertical axis represents the respective bispecific antibodies, and the horizontal axis represents the cellular cytotoxicity (%).

FIG. 45C shows the results of measuring the cellular cytotoxicity against BT-20 of the bispecific antibodies in which the modifications were introduced into the Fc (CH3), the bispecific antibodies in which the anti-CD3 scFv was changed to VL-Linker-VH type, and the bispecific antibodies in which the modifications were introduced into the anti-CD3 scFv. The activity value of the wells to which no test substance was added is taken as 0%, and that of the wells to which 0.5% Triton X-100 was added is taken as 100%, and the cellular cytotoxicity at 48 hours is shown. The vertical axis represents the respective bispecific antibodies, and the horizontal axis represents the cellular cytotoxicity (%).

FIG. 45D shows the results of measuring the cellular cytotoxicity against BT-20 of the bispecific antibodies in which the modification was introduced into the Fc (CH3), the bispecific antibodies in which the anti-CD3 scFv was changed to VL-Linker-VH type, and the bispecific antibodies in which the modifications were introduced into the anti-CD3 scFv. The activity value of the wells to which no test substance was added is taken as 0%, and that of the wells to which 0.5% Triton X-100 was added is taken as 100%, and the cellular cytotoxicity at 48 hours is shown. The vertical axis represents the respective bispecific antibodies, and the horizontal axis represents the cellular cytotoxicity (%).

FIG. 46A shows the results of measuring the cytokine production during cytotoxic assay against BT-20 of the bispecific antibodies in which the modifications were introduced into the Fc (CH3), the bispecific antibodies in which the anti-CD3 scFv was changed to VL-Linker-VH type, and the bispecific antibody in which the modifications were introduced into the anti-CD3 scFv by flow cytometry. FIG. 46(A) shows the concentration of INF-γ in the culture supernatant.

FIG. 46B shows the results of measuring the cytokine production during cytotoxic assay against BT-20 of the bispecific antibodies in which the modifications were introduced into the Fc (CH3), the bispecific antibodies in which the anti-CD3 scFv was changed to VL-Linker-VH type, and the bispecific antibody in which the modification were introduced into the anti-CD3 scFv by flow cytometry. FIG. 46(B) shows the concentration of IL-6 in the culture supernatant.

FIG. 46C shows the results of measuring the cytokine production during cytotoxic assay against BT-20 of the bispecific antibody in which the modifications were introduced into the Fc (CH3), and the bispecific antibodies in which the modifications were introduced into the anti-CD3 scFv by flow cytometry. FIG. 46(C) shows the concentration of INF-γ in the culture supernatant.

FIG. 46D shows the results of measuring the cytokine production during cytotoxic assay against BT-20 of the bispecific antibodies in which the modifications were introduced into the Fc (CH3), and the bispecific antibodies in which the modifications were introduced into the anti-CD3 scFv by flow cytometry. FIG. 46(D) shows the concentration of IL-6 in the culture supernatant.

FIG. 46E shows the results of measuring the cytokine production during cytotoxic assay against BT-20 of the bispecific antibodies in which the modifications were introduced into the Fc (CH3), the bispecific antibodies in which the anti-CD3 scFv was changed to VL-Linker-VH type, and the bispecific antibodies in which the modifications were introduced into the anti-CD3 scFv by flow cytometry. FIG. 46(E) shows the concentration of INF-γ in the culture supernatant.

FIG. 46F shows the results of measuring the cytokine production during cytotoxic assay against BT-20 of the bispecific antibodies in which the modifications were introduced into the Fc (CH3), the bispecific antibodies in which the anti-CD3 scFv was changed to VL-Linker-VH type, and the bispecific antibodies in which the modifications were introduced into the anti-CD3 scFv by flow cytometry. FIG. 46(F) shows the concentration of IL-6 in the culture supernatant.

DESCRIPTION OF EMBODIMENTS

The present invention relates to a bispecific antibody comprising an antigen binding domain that binds to CD3 and an antigen binding domain that binds to a disease-related antigen, or a bispecific antibody fragment thereof (hereinafter also referred to as the bispecific antibody or the bispecific antibody fragment thereof of the present invention).

As the bispecific antibody of the present invention, a bispecific antibody comprising a CD3 binding domain with reduced affinity for CD3, a bispecific antibody comprising an antigen binding domain that binds to CD3 and an antigen binding domain that binds to a disease-related antigen, a bispecific antibody comprising an Fc region having a binding ability to an Fc receptor, and also comprising a CD3 binding domain with reduced affinity for CD3 and an antigen binding domain that binds to a disease-related antigen, a bispecific antibody comprising an Fc region with enhanced affinity for an Fc receptor, and also comprising a CD3 binding domain with reduced affinity for CD3 and an antigen binding domain that binds to a disease-related antigen, and the like are exemplified. The bispecific antibody of the present invention binds to both CD3 and a disease-related antigen, so that a cell having expressed the disease-related antigen can be damaged in a T cell and/or NK cell dependent manner without causing excessive cytokine production.

CD3 in the present invention is used as a synonym for CD3E, T3E, or T-cell surface glycoprotein CD3 epsilon chain. As CD3, for example, human CD3 containing the amino acid sequence represented by GenBank Accession No. NP_000724.1 in NCBI (www.ncbi.nlm.nih.gov) or SEQ ID NO: 138, monkey CD3 containing the amino acid sequence represented by GenBank Accession No. NP_001270544.1 or SEQ ID NO: 139, and the like are exemplified. Further, for example, a polypeptide that is composed of an amino acid sequence in which one or more amino acids are deleted, substituted, or added in the amino acid sequence represented by SEQ ID NO: 138, GenBank Accession No. NP_000724.1, SEQ ID NO: 139, or GenBank Accession No. NP_001270544.1 and that has the function of CD3 is exemplified.

A polypeptide containing an amino acid sequence having generally 70% or more, preferably 80% or more, and more preferably 90% or more homology with the amino acid sequence represented by SEQ ID NO: 138, GenBank Accession No. NP_000724.1, SEQ ID NO: 139, or GenBank Accession No. NP_001270544.1, and most preferably, a polypeptide that is composed of an amino acid sequence having 95% or more, 96% or more, 97% or more, 98% or more, and 99% or more homology and that has the function of CD3 are also included in the CD3 of the present invention.

The polypeptide having an amino acid sequence in which one or more amino acid residues are deleted, substituted, or added in the amino acid sequence represented by SEQ ID NO: 138, GenBank Accession No. NP_000724.1, SEQ ID NO: 139, or GenBank Accession No. NP_001270544.1 can be obtained by, for example, introducing a site-specific mutation into a DNA encoding the amino acid sequence represented by SEQ ID NO: 138, GenBank Accession No. NP_000724.1, SEQ ID NO: 139, or GenBank Accession No. NP_001270544.1 using a site-specific mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proceeding of the National Academy of Sciences in USA, 82, 488 (1985)], or the like. The number of amino acids to be deleted, substituted, or added is not particularly limited, but is preferably one to several tens, for example, 1 to 20, and more preferably one to several, for example, 1 to 5 amino acids.

As a gene encoding CD3, for example, the nucleotide sequence of human CD3 represented by SEQ ID NO: 141 or GenBank Accession No. NM_000733.3, the nucleotide sequence of monkey CD3 represented by SEQ ID NO: 142 or GenBank Accession No. NM_001283615.1, and the like are exemplified.

Further, for example, a gene that is composed of a nucleotide sequence in which one or more nucleotides are deleted, substituted, or added in the nucleotide sequence represented by SEQ ID NO: 141, GenBank Accession No. NM_000733.3, SEQ ID NO: 142, or GenBank Accession No. NM_001283615.1 and that contains a DNA encoding a polypeptide having the function of CD3, a gene that is composed of preferably a nucleotide sequence having 60% or more homology, more preferably a nucleotide sequence having 80% or more homology, and further more preferably a nucleotide sequence having 95% or more homology with the nucleotide sequence represented by SEQ ID NO: 141, GenBank Accession No. NM_000733.3, SEQ ID NO: 142, or GenBank Accession No. NM_001283615.1 and that contains a DNA encoding a polypeptide having the function of CD3, a gene that is composed of a DNA which hybridizes with a DNA composed of the nucleotide sequence represented by SEQ ID NO: 141, GenBank Accession No. NM_000733.3, SEQ ID NO: 142, or GenBank Accession No. NM_001283615.1 under stringent conditions, and that contains a DNA encoding a polypeptide having the function of CD3, and the like are also included in the gene encoding the CD3 of the present invention.

The DNA which hybridizes under stringent conditions means, for example, a hybridizable DNA obtained by a colony hybridization method, a plaque hybridization method, a Southern blot hybridization method, a DNA microarray method, or the like using a DNA having the nucleotide sequence represented by SEQ ID NO: 141, GenBank Accession No. NM_000733.3, SEQ ID NO: 142, or GenBank Accession No. NM_001283615.1 as a probe.

Specifically, a DNA that can be identified by performing hybridization at 65° C. in the presence of 0.7 to 1.0 mol/L sodium chloride [Molecular Cloning, A Laboratory Manual, Second Edition, Cold Spring Harbor Laboratory Press (1989), Current Protocols in Molecular Biology, John Wiley & Sons (1987-1997), DNA Cloning 1: Core Techniques, A Practical Approach, Second Edition, Oxford University (1995)] using a filter or a microscope slide on which a DNA derived from a hybridized colony or plaque, or a PCR product or an oligo DNA having the sequence is immobilized, and then washing the filter or the microscope slide under the condition of 65° C. using a 0.1 to 2×SSC solution (the formulation of a 1×SSC solution is composed of 150 mmol/L sodium chloride and 15 mmol/L sodium citrate) can be exemplified. As the hybridizable DNA, for example, a DNA preferably having 60% or more homology, more preferably a DNA having 80% or more homology, and further more preferably a DNA having 95% or more homology with the nucleotide sequence represented by SEQ ID NO: 141, GenBank Accession No. NM_000733.3, SEQ ID NO: 142, or GenBank Accession No. NM_001283615.1 can be exemplified.

A gene polymorphism is often observed in a nucleotide sequence of a gene encoding a eukaryotic protein. A gene in which a small-scale mutation has occurred in a nucleotide sequence due to such a polymorphism among genes used in the present invention is also included in the gene encoding the CD3 in the present invention.

The homology value in the present invention may be a value calculated using a homology search program known to those skilled in the art unless otherwise particularly specified, however, with respect to a nucleotide sequence, a value calculated using a default parameter in BLAST [J. Mol. Biol., 215, 403 (1990)], and the like are exemplified, and with respect to an amino acid sequence, a value calculated using a default parameter in BLAST 2 [Nucleic Acids Research, 25, 3389 (1997), Genome Research, 7, 649 (1997), (www.ncbi.nlm.nih.gov)], and the like are exemplified.

As for the default parameters, G (Cost to open gap) is 5 in the case of a nucleotide sequence and 11 in the case of an amino acid sequence, -E (Cost to extend gap) is 2 in the case of a nucleotide sequence and 1 in the case of an amino acid sequence, -q (Penalty for nucleotide mismatch) is -3, -r (reward for nucleotide match) is 1, -e (expect value) is 10, -W (wordsize) is 11 residues in the case of a nucleotide sequence and 3 residues in the case of an amino acid sequence, -y [Dropoff (X) for blast extensions in bits] is 20 in the case of blastn and 7 in the case of programs other than blastn, -X (X dropoff value for gapped alignment in bits) is 15, and -Z (final X dropoff value for gapped alignment in bits) is 50 in the case of blastn and 25 in the case of programs other than blastn (www.ncbi.nlm.nih.gov).

A polypeptide composed of a partial sequence of the amino acid sequence of CD3 can be produced by a method known to those skilled in the art, and for example, a polypeptide composed of a partial sequence of CD3 can be produced by deleting part of a DNA encoding the amino acid sequence represented by SEQ ID NO: 138, GenBank Accession No. NP_000724.1, SEQ ID NO: 139, or GenBank Accession No. NP_001270544.1 and culturing a transformant transfected with an expression vector containing the resulting DNA.

In addition, for example, a polypeptide having an amino acid sequence in which one or more amino acids are deleted, substituted, or added in a partial sequence of the amino acid sequence represented by SEQ ID NO: 138, GenBank Accession No. NP_000724.1, SEQ ID NO: 139, or GenBank Accession No. NP_001270544.1 can be obtained by the same method as described above based on the polypeptide or the DNA produced by the above method.

Further, a polypeptide composed of a partial sequence of the amino acid sequence of CD3, or a polypeptide having an amino acid sequence in which one or more amino acids are deleted, substituted, or added in a partial sequence of the amino acid sequence of CD3 can also be produced using a chemical synthesis method such as a fluorenylmethyloxycarbonyl (Fmoc) method or a t-butyloxycarbonyl (tBoc) method.

As an extracellular domain of CD3 in the present invention, for example, a region or the like in which the amino acid sequence of human CD3 represented by GenBank Accession No. NP_000724.1 is predicted using a known transmembrane region prediction program SOSUI (sosui.proteome.bio.tuat.ac.jp), TMHMM ver. 2 (www.cbs.dtu.dk), ExPASy Proteomics Server (Ca.expasy-.org), or the like is exemplified. Specifically, as the extracellular domain of CD3, the amino acid sequence represented by positions 22 to 126 of SEQ ID NO: 140 or GenBank Accession No. NP_000724.1 is exemplified.

Examples of the function of CD3 include the formation of a subunit structure of a protein complex by directly associating with a T cell receptor (TCR) and involvement in intracellular signal transduction by recognizing an antigen peptide bound to a major histocompatibility gene complex (MHC). Examples of the cell that expresses CD3 include T cells, NKT cells, γδT cells, progenitor cells thereof, and mature thymocytes.

The disease-related antigen in the present invention may be any antigen as long as it is an antigen related to any disease such as a cancer, an immune disease, an allergic disease, an autoimmune disease, a central nervous system disease, or a cardiovascular disease, and examples thereof include a cytokine, a chemokine, a growth factor and a receptor thereof, a cluster of differentiation (hereinafter referred to as CD) antigen, and the like.

Examples of a cytokine or growth factor receptor include receptors for interferon (hereinafter referred to as IFN)-α, IFN-β, IFN-γ, interleukin (hereinafter referred to as IL)-2, IL-3, IL-4, IL-5, IL-6, IL-7, IL-8, IL-9, IL-10, IL-12, IL-13, IL-15, IL-17, IL-18, IL-21, IL-23, IL-27, a granulocyte colony-stimulating factor (G-CSF), a granulocyte-macrophage colony-stimulating factor (GM-CSF), or a macrophage colony-stimulating factor (M-CSF), and the like.

Examples of a chemokine receptor include receptors for SLC, ELC, 1-309, TARC, MDC, MIP-3α, and CTACK.

Examples of a growth factor receptor include receptors for an epidermal growth factor (EGF), a vascular endothelial growth factor (VEGF), angiopoietin, a fibroblast growth factor (FGF), a hepatocyte growth factor (HGF), a platelet-derived growth factor (PDGF), an insulin-like growth factor (IGF), erythropoietin (EPO), TGF-β, iephrin, angiopoietin, a frizzled ligand, or SDF-1, and the like.

Examples of a CD antigen include CD1a, CD1c (BDCA1), CD1d, CD2, CD3, CD4, CD5, CD6, CD7, CD8, CD10, CD11a, CD11b, CD11c, CD14, CD16, CD18, CD19, CD20, CD21, CD22, CD23, CD24, CD25, CD26 (DPP-4), CD27, CD28, CD30, CD32, CD34, CD37, CD38, CD39, CD40, CD43, CD44, CD45, CD47, CD49, CD51, CD52, CD53, CD54, CD55, CD56, CD57, CD59, CD62E, CD62L, CD62P, CD64, CD66a (CEACAM1), CD66b (NCA-95), CD66c (NCA-50/90), CD66d (CGM1), CD66e (CEA), CD66f (PSG), CD68, CD69, CD70, CD72, CD73, CD74, CD75, CD76, CD77, CD78, CD79a, CD79b, CD80 (B7.1), CD81, CD82, CD83, CD84 (SLAMF5), CD85a (ILT-5), CD85b (ILT8), CD85c (LIR8), CD85d (ILT4), CD85f (ILT11), CD85g (ILT7), CD85h (ILT1), CD85i (LIR6a), CD85j (ILT2), CD85k (ILT3), CD85m (ILT10), CD86 (B7.2), CD87, CD89, CD94 (NKG2), CD95 (Fas), CD98, CD103, CD107a (LAMP1), CD114 (G-CSFR), CD115 (M-CSFR), CD116 (GM-CSFR), CD117 (SCF-R), CD119 (IFNGR1), CD121a (IL-1R1), CD122 (IL-2Rb), CD123 (IL-3Ra), CD124 (IL-4Ra), CD125 (IL-5Ra), CD126 (IL-6Ra), CD127 (IL-7Ra), CD134 (OX40), CD135 (FLT3), CD137 (4-1BB), CD138 (Syndecan-1), CD140 (PDGFR), CD146 (MUC18), CD147 (EMMRRIN), CD152 (CTLA-4), CD158a (KIR2DL1), CD158b1 (KIR2DL2), CD158b2 (KIR2DL3), CD158c (KIR2DS6), CD158d (KIR2DL4), CD158e1 (KIR3DL1), CD158e2 (KIR3DS1), CD158f (KIR2DL5), CD158g (KIR2DS5), CD158h (KIR2DS1), CD158i (KIR2DS4), CD158j (KIR2DS2), CD158k (KIR3DL2), CD159a (NKG2A), CD159c (NKG2C), CD161 (NKRP1A), CD162 (PSGL-1), CD163, CD169 (SIGLEC1), CD178 (FasL), CD183 (CXCR3), CD184 (CXCR4), CD185 (CXCR5), CD191 (CCR1), CD193 (CCR3), CD194 (CCR4), CD195 (CCR5), CD196 (CCR6), CD197 (CCR7), CD198 (CCR8), CD199 (CCR9), CD200 (OX2), CD206 (MMR), CD207 (Langerin), CD209 (DC-SIGN), CD212 (IL-12Rβ1), CD213a1 (IL-13Ra1), CD213a2 (IL-13Ra2), CD215 (IL-15RA), CD217 (IL-17R), CD218a (IL-18Ra), CD218b (IL-18Rβ), CD223 (LAG3), CD226 (DNAM-1), CD229 (SLAMF3), CD252 (OX40L), CD269 (BCMA), CD272 (BTLA), CD274 (PD-L1), CD276 (B7H3), CD278 (ICOS), CD279 (PD-1), CD281 (TLR1), CD282 (TLR2), CD283 (TLR3), CD284 (TLR4), CD286 (TLR6), CD288 (TLR8), CD289 (TLR9), CD294 (CRTH2), CD301 (MGL), CD302 (DCL1), CD303 (BDCA2), CD304 (BDCA4), CD317 (BST2), CD324 (E-cadherin), CD326 (EpCAM), CD357 (GITR), CD358 (DR6), CD360 (IL-21R), CD365 (TIM-1), CD366 (TIM-3), CD369 (DECTIN-1), CD370 (CLEC9A), human leukocyte antigen (HLA)-Class II, HLA-I, and the like.

Other examples of the antigen of an antibody related to a cancer, an immune disease, an allergic disease, an autoimmune disease, a central nervous system or cardiovascular disease, or the like include gangliosides GM1, GM2, GD2, and GD3, Lewis X, Lewis Y, glypican-3, claudin, ASCT-2, CD3, CD4, CD40, a CD40 ligand, a B7 family molecule (for example, CD80, CD86, CD274, B7-DC, B7-H2, B7-H3, or B7-H4), a ligand for a B7 family molecule (for example, CD28, CTLA-4, ICOS, PD-1, or BTLA), OX-40, an OX-40 ligand, CD137, a tumor necrosis factor (TNF) receptor family molecule (for example, DR3, DR4, DR5, BAFFR, LIGHT, TNFR1, or TNFR2), a TNF-related apoptosis-inducing ligand receptor (TRAIL) family molecule, a receptor family of a TRAIL family molecule (for example, TRAIL-R1, TRAIL-R2, TRAIL-R3, or TRAIL-R4), a receptor activator of nuclear factor kappa B ligand (RANK), a RANK ligand, CD25, a folic acid receptor, Mesothelin, SIGLEC8, a cytokine/chemokine receptor [for example, IL-1RT1, IL-12Rβ2, IL-17Rβ, IL-23R, IL-27Rα, IL-31R, IL-33Rα, IL-36R, a transforming growth factor (TGF) βRII, CCR2, CCR10, CXCR1, or CXCR2], an NK cell receptor (for example, NKG2D, E4BP4, NKp30, NKp44, NKp46, or AhR) a T cell receptor (for example, TCRα/β, TCR Vβ11, TCRγ/δ, TSLPR, SLAM, SLAMF6, LAP, GARP, SR-A1, CD200R, DCR3, or TIGIT), a B cell receptor (for example, BLYS, APRIL, or TSLPR), a dendritic cell receptor (for example, FCER1A, TLR7, CADM1, XCR1, BTLA, SIRPA, DCIR, TROP2, AXL, SIGLEC6, SIGLEC15, CX3CR1, S100A8, S100A9, or ASGR1), and the like.

The antibody of the present invention is a protein derived from a gene (referred to as "antibody gene") encoding all or part of a heavy chain variable region, a heavy chain constant region, a light chain variable region, and a light chain constant region constituting an immunoglobulin. The antibody of the present invention also includes an antibody or an antibody fragment having any immunoglobulin class and subclass.

The heavy chain (H chain) refers to a polypeptide having a higher molecular weight among the two types of polypeptides constituting an immunoglobulin molecule. The heavy chain determines the antibody class and subclass. IgA, IgD, IgE, IgG, and IgM include an a chain, a δ chain, an ε chain, a γ chain, and a chain as the heavy chain, respectively, and the heavy chain constant region is characterized by a different amino acid sequence. The light chain (L chain) refers to a polypeptide having a lower molecular weight among the two types of polypeptides constituting an immunoglobulin molecule. In the case of a human antibody, there exist two types, a κ chain and a λ chain, in the light chain.

The variable region (V region) generally refers to a region that is present in an amino acid sequence at the N-terminal side of an immunoglobulin and is rich in diversity. Because a part other than the variable region has a structure with less diversity, it is called a constant region (C region). The respective variable regions of the heavy chain and the light chain are associated to form an antigen binding site and determine the binding property of the antibody to the antigen.

In the heavy chain of a human antibody, the variable region corresponds to the amino acid sequence at positions 1 to 117 according to the EU index of Kabat et al. (Kabat et al., Sequences of proteins of immunological interest, 1991 Fifth edition) (hereinafter, also simply referred to as EU index), and the constant region corresponds to the amino acid sequence downstream of position 118. In the light chain of a human antibody, the amino acid sequence at positions 1 to 107 numbered according to Kabat et al. (Kabat numbering) corresponds to the variable region, and the amino acid sequence downstream of position 108 corresponds to the constant region. Hereinafter, the heavy chain variable region or the light chain variable region is abbreviated as VH or VL, respectively.

The antigen binding site is a site that recognizes and binds to an antigen in an antibody, and refers to a site that forms a complementary conformation with an antigenic determinant (epitope). In the antigen binding site, a strong intermolecular interaction occurs with the antigenic determinant. The antigen binding site is constituted by VH and VL including at least three complementarity determining regions (CDRs). In the case of a human antibody, VH and VL each include three CDRs. These CDRs are referred to as CDR1, CDR2, and CDR3, respectively, in order from the N-terminal side.

In the constant region, the heavy chain constant region and the light chain constant region are denoted by CH and CL, respectively. The CH is classified into an α chain, a δ chain, an ε chain, a γ chain, and a chain which are subclasses of the heavy chain. The CH is constituted by a CH1 domain, a hinge domain, a CH2 domain, and a CH3 domain arranged in order from the N-terminal side, and the CH2 domain and the CH3 domain together are called an Fc region. On the other hand, the CL is classified into two subclasses called a Cλ chain and a Cκ chain.

The anti-CD3 antibody of the present invention refers to a monoclonal antibody that specifically recognizes and binds to the extracellular domain of CD3. Further, the antibody of the present invention also includes a polyclonal antibody and an oligoclonal antibody.

In the present invention, the binding of the bispecific antibody or the bispecific antibody fragment thereof to CD3 or a disease-related antigen can be confirmed by a method in which the binding affinity of the antibody to a cell having expressed CD3 or a disease-related antigen is confirmed using, for example, a known immunological detection method, preferably a fluorescent cell staining method, or the like. Further, it is also possible to use known immunological detection methods [Monoclonal Antibodies—Principles and Practice, Third Edition, Academic Press (1996), Antibodies—A Laboratory Manual, Cold Spring Harbor Laboratory (1988), Monoclonal Antibody Experimental Manual, Kodansha Scientific Ltd. (1987)], and the like in combination.

A monoclonal antibody is an antibody secreted by an antibody-producing cell maintaining monoclonality, and recognizes a single epitope (also referred to as an antigenic determinant). The monoclonal antibody molecules have the same amino acid sequence (primary structure) and have a single structure. A polyclonal antibody refers to a population of antibody molecules secreted by antibody-producing cells of different clones. An oligoclonal antibody refers to a population of antibody molecules in which multiple different monoclonal antibodies are mixed.

The epitope refers to a structural site of an antigen which an antibody recognizes and binds to. Examples of the epitope include a single amino acid sequence, a conformation composed of an amino acid sequence, an amino acid sequence to which a sugar chain is bound, and a conformation composed of an amino acid sequence to which a sugar chain is bound, each of which a monoclonal antibody recognizes and binds to, and the like.

As the monoclonal antibody of the present invention, an antibody produced by a hybridoma, and a genetically recombinant antibody produced by a transformant transformed with an expression vector containing an antibody gene can be exemplified.

The hybridoma can be prepared by, for example, preparing an antigen, obtaining an antibody-producing cell having antigen specificity from an animal immunized with the antigen, and then fusing the antibody-producing cell with a myeloma cell. A desired monoclonal antibody can be obtained by culturing the hybridoma or by administering the hybridoma to an animal to convert the hybridoma into an ascites tumor, separating the culture solution or the ascites, followed by purification. As the animal to be immunized with the antigen, any animal can be used as long as it can produce the hybridoma, however, a mouse, a rat, a hamster, a rabbit, or the like is preferably used. In addition, the hybridoma can also be produced by obtaining a cell having an antibody-producing ability from such an immunized animal, subjecting the cell to in vitro immunization, and then fusing the cell with a myeloma cell.

Examples of the genetically recombinant antibody of the present invention include antibodies produced using a gene recombination technique such as a recombinant mouse antibody, a recombinant rat antibody, a recombinant hamster antibody, a recombinant rabbit antibody, a human chimeric antibody (also referred to as a chimeric antibody), a humanized antibody (also referred to as a CDR-grafted antibody), and a human antibody. In the genetically recombinant antibody, it is possible to determine which animal species the heavy chain and the light chain variable regions and constant regions derived from are applied according to the targeted animal species and the purpose. For example, when the targeted animal species is a human, as the variable region, one derived from a human or a non-human animal such as a mouse can be adopted, and as the constant region and the linker, those derived from a human can be adopted.

The chimeric antibody refers to an antibody composed of VH and VL of an antibody of an animal other than a human (non-human animal) and CH and CL of a human antibody. As the non-human animal, any animal such as a mouse, a rat, a hamster, or a rabbit can be used as long as it can produce a hybridoma. The chimeric antibody can be produced by obtaining cDNAs encoding VH and VL from a hybridoma derived from a non-human animal that produces a monoclonal antibody, inserting each of the cDNAs into an expression vector for animal cells having DNAs encoding CH and CL of a human antibody, thereby constructing an expression vector for a chimeric antibody, and then introducing the vector into an animal cell to cause expression.

The humanized antibody refers to an antibody in which CDRs of VH and VL of a non-human animal antibody are grafted in the corresponding CDRs of VH and VL of a human antibody. A region other than the CDRs of VH and VL is referred to as a framework region (hereinafter referred to as FR). The humanized antibody can be produced by constructing a cDNA encoding the amino acid sequence of VH composed of the amino acid sequence of CDR of VH of a non-human animal antibody and the amino acid sequence of FR of VH of an arbitrary human antibody, and a cDNA encoding the amino acid sequence of VL composed of the amino acid sequence of CDR of VL of a non-human animal antibody and the amino acid sequence of FR of VL of an arbitrary human antibody, inserting each of the cDNAs into an expression vector for animal cells having DNAs encoding CH and CL of a human antibody, thereby constructing an expression vector for a humanized antibody, and then introducing the vector into an animal cell to cause expression.

The human antibody originally refers to an antibody that is naturally present in a human body, but also includes antibodies obtained from a human antibody phage library and a human antibody-producing transgenic animal, each of which is produced by recent advancement of genetic engineering, cellular engineering, or developmental engineering technology, and the like.

The antibody that is naturally present in a human body can be obtained by, for example, infecting human peripheral blood lymphocytes with an EB virus or the like so as to immortalize the lymphocytes, culturing a lymphocyte that produces the antibody by cloning, and then purifying the antibody from the culture supernatant.

The human antibody phage library is a library in which an antibody fragment such as Fab or scFv is expressed on a phage surface by inserting an antibody gene prepared from a human B cell into a phage gene. It is possible to collect a phage having expressed an antibody fragment having a desired antigen binding activity on the surface from the library using a binding activity to a substrate on which an antigen is immobilized as an index. The antibody fragment can be further converted into a human antibody molecule composed of two complete H chains and two complete L chains using a genetic engineering technique.

The human antibody-producing transgenic animal means an animal in which a human antibody gene is incorporated into a cell. Specifically, for example, a human antibody-producing transgenic mouse can be produced by introducing a human antibody gene into a mouse ES cell, implanting the ES cell in a mouse early embryo, and then allowing the embryo to develop into an individual. A human antibody derived from the human antibody-producing transgenic animal can be prepared by obtaining a hybridoma using a conventional hybridoma production method that is performed for a non-human animal, and culturing the hybridoma to produce and accumulate the antibody in the culture supernatant.

The CH of the genetically recombinant antibody may be any as long as it belongs to a human immunoglobulin, but is preferably CH of human immunoglobulin G (hIgG) class. Further, it is possible to use CH of any subclass such as hIgG1, hIgG2, hIgG3, and hIgG4 which belong to the hIgG class. In addition, the CL of the genetically recombinant antibody may be any as long as it belongs to a human immunoglobulin, and CL of the κ class or the λ class can be used.

In the present invention, the antibody fragment is a protein that includes an antigen binding site and has an antigen binding activity to the antigen. Examples thereof include Fab, Fab', $F(ab')_2$, scFv, a diabody, dsFv, VHH, a peptide including CDR, and the like.

The Fab is an antibody fragment, which has a molecular weight of about 50,000 and has an antigen binding activity, and in which about a half of an H chain at the N-terminal side and the entire L chain are bound via a disulfide bond (S—S bond) among the fragments obtained by treating an IgG antibody with a protease papain (cleaved at an amino acid residue at position 224 in the H chain). A polypeptide chain of Fab including VH and CH1 is referred to as a heavy chain (H chain) of Fab or VH-CH1. Further, a polypeptide chain of Fab including VL and CL is referred to as a light chain (L chain) of Fab or VL-CL.

The $F(ab')_2$ is an antibody fragment, which has a molecular weight of about 100,000 and has an antigen binding activity, and is slightly larger than a molecule obtained by binding Fabs via an S—S bond in the hinge region among the fragments obtained by treating IgG with a protease pepsin (cleaved at an amino acid residue at position 234 in the H chain).

The Fab' is an antibody fragment, which has a molecular weight of about 50,000 and has an antigen binding activity, obtained by cleaving the S—S bond in the hinge region of the above $F(ab')_2$.

The scFv is a VH-P-VL or VL-P-VH polypeptide in which one VH and one VL are linked using an appropriate peptide linker (P) of 12 or more residues, and is an antibody fragment having an antigen binding activity.

The diabody is an antibody fragment in which scFvs having the same or different antigen binding specificity form a dimer, and is an antibody fragment having a bivalent antigen binding activity to the same antigen or antigen binding activities each specific to different antigens.

The dsFv refers to a molecule obtained by binding polypeptides in which one amino acid residue in each of VH and VL is substituted with a cysteine residue via an S—S bond between the cysteine residues.

The VHH (also referred to as a nanobody) refers to a heavy chain variable region in a VHH antibody, and can bind to an antigen without the presence of another polypeptide.

The VHH antibody is an antibody present in an animal of the family Camelidae such as an alpaca and an elasmobranch such as a shark, and does not include a light chain or CH1, and is composed only of a heavy chain.

The peptide including CDR is configured to include at least one region of CDRs of VH or VL. A peptide including multiple CDRs can be produced by binding CDRs either directly or through an appropriate peptide linker. The peptide including CDR can be produced by constructing DNAs encoding CDRs of VH and VL of the bispecific antibody of the present invention, inserting the DNAs into an expression vector for a prokaryote or an expression vector for a eukaryote, and then introducing the expression vector into a prokaryote or a eukaryote to cause expression. In addition, the peptide including CDR can also be produced by a chemical synthesis method such as an Fmoc method or a tBoc method.

In the present invention, the bispecific antibody fragment is essentially composed of a partial structure of a bispecific antibody and is a bispecific antibody fragment having an antigen binding activity to two types of antigens.

A fusion protein in which the bispecific antibody fragment of the present invention is bound to an Fc region, an Fc fusion protein in which the Fc region is bound to a naturally occurring ligand or receptor (also referred to as immunoadhesin), an Fc fusion protein in which multiple Fc regions are fused, and the like are also included in the present invention. In addition, an Fc region including an amino acid residue modification aiming at enhancing or deleting the effector activity of the antibody, stabilizing the antibody, and controlling the blood half-life can also be used for the bispecific antibody of the present invention.

The bispecific antibody of the present invention refers to a polypeptide or a protein having two types of antigen binding domains with different specificities. The respective antigen binding domains of the bispecific antibody may bind to different epitopes of a single antigen or may bind to different antigens.

In the present invention, the antigen binding domain is a partial structure having a function of specifically recognizing and binding to an antigen. The antigen binding domain of the present invention may be in any form of, for example, a polypeptide, a protein molecule, and a fragment thereof that can be produced by a gene recombination technique such as an antibody, an antibody fragment thereof, a ligand, a receptor, and a naturally occurring interacting molecule, and a conjugate body with a low-molecular weight molecule or a natural product of the protein molecule, or the like.

The two types of antigen binding domains of the bispecific antibody of the present invention are a CD3 binding domain and a disease-related antigen binding domain. When a plurality of disease-related antigen binding domains are included, they may bind to the same antigen or different antigens.

The bispecific antibody of the present invention comprises an Fc region having a binding ability to an Fc receptor, a CD3 binding domain, and a disease-related antigen binding domain, and the C terminus of the Fc region is bound to the CD3 binding domain directly or through a linker.

The CD3 binding domain in the present invention refers to an antigen binding domain that binds to CD3.

The disease-related antigen binding domain in the present invention refers to an antigen binding domain that binds to a disease-related antigen.

The CD3 binding domain in the present invention may be any as long as it specifically recognizes and binds to CD3, and a CD3 binding domain comprising a CDR sequence derived from an anti-CD3 antibody, a CD3 binding domain comprising VH and VL derived from an anti-CD3 antibody, and the like are exemplified. The CD3 antigen binding domain comprising a CDR sequence or VH and VL derived from an anti-CD3 antibody is preferably scFv.

In the present invention, the disease-related antigen binding domain may be any as long as it specifically recognizes and binds to a disease-related antigen, and is preferably Fab of an antibody or a variable region composed of VH and VL thereof.

In the present invention, the binding of a polypeptide, an antibody, an antibody fragment thereof, a bispecific antibody, or a bispecific antibody fragment thereof to CD3 and/or a disease-related antigen can be confirmed, for example, by a method in which the binding affinity of the antibody to a cell having expressed an antigen to be evaluated is confirmed using a known immunological detection method, preferably a fluorescent cell staining method, or the like. Further, it is also possible to use known immunological detection methods [Monoclonal Antibodies—Principles and Practice, Third Edition, Academic Press (1996), Antibodies—A Laboratory Manual, Cold Spring Harbor Laboratory (1988), Monoclonal Antibody Experimental Manual, Kodansha Scientific Ltd. (1987)], and the like in combination.

As the bispecific antibody or the bispecific antibody fragment thereof of the present invention, for example, an anti-CD3 bispecific antibody with a reduced ability to induce cytokine production in the presence of CD3-positive T cells and disease-related antigen-positive cells as compared with an anti-CD3 bispecific antibody containing a CD3 binding domain derived from an anti-CD3 monoclonal antibody SP34 (U.S. Pat. No. 10,066,015) as a CD3 binding domain is exemplified. Such a bispecific antibody or a bispecific antibody fragment thereof is preferred in that it has few side effects such as chills, nausea, malaise, headache, fever, tachycardia, and/or blood pressure fluctuation due to cytokine production, and is less likely to cause cytokine release syndrome.

In the present invention, the ability to induce cytokine production refers to an activity to induce cytokine production by a T cell, a target cell, an NK cell, or the like by binding of the bispecific antibody or the bispecific antibody fragment thereof of the present invention to CD3 on the T cell, an Fc receptor on the NK cell, and/or a disease-related antigen on the target cell.

A cytokine whose production is preferably reduced may be any cytokine as long as it is a cytokine associated with a side effect caused by the above-mentioned excessive or unnecessary cytokine production, and for example, inflammatory cytokines such as interferon-γ (IFN-γ), tumor necrosis factor-α (TNF-α), and interleukin-6 (IL-6), IL-2, IL-4, IL-10, and the like are exemplified.

The bispecific antibody or the bispecific antibody fragment thereof of the present invention is preferably one that binds to CD3 and a disease-related antigen expressed on different cells.

The bispecific antibody or the bispecific antibody fragment thereof of the present invention is preferably one that induces cell death of a target cell by binding to CD3 on a T cell and a disease-related antigen on the target cell, and is more preferably one that specifically damages only a target cell in the presence of a CD3-positive T cell and the target cell, and does not exhibit cellular cytotoxicity in the absence of either the CD3-positive cell or the target cell.

Examples of the mechanism of the cellular cytotoxicity of the bispecific antibody or the bispecific antibody fragment thereof of the present invention include an ADCC activity, a CDC activity, an ADCP activity, an ADTC activity, and the like.

That is, as the bispecific antibody or the bispecific antibody fragment thereof of the present invention, specifically, a bispecific antibody or a bispecific antibody fragment thereof that specifically induces cell injury and/or cell death of a disease-related antigen-positive cell when it binds to both a CD3-positive cell and the disease-related antigen-positive cell, and the like are exemplified.

The number of binding domains to a certain antigen included in a single molecule of a bispecific antibody refers to a binding valence. For example, in the present invention, when a single molecule of a bispecific antibody has two antigen binding domains that bind to CD3 and two antigen binding site domains that bind to a disease-specific antigen, the bispecific antibody bivalently binds to each of CD3 and the disease-specific antigen.

Further, an antibody containing multiple antigen binding domains bound to one another through an appropriate linker such as a linker containing an immunoglobulin domain or a fragment thereof is also included in the bispecific antibody of the present invention.

In the present invention, the immunoglobulin domain used as the linker includes a peptide that has an amino acid sequence similar to that of an immunoglobulin and is composed of about 100 amino acid residues in which at least two cysteine residues are present as a smallest unit. In the present invention, the immunoglobulin domain also includes a polypeptide including multiple immunoglobulin domains, each of which is the smallest unit described above. Examples of the immunoglobulin domain include VH, CH1, CH2, and CH3 of an immunoglobulin heavy chain, and VL and CL of an immunoglobulin light chain, and the like.

The animal species of the immunoglobulin is not particularly limited, but is preferably a human. In addition, the subclass of the constant region of the immunoglobulin heavy chain may be any of IgD, IgM, IgG1, IgG2, IgG3, IgG4, IgAQ1, IgA2, and IgE, and preferably, IgG-derived and IgM-derived subclasses are exemplified. In addition, the subclass of the constant region of the immunoglobulin light chain may be either of κ and λ.

Further, the immunoglobulin domain is also present in proteins other than the immunoglobulin, and for example, immunoglobulin domains included in proteins belonging to the immunoglobulin superfamily such as a major histocompatibility antigen (MHC), CDT, B7, and a T cell receptor (TCR) are exemplified. As the immunoglobulin domain used for the bispecific antibody of the present invention, any immunoglobulin domain can be applied.

In the case of a human IgG, CH1 refers to a region having the amino acid sequence at positions 118 to 215 indicated by the EU index. Similarly, CH2 refers to a region having the amino acid sequence at positions 231 to 340 indicated by the EU index of Kabat et al., and CH3 refers to a region having the amino acid sequence at positions 341 to 447 indicated by the EU index of Kabat et al. Between CH1 and CH2, an amino acid region which is rich in flexibility called a hinge region (hereinafter sometimes referred to as a hinge) is present. The hinge region refers to a region having the amino acid sequence at positions 216 to 230 indicated by the EU index of Kabat et al.

The CL refers to a region having the amino acid sequence at positions 108 to 214 indicated by Kabat numbering in the case of the κ chain of a human antibody, and refers to a region having the amino acid sequence at positions 108 to 215 in the case of the λ chain.

As the Fc region contained in the bispecific antibody or the bispecific antibody fragment thereof of the present invention, an Fc region derived from an antibody of any animal species can be used, but a human-derived Fc region is preferred, and an Fc region derived from IgG1 is particularly preferred.

In the present invention, the "Fc region having a binding ability to an Fc receptor" refers to an Fc region having a binding ability to various Fc receptors to at least such an extent that an effector activity such as an ADCC activity is exhibited through an Fc receptor. Specific examples thereof include an Fc region of human IgG1, an Fc region of human IgG3, an Fc region of mouse IgG2a, and the like. In addition, an Fc region having an enhanced binding ability to an Fc receptor is also included in the Fc region having a binding ability to an Fc receptor.

The "Fc region having a binding ability to an Fc receptor" contained in the bispecific antibody or the bispecific antibody fragment thereof of the present invention is preferably an Fc region having a binding ability to FcγR, and more preferably an Fc region having a binding ability to FcγRIIIA.

Further, as the "Fc region having a binding ability to an Fc receptor" contained in the bispecific antibody or the bispecific antibody fragment thereof of the present invention, "an Fc region having enhanced affinity for an Fc receptor" is also preferred.

The Fc region having enhanced affinity for an Fc receptor may be any as long as the affinity for an Fc receptor is enhanced as compared with the Fc region of a naturally occurring antibody, but examples thereof include an Fc region including a sugar chain modification, an Fc region including an amino acid residue modification, and the like.

As the Fe including a sugar chain modification, for example, an Fc region in which the addition amount of α1,6-fucose is reduced or deleted or an Fc region in which an amino acid modification for enhancing the affinity for an Fc receptor (a modification with a natural amino acid residue or a non-natural amino acid residue) is added, or the like is exemplified.

As the Fc region including an amino acid residue modification, for example, an Fc region including at least one amino acid residue modification selected from P247I, A339D, F243L, R292P, Y300L, P396L, T393A, H433P, S239D, S298A, A330L, 1332E, E333A, and K334A in the human IgG1 constant region, and amino acid modifications described in Current Opinion in Biotechnology 2009, 20: 685-691 is exemplified.

The notation for the following amino acid residue modification is expressed by [one-letter code for amino acid residue before modification], [amino acid position indicated by the EU index], and [one-letter code for amino acid residue after modification] in this order.

The Fc region or the antibody constant region is preferably one of the IgG class, and a part of the amino acid sequence thereof may be deleted, added, substituted, and/or inserted. In addition, all or some of the fragments of the amino acid sequence composed of CH1, a hinge, CH2, and CH3 of the heavy chain of IgG can be appropriately combined and used. Further, the amino acid sequences thereof can also be used by partially deleting or changing the order.

The subclass of IgG of the Fc region or the antibody constant region used in the bispecifie antibody of the present invention is not particularly limited, and it may be an Fc region or a constant region derived from any subclass of IgG1, IgG2, IgG3, and IgG4, but IgG1 is preferred.

In the case of the Fc region or the heavy chain constant region of IgG1, for example, an Fc region or a heavy chain constant region including a deletion of amino acid residues at positions 216 to 220 of the hinge region and at least one modification selected from the amino acid residue modifications of C220S, H435R, and Y436F, an Fc region or a constant region including a deletion of amino acid residues at positions 216 to 220 of the hinge region and an amino acid residue modification of C220S, and an Fc region or a heavy chain constant region including at least one modification selected from S354C, T366W, Y349C, T366S, L368A, and Y407V are exemplified.

Each of two polypeptide chains constituting the Fc region of the present invention is also referred to as an Fc polypeptide chain or simply an Fc chain.

In the bispecific antibody of the present invention, one CD3 binding domain is bound to any one of the Fc chains of the Fc region directly or through a linker. Therefore, the Fc region in the present invention is constituted by an Fc region composed of "an Fc chain" and "an Fc chain in which a CD3 binding domain is bound to the C terminus of the Fc chain".

Further, examples of the heavy chain constant region comprising the Fc region in the present invention include a heavy chain constant region composed of "a polypeptide chain of CH" and "a CH chain in which a CD3 domain is bound to the C terminus of the polypeptide chain of CH", and a constant region, which is a constant region composed of "a polypeptide chain of CH (also referred to as CH1-Fc)" and "a polypeptide chain in which CL is fused to an Fc chain (hereinafter abbreviated as CL-Fc)", and in which a CD3 binding domain is bound to the C terminus of either one of the polypeptide chains, and the like. The CD3 binding domain may be bound to either polypeptide chain of the two polypeptide chains constituting the above-mentioned Fc region or constant region.

Further, the production can also be carried out by bonding VH or VL, VH-CH or VL-CL constituting the CD3 binding domain, to each of the polypeptide chains included in the Fc region or the heavy chain constant region.

The Fc region or the constant region included in the bispecific antibody of the present invention forms a heterodimer, since the CD3 binding domain is bound to either one of the two polypeptide chains constituting each region as described above. It may include any modification of addition, deletion, and substitution as long as this heterodimer structure can be formed.

Specifically, when it is composed of two Fc polypeptide chains or CH polypeptide chains, a heterodimer can be formed by adding an appropriate amino acid residue substitution to the CH3 domain. For example, by adding amino acid residue substitutions of S354C and T366W to one of the two Fc polypeptide chains, and adding amino acid residue substitutions of Y349C, T366S, L368A, and Y407V to the other, a heterodimer of the Fc region or the CH region can be formed [Knobs into Holes modification (Nature Biotechnology, vol. 16: 677-681, 1998)]. This modification is also referred to as KIH modification.

When the KIH modification is added to the Fc region included in the bispecific antibody of the present invention, Knobs or Holes modifications may be added to either polypeptide chain whether or not the CD3 binding domain is bound to either of the two polypeptide chains constituting the Fc region. Further, the KIH modification excluding the modifications (S354C and Y349C) for forming a disulfide bond can also be adapted to the CH3 moiety. In this case, an amino acid residue substitution of T366W is added to one of the two Fc polypeptide chains, and amino acid residue substitutions of T366S, L368A, and Y407V are added to the other.

Specific examples of the amino acid sequence of the Fc region into which the KIH modification is introduced include, but are not limited to, an Fc region comprising a polypeptide comprising the amino acid sequence represented by SEQ ID NO: 147 and a polypeptide comprising the amino acid sequence represented by SEQ ID NO: 148, an Fc region comprising a polypeptide comprising the amino acid sequence represented by SEQ ID NO: 149 and a polypeptide comprising the amino acid sequence represented by SEQ ID NO: 150, an Fc region comprising a polypeptide comprising the amino acid sequence represented by SEQ ID NO: 151 and a polypeptide comprising the amino acid sequence represented by SEQ ID NO: 152, and an Fc region comprising a polypeptide comprising the amino acid sequence represented by SEQ ID NO: 153 and a polypeptide comprising the amino acid sequence represented by SEQ ID NO: 154.

Further, as a CH region composed of two hetero CH chains (hereinafter, hetero CH region), a hetero CH region comprising a CH polypeptide chain and CL-Fc is exemplified, and a CH region comprising a CH polypeptide chain comprising C220S, and CL-Fc comprising a deletion of amino acid residues 216-220 and C214S, a CH region comprising a CH polypeptide comprising C220S, and CL-Fc comprising a deletion of amino acid residues 216-220 and C214S and H435R, and a CH region comprising a CH polypeptide comprising C220S, and CL-Fc comprising a deletion of amino acid residues 216-220 and C214S, H435R, and Y436F are more preferred.

The CD3 binding domain of the present invention may be a single chain or a polymer composed of a plurality of polypeptide chains as long as it has an antigen binding ability to CD3. As the CD3 antigen binding domain, for example, a CD3 binding domain comprising three or six CDR sequences of an antibody against CD3, or a CD3 binding domain comprising VH and VL of an antibody against CD3 is exemplified, and Fab, Fab', scFv, dsFv, and VHH are preferred, and Fab and scFv are more preferred. In addition, a ligand molecule or a receptor molecule for a cell surface antigen can also be used in the same manner.

When the CD3 binding domain of the present invention is scFv, as the scFv, one in which VH, a linker, and VL are bound in this order from the N-terminal side (referred to as VH-linker-VL type or HL type), and one in which VL, a linker, and VH are bound in this order (referred to as VL-linker-VH type or LH type) are known, and either can be used as the scFv of the present invention.

When the CD3 binding domain of the present invention is scFv, a modification may be added to the framework of scFv. As an example of the modification, for example, a modification for enhancing the physicochemical stability, a modification for improving the productivity, a modification of an amino acid on the interaction surface of VH and VL of scFv, and the like are contemplated. Specifically, a modification (CC modification) in which an amino acid at position 44 (according to Kabat numbering) of VH of scFv is substituted with Cys and an amino acid at position 100 (according to Kabat numbering) of VL is substitute with Cys, a modification (SE modification) in which an amino acid at position 44 of VH is substituted with Ser and an amino acid at position 100 of VL is substituted with Glu, and the like are exemplified.

The affinity of the CD3 binding domain of the present invention for CD3 is preferably reduced. The phrase "the affinity of the CD3 binding domain is reduced" indicates, for example, that the dissociation constant ($K_D$) for CD3 is $6\times10^{-8}$ or more. The dissociation constant ($K_D$) of the CD3 binding domain for CD3 is more preferably $7\times10^{-8}$ or more, further more preferably $8\times10^{-8}$ or more, and still further more preferably $9\times10^{-8}$ or more. In addition, the phrase "the affinity of the CD3 binding domain for CD3 is reduced" indicates, for example, that the dissociation constant for CD3 is larger than that of an anti-CD3 monoclonal antibody SP34 or KM14.

As the dissociation constant of the CD3 binding domain of the present invention, for example, a value calculated by a surface plasmon resonance (SPR) method using Biacore T100 (GE Healthcare) is exemplified.

As one embodiment of the CD3 binding domain of the present invention, one in which the amino acid sequence of CDR or VH/VL has 80% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more homology with the amino acid sequence of CDR or VH/VL of an anti-CD3 monoclonal antibody SP34 or KM14 serving as a comparison control, and further, the affinity for CD3 is reduced by preferably 10% or more, more preferably 20% or more, and further more preferably 30% or more as compared with that of SP34 or KM14 is exemplified.

As one embodiment of the CD3 binding domain of the present invention, one in which the amino acid sequence of CDR or VH/VL has 80% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more homology with the amino acid sequence of an anti-CD3 monoclonal antibody SP34 serving as a comparison control, and further, the affinity is reduced by 70% or more, preferably 80% or more, more preferably 85% or more, and further more preferably 90% or more as compared with that of SP34 is exemplified.

Further, as one embodiment of the CD3 binding domain of the present invention, one in which the amino acid sequence of CDR or VH/VL has 80% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more homology with the amino acid sequence of an anti-CD3 monoclonal antibody KM14 serving as a comparison control, and further, the affinity is reduced by preferably 10% or more, more preferably 15% or more, further more preferably 30% or more, and still further more preferably 40% or more as compared with that of KM14 is exemplified.

In the present invention, the phrase "the affinity is reduced by A % or more" means that when the dissociation constant of a CD3 binding domain of a comparison control for CD3 is represented by $K_{D0}$ and the dissociation constant of a CD3 binding domain to be tested for CD3 is represented by $K_{D1}$, the ratio thereof. $K_{D0}/K_{D1}$ is (100-A) % or less.

In the present invention, an antibody comprising the amino acid sequences of VH and VL of an anti-CD3 monoclonal antibody SP34 or the amino acid sequences of six CDRs of SP34 is called SP34 clone.

In the present invention, an antibody comprising the amino acid sequences of VH and VL of an anti-CD3 monoclonal antibody KM14 or the amino acid sequences of six CDRs of KM14 is called KM14 clone.

In the present invention, the linker may have any molecular structure as long as it can bind the Fc region and the CD3 binding domain, or the Fc region and the disease-related antigen binding domain, and for example, an immunoglobulin domain or a fragment thereof and a peptide chain, and the like are exemplified, but a peptide chain is preferred. As the amino acid sequence of the peptide chain, for example, a so-called GS linker composed of SGGGG or a repeating sequence of SGGGG, a linker composed of EAAAK or a repeating sequence thereof, a linker composed of an amino acid sequence called PAPAP, or a sequence derived from a hinge region of an antibody and a constant region such as a CH1 domain, or a modified sequence thereof, or the like is exemplified.

The bispecific antibody or the bispecific antibody fragment thereof of the present invention may have one or two or more disease-related antigen binding domains.

The disease-related antigen binding domain may be bound to the Fc region directly or through a linker. Further, it may be bound to the C-terminal side or the N-terminal side of the Fc region, and is preferably bound to the C-terminal side. When one CD3 binding domain is bound to the C-terminal side of the Fc region, the CD3 binding domain may be bound to either polypeptide chain of the two polypeptide chains constituting the Fc region.

The disease-related antigen binding domain in the present invention may be a single chain or a polymer composed of a plurality of polypeptide chains as long as it has an antigen binding ability to a disease-related antigen. As the disease-related antigen binding domain, for example, an antigen binding domain comprising three or six CDR sequences of an antibody against a disease-related antigen, or an antigen binding domain comprising VH and VL of an antibody against a disease-related antigen is exemplified, and Fab, Fab', scFv, dsFv, VHH, and the like are exemplified. It is preferably an antigen binding domain composed of VH and VL or Fab. In addition, a ligand molecule or a receptor molecule for a cell surface antigen can also be used in the same manner.

The antibody against a disease-related antigen is preferably a monoclonal antibody, and an antibody having any specificity as long as it is an antibody that can be genetically modified such as a monoclonal antibody known to specifically recognize and bind to an antigen related to each disease or a monoclonal antibody which has already been launched on the market as an antibody drug can also be used as the disease-related antigen binding domain to be comprised in the anti-CD3 bispecific antibody of the present invention.

An antibody or a bispecific antibody fragment thereof, in which one or more amino acid residues are deleted, added, substituted, or inserted in the amino acid sequence constituting the bispecific antibody or the bispecific antibody fragment thereof of the present invention, and which has the same activity as that of the antibody or the antibody fragment thereof described above, is also included in the bispecific antibody or the bispecific antibody fragment thereof of the present invention.

The number of amino acids to be deleted, substituted, inserted, and/or added is one or more, and is not particularly limited, and is a number such that deletion, substitution, insertion, or addition can be carried out using a well-known technique such as a site-specific mutagenesis method described in Molecular Cloning, The Second Edition, Cold Spring Harbor Laboratory Press (1989), Current Protocols in Molecular Biology, John Willy & Sons (1987-1997), Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci USA, 82, 488 (1985), or the like. For example, it is generally one to several tens, preferably 1 to 20, more preferably 1 to 10, and further more preferably 1 to 5.

The above description that one or more amino acid residues in the amino acid sequence of the bispecific antibody of the present invention are deleted, substituted, inserted, or added indicates as follows. The description means that there is a deletion, substitution, insertion, or addition of one or multiple amino acid residues in any one or multiple amino acid sequences in the same sequence. Further, such a deletion, substitution, insertion, or addition may sometimes occur simultaneously, and the amino acid residues to be substituted, inserted, or added may be either a natural type or an unnatural type.

Examples of the natural amino acid residue include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

Hereinafter, preferred examples of mutually substitutable amino acid residues are shown. Amino acid residues included in the same group can be mutually substituted.

group A: leucine, isoleucine, norleucine, valine, norvaline, alanine, 2-aminobutanoic acid, methionine, O-methylserine, t-butyl glycine, t-butyl alanine, and cyclohexylalanine group B: aspartic acid, glutamic acid, isoaspartic acid, isoglutamic acid, 2-aminoadipic acid, and 2-aminosuberic acid group C: asparagine and glutamine group D: lysine, arginine, ornithine, 2,4-diaminobutanoic acid, and 2,3-diaminopropionic acid group E: proline, 3-hydroxyproline, and 4-hydroxyproline group F: serine, threonine, and homoserine group G: phenylalanine and tyrosine The bispecific antibody of the present invention also includes an antibody containing any amino acid residue having undergone a post-translational modification. Examples of the post-translational modification include a deletion of a lysine residue at the C terminus of an H chain (lysine clipping), a substitution of a glutamine residue at the N terminus of a polypeptide with pyroglutamate (pyroGlu), and the like [Beck et al., Analytical Chemistry, 85, 715-736 (2013)].

As the bispecific antibody or the bispecific antibody fragment thereof of the present invention, specifically, for example, any one bispecific antibody or bispecific antibody fragment thereof selected from the group consisting of the following (1) to (3), and the like are exemplified:

(1) an anti-CD3 bispecific antibody or a bispecific antibody fragment thereof comprising an Fc region having a binding ability to an Fc receptor, and one CD3 binding domain bound to the C-terminal side of the Fc region, and further comprising one or more disease-related antigen binding domains at the N-terminal side of the Fc region;

(2) an anti-CD3 bispecific antibody or a bispecific antibody fragment thereof comprising an Fc region having a binding ability to an Fc receptor, and one CD3 binding domain bound to the C-terminal side of the Fc region, and further comprising one or more disease-related antigen binding domains at the C-terminal side of the Fc region; and (3) an anti-CD3 bispecific antibody or a bispecific antibody fragment thereof comprising an Fc region having a binding ability to an Fc receptor, and one CD3 binding domain bound to the C-terminal side of the Fc region, and further comprising one or more disease-related antigen binding domains at the C-terminal side of the Fc region, and one or more disease-related antigen binding domains at the N-terminal side of the Fc region.

As one embodiment of the present invention, a bispecific antibody or a bispecific antibody fragment thereof, which is the anti-CD3 bispecific antibody or the bispecific antibody fragment thereof described in the above (1), and is a bispecific antibody in which the Fc region forms a heterodimer with Knobs into Holes modification (Nature Biotechnology, vol. 16: 677-681, 1998) (also referred to as KIH modification) or a modification excluding modifications (S354C and Y349C) for forming a disulfide bond from the KIH modification introduced into the CH3 moiety, and the CD3 binding domain is bound to either one of the C termini of the heterodimer through a linker, and in which the disease-related antigen binding domain is bound to one or both of the N termini of the heterodimer is exemplified.

As one embodiment of the present invention, the following (a), (b), and (c) are exemplified, each of which is the anti-CD3 bispecific antibody or the bispecific antibody fragment thereof described in the above (1), and in which a heterodimer composed of CH1-Fc and CL-Fc is formed by bonding CL and CH1 to the N-terminal sides of the two polypeptide chains of the Fc region, respectively, and the CD3 binding domain is bound to the C terminus of either one of CH1-Fc and CL-Fc through a linker:

(a) a bispecific antibody or a bispecific antibody fragment thereof, in which one disease-related antigen binding domain is formed by bonding VH and VL to the N termini of CH1-Fc and CL-Fc, respectively;

(b) a bispecific antibody or a bispecific antibody fragment thereof, in which one disease-related antigen binding domain is formed by bonding VL and VH to the N termini of CH1-Fc and CL-Fc, respectively; and (c) a bispecific antibody or a bispecific antibody fragment thereof, in which Fab, VHH, and/or scFv is bound to the N terminus of CH1-Fc and/or CL-Fc, and one or more disease-related antigen binding domains are comprised.

Among them, it is preferred that VL and VH or VH and VL are bound to the N termini of CH1-Fc and CL-Fc, respectively, and it is more preferred that VH and VL are bound to the N termini of CH1-Fc and CL-Fc, respectively.

Further, the amino acid sequences of CH1-Fc and CL-Fc are preferably subjected to amino acid modifications so as to form a heterodimer when the sequences are expressed in cells, and specifically, it is preferred to include deletion of 216-220 and amino acid residue modifications of C214S, H435R, and Y436F in CL-Fc, and an amino acid residue modification of C220S in CH1-Fc. These modifications may be introduced simultaneously with either of the KIH modification or the modification excluding the modifications for forming a disulfide bond from the KIH modification may be introduced.

Examples of the disease-related antigen binding domain include Fab, a variable region composed of VH and VL, VHH, scFv, and the like. Specifically, it is preferred that as the disease-related antigen binding domain, Fab is bound to both of the N termini of the heterodimer. Either of the polypeptide chains of VH-CH1 and VL-CL that form Fab may be bound to the N terminus of the Fc region, but it is more preferred that VH-CH1 is bound thereto.

As one embodiment of the present invention, a bispecific antibody or a bispecific antibody fragment thereof, which is the anti-CD3 bispecific antibody or the bispecific antibody fragment thereof described in the above (2), and in which a heterodimer of CH1-Fc and CL-Fc is formed by bonding CL and CH1 to the N-terminal sides of the two polypeptide chains of the Fc region, respectively, and the CD3 binding domain is bound to the C terminus of either one of CH1-Fc and CL-Fc through a linker, wherein Fab, VHH, and/or scFv is bound as a disease-related antigen binding domain to the C-terminal side of CH1-Fc and/or CL-Fc is exemplified.

At this time, the disease-related antigen binding domain may be directly bound to CH1-Fc and/or CL-Fc, or may be bound through a linker, or may be bound to the further C-terminal side of the CD3 binding domain.

The amino acid sequence of the heterodimer is preferably subjected to amino acid modifications so as to form a heterodimer when the sequence is expressed in cells, and specifically, it is desirably subjected to a deletion of amino acid residues at 216-220 and amino acid residue modifications of C214S, H435R, and Y436F in CL-Fc, and an amino acid residue modification of C220S in CH1-Fc.

As another embodiment of the present invention, a bispecific antibody which is the anti-CD3 bispecific antibody or the bispecific antibody fragment thereof described in the above (2), and in which Knobs into Holes modification or a modification other than S354C and Y349C in the KIH modification is added to the Fc region, and one or more disease-related antigen binding domains are comprised at the C-terminal side of a heterodimer that forms the Fc region is exemplified. Examples of the disease-related antigen binding domain include Fab, an antibody variable region composed of VH and VL, VHH, scFv, and the like. The disease-related antigen binding domain may be directly bound to CH1-Fc and/or CL-Fc, or may be bound through a linker, or may be bound to the further C-terminal side of the CD3 binding domain.

As one embodiment of the present invention, a bispecific antibody or a bispecific antibody fragment thereof, which is the anti-CD3 bispecific antibody or the bispecific antibody fragment thereof described in the above (3), and in which a heterodimer composed of CH1-Fc and CL-Fc is formed by bonding CL and CH1 to the N-terminal sides of the two polypeptide chains of the Fc region, respectively, and the CD3 binding domain is bound to the C terminus of either one of CH1-Fc and CL-Fc through a linker, wherein one or more disease-related antigen binding domains are comprised at the N-terminal sides of CH1-Fc and CL-Fc, and further, one or more disease-related antigen binding domains are comprised also at the C-terminal sides of CH1-Fc and CL-Fc is exemplified.

As for the disease-related antigen binding domain bound to the N-terminal side of CH1-Fc and/or CL-Fc, one disease-related antigen binding domain may be formed by bonding VH and VL (or VL and VH) to the N termini of CH1-Fc and CL-Fc, respectively, or at least one disease-related antigen binding domain may be formed by bonding Fab, VHH, and/or scFv to the N terminus of at least one of CH1-Fc and CL-Fc.

Further, as the disease-related antigen binding domain, it is preferred that one disease-related antigen binding domain is formed by bonding VH and VL (or VL and VH) to the N termini of each CH1-Fc and CL-Fc, respectively, and it is more preferred that VH and VL are bound to the N termini of each CH1-Fc and CL-Fc, respectively.

The disease-related antigen binding domain bound to the C-terminal side of CH1-Fc and/or CL-Fc may be directly bound to the polypeptide chain thereof, or may be bound through a linker, or may be bound through the CD3 binding domain. Examples of the disease-related antigen binding domain include Fab, VHH, scFv, and the like.

Further, the amino acid sequences of CH1-Fc and CL-Fc are preferably subjected to amino acid modifications so as to form a heterodimer when the sequence is expressed in cells, and specifically, it is preferred that CL-Fc is subjected to a deletion of amino acid residues at 216-220 and amino acid residue modifications of C214S, H435R, and Y436F, and CH1-Fc is subjected to an amino acid residue modification of C220S.

As another embodiment of the present invention, a bispecific antibody or a bispecific antibody fragment thereof which is the anti-CD3 bispecific antibody or the bispecific antibody fragment thereof described in the above (3), and in which Knobs into Holes modification or a modification other than S354C and Y349C in the KIH modification is added to the Fc region, and one or more disease-related antigen binding domains are comprised at the N-terminal side of a heterodimer of the Fc region, and further one or more disease-related antigen binding domains are comprised also at the C-terminal side of the heterodimer of the Fc region is exemplified.

Examples of the disease-related antigen binding domain include Fab, VHH, scFv, and the like. When Fab is bound as the disease-related antigen binding domain to the N-terminal side of the heterodimer, either of VH-CH1 and VL-CL polypeptide chains that form Fab may be bound to the N terminus of the Fc region, but it is more preferred that VH-CH1 is bound thereto.

Further, the disease-related antigen binding domain bound to the C-terminal side of the heterodimer may be directly bound to the C terminus of the heterodimer, or may be bound through a linker, or may be bound to the further C-terminal side of the CD3 binding domain.

In any of the embodiments described in the above (1) to (3), as the Fc region having the binding ability to an Fc receptor, an Fc region having enhanced affinity for an Fc receptor can also be used in the same manner.

In any of the embodiments described in the above (1) to (3), by bonding VH and VL constituting the CD3 binding domain to two polypeptide chains constituting the Fc region, respectively, the anti-CD3 bispecific antibody or the bispecific antibody fragment thereof in which one CD3 binding domain is bound to the C terminus of the Fc region can be produced.

The anti-CD3 bispecific antibody or the bispecific antibody fragment thereof of the present invention can also be produced by utilizing a known heterodimer production technology other than the above. Examples of the known technology include CrossMAb technology, BEAT technology, XmAb technology, ART-Ig technology, and Azymetric technology (all described in Nat Rev Drug Discov. 18: 585-608, 2019), and other heterodimer production technologies described in Nat Rev Drug Discov. 18: 585-608, 2019, and the like.

As a more preferred embodiment of the present invention, a bispecific antibody or a bispecific antibody fragment thereof, wherein the CD3 binding domain is scFv is exemplified.

As a still more preferred embodiment of the present invention, a bispecific antibody or a bispecific antibody fragment thereof, wherein the dissociation constant ($K_D$) of the CD3 binding domain for CD3 is $6\times10^{-8}$ or more, $7\times10^{-8}$ or more, $8\times10^{-8}$ or more, or $9\times10^{-8}$ or more is exemplified.

As one embodiment of the present invention, a bispecific antibody or a bispecific antibody fragment thereof, wherein the dissociation constant of the CD3 binding domain for CD3 is larger than that of an anti-CD3 monoclonal antibody SP34 or KM14 serving as a comparison control is exemplified.

As one embodiment of the present invention, a bispecific antibody or a bispecific antibody fragment thereof, wherein the amino acid sequence of CDR or VH/VL of the CD3 binding domain has 90% or more homology with the amino acid sequence of CDR or VH/VL of the CD3 binding domain of the anti-CD3 monoclonal antibody SP34 or KM14 serving as a comparison control, and the affinity is reduced by 10% or more as compared with that of the anti-CD3 antibody SP34 or KM14 is exemplified.

As a more preferred embodiment of the present invention, a bispecific antibody, wherein the antibody has an ADCC activity and an ADTC activity against a cell that expresses a disease-related antigen, and the induction of cytokine production is suppressed during cell injury of the disease-related antigen-expressing cell is exemplified.

As a still more preferred embodiment, a bispecific antibody or a bispecific antibody fragment thereof, wherein the amino acid sequence of the linker between the Fc region and the CD3 binding domain is one selected from (SGGGG)n (n=1 to 3), (EAAAK)n (n=1 to 3), or PAPAP is exemplified.

As the CD3 binding domain in the present invention, specifically, a CD3 binding domain in which the amino acid sequences of CDRs 1 to 3 of VH (HCDRs 1 to 3) and CDRs 1 to 3 of VL (LCDRs 1 to 3) of the CD3 binding domain have 90% or more homology with the amino acid sequences of HCDRs 1 to 3 and LCDRs 1 to 3, respectively, of any one selected from the following (a) to (h) is exemplified:

(a) HCDRs 1 to 3 comprising the amino acid sequences represented by SEQ ID NOS: 118 to 120, respectively, and LCDRs 1 to 3 comprising the amino acid sequences represented by SEQ ID NOS: 121 to 123, respectively;

(b) HCDRs 1 to 3 comprising the amino acid sequences represented by SEQ ID NOS: 83 to 85, respectively, and LCDRs 1 to 3 comprising the amino acid sequences represented by SEQ ID NOS: 86 to 88, respectively;

(c) HCDRs 1 to 3 comprising the amino acid sequences represented by SEQ ID NOS: 98 to 100, respectively, and LCDRs 1 to 3 comprising the amino acid sequences represented by SEQ ID NOS: 132, 96, and 97, respectively;

(d) HCDRs 1 to 3 comprising the amino acid sequences represented by SEQ ID NOS: 98 to 100, respectively, and LCDRs 1 to 3 comprising the amino acid sequences represented by SEQ ID NOS: 133, 96, and 97, respectively;

(e) HCDRs 1 to 3 comprising the amino acid sequences represented by SEQ ID NOS: 98, 134, and 100, respectively, and LCDRs 1 to 3 comprising the amino acid sequences represented by SEQ ID NOS: 95 to 97, respectively;

(f) HCDRs 1 to 3 comprising the amino acid sequences represented by SEQ ID NOS: 98, 135, and 100, respectively, and LCDRs 1 to 3 comprising the amino acid sequences represented by SEQ ID NOS: 95 to 97, respectively;

(g) HCDRs 1 to 3 comprising the amino acid sequences represented by SEQ ID NOS: 98, 136, and 100, respectively, and LCDRs 1 to 3 comprising the amino acid sequences represented by SEQ ID NOS: 95 to 97, respectively; and (h) HCDRs 1 to 3 comprising the amino acid sequences represented by SEQ ID NOS: 98, 137, and 100, respectively, and LCDRs 1 to 3 comprising the amino acid sequences represented by SEQ ID NOS: 95 to 97, respectively.

As the CD3 binding domain in the present invention, specifically, a CD3 binding domain in which the amino acid sequences of VH and VL of the CD3 binding domain have 80% or more homology with the amino acid sequences of VH and VL, respectively, of any one selected from the following (aa) to (rr) is exemplified:

(aa) VH comprising the amino acid sequence represented by SEQ ID NO: 124 and VL comprising the amino acid sequence represented by SEQ ID NO: 125;

(bb) VH comprising the amino acid sequence represented by SEQ ID NO: 115 and VL comprising the amino acid sequence represented by SEQ ID NO: 116;

(cc) VH comprising the amino acid sequence represented by SEQ ID NO: 94 and VL comprising the amino acid sequence represented by SEQ ID NO: 126;

(dd) VH comprising the amino acid sequence represented by SEQ ID NO: 94 and VL comprising the amino acid sequence represented by SEQ ID NO: 127;

(ee) VH comprising the amino acid sequence represented by SEQ ID NO: 128 and VL comprising the amino acid sequence represented by SEQ ID NO: 93;

(ff) VH comprising the amino acid sequence represented by SEQ ID NO: 129 and VL comprising the amino acid sequence represented by SEQ ID NO: 93;

(gg) VH comprising the amino acid sequence represented by SEQ ID NO: 130 and VL comprising the amino acid sequence represented by SEQ ID NO: 93;

(hh) VH comprising the amino acid sequence represented by SEQ ID NO: 131 and VL comprising the amino acid sequence represented by SEQ ID NO: 93;

(ii) VH comprising the amino acid sequence represented by SEQ ID NO: 159 and VL comprising the amino acid sequence represented by SEQ ID NO: 165;

(jj) VH comprising the amino acid sequence represented by SEQ ID NO: 160 and VL comprising the amino acid sequence represented by SEQ ID NO: 165;

(kk) VH comprising the amino acid sequence represented by SEQ ID NO: 161 and VL comprising the amino acid sequence represented by SEQ ID NO: 166;

(ll) VH comprising the amino acid sequence represented by SEQ ID NO: 162 and VL comprising the amino acid sequence represented by SEQ ID NO: 166;

(mm) VH comprising the amino acid sequence represented by SEQ ID NO: 168 and VL comprising the amino acid sequence represented by SEQ ID NO: 180;

(nn) VH comprising the amino acid sequence represented by SEQ ID NO: 169 and VL comprising the amino acid sequence represented by SEQ ID NO: 181;

(oo) VH comprising the amino acid sequence represented by SEQ ID NO: 170 and VL comprising the amino acid sequence represented by SEQ ID NO: 182;

(pp) VH comprising the amino acid sequence represented by SEQ ID NO: 171 and VL comprising the amino acid sequence represented by SEQ ID NO: 183;

(qq) VH comprising the amino acid sequence represented by SEQ ID NO: 172 and VL comprising the amino acid sequence represented by SEQ ID NO: 184; and (rr) VH comprising the amino acid sequence represented by SEQ ID NO: 173 and VL comprising the amino acid sequence represented by SEQ ID NO: 185.

As the CD3 binding domain in the present invention, a CD3 binding domain which binds to CD3 competitively with a CD3 binding domain comprising any one selected from the above (a) to (h), (aa) to (rr), and anti-CD3 monoclonal antibodies SP34 and KM14, a CD3 binding domain which binds to an epitope on CD3 to which a CD3 binding domain comprising any one selected from the above (a) to (h), (aa) to (rr), and anti-CD3 monoclonal antibodies SP34 and KM14 binds, and a CD3 binding domain which binds to an epitope included in an epitope to which a CD3 binding domain comprising any one selected from the above (a) to (h), (aa) to (rr), and anti-CD3 monoclonal antibodies SP34 and KM14 binds are exemplified.

As the epitope present on the CD3 molecule to which the CD3 binding domain of the present invention binds, an amino acid sequence from the N terminus to position 27 of the amino acid sequence of human CD3 is exemplified. Both the anti-CD3 monoclonal antibodies SP34 and KM14 bind to this epitope, and therefore, preferred examples of the epitope for CD3 in the present invention include an epitope containing at least one amino acid residue contained in the amino acid sequence from the N terminus to position 27 of the amino acid sequence of CD3, an epitope having a conformation composed of the amino acid sequence, and the like.

An antibody that binds competitively with the anti-CD3 monoclonal antibody SP34 and/or KM14 described above, and an antibody that binds to the epitope to which the antibody binds can be obtained by performing an antibody binding assay using an amino acid sequence at positions 1 to 27 of the amino acid sequence of human CD3.

Specific examples of the anti-CD3 bispecific antibody of the present invention include a bispecific antibody containing the CD3 binding domain described above.

The CD3 binding domain of the present invention can also be applied for the purpose of producing an anti-CD3 bispecific antibody whose ability to induce cytokine production is suppressed, and also for the purpose of suppressing the induction of excessive cytokine production of the anti-CD3 bispecific antibody.

The bispecific antibody or the bispecific antibody fragment thereof of the present invention also includes a bispecific antibody or a bispecific antibody fragment thereof having an effector activity.

The effector activity refers to an antibody-dependent cellular cytotoxicity activity caused through the Fc region of the antibody, and examples thereof include an ADCC activity, a complement-dependent cytotoxicity activity (CDC activity), an antibody-dependent cellular phagocytosis activity (ADCP activity) caused by phagocytes such as macrophages or dendritic cells, an opsonin effect, and the like.

In the present invention, the ADCC activity and the CDC activity can be measured using a known measurement method [Cancer Immunol. Immunother., 36, 373 (1993)].

The ADCC activity refers to an activity in which an antibody bound to an antigen on a target cell activates an immune cell (a natural killer cell or the like) when the antibody binds to an Fc receptor of the immune cell through the Fc region of the antibody so as to damage the target cell.

The Fc receptor (FcR) is a receptor that binds to the Fc region of the antibody, and induces various effector activities by binding of the antibody. Each FcR corresponds to the subclass of the antibody, and IgG, IgE, IgA, and IgM bind specifically to FcγR, FcεR, FcαR, and FcμR, respectively. Further, in the FcγR, there are subtypes of FcγRI (CD64), FcγRII (CD32), and FcγRIII (CD16), and the subtypes have isoforms of FcγRIA, FcγRIB, FcγRIC, FcγRIIA, FcγRIIB, FcγRIIC, FcγRIIIA, and FcγRIIIB, respectively. The different types of FcγRs are present on different cells [Annu. Rev. Immunol. 9: 457-492 (1991)]. In humans, FcγRIIIB is expressed specifically in neutrophils, and FcγRIIIA is expressed in monocytes, natural killer cells (NK cells), macrophages, and some T cells. An NK cell-dependent ADCC activity is induced through the binding of the antibody to FcγRIIIA.

The CDC activity refers to an activity in which an antibody bound to an antigen on a target cell activates a series of cascades (complement activation pathways) composed of complement-related proteins in the blood so as to damage the target cell. In addition, a protein fragment generated by the activation of the complement induces the migration and activation of an immune cell. The cascade of CDC activity starts when C1q first binds to the Fc region, and subsequently binds to C1r and C1s that are two serine proteases so as to form a C1 complex.

The CDC activity or the ADCC activity of the bispecific antibody or the bispecific antibody fragment thereof of the present invention against an antigen-expressing cell can be evaluated by a known measurement method [Cancer Immunol. Immunother., 36, 373 (1993)].

As a method for controlling the effector activity of the bispecific antibody of the present invention, a method for controlling the amount of fucose (also referred to as core fucose) that is α-1,6-linked to N-acetylglucosamine (GlcNAc) present at the reducing end of an N-linked complex sugar chain that binds to asparagine (Asn) at position 297 of the Fc region (a constant region composed of CH2 and CH3 domains) of the antibody (WO 2005/035586, WO 2002/31140, and WO 00/61739), a method for controlling by modifying an amino acid residue of the Fc region of the antibody (WO 00/42072), and the like are known.

By controlling the amount of core fucose that binds to the bispecific antibody, the ADCC activity of the antibody can be increased or decreased. For example, as a method for decreasing the content of core fucose that binds to the N-linked complex sugar chain bound to Fc of the antibody, by expressing the bispecific antibody using an α1,6-fucosyltransferase gene-deficient host cell, the bispecific antibody having high ADCC can be obtained. On the other hand, as a method for increasing the content of fucose that binds to the N-linked complex sugar chain bound to Fe of the bispecific antibody, by expressing the antibody using a host cell transfected with an α1,6-fucosyltransferase gene, the bispecific antibody having a low ADCC activity can be obtained.

In addition, the ADCC activity or the CDC activity can be increased or decreased by modifying an amino acid residue in the Fc region of the bispecific antibody. For example, by using the amino acid sequence of the Fc region described in US Patent Application Publication No. 2007/0148165, the CDC activity of the bispecific antibody can be increased. Further, by performing an amino acid modification described in U.S. Pat. Nos. 6,737,056, 7,297,775, 7,317,091, or the like, the ADCC activity or the CDC activity can be increased or decreased.

Further, a bispecific antibody in which the effector activity is controlled may be obtained by combining the above-mentioned methods.

The stability of the bispecific antibody of the present invention can be evaluated by measuring the amount of an aggregate (oligomer) formed in a purification process or in a sample stored under certain conditions. That is, when the amount of the aggregate decreases under the same conditions, it is evaluated that the stability of the antibody has been improved. The amount of the aggregate can be measured by separating an aggregated antibody and a non-aggregated antibody using appropriate chromatography including gel filtration chromatography.

The productivity of the bispecific antibody of the present invention can be evaluated by measuring the amount of an antibody produced from the antibody-producing cell in a culture solution. More specifically, the productivity can be evaluated by measuring the amount of the antibody contained in a culture supernatant obtained by removing the producing cell from the culture solution using an appropriate method such as an HPLC method or an ELISA method.

The bispecific antibody or the bispecific antibody fragment of the present invention includes a derivative of an antibody in which a radioisotope, a low-molecular weight drug, a high-molecular weight drug, a protein, an antibody drug, or the like is bound chemically or by genetic engineering to the bispecific antibody or the bispecific antibody fragment thereof of the present invention.

The derivative of the antibody in the present invention can be produced by binding a radioisotope, a low-molecular weight drug, a high-molecular weight drug, an immunostimulant, a protein, an antibody drug, or the like to the N-terminal side or the C-terminal side of an H chain or an L chain of the bispecific antibody or the bispecific antibody fragment thereof of the present invention, an appropriate substituent or a side chain in the antibody or the antibody fragment thereof, further, a sugar chain in the antibody or the antibody fragment thereof, or the like using a chemical method [Introduction to Antibody Engineering, Chijin Shokan Co., Ltd. (1994)].

Further, the derivative of the antibody in the present invention can be produced by a genetic engineering technique in which a DNA encoding the bispecific antibody or the bispecific antibody fragment thereof of the present invention is ligated to a DNA encoding a desired protein or antibody drug, the resultant is inserted into an expression vector, and the expression vector is introduced into an appropriate host cell to cause expression.

Examples of the radioisotope include $^{111}$In, $^{131}$I, $^{125}$I, $^{90}$Y, $^{64}$Cu, $^{99}$Tc, $^{77}$Lu, $^{211}$At, and the like. The radioisotope can be directly bound to the antibody by a chloramine T method or the like. In addition, a substance that chelates the radioisotope may be bound to the antibody. Examples of the chelating agent include 1-isothiocyanatobenzyl-3-methyldiethylenetriaminepentaacetic acid (MX-DTPA) and the like.

Examples of the low-molecular weight drug include anticancer agents such as an alkylating agent, a nitrosourea agent, an antimetabolite, an antibiotic, a plant alkaloid, a topoisomerase inhibitor, a hormonal therapy agent, a hormone antagonist, an aromatase inhibitor, a P-glycoprotein inhibitor, a platinum complex derivative, an M-phase inhibitor, or a kinase inhibitor [Clinical oncology, Japanese Journal of Cancer and Chemotherapy (1996)], anti-inflammatory agents such as a steroidal agent such as hydrocortisone or prednisone, a nonsteroidal agent such as aspirin or indomethacin, an immunomodulatory agent such as gold thiomalate or penicillamine, an immunosuppressive agent such as cyclophosphamide or azathioprine, or an antihistamine agent such as chlorpheniramine maleate or clemastine [Inflammation and anti-inflammatory therapy, Ishiyaku Publishers, Inc. (1982)], and the like.

Examples of the anticancer agent include amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (Adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, peplomycin, estramustine, paclitaxel (Taxol), docetaxel (Taxotere), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (Iressa), imatinib (ST1571), erlotinib, an FMS-like tyrosine kinase 3 (Flt3) inhibitor, a vascular endothelial growth factor receptor (VEGFR) inhibitor, a fibroblast growth factor receptor (FGFR) inhibitor, an epidermal growth factor receptor (EGFR) inhibitor such as Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, a progestin, an estrogen, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, bortezomib, allopurinol, calicheamicin, ibritumomab tiuxetan, targretin, ozogamine, clarithromycin, leucovorin, ketoconazole, aminoglutethimide, suramin, methotrexate, or maytansinoid, or a derivative thereof, and the like.

Examples of a method for binding a low-molecular weight drug to the bispecific antibody or the bispecific antibody fragment thereof of the present invention include a method for binding between amino groups of the drug and the antibody via glutaraldehyde, a method for binding an amino group of the drug to a carboxyl group of the antibody via a water-soluble carbodiimide, and the like.

Examples of the high-molecular weight drug include polyethylene glycol (PEG), albumin, dextran, polyoxyethylene, a styrene-maleic acid copolymer, polyvinylpyrrolidone, a pyran copolymer, hydroxypropyl methacrylamide, and the like. By binding such a high-molecular weight compound to the bispecific antibody or the antibody fragment of the present invention, an effect such as (1) improvement of the stability against various chemical, physical, or biological factors, (2) significant extension of the blood half-life, or (3) elimination of immunogenicity or suppression of antibody production is expected [Bioconjugate pharmaceutical, Hirokawa-Shoten Ltd. (1993)].

Examples of a method for binding PEG to the bispecific antibody of the present invention include a method for reacting with a PEGylation reagent, and the like [Bioconjugate pharmaceutical, Hirokawa-Shoten Ltd. (1993)]. Examples of the PEGylation reagent include a modifying agent to an ε-amino group of lysine (JP-A-S61-178926), a modifying agent to a carboxyl group of aspartic acid and glutamic acid (JP-A-S56-23587), a modifying agent to a guanidino group of arginine (JP-A-H2-117920), and the like.

The immunostimulant may be a natural product known as an immunoadjuvant, and specific examples thereof include a drug that enhances immunity such as a $\beta(1\rightarrow3)$ glucan (for example, lentinan or schizophyllan) or α-galactosylceramide (KRN7000), and the like.

Examples of the protein include a cytokine or a growth factor that activates immunocompetent cells such as NK cells, macrophages, or neutrophils, or a toxic protein, and the like.

Examples of the cytokine or the growth factor include interferon (hereinafter referred to as IFN)-α, IFN-β, IFN-γ, interleukin (hereinafter referred to as IL)-2, IL-5, IL-6, IL-10, IL-12, IL-15, IL-18, IL-21, IL-23, a tumor necrosis factor (TNF)-α, TNF-β, a granulocyte colony-stimulating factor (G-CSF), a granulocyte-macrophage colony-stimulating factor (GM-CSF), a macrophage colony-stimulating factor (M-CSF), and the like.

Examples of the toxic protein include ricin, diphtheria toxin, ONTAK, and the like, and also include a protein toxin in which a mutation is introduced into a protein for regulating toxicity.

A fusion antibody with a protein or an antibody drug can be produced by ligating a cDNA encoding the protein to a cDNA encoding the bispecific antibody or the antibody fragment of the present invention to construct a DNA encoding the fusion antibody, inserting the DNA into an expression vector for a prokaryote or a eukaryote, and then introducing the expression vector into a prokaryote or a eukaryote to cause expression.

When the derivative of the antibody is used for a detection method or a quantitative determination method, or as a reagent for detection, a reagent for quantitative determination, or a diagnostic agent, examples of the drug to be bound to the bispecific antibody or the antibody fragment thereof of the present invention include a labeling substance to be used for a general immunological detection method or measurement method. Examples of the labeling substance include an enzyme such as alkaline phosphatase, peroxidase, or luciferase, a luminescent substance such as acridinium ester or lophine, or a fluorescent substance such as fluorescein isothiocyanate (FITC) or tetramethylrhodamine isothiocyanate (RITC), Alexa (registered trademark) Fluor 488, or R-phycoerythrin (R-PE), and the like.

In the present invention, the bispecific antibody and the bispecific antibody fragment thereof having cellular cytotoxicity such as a CDC activity or an ADCC activity are included. The CDC activity or the ADCC activity of the bispecific antibody or the bispecific antibody fragment thereof of the present invention against an antigen-expressing cell can be evaluated by a known measurement method [Cancer Immunol. Immunother., 36, 373 (1993)].

Further, the present invention relates to a composition containing a bispecific antibody or a bispecific antibody fragment thereof that specifically recognizes and binds to CD3 and a disease-related antigen or a therapeutic agent for a disease associated with at least one of CD3 and a disease-related antigen, preferably a disease involved in a cell that expresses a disease-related antigen, containing the bispecific antibody or the bispecific antibody fragment thereof as an active ingredient.

The disease associated with at least one of CD3 and a disease-related antigen may be, for example, any as long as it is a disease associated with at least one of CD3 and a disease-related antigen, and for example, a malignant tumor, a cancer, and the like are exemplified.

The therapeutic agent containing the bispecific antibody or the bispecific antibody fragment thereof of the present invention, or a derivative thereof may contain only the bispecific antibody or the bispecific antibody fragment thereof or a derivative thereof as an active ingredient, however, in general, it is preferably provided as a pharmaceutical preparation produced using an arbitrary method known in the technical field of pharmaceutics by mixing it together with one or more pharmacologically acceptable carriers.

As the route of administration, it is preferred to use the most effective route in the treatment, and for example, oral administration or parenteral administration such as intraoral, intra-airway, intrarectal, subcutaneous, intramuscular, or intravenous administration is exemplified. Above all, intravenous administration is preferred.

Examples of a dosage form include a spray, a capsule, a tablet, a powder, a granule, a syrup, an emulsion, a suppository, an injection, an ointment, a tape, and the like.

A dose or administration frequency varies depending on a target therapeutic effect, an administration method, a treatment duration, an age, a body weight, etc., but is generally 10 μg/kg to 10 mg/kg per day for an adult.

Further, the present invention relates to a reagent for immunologically detecting or measuring at least one of CD3 and a disease-related antigen, or a diagnostic agent for a disease associated with at least one of CD3 and a disease-related antigen, preferably a disease involved in a cell that expresses a disease-related antigen, each of which contains the bispecific antibody or the bispecific antibody fragment thereof of the present invention. In addition, the present invention relates to a method for immunologically detecting or measuring at least one of CD3 and a disease-related antigen, a therapeutic method for a disease associated with at least one of CD3 and a disease-related antigen, preferably a disease involved in a cell that expresses a disease-related antigen, or a diagnostic method for a disease associated with at least one of CD3 and a disease-related antigen, preferably a disease involved in a cell that expresses a disease-related antigen, each of which uses the bispecific antibody or the bispecific antibody fragment thereof of the present invention.

Examples of a method for detecting or measuring the amount of at least one of CD3 and a disease-related antigen in the present invention include any known methods. For example, an immunological detection or measurement method and the like are exemplified.

The immunological detection or measurement method is a method for detecting or measuring the amount of an antibody or the amount of an antigen using a labeled antigen or antibody. Examples of the immunological detection or measurement method include a radioimmunoassay method (RIA), an enzyme immunoassay method (EIA or ELISA), a fluorescence immunoassay method (FIA), a luminescent immunoassay method, a Western blotting method, a physicochemical method, and the like.

By detecting or measuring a cell having expressed at least one of CD3 and a disease-related antigen using the bispecific antibody or the bispecific antibody fragment thereof of the present invention, it is possible to diagnose a disease associated with at least one of CD3 and a disease-related antigen, preferably a disease involved in a cell that expresses a disease-related antigen.

It is possible to use a known immunological detection method for detecting a cell having expressed at least one of CD3 and a disease-related antigen, but for example, an immunoprecipitation method, an immunocytological staining method, an immunohistological staining method, or a fluorescent antibody staining method, and the like are exemplified. In addition, for example, a fluorescent antibody staining method such as an FMAT 8100 HTS system (manufactured by Applied Biosystems, Inc.), and the like are also exemplified.

A biological sample to be subjected to detection or measurement of at least one of CD3 and a disease-related antigen in the present invention includes, for example, a tissue cell, blood, plasma, serum, pancreatic juice, urine, feces, a tissue fluid, a culture solution, and the like, and is not particularly limited as long as the sample may contain a cell having expressed at least one of CD3 and a disease-related antigen.

The diagnostic agent containing the bispecific antibody or the bispecific antibody fragment thereof of the present invention, or a derivative thereof may contain a reagent for performing an antigen-antibody reaction or a reagent for detecting the reaction in accordance with a target diagnostic method. Examples of the reagent for performing an antigen-antibody reaction include a buffer, a salt, and the like.

Examples of the reagent for detection include a reagent, which is used for a general immunological detection or measurement method, such as a labeled secondary antibody that binds to the bispecific antibody or the bispecific antibody fragment thereof, or a derivative thereof, or a substrate corresponding to a label.

Hereinafter, a method for producing the bispecific antibody of the present invention, a method for evaluating the activity of the bispecific antibody or the bispecific antibody fragment thereof, and a therapeutic method and a diagnostic method for a disease using the bispecific antibody or the bispecific antibody fragment thereof will be specifically described.

1. Method for Producing Monoclonal Antibody

A method for producing a monoclonal antibody in the present invention includes the following operation steps. That is, (1) at least one of the purification of an antigen to be used as an immunogen and the production of a cell in which the antigen is overexpressed on the cell surface, (2) a step of preparing an antibody-producing cell by immunizing an animal with the antigen, followed by collecting the blood and examining an antibody titer thereof to determine when to resect the spleen or the like, (3) preparing a myeloma cell (myeloma), (4) fusing the antibody-producing cell with the myeloma, (5) screening a hybridoma group that produces a target antibody, (6) separating (cloning) a monoclonal cell from the hybridoma group, (7) in some cases, culturing the hybridoma for producing a monoclonal antibody in a large amount, or breeding an animal implanted with the hybridoma, (8) investigating the bioactivity of the monoclonal antibody produced in this manner, and the antigen binding specificity thereof, or examining the characteristics as a labeling reagent, and the like.

Hereinafter, a method for producing a monoclonal antibody that binds to CD3 and a monoclonal antibody that binds to a disease-related antigen, which are used for producing the bispecific antibody that binds to CD3 and a disease-related antigen in the present invention, will be described in detail in accordance with the above-mentioned steps. The method for producing the antibodies is not limited thereto, and for example, an antibody-producing cell other than a spleen cell, and a myeloma can also be used.

(1) Purification of Antigen

A cell allowed to express a disease-related antigen or CD3 can be obtained by introducing an expression vector containing a cDNA encoding the full length of a disease-related antigen or CD3 or a partial length thereof into *E. coli*, yeast, an insect cell, an animal cell, or the like. In addition, at least one of CD3 and a disease-related antigen is purified from various human cultured tumor cells or human tissues or the like in which at least one of CD3 and a disease-related antigen is expressed in a large amount and can be used as an antigen. In addition, the cultured tumor cell or the tissue or the like can also be used as an antigen as it is. Further, a synthetic peptide having a partial sequence of CD3 or a disease-related antigen is prepared by a chemical synthesis method such as an Fmoc method or a tBoc method and can also be used as an antigen.

CD3 or a disease-related antigen used in the present invention can be produced using a method described in Molecular Cloning, A Laboratory Manual, Second Edition, Cold Spring Harbor Laboratory Press (1989), or Current Protocols In Molecular Biology, John Wiley & Sons (1987-1997), or the like, for example, by expressing a DNA encoding the CD3 or the disease-related antigen in a host cell using the following method.

A recombinant vector is produced by inserting a full-length cDNA containing a region encoding CD3 or a disease-related antigen downstream of a promoter in an appropriate expression vector. A DNA fragment that has been prepared based on the full-length cDNA and has an appropriate length and contains a region encoding a polypeptide may be used in place of the full-length cDNA. Subsequently, by introducing the obtained recombinant vector into a host cell suitable for the expression vector, a transformant that produces CD3 or a disease-related antigen can be obtained.

As the expression vector, any vector can be used as long as it can autonomously replicate or can be integrated into a chromosome in a host cell to be used, and contains an appropriate promoter at a position capable of transcribing a DNA encoding CD3 or a disease-related antigen.

As the host cell, any cell, for example, a microorganism belonging to the genus *Escherichia* such as *E. coli* or the like, yeast, an insect cell, an animal cell, or the like, can be used as long as it can express a target gene.

When a prokaryote such as *E. coli* is used as the host cell, the recombinant vector is preferably a vector that can autonomously replicate in the prokaryote, and also contains a promoter, a ribosomal binding sequence, a DNA containing a region encoding CD3 or a disease-related antigen, and a transcription termination sequence. In addition, the transcription termination sequence is not necessarily needed for the recombinant vector, however, it is preferred that the transcription termination sequence is placed immediately downstream of a structural gene. Further, the recombinant vector may contain a gene that controls the promoter.

As the recombinant vector, it is preferred to use a plasmid in which the distance between a Shine-Dalgamo sequence, which is a ribosomal binding sequence, and a start codon is adjusted to an appropriate distance (for example, 6 to 18 nucleotides).

In addition, in the nucleotide sequence of the DNA encoding CD3 or a disease-related antigen, it is possible to substitute a nucleotide so as to obtain an optimal codon for expression in a host, and as a result, the production rate of the target CD3 or disease-related antigen can be improved.

As the expression vector, any vector can be used as long as it can exhibit its function in a host cell to be used, and examples thereof include pBTrp2, pBTac1, pBTac2 (each of which is manufactured by Roche Diagnostics K.K.), pKK233-2 (manufactured by Pharmacia Corporation), pSE280 (manufactured by Invitrogen), pGEMEX-1 (manufactured by Promega Corporation), pQE-8 (manufactured by QIAGEN N.V.), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corporation), pTrs30 [prepared from *E. coli* JM109/pTrS30 (FERM BP-5407)], pTrs32 [prepared from *E. coli* JM109/pTrS32 (FERM BP-5408)], pGHA2 [prepared from *E. coli* IGHA2 (FERM BP-400), JP-A-S60-221091], pGKA2 [prepared from *E. coli* IGKA2 (FERM BP-6798), JP-A-S60-221091], pTerm2 (U.S. Pat. Nos. 4,686,191, 4,939,094, or U.S. Pat. No. 5,160,735), pSupex, pUB110, pTP5, pC194, pEG400 [J. Bacteriol., 172, 2392 (1990)], pGEX (manufactured by Pharmacia Corporation), pET System (manufactured by Novagen, Inc.), pME18SFL3 (manufactured by Toyobo Co., Ltd.), and the like.

The promoter may be any as long as it functions in a host cell to be used. Examples thereof include promoters derived from *E. coli*, a phage, or the like such as a trp promoter (Ptrp), a lac promoter, a PL promoter, a PR promoter, or a T7 promoter. In addition, examples thereof also include artificially designed and modified promoters such as a tandem promoter in which two Ptrp promoters are linked in tandem, a tac promoter, a lacT7 promoter, or a let I promoter, and the like.

Examples of the host cell include *E. coli* XL1-Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, *E. coli* DH5a, and the like.

As a method for introducing a recombinant vector into a host cell, any method can be used as long as it is a method for introducing a DNA into a host cell to be used, and examples thereof include a method using calcium ions [Proc. Natl. Acad. Sci. USA, 69, 2110 (1972), Gene, 17, 107 (1982), Molecular & General Genetics, 168, 111 (1979)].

When an animal cell is used as a host, as the expression vector, any vector can be used as long as it functions in an animal cell, and examples thereof include pcDNAI (manufactured by Invitrogen), pcDM8 (manufactured by Funakoshi Co., Ltd.), pAGE107 [JP-A-H3-22979; Cytotechnology, 3, 133 (1990)], pAS3-3 (JP-A-H2-227075), pCDM8 [Nature, 329, 840 (1987)], pcDNAI/Amp (manufactured by Invitrogen), pcDNA3.1 (manufactured by Invitrogen), pREP4 (manufactured by Invitrogen), pAGE103 [J. Biochemistry, 101, 1307 (1987)], pAGE210, pME18SFL3, pKANTEX93 (WO 97/10354), and the like.

As the promoter, any promoter can be used as long as it can exhibit its functions in an animal cell, and examples thereof include a cytomegalovirus (CMV) immediate early (IE) gene promoter, an SV40 early promoter, a retrovirus promoter, a metallothionein promoter, a heat-shock promoter, an SRα promoter, or a Moloney murine leukemia virus promoter or enhancer. In addition, a human CMV IE gene enhancer may be used together with the promoter.

Examples of the host cell include a human Burkitt's lymphoma cell Namalwa, an African Green Monkey kidney-derived cell COS, a Chinese hamster ovary-derived cell CHO, a human leukemia cell HBT5637 (JP-A-S63-000299), and the like.

As a method for introducing a recombinant vector into a host cell, any method can be used as long as it is a method for introducing a DNA into an animal cell, and examples thereof include an electroporation method [Cytotechnology, 3, 133 (1990)], a calcium phosphate method (JP-A-H2-227075), a lipofection method [Proc. Natl. Acad. Sci. USA, 84, 7413 (1987)], and the like.

CD3 or a disease-related antigen can be produced by culturing a transformant derived from a microorganism or an animal cell or the like having a recombinant vector incorporating a DNA encoding CD3 or a disease-related antigen obtained as described above in a culture medium, allowing the transformant to produce and accumulate the CD3 or the disease-related antigen in the culture, and then collecting it from the culture. A method for culturing the transformant in a culture medium can be carried out according to a usual method used for culturing a host.

In the case of causing expression in a cell derived from a eukaryote, it is possible to obtain CD3 or a disease-related antigen to which a sugar or a sugar chain is added.

When culturing a microorganism transformed with a recombinant vector using an inducible promoter, an inducer may be added to a culture medium as needed. For example, when a microorganism transformed with a recombinant vector using a lac promoter is cultured, isopropyl-β-D-thiogalactopyranoside or the like may be added to a culture medium, and when a microorganism transformed with a recombinant vector using a trp promoter is cultured, indoleacrylic acid or the like may be added to a culture medium.

Examples of the culture medium in which the transformant obtained using an animal cell as a host is cultured include RPMI 1640 medium [The Journal of the American Medical Association, 199, 519 (1967)], Eagle's MEM medium [Science, 122, 501 (1952)], Dulbecco's modified MEM medium [Virology, 8, 396 (1959)], Medium 199 [Proc. Soc. Exp. Biol. Med., 73, 1 (1950)], Iscove's modified Dulbecco's medium (IMDM), which are generally used, or a culture medium in which fetal bovine serum (FBS) or the like is added to any of these culture media, and the like. The culture is usually carried out under the conditions of pH 6 to 8 and 30 to 40° C. in the presence of 5% $CO_2$ for 1 to 7 days. In addition, during the culture, an antibiotic such as kanamycin or penicillin may be added to the culture medium as needed.

As a method for expressing a gene encoding CD3 or a disease-related antigen, a method of secretory production, fused protein expression, or the like [Molecular Cloning, A Laboratory Manual, Second Edition, Cold Spring Harbor Laboratory Press (1989)] can be used in addition to direct expression. Examples of a method for producing CD3 or a disease-related antigen include a method for producing it in a host cell, a method for secreting it out of a host cell, and a method for producing it on an outer membrane of a host cell, and an appropriate method can be selected by changing a host cell to be used or the structure of CD3 or a disease-related antigen to be produced.

For example, an antigen fusion protein can be produced by preparing a DNA in which a DNA encoding an Fc region of an antibody, a DNA encoding glutathione S-transferase (GST), a DNA encoding a FLAG tag, a DNA encoding a Histidine tag, or the like is ligated to a DNA encoding an amino acid sequence of an extracellular domain, followed by expression and purification. Specific examples thereof include an Fc-fusion protein in which an extracellular domain of CD3 or a disease-related antigen is bound to an Fc region of human IgG, and a fusion protein of an extracellular domain of CD3 or a disease-related antigen with glutathione S-transferase (GST).

When CD3 or a disease-related antigen is produced in a host cell or on an outer membrane of a host cell, CD3 or a disease-related antigen can be actively secreted out of the host cell using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)], or a method described in JP-A-H05-336963, WO 94/23021, or the like. In addition, the production amount of CD3 or a disease-related antigen can also be increased by utilizing a gene amplification system using a dihydrofolate reductase gene or the like (JP-A-H2-227075).

The produced CD3 or disease-related antigen can be isolated and purified, for example, as follows.

When CD3 or a disease-related antigen is expressed in cells in a dissolved state, the cells are collected by centrifugation after completion of the culture, suspended in an aqueous buffer solution, followed by homogenization of the cells using an ultrasonic homogenizer, a French press, a Manton Gaulin homogenizer, a Dyno mill, or the like, whereby a cell-free extract solution is obtained. It is possible to obtain a purified protein from a supernatant obtained by centrifugation of the cell-free extract solution using methods such as general protein isolation and purification methods, that is, a solvent extraction method, a salting-out method using ammonium sulfate or the like, a desalting method, a precipitation method using an organic solvent, anion exchange chromatography using a resin such as diethylaminoethyl (DEAE)-Sepharose or DIAION HPA-75 (manufactured by Mitsubishi Chemical Corporation), cation exchange chromatography using a resin such as S-Sepharose FF (manufactured by Pharmacia Corporation), hydrophobic chromatography using a resin such as Butyl Sepharose or Phenyl Sepharose, a gel filtration method using a molecular sieve, affinity chromatography, a chromatofocusing method, electrophoresis such as isoelectric focusing electrophoresis, and the like alone or in combination.

When CD3 or a disease-related antigen is expressed in cells by forming an insoluble body, the cells are collected and then homogenized in the same manner as described above, followed by centrifugation, whereby the insoluble body of the CD3 or the disease-related antigen is collected as a precipitated fraction. The collected insoluble body of the CD3 or the disease-related antigen is solubilized with a protein denaturing agent. The CD3 or the disease-related antigen is returned to a normal conformation by diluting or dialyzing the solubilized solution, and thereafter, a purified protein of a polypeptide can be obtained by the same isolation and purification methods as described above.

When CD3 or a disease-related antigen, or a derivative thereof such as a sugar-modified body thereof is extracellularly secreted, the CD3 or the disease-related antigen, or the derivative thereof such as a sugar-modified body thereof can be collected in a culture supernatant. The culture supernatant is subjected to a treatment using a method such as centrifugation in the same manner as described above, thereby obtaining a soluble fraction, and then, by using the same isolation and purification methods as described above, a purified protein can be obtained from the soluble fraction.

In addition, CD3 or a disease-related antigen used in the present invention can also be produced using a chemical synthesis method such as an Fmoc method or a tBoc method. Specifically, for example, chemical synthesis can be carried out by utilizing a peptide synthesizer manufactured by Advanced Chemtech, Inc., PerkinElmer, Inc., Pharmacia Corporation, Protein Technology Instrument, Inc., Synthecell-Vega Biomolecules Corporation, Perceptive, Inc., Shimadzu Corporation, or the like.

(2) Step of Preparing Antibody-Producing Cell

An animal such as a mouse, a rat, a hamster, a rabbit, cattle, or an alpaca is immunized with the antigen obtained in (1), and an antibody-producing cell in the spleen, the lymph node, or the peripheral blood of the animal is collected. In addition, as the animal, for example, a transgenic mouse that produces a human-derived antibody described in the document of Tomizuka. et al. [Tomizuka. et al., Proc Natl Acad Sci USA., 97, 722 (2000)], a conditional knockout mouse of CD3 or a disease-related antigen for enhancing immunogenicity, or the like is exemplified as an immunized animal.

The immunization is performed by administering an antigen together with an appropriate adjuvant such as a Freund's complete adjuvant, an aluminum hydroxide gel, *Bordetella pertussis* vaccine, or the like. As a method for administration of an immunogen when immunizing a mouse, any method of subcutaneous injection, intraperitoneal injection, intravenous injection, intradermal injection, intramuscular injection, footpad injection, and the like may be used, but intraperitoneal injection, footpad injection, or intravenous injection is preferred. When the antigen is a partial peptide, a conjugate of the antigen with a carrier protein such as BSA (bovine serum albumin) or KLH (Keyhole Limpet hemocyanin) is produced and used as an immunogen.

The administration of the antigen is performed 5 to 10 times every 1 to 2 weeks after the first administration. On day 3 to 7 after each administration, the blood is collected from a venous plexus of the fundus, and the antibody titer of the serum thereof is measured using an enzyme immunoassay method [Antibodies—A Laboratory Manual, Cold Spring Harbor Laboratory (1988)] or the like. If an animal whose serum shows a sufficient antibody titer against the antigen used for the immunization is used as a supply source for the antibody-producing cell for fusion, the effect of the subsequent operation can be enhanced.

On day 3 to 7 after the final administration of the antigen, a tissue including the antibody-producing cell such as the spleen is resected from the immunized animal, and the antibody-producing cell is collected. The antibody-producing cell is a lymphocyte that is a plasma cell and a progenitor cell thereof, and the cell may be obtained from any site of an individual and can be generally obtained from the spleen, lymph node, bone marrow, tonsil, peripheral blood, or an appropriate combination thereof, or the like, but spleen cells are most generally used. When spleen cells are used, the spleen is shredded and loosened, followed by centrifugation, and then, red blood cells are removed, whereby the antibody-producing cells for fusion are obtained.

(3) Step of Preparing Myeloma

As a myeloma, a cell that is derived from a mammal such as a mouse, a rat, a guinea pig, a hamster, a rabbit, or a human, and that has no ability of autoantibody production can be used, however, generally, an established cell line obtained from a mouse, for example, an 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)], or the like is used. The cell line is subcultured in a suitable culture medium, for example, a culture medium such as an 8-azaguanine medium [RPMI 1640 medium supplemented with glutamine, 2-mercapto-ethanol, gentamicin, FCS, and 8-azaguanine], Iscove's modified Dulbecco's medium (hereinafter referred to as "IMDM"), or Dulbecco's modified Eagle medium (hereinafter referred to as "DMEM"). The above-mentioned cell line is subcultured in a normal culture medium (for example, DMEM medium containing 10% FCS) 3 to 4 days before cell fusion, and $2\times10^7$ or more cells are ensured on the day of performing the fusion.

(4) Cell Fusion

The antibody-producing cells for fusion obtained in (2) and the myeloma cells obtained in (3) are well washed with Minimum Essential Medium (MEM) or PBS (1.83 g of disodium phosphate, 0.21 g of monopotassium phosphate, 7.65 g of sodium chloride, 1 L of distilled water, pH 7.2), and mixed to give the antibody-producing cells for fusion: the myeloma cells=5:1 to 10:1, followed by centrifugation, and then, the supernatant is removed. After the precipitated cell clusters are well loosened, a mixed solution of polyethylene glycol 1000 (PEG-1000), MEM medium, and dimethyl sulfoxide is added thereto while stirring at 37° C. Further, 1 to 2 mL of MEM medium is added thereto every 1 to 2 minutes several times, and then, MEM medium is added thereto so that the total amount becomes 50 mL. After centrifugation, the supernatant is removed, the precipitated cell clusters are gently loosened, and then, the cells are gently suspended in HAT medium [a normal culture medium supplemented with hypoxanthine, thymidine, and aminopterin]. The resulting suspension is cultured in a 5% $CO_2$ incubator at 37° C. for 7 to 14 days.

In addition, the cell fusion can also be carried out by the following method. The spleen cells and the myeloma cells are well washed with a serum-free culture medium (for example, DMEM), or phosphate buffered saline (hereinafter referred to as "phosphate buffer solution"), and mixed so that the cell count ratio of the spleen cells to the myeloma cells becomes about 5:1 to 10:1, followed by centrifugation. The supernatant is removed, and after the precipitated cell clusters are well loosened, 1 mL of a serum-free culture medium containing 50% (w/v) polyethylene glycol (molecular weight: 1000 to 4000) is added dropwise thereto while stirring. Thereafter, 10 mL of the serum-free culture medium is slowly added thereto, followed by centrifugation. The supernatant is removed again, the precipitated cells are suspended in an appropriate amount of a normal culture medium containing a hypoxanthine-aminopterin-thymidine (HAT) solution and human interleukin 2 (IL-2) (hereinafter referred to as HAT medium), and the suspension is dispensed in each well of a culture plate (hereinafter referred to as a plate), and then, the cells are cultured in the presence of 5% carbon dioxide gas at 37° C. for about 2 weeks. During the course of the culture, the HAT medium is supplemented as appropriate.

(5) Selection of Hybridoma Group

When the myeloma cell used for the fusion is an 8-azaguanine resistant strain, that is, a hypoxanthine-guanine-phosphoribosyltransferase (HGPRT)-deficient strain, the unfused myeloma cell and a fused cell of the myeloma cells cannot survive in the HAT medium. On the other hand, a fused cell of the antibody-producing cells, and a hybridoma of the antibody-producing cell and the myeloma cell can survive in the HAT medium, however, the life span of the fused cell of the antibody-producing cells is reached shortly. Therefore, by continuing the culture in the HAT medium, only the hybridoma of the antibody-producing cell and the myeloma cell survives, and as a result, the hybridoma can be obtained.

For a hybridoma grown in a colony form, medium replacement with a culture medium obtained by removing aminopterin from the HAT medium (hereinafter referred to as HT medium) is performed. Thereafter, a portion of the culture supernatant is collected, and a hybridoma that produces an antibody can be selected using the below-mentioned antibody titer measurement method. Examples of the antibody titer measurement method include various known techniques such as a radioisotopic immunoassay method (RIA method), a solid-phase enzyme immunoassay method (ELISA method), a fluorescent antibody method, and a passive hemagglutination reaction method, but an RIA method or an ELISA method is preferred from the viewpoint of detection sensitivity, rapidity, accuracy, a possibility of automation of an operation, and the like.

The hybridoma determined to produce a desired antibody by measuring the antibody titer is transferred to another plate, and cloning is performed. Examples of the cloning method include a limiting dilution method in which culture is performed by dilution so that one cell is contained in one well of a plate, a soft agar method in which culture is performed in a soft agar medium to collect colonies, a method in which one cell is isolated using a micromanipulator, a method in which one cell is isolated using a cell sorter, and the like.

For a well in which the antibody titer is observed, for example, cloning by a limiting dilution method is repeated 2 to 4 times, and the cell in which the antibody titer is stably observed is selected as a hybridoma strain that produces a monoclonal antibody against CD3 or a disease-related antigen.

(6) Preparation of Monoclonal Antibody

The monoclonal antibody-producing hybridoma obtained in (5) is intraperitoneally injected into a mouse or a nude mouse at the age of 8 to 10 weeks having been subjected to a pristane treatment [0.5 mL of 2,6,10,14-tetramethylpentadecane (Pristane) is intraperitoneally administered, followed by breeding for 2 weeks]. In 10 to 21 days, the hybridoma is converted into an ascites tumor. The ascites is collected from this mouse, followed by removing solids by centrifugation, and then salting out with 40 to 50% ammonium sulfate. Thereafter, purification is performed by a caprylic acid precipitation method, a DEAE-Sepharose column, a protein A column, or a gel filtration column, and then, an IgG or IgM fraction is collected and a purified monoclonal antibody is prepared. In addition, by growing the hybridoma in the peritoneal cavity of a mouse of the same strain (for example, BALB/c) or a Nu/Nu mouse, a rat, a guinea pig, a hamster, a rabbit, or the like, ascites containing a large amount of a monoclonal antibody that binds to CD3 or a disease-related antigen can be obtained.

After culturing the monoclonal antibody-producing hybridoma obtained in (5) in RPMI 1640 medium supplemented with 10% FBS, or the like, the supernatant is removed by centrifugation, and the residue is suspended in GIT medium or Hybridoma-SFM medium supplemented with 5% Daigo's GF21, or the like, and then cultured for 3 to 7 days by flask culture, spinner culture, bag culture, or the like. The obtained cell suspension is centrifuged, and purification from the obtained supernatant is performed using a protein A column or a protein G column, and then, an IgG fraction is collected, whereby a purified monoclonal antibody can also be obtained. As a simple method for the purification, it is also possible to utilize a commercially available monoclonal antibody purification kit (for example, MabTrap GII kit manufactured by Amersham Pharmacia Biotech), or the like.

The determination of the subclass of the antibody is carried out by an enzyme immunoassay method using a subclass typing kit. The quantitative determination of a protein amount can be carried out by a Lowry method or a method of calculation from the absorbance at 280 nm [1.4 ($OD_{280}$)=1 mg/mL immunoglobulin].

(7) Binding Assay of Monoclonal Antibody to CD3 or Disease-Related Antigen

The anti-CD3 bispecific antibody of the present invention includes a CD3 binding domain with reduced affinity for CD3, and the CD3 binding domain can be established using the anti-CD3 monoclonal antibody SP34 or KM14 as a control in the above-mentioned binding assay.

For example, a desired CD3 binding domain can be established by screening an antibody with affinity reduced by 10% or more as compared with the anti-CD3 monoclonal antibody SP34 or KM14 from an anti-CD3 monoclonal antibody library. Further, an antibody library in which a random mutation is introduced into the amino acid sequence of CDR or an FR region is produced based on the amino acid sequence of CDR or VH/VL of the anti-CD3 monoclonal antibody SP34 or KM14, and a desired CD3 binding domain can be established by screening an antibody with affinity reduced by 10% or more as compared with the anti-CD3 monoclonal antibody SP34 or KM14 from the library.

The binding activity of the monoclonal antibody to CD3 or a disease-related antigen can be measured by a binding assay system such as an Ouchterlony method, an ELISA method, an RIA method, a flow cytometry method (FCM), or a surface plasmon resonance (SPR) method.

The Ouchterlony method is simple, but a concentration operation is needed when the concentration of the antibody is low. On the other hand, when the ELISA method or the RIA method is used, by allowing a culture supernatant to directly react with an antigen-adsorbed solid phase and further by using antibodies corresponding to various immunoglobulin isotypes and subclasses as secondary antibodies, it is possible to identify the isotype and subclass of the antibody and also to measure the binding activity of the antibody.

As a specific example of the procedure, the purified or partially purified recombinant CD3 or a disease-related antigen is adsorbed to a solid phase surface of a 96-well plate for ELISA or the like, and then, the solid phase surface to which the antigen is not adsorbed is blocked with a protein unrelated to the antigen, for example, bovine serum albumin (BSA). After an ELISA plate is washed with phosphate buffer saline (PBS) and PBS containing 0.05% Tween 20 (Tween-PBS) or the like, a serially diluted first antibody (for example, mouse serum, a culture supernatant, or the like) is allowed to react therewith, and then, the antibody is bound to the antigen immobilized on the plate. Subsequently, as a second antibody, an anti-immunoglobulin antibody labeled with biotin, an enzyme (horse radish peroxidase (HRP), alkaline phosphatase (ALP), or the like), a chemiluminescent substance or a radioactive compound, or the like, is dispensed to allow the second antibody to react with the first antibody bound to the plate. After well washing with Tween-PBS, a reaction according to the labeling substance of the second antibody is performed, and a monoclonal antibody that specifically reacts with the target antigen is selected.

In the FCM method, the binding activity of an antibody to an antigen-expressing cell can be measured [Cancer Immunol. Immunother., 36, 373 (1993)]. The fact that an antibody binds to a membrane protein antigen expressed on a cell membrane means that the antibody recognizes the conformation of a naturally occurring antigen and binds thereto.

Examples of the SPR method include a kinetics analysis by Biacore. For example, by using Biacore T100, the kinetics in binding of an antigen and a test substance is measured, and the result is analyzed with an analysis software attached to an instrument. As a specific example of the procedure, after fixing an anti-mouse IgG antibody to a sensor chip CM5 by an amine coupling method, a test substance such as a hybridoma culture supernatant or a purified monoclonal antibody is allowed to flow and bind in an appropriate amount, further the antigen at multiple known concentrations is allowed to flow, and then, binding and dissociation are measured. Subsequently, a kinetics analysis by a 1:1 binding model is performed for the obtained data using the software attached to the instrument to obtain various parameters. Alternatively, after fixing CD3 or a disease-related antigen onto the sensor chip by, for example, an amine coupling method, a purified monoclonal antibody at multiple known concentrations is allowed to flow, and then, binding and dissociation are measured. A kinetics analysis by a 1:1 binding model or a bivalent binding model is performed for the obtained data using the software attached to the instrument to obtain various parameters.

In addition, in the present invention, it is possible to select an antibody that binds to CD3 or a disease-related antigen competitively with the antibody against CD3 or a disease-related antigen by allowing a test antibody to coexist in the above-mentioned binding assay system to cause a reaction. That is, by screening an antibody whose binding to an antigen is inhibited when a test antibody is added, it is possible to obtain an antibody that competes with the antibody obtained above for binding to CD3 or a disease-related antigen.

(8) Identification of Epitope for Monoclonal Antibody against CD3 or Disease-Related Antigen In the present invention, the identification of an epitope which the antibody recognizes and binds to can be carried out as follows.

For example, a partially deficient variant of an antigen, a mutant of an antigen in which an amino acid residue different among species is modified, or a mutant of an antigen in which a specific domain is modified is produced, and if the reactivity of an antibody against the deficient variant or the mutant is lowered, it becomes clear that the deficient site or the amino acid modification site is an epitope for the antibody. Such a partially deficient variant or a mutant of an antigen may be obtained as a secretory protein using a suitable host cell, for example, *E. coli*, yeast, a plant cell, a mammalian cell, or the like, or may be prepared as an antigen-expressing cell by expressing it on a cell membrane of a host cell. In the case of a membrane-associated antigen, in order to express it while maintaining the conformation of the antigen, it is preferred to express it on the membrane of a host cell. In addition, it is also possible to confirm the reactivity of the antibody by producing a synthetic peptide mimicking the primary structure or the conformation of the antigen. As for a synthetic peptide, a method for producing various partial peptides of the molecule thereof using a known peptide synthesis technique, and the like are exemplified.

For example, with respect to the extracellular domain of human and mouse CD3 or a disease-related antigen, it is possible to identify an epitope for an antibody by producing a chimeric protein in which domains constituting the respective regions are appropriately combined, and then confirming the reactivity of the antibody with the protein. Thereafter, it is possible to specify the epitope in more detail by variously synthesizing an oligopeptide of the corresponding region or a mutant or the like of the peptide using an oligopeptide synthesis technique well known to those skilled in the art, and then confirming the reactivity of the antibody with the peptide. As a simple method for obtaining many types of oligopeptides, a commercially available kit [for example, SPOTs Kit (manufactured by Genosys Biotechnologies, Inc.), a series of multipin peptide synthesis kits (manufactured by Chiron Corporation) using a multipin synthesis method, or the like] can also be utilized.

An antibody that binds to the same epitope as an epitope to which an antibody that binds to CD3 or a disease-related antigen binds can be obtained by identifying an epitope for an antibody obtained in the above-mentioned binding assay system, producing a partial synthetic peptide of the epitope, a synthetic peptide mimicking the conformation of the epitope, a recombinant of the epitope, or the like, and then performing immunization therewith.

For example, if the epitope is a membrane protein, an antibody specific to the epitope can be more efficiently produced by producing a recombinant fusion protein in which the entire extracellular domain or a part of the extracellular domain is linked to an appropriate tag, for example, a FLAG tag, a Histidine tag, a GST protein or an antibody Fc region, or the like, and performing immunization with the recombinant protein.

2. Production of Genetically Recombinant Antibody

As production examples of the genetically recombinant antibody, methods for producing a chimeric antibody, a humanized antibody, and a human antibody will be described below, although the methods are schematically described in P. J. Delves., ANTIBODY PRODUCTION ESSENTIAL TECHNIQUES., 1997 WILEY, P. Shepherd and C. Dean. Monoclonal Antibodies., 2000 OXFORD UNIVERSITY PRESS, and J. W. Goding., Monoclonal Antibodies: principles and practice., 1993 ACADEMIC PRESS, and the like. In addition, genetically recombinant mouse, rat, hamster, and rabbit antibodies can also be produced using the same method.

(1) Acquisition of cDNA Encoding V Region of Monoclonal Antibody from Hybridoma

Acquisition of cDNAs encoding VH and VL of a monoclonal antibody can be carried out, for example, as follows.

First, mRNA is extracted from a hybridoma that produces a monoclonal antibody, and cDNAs are synthesized. Subsequently, the synthesized cDNAs are each cloned into a vector such as a phage or a plasmid, thereby producing a cDNA library. A recombinant phage or a recombinant plasmid containing a cDNA encoding VH or VL is isolated from the library using a DNA encoding a C region part or a V region part of the antibody as a probe, respectively. The entire nucleotide sequence of VH or VL in the isolated recombinant phage or recombinant plasmid is determined, and then, the entire amino acid sequence of VH or VL is deduced from the nucleotide sequence.

As a non-human animal used for producing a hybridoma, a mouse, a rat, a hamster, a rabbit, or the like is used, but any animal can be used as long as a hybridoma can be produced.

In the preparation of the total RNA from a hybridoma, a guanidine thiocyanate-cesium trifluoroacetate method [Methods in Enzymol., 154, 3 (1987)], or a kit such as RNA easy Kit (manufactured by QIAGEN N.V.), or the like is used.

In the preparation of mRNA from the total RNA, an oligo (dT)-immobilized cellulose column method [Molecular Cloning, A Laboratory Manual, Second Edition, Cold Spring Harbor Laboratory Press (1989)], or a kit such as Oligo-dT30<Super> mRNA Purification Kit (manufactured by Takara Bio, Inc.), or the like is used. Further, it is also possible to prepare mRNA using a kit such as Fast Track mRNA Isolation Kit (manufactured by Invitrogen), or QuickPrep mRNA Purification Kit (manufactured by Pharmacia Corporation).

In the synthesis of cDNAs and the production of a cDNA library, a known method [Molecular Cloning, A Laboratory Manual, Second Edition, Cold Spring Harbor Laboratory Press (1989), Current Protocols in Molecular Biology, Supplement 1, John Wiley & Sons (1987-1997)], or a kit such as SuperScript Plasmid System for cDNA Synthesis and Plasmid Cloning (manufactured by Invitrogen) or ZAP-cDNA Synthesis Kit (manufactured by Stratagene Corporation), or the like is used.

When the cDNA library is produced, as the vector into which a cDNA synthesized using mRNA extracted from a hybridoma as a template is incorporated, any vector can be used as long as it can incorporate the cDNA.

For example, ZAP Express [Strategies, 5, 58 (1992)], pBluescript II SK(+) [Nucleic Acids Research, 17, 9494 (1989)], XZAP II (manufactured by Stratagene Corporation), Xgt 10, Xgt 11 [DNA Cloning: A Practical Approach, I, 49 (1985)], Lambda BlueMid (manufactured by Clontech Laboratories, Inc.), XExCell, pT7T3-18U (manufactured by Pharmacia Corporation), pcD2 [Mol. Cell. Biol., 3, 280 (1983)], pUC18 [Gene, 33, 103 (1985)], or the like is used.

As *E. coli* into which a cDNA library constructed by a phage or a plasmid vector is introduced, any *E. coli* can be used as long as it can introduce, express, and maintain the cDNAlibrary. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)], or the like is used.

In the selection of a cDNA clone encoding VH or VL of a non-human antibody from the cDNA library, a colony hybridization method using an isotope or a fluorescently labeled probe, or a plaque hybridization method [Molecular Cloning, A Laboratory Manual, Second Edition, Cold Spring Harbor Laboratory Press (1989)], or the like is used.

In addition, it is also possible to prepare a cDNA encoding VH or VL by preparing a primer and performing a polymerase chain reaction method [hereinafter referred to as a PCR method, Molecular Cloning, A Laboratory Manual, Second Edition, Cold Spring Harbor Laboratory Press (1989), Current Protocols in Molecular Biology, Supplement 1, John Wiley & Sons (1987-1997)] using a cDNA synthesized from mRNA or a cDNA library as a template.

The selected cDNA is cleaved with an appropriate restriction enzyme or the like, and then cloned into a plasmid such as pBluescript SK(−) (manufactured by Stratagene Corporation), and the nucleotide sequence of the cDNA is determined by a commonly used nucleotide sequence analysis method or the like. For example, after performing a reaction such as a dideoxy method [Proc. Natl. Acad. Sci. USA, 74, 5463 (1977)], an analysis is performed using an automatic nucleotide sequence analyzer such as A.L.F. DNA sequencer (manufactured by Pharmacia Corporation).

By deducing the entire amino acid sequence of each of VH and VL from the determined entire nucleotide sequence and comparing it with the entire amino acid sequence of each of VH and VL of a known antibody [Sequences of Proteins of Immunological Interest, US Dept. Health and Human Services (1991)], it is confirmed whether or not the obtained cDNA encodes the complete amino acid sequence of each of VH and VL of the antibody containing a secretion signal sequence.

With respect to the complete amino acid sequence of each of VH and VL of the antibody containing a secretion signal sequence, by comparison with the entire amino acid sequence of each of VH and VL of a known antibody [Sequences of Proteins of Immunological Interest, US Dept. Health and Human Services (1991)], the length of the secretion signal sequence and the N-terminal amino acid sequence can be deduced, and further the subgroup to which these belong can be identified.

In addition, the amino acid sequence of each of CDRs of VH and VL can be deduced by comparison with the amino acid sequence of each of VH and VL of a known antibody [Sequences of Proteins of Immunological Interest, US Dept. Health and Human Services (1991)].

Further, with respect to the obtained complete amino acid sequence of each of VH and VL, it is possible to confirm whether or not the complete amino acid sequence of each of VH and VL is new by, for example, performing a homology search by the BLAST method [J. Mol. Biol., 215, 403 (1990)] or the like using an arbitrary database such as SWISS-PROT or PIR-Protein.

(2) Construction of Expression Vector for Genetically Recombinant Antibody

An expression vector for a genetically recombinant antibody can be constructed by cloning a DNA encoding at least one of CH and CL of a human antibody into an expression vector for animal cells.

As a C region of a human antibody, CH and CL of an arbitrary human antibody can be used, and for example, CH of γ1 subclass and CL of κ class of a human antibody, or the like can be used. As a DNA encoding each of CH and CL of a human antibody, a cDNA is used, but it is also possible to use a chromosomal DNA composed of an exon and an intron.

As the expression vector for animal cells, any vector can be used as long as it can incorporate a gene encoding a C region of a human antibody and express the gene, and for example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)], INPEP4 (manufactured by Biogen-IDEC, Inc.), N5KG1val (U.S. Pat. No. 6,001,358), N5KG4PE R409K (described in WO 2006/033386), an N5KG2 vector (described in WO 2003/033538), a transposon vector (WO 2010/143698), or the like can be used.

As a promoter and an enhancer of the expression vector for animal cells, an SV40 early promoter [J. Biochem., 101, 1307 (1987)], Moloney murine leukemia virus LTR [Biochem. Biophys. Res. Commun., 149, 960 (1987), a CMV promoter (U.S. Pat. No. 5,168,062), or a promoter [Cell, 41, 479 (1985)] and an enhancer [Cell, 33, 717 (1983)] of an immunoglobulin H chain, or the like can be used.

In the expression of a genetically recombinant antibody, a vector carrying both genes of the antibody H chain and L chain (tandem-type vector) [J. Immunol. Methods, 167, 271 (1994)] is used from the viewpoints of ease of construction of the vector, ease of introduction into an animal cell, balance of the expression levels of the antibody H chain and L chain in the cell, and the like, however, multiple vectors separately carrying each of the genes of the antibody H chain and L chain (separate-type vectors) can also be used in combination.

As the tandem-type expression vector for a genetically recombinant antibody, pKANTEX93 (WO 97/10354), pEE18 [Hybridoma, 17, 559 (1998)], N5KG1val (U.S. Pat. No. 6,001,358), N5KG4PE R409K (described in WO 2006/033386), an N5KG2 vector (described in WO 2003/033538), a Tol2 transposon vector (WO 2010/143698), or the like is used.

(3) Construction of Expression Vector for Chimeric Antibody

By cloning the cDNA encoding VH or VL of a non-human antibody obtained in (1) upstream of each gene encoding CH or CL of a human antibody in the expression vector for a genetically recombinant antibody obtained in (2), an expression vector for a chimeric antibody can be constructed.

First, in order to ligate the cDNA encoding VH or VL of a non-human antibody at the 3'-end side to CH or CL of a human antibody at the 5'-end side, cDNAs of VH and VL designed so that the nucleotide sequence of a ligation region encodes an appropriate amino acid and becomes an appropriate restriction enzyme recognition sequence are produced. Subsequently, the produced cDNAs of VH and VL are each cloned upstream of each gene encoding CH or CL of a human antibody in the expression vector for a genetically recombinant antibody obtained in (2) so that they are expressed in an appropriate form, whereby an expression vector for a chimeric antibody is constructed.

In addition, each cDNA encoding VH or VL of a non-human antibody is amplified by a PCR method using a synthetic DNA containing an appropriate restriction enzyme recognition sequence at both ends, and is cloned into the expression vector for a genetically recombinant antibody obtained in (2), whereby an expression vector for a chimeric antibody can also be constructed.

(4) Production of cDNA Encoding V Region of Humanized Antibody

A cDNA encoding VH or VL of a humanized antibody can be produced as follows. First, each amino acid sequence of a framework region (hereinafter referred to as FR) of VH or VL of a human antibody to be grafted with the amino acid sequence of a CDR of VH or VL of a non-human antibody obtained in (1) is selected.

As the amino acid sequence of FR to be selected, any amino acid sequence can be used as long as it is derived from a human antibody. For example, an amino acid sequence of FR of a human antibody registered in a database such as Protein Data Bank, or a common amino acid sequence in each subgroup of FR of a human antibody [Sequences of Proteins of Immunological Interest, US Dept. Health and Human Services (1991)], or the like is used. In order to suppress a decrease in the binding activity of an antibody, an amino acid sequence of human FR having a homology as high as possible (60% or more) with the amino acid sequence of FR of VH or VL of the original non-human antibody is selected.

Subsequently, each of the amino acid sequences of CDRs of the original non-human antibody is grafted to the selected amino acid sequence of FR of VH or VL of a human antibody, and each amino acid sequence of VH or VL of a humanized antibody is designed. By converting the designed amino acid sequence into a DNA sequence in consideration of the usage frequency of codons found in the nucleotide sequence of the antibody gene [Sequences of Proteins of Immunological Interest, US Dept. Health and Human Services (1991)], each cDNA sequence of VH or VL of a humanized antibody is designed.

Based on the designed cDNA sequence, several synthetic DNAs having a length of around 100 to 150 nucleotides are synthesized and a PCR reaction is performed using them. In this case, from the viewpoint of the reaction efficiency in the PCR reaction and the length of a synthesizable DNA, preferably 4 to 6 synthetic DNAs are designed for each of the H chain and the L chain. In addition, it is also possible to synthesize and use a synthetic DNA having a full-length variable region.

Further, by introducing an appropriate restriction enzyme recognition sequence at the 5' end of the synthetic DNA located at both ends, a cDNA encoding VH or VL of a humanized antibody can be easily cloned into the expression vector for a genetically recombinant antibody obtained in (2). After a PCR reaction, each amplification product is cloned into a plasmid such as pBluescript SK(−) (manufactured by Stratagene Corporation), the nucleotide sequence is determined by the same method as described in (1), and thus a plasmid containing a DNA sequence encoding the amino acid sequence of VH or VL of a desired humanized antibody is obtained.

(5) Modification of Amino Acid Sequence of V Region of Humanized Antibody

The antigen binding activity of a humanized antibody prepared merely by grafting only CDRs of VH and VL of a non-human antibody to FRs of VH and VL of a human antibody is reduced as compared with that of the original non-human antibody [BIO/TECHNOLOGY, 9, 266 (1991)]. For this reason, the reduced antigen binding activity of the humanized antibody can be increased by identifying amino acid residues directly involved in the binding to an antigen, amino acid residues interacting with the amino acid residues of CDRs, and amino acid residues maintaining the conformation of the antibody and indirectly involved in the binding to an antigen in the amino acid sequences of FRs of VH and VL of the human antibody, and substituting the amino acid residues with the amino acid residues of the original non-human antibody.

In order to identify the amino acid residues of FR involved in the antigen binding activity, it is possible to construct and analyze the conformation of the antibody using X-ray crystallography [J. Mol. Biol., 112, 535 (1977)], or computer modeling [Protein Engineering, 7, 1501 (1994)], or the like. Further, it is possible to obtain a modified humanized antibody having a necessary antigen binding activity by producing several types of variants for each antibody, and repeatedly examining the correlation with each antigen binding activity thereof through trial and error.

The amino acid residues of FRs of VH and VL of a human antibody can be modified by performing the PCR reaction described in (4) using a synthetic DNA for modification. With respect to the amplification product after the PCR reaction, the nucleotide sequence is determined to confirm that the desired modification has been carried out by the method described in (1).

(6) Construction of Expression Vector for Humanized Antibody

An expression vector for a humanized antibody can be constructed by cloning each cDNA encoding VH or VL of the constructed humanized antibody upstream of each gene encoding CH or CL of a human antibody of the expression vector for a genetically recombinant antibody obtained in (2).

For example, the cloning is performed upstream of each gene encoding CH or CL of a human antibody in the expression vector for a genetically recombinant antibody obtained in (2) by introducing an appropriate restriction enzyme recognition sequence at the 5' end of the synthetic DNA located at both ends among the synthetic DNAs used when constructing VH or VL of the humanized antibody obtained in (4) and (5) so that they are expressed in an appropriate form.

(7) Construction of Expression Vector for Human Antibody

When a hybridoma that produces a monoclonal antibody is established using an animal that produces a human antibody as an immunized animal, the amino acid sequences and the cDNA sequences of VH and VL of a human antibody can be obtained in (1). Therefore, by cloning each gene encoding VH or VL of a human antibody obtained in (1) upstream of each gene encoding CH or CL of a human antibody of the expression vector for a genetically recombinant antibody obtained in (2), an expression vector for a human antibody can be constructed.

(8) Transient Expression of Genetically Recombinant Antibody

By transiently expressing a genetically recombinant antibody using the expression vector for a genetically recombinant antibody obtained in (3), (6), or (7), or an expression vector obtained by modification thereof, the antigen binding activities of many types of genetically recombinant antibodies obtained can be efficiently evaluated.

As a host cell into which the expression vector is introduced, any cell can be used as long as it is a host cell capable of expressing a genetically recombinant antibody, and for example, a COS-7 cell [American Type Culture Collection (ATCC) number: CRL1651] is used. In the introduction of the expression vector into a COS-7 cell, a DEAE-dextran method [Methods in Nucleic Acids Res., CRC press (1991)], a lipofection method [Proc. Natl. Acad. Sci. USA, 84, 7413 (1987)], or the like is used.

After the introduction of the expression vector, the expression level and the antigen binding activity of the genetically recombinant antibody in a culture supernatant are measured using an enzyme immunoassay method [Monoclonal Antibodies-Principles and practice, Third Edition, Academic Press (1996), Antibodies—A Laboratory Manual, Cold Spring Harbor Laboratory (1988), Monoclonal Antibody Experimental Manual, Kodansha Scientific Ltd. (1987)], or the like.

(9) Acquisition of Stable Expression Cell Line of Genetically Recombinant Antibody and Preparation of Genetically Recombinant Antibody A transformant that stably expresses a genetically recombinant antibody can be obtained by introducing the expression vector for a genetically recombinant antibody obtained in (3), (6), or (7) into an appropriate host cell.

As the introduction of the expression vector into a host cell, for example, an electroporation method [JP-A-H2-257891, Cytotechnology, 3, 133 (1990)], a calcium ion method, an electroporation method, a spheroplast method, a lithium acetate method, a calcium phosphate method, a lipofection method, and the like are exemplified. In addition, as a method for introducing a gene into an animal described below, for example, a microinjection method, a method for introducing a gene into an ES cell using electroporation or a lipofection method, a nuclear transfer method, and the like are exemplified.

As a host cell into which the expression vector for a genetically recombinant antibody is introduced, any cell can be used as long as it is a host cell capable of expressing a genetically recombinant antibody. For example, mouse SP2/0-Ag14 cells (ATCC CRL 1581), mouse P3X63-Ag8.653 cells (ATCC CRL 1580), Chinese hamster CHO-K1 cells (ATCC CCL-61), DUKXB11 (ATCC CCL-9096), Pro-5 cells (ATCC CCL-1781), CHO—S cells (Life Technologies, Cat No. 11619), dihydrofolate reductase gene (dhfr)-deficient CHO cells (CHO/DG44 cells) [Proc. Natl. Acad. Sci. USA, 77, 4216 (1980)], Lec13 cells having acquired lectin resistance [Somatic Cell and Molecular Genetics, 12, 55 (1986)], α1,6-fucosyltransferase gene-deficient CHO cells (WO 2005/035586 and WO 02/31140), Rat YB2/3HL.P2.G11.16Ag.20 cells (ATCC No.: CRL 1662), and the like are used.

In addition, it is also possible to use a host cell in which the activity of a protein such as an enzyme involved in the synthesis of intracellular sugar nucleotide GDP-fucose, a protein such as an enzyme involved in sugar chain modification such that the 1-position of fucose is α-linked to the 6-position of N-acetylglucosamine at the reducing end of an N-glycoside-linked complex sugar chain, a protein involved in the transport of intracellular sugar nucleotide GDP-fucose to the Golgi body, or the like is decreased or lost, for example, an α1,6-fucosyltransferase gene-deficient CHO cell (WO 2005/035586 and WO 02/31140), or the like.

After introduction of the expression vector, a transformant that stably expresses a genetically recombinant antibody is selected by culturing the transformant in a culture medium for culturing animal cells containing a drug such as G418 sulfate (hereinafter referred to as G418) (JP-A-H2-257891).

As the culture medium for culturing animal cells, RPMI 1640 medium (manufactured by Invitrogen), GIT medium (manufactured by Nippon Pharmaceutical Co., Ltd.), EX-CELL 301 medium (manufactured by JRH Biosciences, Inc.), EX-CELL 302 medium (manufactured by JRH Bioscience, Inc.), EX-CELL 325 medium (manufactured by JRH Bioscience., Inc.), IMDM medium (manufactured by Invitrogen) or Hybridoma-SFM medium (manufactured by Invitrogen), or a culture medium in which any of various additives such as FBS is added to any of these culture media, or the like is used. By culturing the obtained transformant in the culture medium, a genetically recombinant antibody is expressed and accumulated in the culture supernatant. The expression level and the antigen binding activity of the genetically recombinant antibody in the culture supernatant can be measured by an ELISA method or the like. In addition, the expression level of the genetically recombinant antibody produced by the transformant can be increased by utilizing a DHFR amplification system (JP-A-H2-257891) or the like.

The genetically recombinant antibody can be purified using a protein A column from the culture supernatant of the transformant [Monoclonal Antibodies—Principles and Practice, Third Edition, Academic Press (1996), Antibodies—A Laboratory Manual, Cold Spring Harbor Laboratory (1988)]. In addition, the purification can also be carried out by combining methods used for purifying a protein such as gel filtration, ion exchange chromatography, and ultrafiltration.

The molecular weight of an H chain, an L chain, or the entire antibody molecule of a purified genetically recombinant antibody can be measured using a polyacrylamide gel electrophoresis method [Nature, 227, 680 (1970)], or a Western blotting method [Monoclonal Antibodies—Principles and Practice, Third Edition, Academic Press (1996), Antibodies—A Laboratory Manual, Cold Spring Harbor Laboratory (1988)], or the like.

3. Designing of Bispecific Antibody

The bispecific antibody of the present invention can be produced by designing each of a CD3 binding domain, an Fc region or a constant region including an Fc region, and a disease-related antigen binding domain, and designing a bispecific antibody in which these are linked.

3-1. Designing of CD3 Binding Domain

For the CD3 binding domain, a desired CD3 binding domain can be obtained using the method described in the above 1, and a cDNA sequence encoding the amino acid sequence of the CDRs or variable regions contained in each binding domain can be determined using the method described in the above 2.

3-2. Designing of Fc Region or Constant Region Including Fc Region

In the Fc region or the heavy chain constant region including the Fc region in the present invention, one CD3 binding domain is bound at the C-terminal side. Therefore, in the two Fc chains contained in the Fc region or the two CH chains contained in the heavy chain constant region, even if one CD3 binding domain such as scFv or dsFv is bound to either one polypeptide of each chain, one CD3 binding domain may be bound by bonding VH or VL of the CD3 binding domain to each of the two polypeptides.

An amino acid sequence in which amino acid residue substitutions of S354C and T366W are added to one CH3 domain, and an amino acid sequence in which amino acid residue substitutions of Y349C, T366S, L368A, and Y407V are added to the other CH3 domain so that the Fc polypeptide chain or CH1-Fc, to which the amino acid sequence of the CD3 binding domain is linked, and the other Fc polypeptide chain or CL-Fc can form a heterodimer structure, are produced.

Further, in the case of the hetero CH region of CH1-Fc, to which the amino acid sequence of the CD3 binding domain is linked, and CL-Fc, an amino acid sequence in which an amino acid residue substitution of C220S is added to CH1-Fc, and an amino acid sequence in which a deletion of amino acid residues at 216-220 and an amino acid residue substitution of C214S are added to CL-Fc are produced. In addition, in order to more efficiently form the hetero CH region, amino acid residue substitutions of H435R and Y436F can be further added to CL-Fc, or the above-mentioned amino acid residue substitutions of the CH3 domain can be appropriately combined and used.

3-3. Designing of Disease-Related Antigen Binding Domain

To each polypeptide chain in the Fc region or the CH region produced in 3-2, the amino acid sequence of the binding domain to a desired disease-related antigen is linked. For example, when each of the amino acid sequences of VHNL, VH-CH1VL-Cx, scFv, and VHH of a monoclonal antibody that specifically binds to a disease-related antigen is linked to the N-terminal side of the first or second polypeptide, an anti-CD3 bispecific antibody having a monovalent or bivalent disease-related antigen binding domain can be produced. In addition, if the amino acid sequences of scFv and VHH are linked to the C-terminal side of the first or second polypeptide, a bispecific antibody having a disease-related antigen-binding domain at the C-terminal side in a monovalent manner, or a bispecific antibody having a bivalent or trivalent disease-related antigen-binding domain in total with the binding valence at the N terminus can be produced. When the disease-related antigen binding domain is bivalent or trivalent, whether the respective antigen binding domains bind to the same epitope or different epitopes, production can be carried out. The bispecific antibody has bispecificity or trispecificity in addition to CD3.

4. Production of Bispecific Antibody

Anti-CD3 bispecific antibodies of various molecular types can be produced by the above designing, and some typical ones are illustrated below. Hereinafter, VHNL, scFv, and Fab indicate VHNL, scFv, and Fab of an antibody specific to a disease-related antigen unless otherwise specified.

4-1. Anti-CD3 Bispecific Antibodies Containing Monovalent Disease-Related Antigen-Binding Domain at N Terminus of Fc Region and Monovalent Anti-CD3 Binding Domain at C Terminus of Fc Region VH-CH1-Fc-CD3scFv and VL-CL-Fc VL-CH1-Fc-CD3scFv and VH-CL-Fc VH-CH1-Fc and VL-CL-Fc-CD3scFv VL-CH1-Fc and VH-CL-Fc-CD3scFv VH-CH1-Fc-CD3VH and VL-CL-Fc-CD3VL VL-CH1-Fc-CD3VH and VH-CL-Fc-CD3VL VH-CH1-Fc-CD3VL and VL-CL-Fc-CD3VH VL-CH1-Fc-CD3VL and VH-CL-Fc-CD3VH 4-2. Anti-CD3 Bispecific Antibodies Containing Bivalent Disease-Related Antigen-Binding Domain at N Terminus of Fe Region and Monovalent Anti-CD3 Binding Domain at C Terminus of Fe Region Fab1-Fc-CD3scFv and Fab2-Fc Fab1-Fc and Fab2-Fc-CD3scFv scFv1-CH1-Fc-CD3scFv and scFv2-CL-Fc scFv1-CH1-Fc and scFv2-CL-Fc-CD3scFv scFv1-CH1-Fc-CD3scFv and scFv2-CL-Fc scFv1-CH1-Fc and scFv2-CL-Fc-CD3scFv A bispecific antibody is produced by adding amino acid residue substitutions necessary for forming a heterodimer to the above-mentioned amino acid sequence, and introducing a vector containing a cDNA encoding the amino acid sequence into animal cells for expression. In addition, a bispecifie antibody having no α1,6-fucose can also be produced by introducing the vector into FUT8KO cells for expression. Further, a bispecifie antibody having high ADCC activity can also be produced by adding Fe amino acid residue substitutions. Protein expression and purification can be carried out by the method in the above section 2.

5. Evaluation of Activity of Bispecifie Antibody or Antibody Fragment Thereof of the Present Invention The evaluation of the activity of the purified bispecifie antibody or bispecifie antibody fragment thereof can be carried out as follows.

The binding activity of the bispecifie antibody of the present invention to a cell line having expressed at least one of CD3 and a disease-related antigen can be measured using the binding assay system described in the above 1. (7).

The CDC activity or the ADCC activity against a cell having expressed at least one of CD3 and a disease-related antigen can be measured by a known measurement method [Cancer Immunol. Immunother., 36, 373 (1993)].

The cellular cytotoxicity of the bispecific antibody of the present invention can be measured by the following method. For example, target cells having expressed a disease-related antigen and PBMC are seeded into a dedicated plate, and a bispecific antibody is added thereto, followed by culturing for a certain period of time, and then, a change in cell count is analyzed using a real-time cell analyzer xCELLigence (ACEA Biosciences, Inc.) or the like. Further, fluorescently stained target cells and unstained PBMC are seeded into a 96-well plate, and a bispecific antibody is added thereto, followed by culturing for a certain period of time, and then, dead cell staining is performed, and only viable target cells are counted by flow cytometry, whereby the cellular cytotoxicity is calculated.

The ability to induce cytokine production of the bispecific antibody of the present invention can be measured by the following method. For example, target cells having expressed a disease-related antigen and PBMC are seeded into a 96-well plate, and a bispecific antibody is added thereto, followed by culturing for a certain period of time, and then, the concentration of a cytokine in the culture supernatant is measured using ELISA, Bio-Plex, a suspension array system, or BD Cytometric Bead Array (CBA) kit.

6. Therapeutic Method for Disease Using Bispecific Antibody or Antibody Fragment Thereof of the Present Invention The bispecific antibody or the bispecific antibody fragment thereof of the present invention can be used for a treatment of a disease associated with at least one of CD3 and a disease-related antigen, preferably a disease involved in a cell that expresses a disease-related antigen. As the disease associated with at least one of CD3 and a disease-related antigen, for example, a malignant tumor, a cancer, and the like are exemplified.

Examples of the malignant tumor and the cancer include large intestine cancer, colorectal cancer, lung cancer, breast cancer, glioma, malignant melanoma (melanoma), thyroid cancer, renal cell carcinoma, leukemia, lymphoma, T cell lymphoma, gastric cancer, pancreatic cancer, cervical cancer, endometrial cancer, ovarian cancer, bile duct cancer, esophageal cancer, liver cancer, head and neck cancer, squamous cell cancer, skin cancer, urinary tract cancer, bladder cancer, prostate cancer, choriocarcinoma, pharyngeal cancer, laryngeal cancer, pleural tumor, androblastoma, endometrial hyperplasia, endometriosis, embryoma, fibrosarcoma, Kaposi sarcoma, angioma, cavernous hemangioma, angioblastoma, retinoblastoma, astrocytoma, neurofibroma, oligodendroglioma, medulloblastoma, neuroblastoma, glioma, rhabdomyosarcoma, glioblastoma, osteogenic sarcoma, leiomyosarcoma, Wilms tumor, and the like.

A therapeutic agent containing the bispecific antibody or the bispecific antibody fragment thereof of the present invention or a derivative thereof may contain only the antibody or the antibody fragment thereof or a derivative thereof as an active ingredient, however, in general, it is provided as a pharmaceutical preparation produced using a method known in the technical field of pharmaceutics by mixing it together with one or more pharmacologically acceptable carriers.

Examples of the route of administration include oral administration or parenteral administration such as intraoral, intra-airway, intrarectal, subcutaneous, intramuscular, and intravenous administration. Examples of the dosage form include a spray, a capsule, a tablet, a powder, a granule, a syrup, an emulsion, a suppository, an injection, an ointment, a tape, and the like. Various pharmaceutical preparations can be produced by a conventional method using an excipient, a filler, a binder, a wetting agent, a disintegrating agent, a surfactant, a lubricant, a dispersant, a buffer, a preservative, a solubilizing agent, an antiseptic, a coloring agent, a flavoring agent, a stabilizer, and the like that are generally used.

Examples of the excipient include lactose, fructose, glucose, corn starch, sorbit, crystalline cellulose, sterile water, ethanol, glycerol, physiological saline, a buffer solution, and the like. Examples of the disintegrating agent include starch, sodium alginate, gelatin, calcium carbonate, calcium citrate, dextrin, magnesium carbonate, synthetic magnesium silicate, and the like.

Examples of the binder include methyl cellulose or a salt thereof, ethyl cellulose, gum arabic, gelatin, hydroxypropyl cellulose, polyvinylpyrrolidone, and the like. Examples of the lubricant include talc, magnesium stearate, polyethylene glycol, hydrogenated vegetable oil, and the like.

Examples of the stabilizer include amino acids such as arginine, histidine, lysine and methionine, human serum albumin, gelatin, dextran 40, methyl cellulose, sodium sulfite, sodium metasulfite, and the like.

Examples of other additives include syrup, vaseline, glycerin, ethanol, propylene glycol, citric acid, sodium chloride, sodium nitrite, sodium phosphate, and the like.

Examples of the pharmaceutical preparation suitable for oral administration include an emulsion, a syrup, a capsule, a tablet, a powder, a granule, and the like.

A liquid preparation such as an emulsion or a syrup is produced using water, a saccharide such as sucrose, sorbitol, or fructose, a glycol such as polyethylene glycol or propylene glycol, an oil such as sesame oil, olive oil, or soybean oil, a preservative such as a p-hydroxybenzoic acid ester, a flavor such as strawberry flavor or peppermint, or the like, as an additive.

A capsule, a tablet, a powder, a granule, or the like can be produced using an excipient such as lactose, glucose, sucrose, or mannitol, a disintegrating agent such as starch or sodium alginate, a lubricant such as magnesium stearate or talc, a binder such as polyvinyl alcohol, hydroxypropyl cellulose, or gelatin, a surfactant such as a fatty acid ester, a plasticizer such as glycerin, or the like as an additive.

Examples of the pharmaceutical preparation suitable for parenteral administration include an injection, a suppository, a spray, and the like. An injection is produced using a carrier composed of a salt solution, a glucose solution, or a mixture of both, or the like.

A suppository is produced using a carrier such as cacao butter, a hydrogenated fat, or carboxylic acid. A spray is produced using a carrier which does not stimulate the buccal and airway mucous membranes of a recipient and disperses the monoclonal antibody or the antibody fragment thereof of the present invention as fine particles so as to facilitate absorption thereof, or the like. Examples of the carrier include lactose, glycerin, and the like. In addition, it can also be produced as an aerosol or a dry powder. Further, a component exemplified as the additive for the pharmaceutical preparation suitable for oral administration can also be added in the above-mentioned parenteral preparation.

An effective amount of the bispecific antibody of the present invention and an effective amount to be administered as a combination with a suitable diluent and a pharmacologically usable carrier is 0.0001 mg to 100 mg per kg of the body weight at a time, and is administered at intervals of 2 days to 8 weeks.

7. Diagnostic Method for Disease Using Bispecific Antibody or Bispecific Antibody Fragment Thereof of the Present Invention By detecting or measuring a cell having expressed at least one of CD3 and a disease-related antigen using the bispecific antibody or the bispecific antibody fragment thereof of the present invention, it is possible to diagnose a disease associated with at least one of CD3 and a disease-related antigen, preferably a disease involved in a cell that expresses a disease-related antigen binding domain.

The diagnosis of a malignant tumor or a cancer that is a disease associated with at least one of CD3 and a disease-related antigen can be carried out by, for example, detecting or measuring at least one of CD3 and a disease-related antigen as follows.

First, with respect to biological samples collected from the bodies of multiple healthy subjects, at least one of CD3 and a disease-related antigen is detected or measured by the following immunological method using the bispecific antibody or the bispecific antibody fragment thereof of the present invention, or a derivative thereof, and then, the abundance of at least one of CD3 and a disease-related antigen in the biological samples of the healthy subjects is examined.

Subsequently, the abundance of at least one of CD3 and a disease-related antigen in a biological sample of a test subject is also examined in the same manner, and then, the abundance is compared with the abundance of the healthy subjects. For example, when the abundance of the disease-related antigen of the test subject has increased as compared with that of the healthy subjects, the test subject is diagnosed as having a disease such as a cancer. With respect also to the diagnosis of the other diseases associated with at least one of CD3 and a disease-related antigen, the diagnosis can be carried out in the same manner.

The immunological method is a method for detecting or measuring the amount of an antibody or the amount of an antigen using a labeled antigen or antibody. Examples thereof include a radioimmunoassay method, an enzyme immunoassay method, a fluorescence immunoassay method, a luminescence immunoassay method, a Western blotting method, a physicochemical method, and the like.

Examples of the radioimmunoassay method include a method in which the bispecific antibody or the bispecific antibody fragment thereof of the present invention is allowed to react with an antigen or a cell or the like having expressed an antigen, and further an anti-immunoglobulin antibody or a binding fragment subjected to radiolabeling is allowed to react therewith, followed by measurement with a scintillation counter or the like.

Examples of the enzyme immunoassay method include a method in which the bispecific antibody or the bispecific antibody fragment thereof of the present invention is allowed to react with an antigen or a cell or the like having expressed an antigen, and further an anti-immunoglobulin antibody or a binding fragment subjected to labeling is allowed to react therewith, followed by measurement of a coloring dye with an absorptiometer. For example, a sandwich ELISA method and the like are exemplified.

As a labeling substance used in the enzyme immunoassay method, a known enzyme label [Enzyme Immunoassay Method, IGAKU-SHOIN Ltd. (1987)] can be used. For example, an alkaline phosphatase label, a peroxidase label, a luciferase label, a biotin label, or the like is used.

The sandwich ELISA method is a method in which after an antibody is bound to a solid phase, an antigen that is a detection or measurement target is trapped, and then, a second antibody is allowed to react with the trapped antigen. In the ELISA method, two types of antibodies that are antibodies or antibody fragments binding to an antigen desired to be detected or measured and have different antigen binding sites are prepared, and among them, a first antibody or antibody fragment is adsorbed onto a plate (for example, a 96-well plate) in advance, and subsequently, a second antibody or antibody fragment is labeled with a fluorescent substance such as FITC, an enzyme such as peroxidase, biotin, or the like beforehand. Cells separated from the inside of the living body or a homogenate liquid thereof, tissues or a homogenate liquid thereof, a cell culture supernatant, serum, pleural effusion, ascites, intraocular fluid, or the like is allowed to react with the plate on which the antibody is adsorbed, and thereafter, the labeled antibody or antibody fragment is allowed to react therewith, and then, a detection reaction is performed according to the labeling substance. From a calibration curve prepared by serially diluting an antigen at a known concentration, the antigen concentration in the test sample is calculated.

As the antibody used in the sandwich ELISA method, either a polyclonal antibody or a monoclonal antibody may be used, and an antibody fragment such as Fab, Fab', or $F(ab)_2$ may be used. The combination of the two types of antibodies used in the sandwich ELISA method may be a combination of monoclonal antibodies or antibody fragments thereof that bind to different epitopes, or may be a combination of a polyclonal antibody and a monoclonal antibody or antibody fragments thereof.

As the fluorescence immunoassay method, measurement is performed by, for example, a method described in the document [Monoclonal Antibodies—Principles and Practice, Third Edition, Academic Press (1996), Monoclonal Antibody Experimental Manual, Kodansha Scientific Ltd. (1987)], or the like. As a labeling substance used in the fluorescence immunoassay method, a known fluorescent label [Fluorescent Antibody Method, Soft Science, Inc. (1983)] can be used. For example, FITC, RITC, or the like is used.

As the luminescence immunoassay method, measurement is performed by, for example, a method described in the document [Bioluminescence and Chemiluminescence Clinical Test 42, Hirokawa-Shoten Ltd. (1998)], or the like. As a labeling substance used in the luminescence immunoassay method, a known luminescent label is exemplified, and for example, an acridinium ester, lophine, or the like is used.

As the Western blotting method, measurement is performed by fractionating an antigen or a cell or the like having expressed an antigen by SDS (sodium dodecyl sulfate)-PAGE [Antibodies—A Laboratory Manual Cold Spring Harbor Laboratory (1988)], thereafter blotting the gel onto a polyvinylidene fluoride (PVDF) membrane or a nitrocellulose membrane, allowing an antibody or an antibody fragment that binds to the antigen to react with the membrane, and then further allowing an anti-IgG antibody or an antibody fragment thereof labeled with a fluorescent substance such as FITC, labeled with an enzyme such as peroxidase, or labeled with biotin, or the like to react therewith, followed by visualizing the label. One example is shown below.

First, cells or tissues having expressed a polypeptide containing a desired amino acid sequence are lysed, and 0.1 to 30 g in terms of protein amount per lane is electrophoresed by an SDS-PAGE method under reducing conditions. Subsequently, the electrophoresed protein is transferred to a PVDF membrane and is allowed to react with PBS containing 1 to 10% BSA (hereinafter referred to as BSA-PBS) at room temperature for 30 minutes to perform a blocking operation. Then, the bispecific antibody of the present invention is allowed to react therewith, and the membrane is washed with PBS containing 0.05 to 0.1% Tween 20 (Tween-PBS), and then, a goat anti-mouse IgG labeled with peroxidase is allowed to react therewith at room temperature for 2 hours. By performing washing with Tween-PBS, and detecting a band to which the antibody is bound using ECL Western Blotting Detection Reagents (manufactured by Amersham plc) or the like, an antigen is detected. As the antibody used for detection by Western blotting, an antibody capable of binding to a polypeptide that does not retain a natural conformation is used.

As the physicochemical method, for example, by binding at least one of CD3 which is an antigen and a disease-related antigen to the bispecific antibody or the bispecific antibody fragment thereof of the present invention, an aggregate is formed, and the aggregate is detected. As another physicochemical method, a capillary tube method, a one-dimensional immunodiffusion method, an immunoturbidimetric method, a latex immunoturbidimetric method [Kanai's Manual of Clinical Laboratory Medicine, KANEHARA & Co., LTD. (1998)], or the like can also be used.

In the latex immunoturbidimetric method, when a carrier such as a polystyrene latex having a particle diameter of about 0.1 to 1 m sensitized with an antibody or an antigen is used to cause an antigen-antibody reaction with a corresponding antigen or antibody, the scattered light in a reaction solution is increased and the transmitted light is decreased. The antigen concentration or the like in a test sample is measured by detecting this change as an absorbance or an integrating sphere turbidity.

On the other hand, for the detection or measurement of a cell having expressed at least one of CD3 and a disease-related antigen, a known immunological detection method can be used, but it is preferred to use an immunoprecipitation method, an immunocytological staining method, an immunohistological staining method, a fluorescent antibody staining method, or the like.

As the immunoprecipitation method, a cell or the like having expressed at least one of CD3 and a disease-related antigen is allowed to react with the bispecific antibody or the antibody fragment thereof of the present invention, and then, a carrier having a specific binding ability to an immunoglobulin such as Protein G Sepharose is added thereto, thereby precipitating an antigen-antibody complex.

Alternatively, it can also be carried out by the method as described below. First, the bispecific antibody or the bispecific antibody fragment thereof of the present invention is immobilized on a 96-well plate for ELISA, followed by blocking with BSA-PBS. Subsequently, BSA-PBS is discarded, and the plate is well washed with PBS, and then, a lysate solution of cells or tissues having expressed at least one of CD3 and a disease-related antigen is allowed to react therewith. From the plate after being well washed, an immunoprecipitated material is extracted with a sample buffer for SDS-PAGE, and then detected by the above-mentioned Western blotting.

The immunocytological staining method or the immunohistological staining method is a method in which a cell or a tissue having expressed an antigen or the like is treated with a surfactant or methanol or the like for enhancing the permeability of the antibody in some cases, and then allowed to react with the bispecific antibody of the present invention, and further react with an anti-immunoglobulin antibody or a binding fragment thereof fluorescently labeled with FITC or the like, labeled with an enzyme such as peroxidase, or labeled with biotin, or the like, and thereafter, the label is visualized, and then observed with a microscope. In addition, detection can be carried out by a fluorescent antibody staining method in which a fluorescently labeled antibody is allowed to react with a cell and analyzed with a flow cytometer [Monoclonal Antibodies—Principles and Practice, Third Edition, Academic Press (1996), Monoclonal Antibody Experimental Manual, Kodansha Scientific Ltd. (1987)]. In particular, the bispecific antibody or the bispecific antibody fragment thereof of the present invention enables detection of at least one of CD3 and a disease-related antigen expressed on a cell membrane by a fluorescent antibody staining method.

In addition, when the FMAT 8100 HTS system (manufactured by Applied Biosystems, Inc.) or the like is used among the fluorescent antibody staining methods, it is possible to measure the amount of an antigen or the amount of an antibody without separating the formed antibody-antigen complex from a free antibody or antigen not involved in the formation of the antibody-antigen complex.

EXAMPLES

Hereinafter, description will be made with reference to specific Examples, however, the present invention is not limited to these Examples.

[Example 1] Production of Expression Vectors for Animal Cells for Anti-HER2 Monovalent Antibodies and CD3/HER2 Bispecific Antibodies (1) Production of Expression Vectors for Animal Cells for Anti-HER2 Monovalent Antibodies Expression vectors for animal cells for each of an IgG1-type anti-HER2 monovalent antibody and an IgG4PE (R409K)-type HER2 monovalent antibody [referred to as mvG1 and mvG4PE(R409K), respectively, and each having the structure in FIG. 2(A)](referred to as pKANTEX93mvG1 and pKANTEX93mvG4PE(R409K), respectively) were produced according to the method described in WO 2014/054804.

The monovalent antibody is a heterodimer composed of two different polypeptides, and the polypeptide containing VH is referred to as first polypeptide (VH-CH1-hinge-Fc, also referred to as polypeptide 1), and the polypeptide containing VL is referred to as second polypeptide (VL-CL-hinge-Fc, also referred to as polypeptide 2).

In Table 1, the amino acid sequence and the nucleotide sequence of the CH1-Hinge-Fc moiety of the first polypeptide used in the production of each monovalent antibody are shown.

TABLE 1

| | | IgG1-type anti-HER2 monovalent antibody | IgG4PE(R409K)-type anti-HER2 monovalent antibody |
|---|---|---|---|
| CH1-Hinge-Fc moiety of first | Nucleotide sequence | SEQ ID NO: 1 | SEQ ID NO: 5 |
| polypeptide | Amino acid sequence | SEQ ID NO: 2 | SEQ ID NO: 6 |
| CL-Hinge-Fc moiety of second | Nucleotide sequence | SEQ ID NO: 3 | SEQ ID NO: 7 |
| polypeptide | Amino acid sequence | SEQ ID NO: 4 | SEQ ID NO: 8 |

The IgG4PE(R409K) type shown in Table 1 has a constant region in which the Ser residue at position 228 of the heavy chain constant region of IgG4 was substituted with Pro, the Leu residue at position 235 thereof was substituted with Glu, and the Arg residue at position 409 thereof was substituted with Lys, and does not have ADCC activity.

Further, as the amino acid sequences and the nucleotide sequences of VH and VL of each of the above-mentioned anti-HER2 monovalent antibodies, the amino acid sequences and the nucleotide sequences of VH and VL of an anti-HER2 antibody Trastuzumab (described in Proc. Natl. Acad. Sci. U.S.A. 89: 4285, 1992) were used.

(2) Production of Expression Vectors for Animal Cells for CD3/HER2 Bispecific Antibodies In order to produce heterodimer-type CD3/HER2 bispecific antibodies [FIG. 2(B)] in which anti-CD3 scFv is bound to the C terminus of the first polypeptide of each monovalent antibody through a linker based on the above IgG1-type anti-HER2 monovalent antibody and IgG4PE(R409K)-type anti-HER2 monovalent antibody, expression vectors for animal cells therefor were produced by the method described below.

Using the restriction enzyme sites, a nucleotide sequence encoding a part of the C-terminal portion of the H chain constant region of the first polypeptide of the IgG1-type anti-HER2 monovalent antibody expression vector pKANTEX93mvG1 produced in the above (1) was substituted with a nucleotide sequence encoding a part of the C-terminal portion of the H chain constant region+a peptide linker+anti-CD3 scFv. As a result, an expression vector pKANTEX93mvG1_scT3a for an IgG1-type CD3/HER2 bispecific antibody was obtained.

As the amino acid sequence of the peptide linker, [SerGlyGlyGlyGly (SEQ ID NO: 143)]3 was used. As the amino acid sequence and the nucleotide sequence of the anti-CD3 scFv, the amino acid sequence and the nucleotide sequence of anti-CD3 scFv described in U.S. Pat. No. 7,575,923B2 were used. The amino acid sequence of the anti-CD3 scFv is represented by SEQ ID NO: 9. This sequence is hereinafter referred to as scT3a.

An expression vector pKANTEX93mvG4PE (R409K)_scT3a for an IgG4PE(R409K)-type CD3/HER2 bispecific antibody was obtained from the IgG4PE(R409K)-type anti-HER2 monovalent antibody expression vector pKANTEX93mvG4PE(R409K) produced in the above (1) in the same manner.

The antibody expression vectors produced in the above (1) and in this section were all prepared using *E. coli* Competent Quick DH5α (TOYOBO) as a host and also using PureYield Plasmid Midiprep System (Promega) and used in the following experiments.

[Example 2] Expression and Purification of Anti-HER2 Monovalent Antibodies and CD3/HER2 Bispecific Antibodies By using various antibody expression vectors prepared in Example 1, an IgG1-type anti-HER2 monovalent antibody 4D5_mvG1 (DF) with high ADCC, an IgG4PE(R409K)-type HER2 antibody 4D5_mvG4PE(R409K) (F), an IgG1-type CD3/HER2 bispecific antibody 4D5_mvG1_scT3a (DF) with high ADCC, and an IgG4PE(R409K)-type CD3/HER2 bispecific antibody 4D5_mvG4PE(R409K)_scT3a (F) were obtained by the method described below.

The name of each antibody, the corresponding expression vector, the host cell used, the structure of the Fc sugar chain, and the presence or absence of anti-CD3 scFv are shown in Table 2.

TABLE 2

| Antibody name | Expression vector | Host cell | Presence or absence of α1,6-fucose of Fc sugar chain | Presence or absence of anti-CD3 scFv |
|---|---|---|---|---|
| 4D5_mvG1 (DF) | pKANTEX93mvG1 | FUT8KO CHO | defucosylated | absent |
| 4D5_mvG4PE(R409K) (F) | pKANTEX93mvG4PE(R409K) | CHO/DG44 | fucosylated | absent |
| 4D5_mvG1_scT3a (DF) | pKANTEX93mvG1_scT3a | FUT8KO CHO | defucosylated | present |
| 4D5_mvG4PE(R409K)_scT3a (F) | pKANTEX93mvG4PE(R409K)_scT3a | CHO/DG44 | fucosylated | present |

In the table, CHO/DG44 denotes CHO/DG44 cells derived from Chinese Hamster Ovary (Somatic Cell Mol Genet 12; 555, 1986), and FUT8KO CHO denotes α1,6-fucosyltransferase gene (FUT8)-knocked out CHO/DG44 cells. (U.S. Pat. No. 6,946,292).

To the above-mentioned host cells ($4\times10^6$ cells), 8 μg of each of various expression vectors was added, and gene transfer was carried out by electroporation (Cytotechnology. 3: 133, 1990). After gene transfer, cells were cultured for 2 days in IMDM medium (GIBCO) containing 10% dialyzed bovine serum (hereinafter abbreviated as dFBS), the culture was further continued for about 2 weeks in the culture medium containing 0.5 mg/mL G418 sulfate, whereby G418-resistant strains were obtained. The G418-resistant strains were cultured using Excell 302 medium (SAFC Biosciences, Inc.), and the culture supernatant containing the expressed protein was collected.

By using a column packed with protein A (MabSelect SuRe: GE Healthcare), 1 L of the culture supernatant was loaded therethrough at a flow rate of 0.5 to 1.0 mL/min. The column was washed twice with 10 mL of phosphate buffer saline (PBS), and then, the antibody was eluted with 0.1 M citrate buffer solution (pH 3.9). The obtained eluate was immediately neutralized with 2 M Tris-hydrochloride buffer solution (pH 8.0) and then dialyzed with 10 mM citric acid and 150 mM sodium chloride (pH 6.0) to replace the buffer solution.

The above antibody solution was further subjected to removal of multimers or decomposition products using gel filtration chromatography. A Superdex 200 10/300 GL column (GE Healthcare) was connected to AKTA explore 10S (GE Healthcare), and the flow channel was replaced with 10 mM citric acid and 150 mM sodium chloride (pH 6.0). The prepared antibody solution was added to the column, allowed to pass therethrough at a flow rate of 0.5 mL/min, and collected in fractions of 0.5 mL by a fraction collector. Among the collected fractions, fractions which compose the main peak of $OD_{280}$ chromatogram were collected and pooled as a fraction containing monomer of the target antibody, and the antibody solution was sterilized through a 0.22 μm filter and stored. As a result of subjecting the obtained antibody samples to SDS-PAGE analysis, they all showed the expected molecular weight size, and it was confirmed that the desired antibodies could be obtained. In addition, as a control sample for comparison, an antibody Trastuzumab (DF), lacking of α1,6-fucose in the N-linked sugar chain of the anti-HER2 antibody Trastuzumab, was produced according to the method described in Clin Cancer Res. 13: 1875-1882, 2007, and used in some experiments.

Further, as a negative control, an IgG1-type anti-2,4-dinitrophenyl (DNP) antibody was produced according to the method described in Examples 1 and 2 using a DNA fragment (clone name: DNP2) encoding an anti-2,4-dinitrophenyl (DNP) IgG1 antibody described in Clin Cancer Res. 11(8): 3126-3135, 2005, and used in some experiments.

[Example 3] Evaluation of Antigen Binding Activity of Anti-HER2 Monovalent Antibodies and CD3/HER2 Bispecific Antibodies (1) Evaluation of HER2 Binding Activity The HER2 binding activity of various antibodies obtained in Example 2 was evaluated by binding inhibition experiment against Trastuzumab. First, Trastuzumab (F. Hoffmann-La Roche, Ltd.) was labeled with Alexa 488 using Alexa Fluor 488 Antibody Labeling Kit (Life Technologies, Ltd.), whereby Trastuzumab_Alx was produced. Subsequently, binding inhibition analysis by flow cytometry was performed using an HER2-positive human breast cancer cell line SK-BR-3 (ATCC HTB-30).

Trastuzumab_Alx at a final concentration of 2.0 μg/mL, and each of an unlabeled IgG1 antibody, Trastuzumab, various anti-HER2 monovalent antibodies or CD3/HER2 bispecific antibodies at a final concentration of 105, 21, 4.2, and 0.84 nM were added and allowed to react at 4° C. for 1.5 hours. As a negative control, human serum-derived IgG1/kappa (Millipore, Inc.) at the same concentration was added. After washing, mean fluorescent intensity (MFI) of the binding of SK-BR-3 cells was measured with a flow cytometer Cytomics FC 500 MPL (Beckman Coulter, Inc.). The results are shown in FIG. 4.

As shown in FIG. 4, it was confirmed that Trastuzumab, various anti-HER2 monovalent antibodies, and various CD3/HER2 bispecific antibodies inhibit the binding of Trastuzumab_Alx in antibody concentration-dependent manner and have binding activity specific to HER2. It was revealed that the binding activity to HER2 was comparable among four antibodies: the anti-HER2 monovalent antibodies and the CD3/HER2 bispecific antibodies.

(2) Evaluation of CD3 Binding Activity

The CD3 binding activity of various antibodies obtained in Example 2 was evaluated based on the binding activity to commercially available frozen T cells (AllCells, Inc.). Each of the various antibodies was added to T cells at a final concentration of 10 μg/mL and allowed to react at 4° C. for 1 hour. After washing, Goat anti-Human IgG $F(ab)_2$-FITC (Acris Antibodies GmbH) diluted to 30 μg/mL was added thereto and allowed to react at 4° C. for 1 hour.

As a positive control, 30 μg/mL of an anti-CD3 antibody OKT-3 (abcam. plc) was used as the primary antibody, and Goat anti-mouse IgG $F(ab)_2$-FITC (Dako, Inc.) was used as the secondary antibody. After washing, the MFI of the antibody bound to T cells was measured with a flow cytometer Cytomics FC 500 MPL (Beckman Coulter, Inc.). The results are shown in FIG. 5.

As shown in FIG. 5, among the antibodies evaluated, the CD3/HER2 bispecific antibodies 4D5_mvG1_scT3a (DF) and 4D5_mvG4PE(R409K)_scT3a (F) both bound to T cells at a comparable level. On the other hand, Trastuzumab and the anti-HER2 monovalent antibodies 4D5_mvG1 (DF) and 4D5_mvG4PE(R409K) (F) did not bind to T cells. From the above results, it was revealed that 4D5_mvG1_scT3a (DF) and 4D5_mvG4PE(R409K)_scT3a (F) can bind to CD3 with a comparable strength.

[Example 4] Evaluation of Cellular Cytotoxicity of Anti-HER2 Monovalent Antibodies and CD3/HER2 Bispecific Antibodies With respect to various antibodies produced in Example 2, the cellular cytotoxicity including both ADCC activity through Fc region and ADTC activity by binding to CD3 was measured by the following method using a real-time cell analyzer xCELLigence (ACEA Biosciences, Inc.), which detects the amount of cancer cells adhered to a plate over time. It utilizes the fact that the electrical resistance value changes as the amount of cells on the plate changes. That is, the cell index value obtained by this measurement shows a positive correlation with the amount of cells on the plate.

It is known that NK cells that mainly express an Fc receptor FcγRIIIA are the main effector cells for ADCC activity and T cells that express CD3 are the main effector cells for ADTC activity, and therefore, by using mononuclear cells derived from human peripheral blood (PBMC) including both as the effector, and using an HER2-positive cancer cell line as the target, the cellular cytotoxicity including both ADCC activity and ADTC activity of various antibodies can be measured.

First, RPMI 1640 medium (supplemented with 10% FBS) was added to E-plate VIEW 16 (ACEA Biosciences, Inc.) to perform baseline correction. HER2-moderate expression breast cancer cell line BT-20 cells (ATCC HTB-19) or HER2-low expression MCF-7 cells (ATCC HTB-22) were detached from the flask with 0.02% EDTA (Nacalai Tesque, Inc.) and washed with PBS, and then diluted to $2.0\times10^5$ cells/mL with RPMI 1640 (10% FBS, 10 μg/mL gentamicin), and the resultant was added to the above plate at 50 μL/well.

After incubating the plate in a $CO_2$ incubator for 30 minutes, the measurement of the cell index value was started. After approximately 20 hours, PBMC collected from healthy human peripheral blood by density-gradient method was diluted to $1\times10^6$ cells/mL, and added to the above plate at 50 μL/well, and each of various antibodies prepared at a concentration 4 times higher than the final concentration was added thereto at 50 μL/well, and the measurement was started again. The final data were normalized by the value of the amount of cancer cells immediately before the addition of the antibodies. The obtained results are shown in FIGS. 6 to 8.

FIG. 6 shows the cell index in the case of only BT-20 cells, or when PBMC was added to BT-20 cells, or when the IgG1-type anti-HER2 monovalent antibody 4D5_mvG1 (DF) (final concentration 50 nM) or the IgG4PE(R409K)-type CD3/HER2 bispecific antibody 4D5_mvG4_scT3a (F) (final concentration 50 nM) or a mixture thereof (a mixed liquid in which the final concentration of each antibody was 25 nM) was further added thereto.

In FIG. 6, the difference between the amount of cancer cells when the target cells and PBMC were added and the amount of cancer cells when the antibody was further added is regarded as the cellular cytotoxicity of the antibodies. As shown in FIG. 6, 4D5_mvG1 (DF) and 4D5_mvG4PE (R409K)_scT3a (F) each have moderate cellular cytotoxicity, and the mixture obtained by mixing a half amount of each of these antibodies has high cellular cytotoxicity above the cellular cytotoxicity of each of 4D5_mvG1 (DF) and 4D5_mvG4PE(R409K)_scT3a (F) alone.

As shown in Table 2, the IgG1-type anti-HER2 monovalent antibody 4D5_mvG1 (DF) has an IgG1-type constant region in which N-linked sugar chains deficient in α1,6-fucose are bound, and has a high ADCC activity through the FcγRIIIA binding activity, but has no CD3 binding site and therefore does not have ADTC activity as described in WO 2014/054804.

As shown in Table 2, the IgG4PE(R409K)-type CD3/HER2 bispecific antibody 4D5_mvG4(R409K)_scT3a (F) has an IgG4-type constant region with sugar chains that α1,6-fucose is added and has been subjected to introduction of an amino acid residue modification for reducing the effector activity, and therefore has a molecular structure having no or a very low ability to induce ADCC activity, but having a CD3-mediated ADTC activity.

The cellular cytotoxicity of the group in which these two types of antibodies were added at 25 nM each was higher than that of each of the groups in which only 4D5_mvG1 (DF) or 4D5_mvG4PE(R409K)_scT3a (F) was added at 50 nM, and it was revealed that synergistic cellular cytotoxicity is exhibited by mixing a molecule having only ADCC activity and a molecule having only ADTC activity.

Therefore, the results show that as compared with the case where an antibody having only ADCC activity or an antibody having only ADTC activity is allowed to act on cancer cells alone, the anti-tumor effect is higher in the case where a half amount of each of these antibodies is simultaneously allowed to act on cancer cells.

In addition, 4D5_mvG1 (DF) and 4D5_mvG4PE(R409K)_scT3a (F) both have moderate cellular cytotoxicity, and the fact that the activity of one of them is not saturated at the same concentration indicates that the effective concentration ranges for ADCC activity and ADTC activity do not significantly deviate from each other in this experiment.

FIG. 7 shows the cell index in the case of only BT-20 cells, or when PBMC was added to BT-20 cells, or when a mixture of 4D5_mvG1 (DF) and 4D5_mvG4_scT3a (F) (a mixed liquid containing the antibodies at 0.3 nM each) or the IgG1-type CD3/HER2 bispecific antibody 4D5_mvG1_scT3a (DF) (0.6 nM) was further added thereto.

The results of comparing the cellular cytotoxicity between the mixture of 4D5_mvG1 (DF) and 4D5_mvG4PE (R409K)_scT3a (F) (0.3 nM each) and 4D5_mvG1_scT3a (DF) (0.6 nM) are shown in FIG. 7.

As shown in FIG. 7, 4D5_mvG1_scT3a (DF) exhibited a further higher anti-tumor effect than the case where 4D5_mvG1 (DF) and 4D5_mvG4PE(R409K)_scT3a (F) are simultaneously added.

As shown in Table 2, 4D5_mvG1_scT3a (DF) has a molecular structure having high ADCC activity due to the IgG1-type constant region in which N-linked sugar chains deficient in α1,6-fucose is bound, and CD3-mediated ADTC activity.

Therefore, the high anti-tumor effect of the combined use of the molecule having only an ADCC activity and the molecule having only an ADTC activity shown in FIG. 6 is further enhanced by allowing the same molecule to have both ADCC and ADTC activities, and the synergistic effect is enhanced.

FIGS. 8 (A) to 8 (E) show the cell index in the case of only MCF-7 cells, or when PBMC was added to MCF-7 cells, or when an anti-HER2 antibody Trastuzumab (DF), the IgG1-type anti-HER2 monovalent antibody 4D5_mvG1 (DF), the IgG4PE(R409K)-type CD3/HER2 bispecific antibody 4D5_mvG4PE(R409K)_scT3a (F), or the IgG1-type CD3/HER2 bispecific antibody 4D5_mvG1_scT3a (DF) (all at a final concentration of 50 nM) was further added thereto.

As shown in FIGS. 8(A) to 8(E), it was revealed that Trastuzumab (DF), 4D5_mvG1 (DF), and 4D5_mvG4PE (R409K)_scT3a (F) all exhibit almost no cellular cytotoxicity against MCF-7 cells, but 4D5_mvG1_scT3a (DF) exhibits very high cellular cytotoxicity against MCF-7 cells.

The results showed that an antibody having ADCC activity and ADTC activity in one molecule can exhibit extremely high anti-tumor effect also on cancer cells, against which an antibody having only ADCC activity or an antibody having only ADTC activity exhibit almost no cellular cytotoxicity.

[Example 5] Examination of Linker Sequence of CD3/HER2 Bispecific Antibodies

In this section, with respect to the CD3/HER2 bispecific antibody 4D5_mvG1_scT3a (DF), bispecific antibodies in which the type and length of the sequence of the peptide linker that connects the C terminus of CH3 of the first polypeptide and the anti-CD3 scFv were changed were produced, and the effect of the peptide linker on the biological activity was examined.

In Table 3, the name of each of the produced CD3/HER2 bispecific antibodies, and the amino acid sequence of the peptide linker and the structure thereof are shown.

Among the antibodies shown in Table 3, H1 and H3 are bispecific antibodies having a peptide linker including one turn or three turns of α-helix, respectively, and Pro is a bispecific antibody having a peptide linker containing proline. The peptide linkers contained in these antibodies have a rigid structure as compared with a [SerGlyGlyGlyGly (SEQ ID NO: 143)]~(n is 1 to 3) linker (Chen X, et al. Adv. Drug Deliv. Rev. 65: 1357-1369, 2013). Therefore, by comparing the biological activities of various bispecific antibodies having the above-mentioned different peptide linker, it is possible to know the effects of the rigidity and length of the linker moiety on the cellular cytotoxicity of the CD3/HER2 bispecific antibody.

Expression vectors for animal cells for various bispecific antibodies shown in Table 3 were produced by replacing a gene fragment containing a nucleotide sequence encoding the C terminus of the first polypeptide-[SerGlyGlyGlyGly (SEQ ID NO: 143)]$_3$ linker-anti-CD3 scFv with a gene fragment containing a nucleotide sequence encoding the C terminus of the first polypeptide-a peptide linker shown in Table 3-anti-CD3 scFv by using the restriction enzyme site EcoT22I-BamHI of the bispecific antibody expression vector pKANTEX93mvG1_scT3a produced in Example 1.

These expression vectors were introduced into FUT8KO CHO cells by the method described in Example 2 to express proteins, and the proteins were purified. In the case of G1, G2, H1, H3, and Pro among the produced bispecific antibodies, the purified proteins obtained showed the expected molecular weight size analyzed by SDS-PAGE, and it could be confirmed that the desired antibodies were obtained.

The HER2 and CD3 binding activities of various bispecific antibodies produced were measured by the method described in Example 3. The obtained results are shown in FIGS. 9 and 10. From FIG. 9, it was revealed that 4D5_mvG1_scT3a (DF), G1, G2, H1, H3, and Pro all have a comparable HER2 binding activity, and from FIG. 10, it was revealed that all antibodies have CD3 binding activity that does not greatly change although there is a slight variation among the antibodies.

In addition, the cellular cytotoxicity of the bispecific antibodies against BT-20 cells was measured by the method described in Example 3 (final concentration: 0.617 nM). In the comparison control, only the target cells or only the target cells and PBMC (no antibody added) were added. The obtained results are shown in FIGS. 11 and 12.

As shown in FIGS. 11 and 12, it was revealed that the CD3/HER2 bispecific antibodies G1, G2, H1, H3, and Pro

TABLE 3

| | Sequence of Linker | |
|---|---|---|
| Antibody name | Amino acid sequence | Structure |
| 4D5_mvG1_scT3a (DF) | [SerGlyGlyGlyGly (SEQ ID NO: 143)]$_3$ | linear |
| Δlinker | Non | |
| G1 | [SerGlyGlyGlyGly (SEQ ID NO: 143)]$_1$ | linear |
| G2 | [SerGlyGlyGlyGly (SEQ ID NO: 143)]$_2$ | linear |
| H1 | [GluAlaAlaAlaLys (SEQ ID NO: 144)]$_1$ | α-helix forming linker |
| H3 | [GluAlaAlaAlaLys (SEQ ID NO: 144)]$_3$ | α-helix forming linker |
| Pro | ProAlaProAlaPro (SEQ ID NO: 145)] | rigid |

all exhibit cellular cytotoxicity equal to or higher than that of 4D5_mvG1_scT3a (DF). The results showed that the high cellular cytotoxicity of the IgG1-type CD3/HER2 bispecific antibody 4D5_mvG1_scT3a (DF) does not depend on the structure of the linker moiety.

[Example 6] Cellular Cytotoxicity of CD3/HER2 Bispecific Antibodies Against Gastric Cancer Cell Line A gene encoding the amino acid sequence of each polypeptide shown in Table 4 was inserted into an antibody expression vector produced by modifying the pCI vector of Promega Corporation. Here, for example, with respect to an antibody described as DNP2, a negative control antibody using the variable region of an antibody that binds to DNP as the variable region at binding side to the cancer antigen is shown. (F) and (DF) attached at the end of the antibody name are abbreviations for fucosylated and defucosylated, respectively, and indicate the presence or absence of α1,6-fucose added to the sugar chain of the Fc region.

The gene sequence was inserted downstream of a CAG promoter at the heavy chain side (first polypeptide side) and a CMV promoter at the light chain side (second polypeptide side). By using this vector, and as the expression system, Freestyle CHO Expression kit (Thermo Fisher Scientific, Inc.), and CHO—S cells or floating CHO cells in which α1,6-fucosyltransferase gene (FUT8) was knocked out [hereinafter, referred to as CHO (FUT8 KO)], transient expression was performed. Alternatively, as the expression system, even if Expi293 Expression System (Thermo Fisher Scientific, Inc.) and Expi293F cells or Expi293F cells in which FUT8 was knocked out (hereinafter, referred to as Expi293F (FUT8 KO)) were used, the same antibody group can be produced.

Antibody molecules having α1,6-fucose was produced using CHO—S cells or Expi293F cells, and antibody molecules deficient in α1,6-fucose was produced using CHO (FUT8 KO) cells or Expi293F (FUT8 KO) cells.

A cell culture medium was centrifuged, and the supernatant was collected through a 0.2 μm filter (Thermo Scientific, Inc.). From the culture supernatant, a partially purified antibody was obtained by affinity purification using MabSelect SuRe (GE Healthcare). Specifically, after equilibrating the resin packed in the column with PBS, the culture supernatant was added to the column, and the column was washed once with PBS containing Triton X-114 at a final concentration of 0.1% and once with PBS, and then, the antibody was eluted with an elution buffer (100 mM citrate-NaOH, pH 3.9, or 20 mM acetate-NaOH, 50 mM NaCl, pH 3.9).

The obtained antibody solution was neutralized by adding a 1/10 amount of a neutralization buffer (1 M phosphate-NaOH, pH 7.0), and concentration by ultrafiltration was performed using Amicon Ultra-4 Centrifugal Filter Units (Millipore Corporation). The partially purified antibody contains a certain proportion of aggregates, and therefore, in order to separate only a monomer, gel filtration chromatography was performed using an AKTA chromatography system and a Superdex 200 Increase 10 300 GL column (both GE Healthcare).

As the mobile phase, a citrate buffer (10 mM citrate-NaOH, 150 mM NaCl, pH 6.0) was used. Only a monomer fraction was separated, and the absorbance A280 was measured using Nanodrop (Thermo Fisher Scientific, Inc.), and the measurement of the concentration of the antibody solution and preparation were performed.

TABLE 4

Names and Sequences of Produced CD3/HER2 Bispecific Antibodies, and Expressing Cells

| Antibody name | Amino acid sequence of polypeptide 1 | Amino acid sequence of polypeptide 2 | Expression host cells |
|---|---|---|---|
| DNP2_mvG4PE(R409K) (F) | SEQ ID NO: 10 | SEQ ID NO: 11 | CHO-S |
| DNP2_mvG1 (DF) | SEQ ID NO: 12 | SEQ ID NO: 13 | CHO (FUT8 KO) |
| DNP2_mvG4PE(R409K)_scT3a (F) | SEQ ID NO: 14 | SEQ ID NO: 15 | CHO-S |
| DNP2_mvG1_scT3a (DF) | SEQ ID NO: 16 | SEQ ID NO: 17 | CHO (FUT8 KO) |
| DNP2_IgG1 (DF) | SEQ ID NO: 18 | SEQ ID NO: 19 | CHO (FUT8 KO) |
| 4D5_mvG4PE(R409K) (F) | SEQ ID NO: 20 | SEQ ID NO: 21 | CHO-S |
| 4D5_mvG1 (DF) | SEQ ID NO: 22 | SEQ ID NO: 23 | CHO (FUT8 KO) |
| 4D5_mvG4PE(R409K)_scT3a (F) | SEQ ID NO: 24 | SEQ ID NO: 25 | CHO-S |
| 4D5_mvG1_scT3a (DF) | SEQ ID NO: 26 | SEQ ID NO: 27 | CHO (FUT8 KO) |
| 4D5_IgG1 (DF) | SEQ ID NO: 28 | SEQ ID NO: 29 | CHO (FUT8 KO) |

The cellular cytotoxicity of the above bispecific antibodies against human gastric cancer cell line MKN-7 cells (RIKEN BRC RCB0999) that are moderately positive for HER2 was measured by the method described in Example 3 (final concentration: 50 nM). As the comparison control, only the target cells or only the target cells and PBMC (no antibody added) were added. The obtained results are shown in FIG. 13. None of the antibodies in which DNP2 was used for the variable region exhibited cellular cytotoxicity.

On the other hand, the antibodies having only ADCC activity (4D5_mvG1 (DF) and 4D5_IgG1 (DF)) have cellular cytotoxicity, but the activity was weaker than that of the antibody having only ADTC activity (4D5 mvG4PE (R409K)_scT3a (F)). A mixture obtained by mixing a half amount of 4D5_mvG1 (DF) and a half amount of 4D5_mvG4PE(R409K)_scT3a (F) to give 50 nM exhibited a higher activity than the above antibody group. Further, 4D5_mvG1_scT3a (DF) that can exhibit ADCC activity and ADTC activity in one molecular type exhibited the highest cellular cytotoxicity in all antibody groups.

Similarly, the results of measuring the cellular cytotoxicity against human gastric cancer cell line MKN-45 cells (JCRB cell bank JCRB0254) that are moderately positive for HER2 are shown in FIG. 14. The antibodies in which the variable region is DNP2 to serve as a negative control all did not exhibit cellular cytotoxicity. Among the antibodies in which the variable region is 4D5, only 4D5_mvG1_scT3a (DF) exhibited apparent cellular cytotoxicity. From the above results, it was revealed that also for the HER2-positive cell line other than BT-20 cells, the present technique exhibits high cellular cytotoxicity by a synergistic action.

[Example 7] Cellular Cytotoxicity and Cytokine Production in Culture Supernatant of CD3/HER2 Bispecific Antibodies In order to compare the properties of a representative anti-CD3 bispecific antibody as described in the background section and the bispecific antibody produced in the present invention, a comparison control molecule was produced, and the cellular cytotoxicity and the cytokine production in a culture supernatant during cytotoxic assay were measured. As the comparison control molecule, a known anti-CD3 bispecific antibody (an anti-CD3 bispecific antibody having the amino acid sequences represented by SEQ ID NOS: 160, 359, and 399 described in WO 2016/071004) was produced. Hereinafter, this is also referred to as CD3/HER2 FabxscFv.

The expression vector was produced in the same manner as the method shown in Example 6, and the antibody was expressed using Expi293 Expression System (Thermo Scientific, Inc.). The subsequent purification procedure was performed according to the method described in Example 6.

The cellular cytotoxicity of the produced comparison control bispecific antibody and 4D5_mvG1_scT3a (DF) against BT-20 cells was measured by the method described in Example 4. The cell index value of the wells to which the test antibody was not added was taken as 0% activity, and the cell index value of the wells to which 0.5% Triton X-100 was added in place of the test antibody was taken as 100% activity, and the cellular cytotoxicity value of each antibody was calculated from the cell index value on day 2 (48 hours after addition of the antibodies).

The culture supernatant was collected at the same time, and the concentrations of cytokines (IFN-γ, TNF-α, and IL-6) were measured using BD Cytometric Bead Array (CBA) Human Th1/Th2 Cytokine Kit II (BD Pharmingen, Inc.). The results of plotting the cellular cytotoxicity and the cytokine concentration at each concentration on the same graph are shown in FIG. 15. The maximum cellular cytotoxicity was similar between 4D5_mvG1_scT3a (DF) and the control antibody. On the other hand, the degree of cytokine production was significantly different between these two antibodies. That is, in the case of the control antibody, an increase in cytokine production was observed along with an increase in cellular cytotoxicity in antibody concentration-dependent manner, and it was revealed that the difference between the concentration range in which cellular cytotoxicity is exhibited and the concentration range in which cytokine production is induced is small. On the other hand, in the case of 4D5_mvG1_scT3a (DF), an increase in cytokine production with an increase in cellular cytotoxicity was hardly observed.

[Example 8] Designing of Various Molecular Types of CD3/HER2 Bispecific Antibodies In Examples 1 to 7, the process for producing the heterodimer-type CD3/HER2 bispecific antibodies [FIG. 2(B)] in which anti-CD3 scFv is bound to the C terminus of the first polypeptide based on the IgG1-type anti-HER2 monovalent antibody, and the results of evaluation of their activity are shown. From the results, it was found for the first time that by exhibiting ADCC activity and ADTC activity in one molecule, synergistically high cellular cytotoxicity is exhibited while keeping the ability to induce cytokine production low.

In order to further investigate the molecular types capable of obtaining such a synergistic action of ADCC activity and ADTC activity, each molecular type shown in FIGS. 16(A) to 16(F) was designed. FIG. 16(A) shows a molecule used in the previous Examples. FIG. 16(B) shows a molecule in which anti-CD3 scFv is bound to the C terminus of one heavy chain of a bivalent antibody, and the Fab binding to the cancer antigen is bivalent. In order to produce the hetero heavy chains, Knobs into Holes modification (Nature Biotechnology. Vol 16: 677-681, 1998) is introduced into the CH3 moiety.

FIG. 16(C) shows a molecule which has the same amino acid sequence as that in FIG. 16(A), but has sugar chains to which α1,6-fucose is added by using normal CHO cells as expressing host cells. FIG. 16(D) shows a molecule in which anti-CD3 scFv is bound to the C terminus of the second polypeptide (VL-CL-hinge-Fc) of a monovalent antibody. FIG. 16(E) shows a molecule in which both Fab against the cancer antigen and anti-CD3 scFv are located at the N-terminal side, and in order to produce a hetero heavy chain, Knobs into Holes modification is introduced in the same manner as the above FIG. 16(B). FIG. 16(F) shows a molecule in which anti-CD3 scFv is bound one by one to the C terminus of each of the first and second polypeptides of a monovalent antibody, and as a result, it has two anti-CD3 scFvs in one molecule.

[Example 9] Production of Various Molecules and Evaluation of Cellular Cytotoxicity (1) Production of Designed Bispecific Antibodies The molecules designed in Example 8 were produced in the same manner as the method shown in Example 6. In Table 5, the produced antibodies and the amino acid sequences thereof are shown.

TABLE 5

Names and Sequences of Produced CD3/HER2 Bispecific Antibodies, etc. and Expressing Cells

| Molecular type (Recognition antigen) | Antibody name | Amino acid sequences |
|---|---|---|
| B (DNP) | DNP2_IgG4PE(R409K) (F) | SEQ ID NOS: 30, 31 |
| B (DNP) | DNP2_IgG4PE(R409K)_scT3a (F) | SEQ ID NOS: 32 to 34 |
| B (DNP) | DNP2_IgG1 (DF) | SEQ ID NOS: 35, 36 |
| B (DNP) | DNP2_IgG1_scT3a (DF) | SEQ ID NOS: 37 to 39 |
| B (HER2) | 4D5_IgG4PE(R409K) (F) | SEQ ID NOS: 40, 41 |
| B (HER2) | 4D5_IgG4PE(R409K)_scT3a (F) | SEQ ID NOS: 42 to 44 |
| B (HER2) | 4D5_IgG1 (DF) | SEQ ID NOS: 28, 29 |

TABLE 5-continued

Names and Sequences of Produced CD3/HER2 Bispecific Antibodies, etc. and Expressing Cells

| Molecular type (Recognition antigen) | Antibody name | Amino acid sequences |
|---|---|---|
| B (HER2) | 4D5_IgG1_scT3a (DF) | SEQ ID NOS: 45 to 47 |
| B (GM2) | 8962_IgG1 (DF) | SEQ ID NOS: 48, 49 |
| B (GM2) | 8962_IgG1_scT3a (DF) | SEQ ID NOS: 50 to 52 |
| C (HER2) | 4D5_mvG1 (F) | SEQ ID NOS: 22, 23 |
| C (HER2) | 4D5_mvG1_scT3a (F) | SEQ ID NOS: 26, 27 |
| D (HER2) | 4D5_mvG4PE(R409K)_scT3a (LC) (F) | SEQ ID NOS: 53, 54 |
| D (HER2) | 4D5_mvG1_scT3a (LC) (DF) | SEQ ID NOS: 55, 56 |
| E (HER2) | 4D5_scT3a_IgG1 (DF) | SEQ ID NOS: 57 to 59 |
| E (—) | 4D5mut_scT3a_IgG1 (DF) | SEQ ID NOS: 60 to 62 |
| E (—) | 4D5mut_scSP34(H05')_IgG1 (DF) | SEQ ID NOS: 63 to 65 |
| E (—) | 4D5mut_scSP34_IgG1 (DF) | SEQ ID NOS: 66 to 68 |
| A (—) | 4D5mut_mvG1_scT3a (DF) | SEQ ID NOS: 69, 70 |
| F (DNP) | DNP2_mvG1_(scT3a)2 (DF) | SEQ ID NOS: 71, 72 |

The "molecular type" in Table 5 corresponds to FIGS. 16(B) to 16(F). The molecule having no scFv used as a negative control when evaluating each molecular type is classified as the same molecular type as the molecule having scFv.

The "Antibody name" in Table 5 indicates the characteristics of the molecule in the order of (1) the antibody clone name at the cancer antigen side, (2) the origin and structure of antibody subclass of constant region, (3) the CD3 clone name, and (4) the presence or absence of fucose. The "my" in the antibody name such as mvG1 or mvG4PF(R409K1) indicates an antibody that monovalently binds at the cancer antigen side. The "G1" in the antibody name such as mvG1 or mvG4PE(R409K) indicates that it is composed of Fc derived from IgG1, the "G4PE(R409K)" indicates that it is composed of Fc in which S228P, L235E, and R409K mutations are added to Fc derived from IgG4.

The (F) in Table 5 indicates that it includes fucose, and the (DF) indicates that it does not include fucose. An antibody expressed with (DF) in the antibody name was expressed in CHO (FUT8 KO), and an antibody expressed with (F) was expressed in CHO—S. The "sc" in the antibody name such as scT3a or scSP34 is an abbreviation of scFv, and scSP34 indicates scFv using VH and VL derived from SP34. The (LC) indicates that scFv is bound to a second polypeptide composed of CL-Fc as shown in FIG. 14(D).

The SP34 in molecular type (E) is an anti-CD3 monoclonal antibody described in literature (EMBO J. 1985. 4(2): 337-344; J. Immunol. 1986, 137(4): 1097-100; J. Exp. Med. 1991, 174: 319-326; J. Immunol. 1991, 147(9): 3047-52), and its amino acid sequence is disclosed as SEQ ID NO: 5 and SEQ ID NO: 10 in U.S. Pat. No. 10,066,015, or the like.

The SP34(H05') indicates the sequence of an anti-CD3 antibody with reduced affinity for CD3 by performing amino acid modification of the sequence of the variable region of SP34 (produced in Example 11 described below). The "4D5mut" in Table 5 denotes the variable region of an antibody whose binding affinity for HER2 is completely lost by introducing the modifications of two amino acid residues into the CDRs of the heavy chain variable region of Trastuzumab.

(2) Binding Valence at Cancer Antigen Side and Cellular Cytotoxicity of CD/HER2 and CD3/GM2 Bispecific Antibodies The cellular cytotoxicity of the molecular type (B) shown in Table 5 against BT-20 cells was measured by the method described in Example 4. Each of 4D5_IgG4PE(R409K) (F), 4D5_IgG1 (DF), 4D5 IgG4PE(R409K)_scT3a (F), and 4D5 IgG1_scT3a (DF) was added at a final concentration of 50 nM. For comparison, the cellular cytotoxicity of 4D5_mvG1_scT3a (DF) and 4D5_mvG4PE(R409K)_scT3a (F), each of which is of the molecular type (A), was also measured under the same conditions. The results are shown in FIGS. 17(A) and 17(B).

As shown in FIG. 17(A), 4D5_IgG4PE(R409K) (F) does not have effector activity, and no cellular cytotoxicity was observed only by binding to HER2. As shown in FIG. 17(B), cellular cytotoxicity was observed in both 4D5_IgG4PE (R409K)_scT3a (F) and 4D5_IgG1 (DF), and it was revealed that 4D5_IgG1_scT3a (DF) has higher cellular cytotoxicity than 4D5 IgG4PE(R409K)_scT3a (F). The strength of the activity of 4D5_IgG1_scT3a (DF) in which the Fab in the cancer antigen binding domain is bivalent was comparable to that of 4D5_mvG1_scT3a (DF) in which the Fab in the cancer antigen binding domain is monovalent.

From the above results, it was revealed that the synergistic effect of cellular cytotoxicity due to having ADTC activity and ADCC activity in a single antibody molecule is observed not only when the cancer antigen binding domain is monovalent but also when it is bivalent.

Similarly, the cellular cytotoxicity against human small cell lung cancer cell line SBC-3 cells (JCRB cell bank JCRB0818) was measured for a molecule in which an anti-ganglioside GM2 monoclonal antibody was used as the anti-tumor specific antigen (TSA) antibody of the molecular type (B). Each of 8962 IgG1 (DF), 8962_mvG1_scT3a (DF), and 8962_IgG1_scT3a (DF) was added at a final concentration of 50 nM. The results are shown in FIGS. 18(A) and 18(B).

As a negative control of the anti-TSA antibody variable region, the activity of an antibody molecule containing the variable region of an anti-DNP antibody is shown in FIG. 18(A), and the activity of the antibody molecules containing the variable region of an anti-GM2 monoclonal antibody, which is the test substance, is shown in FIG. 18(B). Under the conditions, cellular cytotoxicity was not observed in 8962 IgG1 (DF) which is an ADCC antibody of bivalent type, but high cellular cytotoxicity was observed in 8962 IgG1_scT3a (DF) that is of bivalent type and has both ADCC and ADTC activities.

(3) Presence or Absence of α1,6-Fucose and Cellular Cytotoxicity of CD3/HER2 Bispecific Antibody The cellular cytotoxicity of the molecular type (C) shown in Table 5 against BT-20 cells was measured by the method described in Example 4. Each of 4D5 mvG4PE(R409K) (F), 4D5_mvG1 (F), 4D5_mvG4PE(R409K)_scT3a (F), and 4D5_mvG1_scT3a (F) was added at a final concentration of 50 nM.

The results are shown in FIG. 19(A). 4D5_mvG4PE (R409K) (F) did not exhibit cellular cytotoxicity (data not show). 4D5_mvG1 (F) and 4D5 mvG4PE(R409K)_scT3a (F) exhibited cellular cytotoxicity, although weakly. Further, it was revealed that 4D5_mvG1_scT3a (F) has higher cellular cytotoxicity than the above-mentioned two molecules. It was revealed that even in the case of having α1,6-fucose, an increase in activity is shown by exhibiting ADCC activity and ADTC activity in one molecule.

However, as shown in FIG. 19(B), according to the comparison with the molecule lacking of α1,6-fucose, 4D5_mvG1 (DF) which is an antibody with a high ADCC activity has stronger cellular cytotoxicity than 4D5_mvG1_scT3a (F), and 4D5_mvG1_scT3a (DF) had even stronger cellular cytotoxicity. From the above results, it was revealed that the phenomenon in which the cellular cytotoxicity is synergistically increased by exhibiting ADCC activity and ADTC activity in one molecule has generality regardless of the presence or absence of α1,6-fucose. Further, it was revealed that higher cellular cytotoxicity is given when high ADCC activity and ATDC activity are exhibited in one molecule by removing α1,6-fucose.

(4) Fusion Position of Anti-CD3 scFv and Cellular Cytotoxicity of CD3/HER2 Bispecific Antibody The cellular cytotoxicity of the molecular type (D) shown in Table 5 against BT-20 cells was measured by the method described in Example 4. Each of 4D5_mvG4PE(R409K), 4D5_mvG1 (DF), 4D5_mvG4PE(R409K)_scT3a (LC) (F), and 4D5_mvG1_scT3a (LC) (DF) was added at a final concentration of 50 nM. The results are shown in FIG. 20(A).

4D5_mvG4PE(R409K)_scT3a (LC) (F) exhibited cellular cytotoxicity comparable to that of 4D5_mvG1 (DF), and 4D5_mvG1_scT3a (LC) (DF) exhibited higher cellular cytotoxicity than these antibodies. Further, the results of comparing the activities of the molecular type (A) and the molecular type (D) in the same manner are shown in FIG. 20(B). When comparison was performed in a combination of 4D5_mvG4PE(R409K)_scT3a (LC) (F) and 4D5_mvG4PE (R409K) scT3a (F), and a combination of 4D5 mvG1 scT3a (LC) (DF) and 4D5_mvG1_scT3a (DF), the antibodies in either combination exhibited substantially comparable cellular cytotoxicity.

That is, it was revealed that even if the anti-CD3 scFv is added to the C terminus of either the first polypeptide or the second polypeptide, neither the increase in ADTC activity nor the increase in the synergistic effect of ADTC activity and ADCC activity in the anti-CD3 bispecific antibodies is affected.

The cellular cytotoxicity of the molecular type (E) shown in Table 5 against BT-20 cells was measured by the method described in Example 4. Each of 4D5_scT3a_IgG1 (DF) and 4D5mut_scT3a_IgG1 (DF) was added at a final concentration was 50 nM, 5 nM, or 0.5 nM. The results are shown in FIG. 21.

4D5_scT3a_IgG1 (DF) exhibited high cellular cytotoxicity at any concentration. 4D5mut_scT3a_IgG1 (DF) does not bind to HER2 as described above but exhibited non-specific cellular cytotoxicity at any concentration.

Similarly, the activity was measured also for 4D5mut_scSP34 IgG1 (DF) and 4D5mut_scSP34(H05')_IgG1 (DF), and the results of comparison with 4D5mut_scT3a_IgG1 (DF) are shown in FIGS. 22A to 22C. All antibodies exhibited non-specific cellular cytotoxicity, but 4D5mut_scSP34(H05')_IgG1 (DF) and 4D5mut_scSP34_IgG1 (DF) exhibited higher cellular cytotoxicity than 4D5mut_scT3a_IgG1 (DF).

The binding affinity of these antibodies for CD3 was measured by Biacore (GE Healthcare). Specifically, an anti-tetra His mouse antibody (QIAGEN N.V.) was immobilized on a CM5 sensor chip at approximately 8000 RU using an amine coupling kit (GE Healthcare). As the coupling buffer, 10 mM sodium acetate (pH 4.5) was used. As the ligand, a His-tag-fused human CD3D&E protein (Sino Biological, Inc.) dissolved in HBS-EP(+) buffer at 5 μg/mL was captured at 5 μL/min for 120 seconds.

Subsequently, bispecific antibody solutions obtained by 2-fold serial dilution for 5 times from 10 μg/mL was added as the analyte at a flow rate of 30 μL/min, and binding reaction between each antibody and the analyte was measured for 2 minutes, and a dissociation reaction was measured for 5 minutes. The measurement was performed by single cycle kinetics method. The obtained sensorgram was analyzed using Bia Evaluation Software (GE Healthcare), and the kinetic constant of each antibody was calculated.

The results are shown in FIGS. 22D to 22G. The $K_D$ value of 4D5mut_scSP34 IgG1 (DF) was $1.26\times10^{-8}$ M, and the $K_D$ value of 4D5mut_scSP34(H05')_IgG1 (DF) was $1.08\times10^{-7}$ M. The $K_D$ values of 4D5mut_scT3a_IgG1 (DF) could not be calculated, but the binding affinity on the sensorgram was observed, and the binding dissociation equilibrium state was reached at about 6 RU at the highest concentration added. 4D5mut_scSP34(H05')_IgG1 (DF) reached a binding dissociation equilibrium state at about 100 RU at the highest concentration added, and therefore, the $K_D$ value of 4D5mut_scT3a_IgG1 (DF) was larger than this and can be determined to be $K_D>1.08\times10^{-7}$ M.

That is, it was demonstrated that by bonding the anti-CD3 scFv not to the C-terminal side, but to the N-terminal side of the Fc region or the constant region, even when the anti-CD3 scFv whose affinity is as low as $K_D>1.08\times10^{-7}$ M, undesired non-specific cytotoxicity irrelevant to specific binding to a disease-related antigen occurs.

(5) Valence of Anti-CD3 scFv and Cellular Cytotoxicity of CD3/HER2 Bispecific Antibody The cellular cytotoxicity of the molecular type (F) shown in Table 5 against BT-20 cells was measured by the method described in Example 4. As a positive control for the cellular cytotoxicity, 4D5_mvG1_scSP34(H05') (DF) was added at 50 nM. Each of 4D5mut_mvG1_scT3a (DF) and DNP2_mvG1_(scT3a)$_2$ (DF) was added at a final concentration of 50 nM, 5 nM, or 0.5 nM. The results are shown in FIGS. 23(A) and 23(B), respectively.

Although none of these molecules bind to HER2, cellular cytotoxicity was not observed at any concentration in 4D5mut_mvG1_scT3a (DF), but antibody concentration-dependent cellular cytotoxicity was observed at 50 nM and 5 nM in DNP2_mvG1_(scT3a)$_2$ (DF). That is, it was demonstrated that by making the anti-CD3 scFv bivalent, non-specific cellular cytotoxicity occurs.

From the results of the above (4) and (5), it was demonstrated that an anti-CD3 bispecific antibody having ADCC and ADTC activity in one molecule, in order to exhibit synergistically high cellular cytotoxicity and not to cause non-specific cellular cytotoxicity of the anti-CD3 bispecific antibody, it is necessary to add the CD3 binding domain monovalently to the C-terminal side of Fc of the anti-CD3 bispecific antibody.

[Example 10] Production of CD3/HER2 Bispecific Antibody Having Anti-CD3 scFv with Strong Affinity and Evaluation of Cellular Cytotoxicity and Cytokine Production The effect of the affinity of the anti-CD3 scFv on the activity of the bispecific antibodies was examined. DNP2_mvG1_scI2C (DF) and 4D5_mvG1_scI2C (DF) having a structure of the molecular type (A) shown in Table 5 were produced in the same manner as the procedure of Example 6 using the amino acid sequence represented by SEQ ID NO: 73 as the anti-CD3 scFv (scFv with VH and VL of clone I2C described in US Patent Publication No. 2011/0275787, the $K_D$ value is around $1\times10^{-8}$). The cellular cytotoxicity of these molecules (final concentration: 50 nM) against BT-20 cells was measured by the method described in Example 4. The results are shown in FIG. 24A.

As shown in FIG. 24A, with respect to the molecules using scT3a as the anti-CD3 scFv (produced in Example 6), cellular cytotoxicity was not observed in DNP2_mvG1_scT3a (DF) which does not specifically bind to HER2, and cellular cytotoxicity was observed in 4D5_mvG1_scT3a (DF) which specifically binds to HER2. On the other hand, with respect to the molecule using the clone scI2C as the anti-CD3 scFv, high cellular cytotoxicity was observed in both DNP2_mvG1_scI2C (DF) and 4D5_mvG1_scI2C (DF) regardless of the presence or absence of specific binding to HER2. Therefore, it was revealed that non-specific cellular cytotoxicity occurs when the clone scI2C is used as the anti-CD3 scFv even if the molecular type is the same.

Subsequently, 4D5_mvG1_scT3a (DF) or 4D5_mvG1_scI2C (DF) and human PBMC were incubated, and the cytokine production amount was measured. Specifically, human PBMC ($1\times10^6$ cells/100 L/tube) and the antibody (final concentration: 100, 10, or 1 μg/mL) were mixed with X-VIVO (registered trademark) 15 serum-free hematopoietic cell medium, and the cells were cultured at 37° C. for 24 hours. The supernatant after culturing was collected, and the cytokine concentration was measured according to the method shown in Example 7. The results are shown in FIG. 24B.

As shown in FIG. 24B, in the 4D5_mvG1_scT3a (DF)-added group, several cytokines whose production was increased at 100 μg/mL were observed, but hardly observed at 10 μg/mL and 1 μg/mL. On the other hand, in 4D5_mvG1_scI2C (DF), significant cytokine production was observed from a low concentration. From the above results, it was revealed that when the clone 12C with strong affinity is used as the anti-CD3 scFv, non-specific cellular cytotoxicity occurs and also significant cytokine production occurs.

[Example 11] Production of CD3/HER2 Bispecific Antibodies Having Anti-CD3 scFv with Adjusted Affinity and Evaluation of Their Activity (1) Designing of Amino Acid Modification From Example 10, it was revealed that it is important to appropriately control the affinity of the anti-CD3 scFv. By using SP34, which is the anti-CD3 monoclonal antibody shown in Example 9 (1), it was attempted to reduce the affinity thereof to an appropriate range by introducing amino acid modification into the CDRs. The nucleotide sequence and the amino acid sequence of scSP34 used as the scFv type, and the amino acid sequence of the CDRs are represented by SEQ ID NOS: 74, 75, and 76 to 81, respectively.

An antibody model structure was prepared based on the amino acid sequence of SP34 by three-dimensional structural modeling using Molecular Operating Environment 2016.08 (Molsis Inc.). Amino acid residues that are present on the surface and are highly likely to contribute to binding were selected as modification candidate residues, and various amino acid-modified CDRs were designed. FIG. 25(A) shows the design of modification introduction of one amino acid, and FIG. 25(B) shows the design of modification introduction of two or more amino acid residues. The amino acid residues shown in bold in the amino acid sequences in the table indicates the amino acid residues after modification. Further, the amino acid sequence of a CDR-modified humanized antibody of SP34 was designed in the same manner as the method described in Example 15(1) of WO 2019/017401, and the amino acid sequences of the frameworks of VL and VH thereof are shown in FIGS. 26(A) and 26(C), and 26(B) and 26(D), respectively.

(2) Production of Antibodies and Affinity Measurement

Some amino acid sequences designed in (1) were actually produced as HER2/CD3 bispecific antibodies in the same manner as the method described in Example 6, and the binding activity thereof was examined. Expi293F cells were used as expressing cells. Affinity measurement was performed according to the method described in Example 9 (4). The results are shown in FIG. 27. It was revealed that as compared with scSP34 which is the anti-CD3 scFv produced from the parent clone SP34, the affinity ($K_D$) can be reduced to the order of 10-7 by introducing amino acid residue modification of one or more amino acid residues.

(3) Cellular Cytotoxicity and Cytokine Production During Cytotoxic Assay

4D5_mvG1_scSP34(H04') (DF) and 4D5_mvG1_scSP34 (H05') (DF), each of which is an HER2/CD3 bispecific antibody having the scSP34 CDR variants scSP34(H04') or scSP34(H05') found in (2) were produced using FUT8KO CHO cells. With respect to these antibodies, cellular cytotoxicity (final concentration of antibody: 400 pM) against BT-20 cells and cytokine production during cytotoxic assay were measured according to the method described in Example 7. The results are shown in FIGS. 28(A) to 28(C) and 29(A) to 29(D), respectively.

As shown in FIGS. 28(A) to 28(C), the cellular cytotoxicity of 4D5_mvG1_scT3a (DF) was slightly higher than that of 4D5_mvG1 (DF), but there was not much difference. On the other hand, it was revealed that 4D5_mvG1_scSP34 (H04') (DF) and 4D5_mvG1_scSP34(H05') (DF) have high cytotoxicity, although it is slightly lower than that of 4D5_mvG1_scSP34 (DF).

As shown in FIGS. 29(A) to 29(D), the amount of each cytokine in the culture supernatant was extremely high for 4D5_mvG1_scSP34 (DF) and significantly lower for 4D5_mvG1_scSP34(H04') (DF), and further lower for 4D5_mvG1_scSP34(H05') (DF). In particular, with respect to IL-2 and IFN-γ, almost no production was observed under the conditions of this experiment for 4D5_mvG1_scSP34 (H04') (DF) and 4D5_mvG1_scSP34(H05') (DF).

The above results revealed that the cellular cytotoxicity and the cytokine production can be controlled by introducing amino acid residue modification into anti-CD3 scFv to adjust the affinity. The amino acid sequence of scSP34 (H04'), which is anti-CD3 scFv with adjusted affinity, is represented by SEQ ID NO: 117, the amino acid sequences of heavy chain CDRs 1 to 3 are represented by SEQ ID NOS: 118 to 120, the amino acid sequences of light chain CDRs 1 to 3 are represented by SEQ ID NOS: 121 to 123, and the amino acid sequences of VH and VL are represented by SEQ ID NOS: 124 and 125. Similarly, the amino acid sequence of scSP34(H05') is represented by SEQ ID NO: 82, the amino acid sequences of heavy chain CDRs 1 to 3 are represented by SEQ ID NOS: 83 to 85, the amino acid sequences of light chain CDRs 1 to 3 are represented by SEQ ID NOS: 86 to 88, and the amino acid sequences of VH and VL are represented by SEQ ID NOS: 115 and 116, respectively.

(4) Non-Specific Cytokine Production

The ability to induce non-specific cytokine production of 4D5_mvG1_scSP34 (DF), 4D5_mvG1_scSP34(H04') (DF), and 4D5_mvG1_scSP34(H05') (DF), or the like was measured in the same manner as the method described in Example 10. As a negative control that does not induce non-specific cytokine production, 4D5_mvG1_scT3a (DF) was used, and as a positive control that induces non-specific cytokine production, 4D5_mvG1_scI2C (DF) was used. The results are shown in FIG. 30.

In terms of all four cytokines measured, significant cytokine production was observed from a low concentration for 4D5_mvG1_scSP34 (DF), but for 4D5_mvG1_scSP34 (H04') (DF) and 4D5_mvG1_scSP34(H05') (DF), the ability to induce cytokine production was reduced, and it was revealed that the reduction degree is correlated with the reduction of the affinity of the anti-CD3 scFv.

[Example 12] Acquisition of Anti-CD3 Monoclonal Antibody from Human Antibody-Producing Mouse, Production of CD3/HER2 Bispecific Antibody with Adjusted Affinity and Evaluation of Activity (1) Immunization of Animal and Preparation of Anti-CD3 Monoclonal Antibody-Producing Cells As an immunogen, an N-terminal non-acetylated peptide of human CD3F conjugated with a KLH protein: $H_2N$-QDGNEEMGGITQTPYKVSISGTTVILTC-KLH (SEQ ID NO: 146) (Scrum Inc.) was administered to human antibody-producing mice [Ishida & Lonberg, IBC's 11th Antibody Engineering, Abstract 2000; Ishida, I. et al., Cloning & Stem Cells 4, 91-102 (2002), and Isamu Ishida (2002) Experimental medicine 20, 6, 846-851] a total of 6 times at 40 μg/mouse. Only at the first immunization, to 20 μL of the antigen solution, an equal amount of TiterMax Gold (TiterMax USA) or Sigma adjuvant system (Sigma-Aldrich Co. LLC) was added as adjuvant.

Dissection was performed 4 days after the final immunization and the lymph node or the spleen was surgically excised. The excised lymph node or spleen was homogenized, and thereafter, the cells were transferred to a tube through a cell strainer (Falcon, Inc.), and centrifuged to precipitate the cells. The obtained spleen cells were mixed with a red blood cell lysis reagent (manufactured by Sigma-Aldrich Co. LLC) and allowed to react with the reagent for 1 minute in a warm water bath at 37° C., followed by dilution with MEM medium, and further the resultant was centrifuged. The obtained spleen cells or lymphoid cells were washed twice with MEM medium, and thereafter subjected to cell fusion.

(2) Production of Anti-CD3 Monoclonal Antibody-Producing Hybridoma

An 8-azaguanine resistant mouse myeloma cell line P3-U1 (P3-X63Ag8U.1, ATCC: CRL-1597, European Journal of Immunology, 6: 511, 1976) was cultured in a culture medium obtained by adding 10% FBS and an antibiotic to RPMI 1640 medium, and expansion culture was performed until a cell count necessary for cell fusion ($3\times10^7$ cells or more) was reached. The mouse spleen cells or lymphoid cells obtained in (1) and the myeloma cells were mixed at a ratio of 2:1 and centrifuged (1500 rpm, 5 minutes). After the cells were loosened, cell fusion was performed using GenomONE-CF (manufactured by Ishihara Sangyo Co., Ltd.). After the reaction on ice for 5 minutes, incubation was performed at 37° C. for 15 minutes.

Thereafter, a culture medium in which 10% FBS, HAT supplement (Thermo Fisher Scientific, Inc.), and an antibiotic were added to Cloning Medium CM-B (Sekisui Medical Co., Ltd.) was added thereto, and the cells were suspended therein at $2.5\times10^6$ cells/18 mL, and the resultant was seeded in an amount of 200 μL into a 96-well plate. The cells were cultured under the conditions of 37° C. and 5% $CO_2$ for 8 to 10 days, and screening of hybridomas described below was performed using the culture supernatant, and each well in which an antibody that shows reactivity specific to the target antigen is produced was selected, and single cell sorting with a cell sorter SH800 (Sony Corporation) was performed, whereby various monoclonal antibody-producing hybridoma were established.

(3) Screening of Anti-CD3 Antibody-Producing Hybridoma

The screening of anti-CD3 antibody-producing hybridomas was performed by flow cytometry. Cells cultured in a flask for floating cell culture were collected, washed twice with PBS, and then suspended in a staining buffer (PBS containing 0.02% EDTA, 0.05% NaN3, and 1% BSA), and prepared so that the viable cell count was 2.0 to $5.0\times10^5$ cells/50 μL. As human CD3 expressing cells, human T lymphoma cell line HuT-78 cells (ATCC TIB-161) were used, and as monkey CD3 expressing cells, HSC-F cells (JCRB cell bank JCRB1164) were used, and both types of cells were stained with CFSE (Sigma-Aldrich Co. LLC, final concentration: 0.2 μM) and VPD450 (BD Biosciences Company, final concentration: 1 μM), respectively. As negative control cells, unstained KHYG-1 cells (JCRB cell bank JCRB156) were used.

These three types of cells were mixed in equal amounts, and the resultant was dispensed into a 96-well plate at 50 μL/well, and incubated on ice for 30 minutes, and then, an equal amount of the undiluted hybridoma supernatant solution was added thereto and mixed therewith, and placed at 4° C. for 30 minutes. After performing centrifugation of the cells and washing with a staining buffer once or twice, 50 μL of Alexa 647 Goat anti-Human IgG (H+L) (Thermo Fisher Scientific, Inc.) prepared at 2 μg/mL using a staining buffer was added thereto, and placed at 4° C. for 30 minutes under shading. After performing centrifugation of the cells and washing with a staining buffer twice, the cells were suspended in a staining buffer, and the fluorescent intensity was measured with a flow cytometer CyAn ADP (Beckman Coulter, Inc.).

By the above procedures (1) to (3), KM14, which is a hybridoma clone that specifically recognizes human CD3 and cynomolgus monkey CD3, was established.

(4) Cloning of Antibody Gene of Hybridoma KM414

The total RNA was extracted from the hybridoma KM14 using QIAGEN Rneasy Plus Mini Kit (QIAGEN N.V.), and 1st strand cDNA was synthesized by a 5' RACE method using SMARTer RACE 5'/3' Kit (Takara Bio Inc.). PCR was performed by PrimeSTAR (registered trademark) Max DNA Polymerase (Takara Bio Inc.) using the universal primers attached to the kit and the primers represented by SEQ ID NOS: 89 and 90, whereby gene fragments having the nucleotide sequences of the light chain and heavy chain variable regions were amplified. The obtained PCR fragments were sequenced using a next generation sequencer Ion PGM (Thermo Fisher Scientific, Inc.) for the light chain and a Sanger sequencer 3130xl Genetic Analyzer (Applied Biosystems, Inc.) for the heavy chain, and the nucleotide sequences of the antibody gene of the anti-CD3 monoclonal antibody KM14 were obtained.

The nucleotide sequences encoding the amino acid sequences of the light chain variable region and the heavy chain variable region of the anti-CD3 monoclonal antibody KM14 are represented by SEQ ID NOS: 91 and 92, respectively. Further, the amino acid sequences obtained by translating these nucleotide sequences are represented by SEQ ID NOS: 93 and 94, respectively, and the amino acid sequences of light chain CDRs 1 to 3 and heavy chain CDRs 1 to 3 are represented by SEQ ID NOS: 95 to 97 and 98 to 100, respectively. In addition, the nucleotide sequence and the amino acid sequence of scKM14 as scFv are represented by SEQ ID NOS: 101 and 102, respectively.

(5) Designing of Amino Acid Residue Modification based on Anti-CD3 Monoclonal Antibody KM14

The affinity for CD3 of scKM14 produced using the variable region of the anti-CD3 monoclonal antibody KM14 is stronger than that of scT3a or scSP34(H05'), which is the anti-CD3 scFv used in the Examples described so far, and it was considered that non-specific cellular cytotoxicity may be occurred by combining with ADCC activity. Therefore, amino acid residue modification of the CDRs of the anti-CD3 monoclonal antibody KM14 was designed according to the method described in Example 11 (1). Some designs are shown in FIG. 31. The amino acid residues in bold in the amino acid sequences in the table indicate the modified amino acid residues.

(6) Production of Bispecific Antibody and Affinity Measurement

Some of the amino acid sequences designed in (5) were actually produced as bispecific antibodies in the same manner as the method described in Example 6 and the binding activity thereof was examined. As an expression system, Expi293 (trademark) Expression System (Thermo Fisher Scientific, Inc.) and Expi293F cells were used. When the antibody is expressed using this cells, α1,6-fucose is added to the antibody molecule, but the measurement of affinity for CD3, and the measurement of cellular cytotoxicity mainly due to ADTC activity, and cytokine production during cytotoxic assay can be carried out.

Affinity measurement was performed according to the method described in Example 9 (4). The results are shown in FIG. 32. It was revealed that as compared with scKM14 which is the anti-CD3 scFv produced from the parent antibody clone KM14, the affinity ($K_D$) can be reduced to the order of 10 by introducing the amino acid residue modification of one or more amino acid residues.

(7) Cellular Cytotoxicity and Cytokine Production During Cytotoxic Assay

The cellular cytotoxicity against BT-20 cells and the cytokine production during cytotoxic assay of the produced antibodies were measured in the same manner as the methods described in Example 3 and Example 7. The final concentration of the test antibodies was set to 400 pM in the measurement of the cellular cytotoxicity and 10 nM in the measurement of the cytokine production. In terms of cellular cytotoxicity, a summary of the results is shown in FIG. 32 described in (6), classifying those having cellular cytotoxicity higher than 4D5_mvG1 (F) and equal to or lower than 4D5_mvG1_scT3a (F) as "+", those having cellular cytotoxicity higher than 4D5_mvG1_scT3a (F) and equal to or lower than 4D5_mvG1_scSP34(H05') (F) as "++", and those having cellular cytotoxicity higher than 4D5_mvG1_scSP34 (H05') (F) and equal to or lower than 4D5_mvG1_scKM14 (F) as "+++".

With respect to 6 variants of mut1-03, mut1-04, mut1-18, mut1-22, mut1-25, and mut1-26, the amino acid sequences of their scFvs are represented by SEQ ID NOS: 103 to 108, respectively, and the detailed results of the cellular cytotoxicity and the cytokine production are shown in FIGS. 33(A) and 33(B), and FIGS. 34(A) and 34(B), respectively. From FIG. 33(A), it was revealed that the cellular cytotoxicity of 4D5_mvG1_scKM14(mut1-25) (F) was slightly lower than that of 4D5_mvG1_scT3a (F).

Further, it was revealed that the cellular cytotoxicity of 4D5_mvG1_scKM14(mut1-03) (F), 4D5_mvG1_scKM14 (mut1-04) (F), 4D5_mvG1_scKM14(mut1-18) (F), and 4D5_mvG1_scKM14(mut1-22) (F) is higher than that of 4D5_mvG1_scT3a (F) and lower than that of 4D5_mvG1_scSP34(H05') (F). In addition, from FIG. 33(B), the activity of 4D5_mvG1_scKM14(mut1-26) (F) was comparable to that of 4D5_mvG1_scSP34(H05') (F). In the drawing, it was revealed that 4D5_mvG1_scKM14 (F) has the highest activity.

With respect to the anti-CD3 monoclonal antibody KM14, which is a parent antibody, and six variants: mut1-03, mut1-04, mut1-18, mut1-22, mut1-25, and mut1-26, the amino acid sequences of VH, VL, and CDRs are shown in Table 6.

TABLE 6

Amino Acid Sequences of VH, VL, and CDRs of KM14 and Modified Antibodies Thereof

| Antibody Name | VH | VL | CDR H1 | CDR H2 | CDR H3 | CDR L1 | CDR L2 | CDR L3 |
|---|---|---|---|---|---|---|---|---|
| KM14 | SEQ ID NO: 94 | SEQ ID NO: 93 | SEQ ID NO: 98 | SEQ ID NO: 99 | SEQ ID NO: 100 | SEQ ID NO: 95 | SEQ ID NO: 96 | SEQ ID NO: 97 |
| mut1-03 | SEQ ID NO: 94 | SEQ ID NO: 126 | SEQ ID NO: 98 | SEQ ID NO: 99 | SEQ ID NO: 100 | SEQ ID NO: 132 | SEQ ID NO: 96 | SEQ ID NO: 97 |
| mut1-04 | SEQ ID NO: 94 | SEQ ID NO: 127 | SEQ ID NO: 98 | SEQ ID NO: 99 | SEQ ID NO: 100 | SEQ ID NO: 133 | SEQ ID NO: 96 | SEQ ID NO: 97 |
| mut1-18 | SEQ ID NO: 128 | SEQ ID NO: 93 | SEQ ID NO: 98 | SEQ ID NO: 134 | SEQ ID NO: 100 | SEQ ID NO: 95 | SEQ ID NO: 96 | SEQ ID NO: 97 |
| mut1-22 | SEQ ID NO: 129 | SEQ ID NO: 93 | SEQ ID NO: 98 | SEQ ID NO: 135 | SEQ ID NO: 100 | SEQ ID NO: 95 | SEQ ID NO: 96 | SEQ ID NO: 97 |
| mut1-25 | SEQ ID NO: 130 | SEQ ID NO: 93 | SEQ ID NO: 98 | SEQ ID NO: 136 | SEQ ID NO: 100 | SEQ ID NO: 95 | SEQ ID NO: 96 | SEQ ID NO: 97 |
| mut1-26 | SEQ ID NO: 131 | SEQ ID NO: 93 | SEQ ID NO: 98 | SEQ ID NO: 137 | SEQ ID NO: 100 | SEQ ID NO: 95 | SEQ ID NO: 96 | SEQ ID NO: 97 |

From FIGS. 34(A) and 34(B), it was found that 4D5_mvG1_scKM14 (F) shows high cytokine production during cytotoxic assay. Cytokine production was reduced for the bispecific antibodies using KM14 variants with adjusted affinity as compared with the one using the original KM14. The production of IFN-γ and IL-6 when each bispecific antibody was added were correlated with the strength of cellular cytotoxicity shown in FIGS. 33(A) and 33(B).

Subsequently, with respect to 4D5_mvG1_scKM14 (DF), 4D5_mvG1_scKM14(mut1-XX) (DF) (XX: 03, 04, 18, 22, 25, or 26), 4D5_mvG1_scSP34(H05') (DF), and 4D5_mvG1 (DF), the cellular cytotoxicity of the produced antibodies against BT-20 cells was measured in the same manner as the method described in Example 3. The final concentration of the test substance was set to 50, 5, and 0.5 nM, and the cell index value of the wells to which no test substance was added was taken as 0% activity, and the cell index value of the wells to which 0.5% Triton X-100 was added was taken as 100% activity, and the cellular cytotoxicity at 48 hours and 120 hours after the addition of the test substance was calculated. The results at 48 hours after the addition of the test substance are shown in FIG. 35(A), and the results at 120 hours after the addition of the test substance are shown in FIG. 35(B).

As shown in FIGS. 35(A) and 35(B), the strength of the antibody concentration-dependent cellular cytotoxicity was correlated with the order among the modified clones shown in FIGS. 33(A) and 33(B) at both measurement times.

(8) Measurement of Cellular Cytotoxicity, etc. in System Using 96-Well Plate

In order to measure the cellular cytotoxicity against BT-20 cells and the cytokine production during cytotoxic assay of the produced bispecific antibodies for many test antibodies, an experimental system using a 96-well plate was constructed and used.

First, BT-20 cells were prepared in RPMI 1640 medium (10% FBS, 10 μg/mL gentamicin) at $2.0\times10^5$ cells/mL, and added to a 96-well plate at 50 μL/well. Subsequently, human immunoglobulin (Japan Blood Products Organization) prepared at 4 mg/mL with RPMI medium, and PBMC derived from healthy human peripheral blood prepared at a cell density of $1\times10^6$ cells/mL were added to the above plate at 50 μL/well each. Finally, each of various bispecific antibodies prepared at 4 times the final concentration was added at 50 μL/well, and the plate was incubated under the conditions of 37° C. and 5% $CO_2$ for 48 hours.

In the measurement of the cellular cytotoxicity, a cell proliferation/cytotoxicity assay kit Cell Counting Kit-8 (Dojindo Laboratories Co., Ltd.) for detecting viable cells was used. The culture supernatant was removed from the 96-well plate after the reaction, followed by washing twice with PBS, and thereafter, the color reaction was performed by adding a coloring reagent, and the absorbance at 450 nm was measured with a plate reader.

The absorbance of the wells into which only the cells were seeded and no test substance was added was taken as 0% activity, and the absorbance of the wells in which the cells were lysed by adding 0.5% Triton X-100 was taken as 100% activity, and the cellular cytotoxicity value was calculated. The measurement of the cytokine production was performed in the same manner as the method described in Example 7 using the culture supernatant after incubation for 48 hours.

With respect to 4D5_mvG1_scKM14(mut1-XX) (DF) (XX: 03, 04, 18, 22, 25, or 26), and CD3/HER2 FabxscFv which is the anti-CD3 bispecific antibody produced in Example 7, the cellular cytotoxicity against BT-20 cells and the cytokine production were measured by the above-mentioned methods. The results of the cellular cytotoxicity are shown in FIG. 41(A), and the results of the cytokine production are shown in FIGS. 41(B) and 41(C).

As shown in FIG. 41(A), with respect to 4D5_mvG1_scKM14(mut1-XX) (DF) (XX: 03, 04, 18, 22, 25, or 26), the antibody concentration-dependent cellular cytotoxicity when each bispecific antibody was added was correlated with the order of activity among the modified clones shown in FIGS. 35(A) and 35(B).

Further, as shown in FIGS. 41(B) and 41(C), the production of IFN-γ and IL-6 for these bispecific antibodies was very low as compared with CD3/HER2 FabxscFv. The cytokine production of these bispecific antibodies was correlated with the strength of the cellular cytotoxicity shown in FIGS. 35(A) and 35(B) and 41(A), and the cytokine production shown in FIGS. 34(A) and 34(B). It was found that the defucosylated bispecific antibodies also show low cytokine production in the same manner as the fucosylated bispecific antibodies.

From the above (6) to (8), it was revealed that by introducing amino acid residue modification into the CDRs of the anti-CD3 monoclonal antibody KM14 so as to adjust the affinity for CD3 within an appropriate range, high cellular cytotoxicity can be exhibited while suppressing the cytokine production during cytotoxicity to a low level.

[Example 13] Production of CD3/Cancer Antigen Bispecific Antibodies Against Various Blood Cancer Antigens and Evaluation of Activity (1) Production of CD3/CCR4 Bispecific Antibody and CD3/CD123 Bispecific Antibody Bispecific antibodies including the variable regions of an antibody against a blood cancer antigen were produced and the cellular cytotoxicity against cell lines derived from blood cancers was examined. The bispecific antibodies shown in Table 7 were produced in accordance with the method described in Example 6.

CD3/CCR4 bispecific antibodies were produced using the amino acid sequences of VL and VH of an anti-CCR4 monoclonal antibody KM2160, a monoclonal antibody that binds to CC-chemokine receptor 4 (CCR4).

As for CD123, for the purpose of comparative verification with a general anti-CD3 bispecific antibody, a CD3/CD123 bispecific antibody XENP14045 was produced as a comparison control based on the amino acid sequences of SEQ ID NOS: 1 to 3 in WO 2017/210443.

XENP14045 is a CD3/CD123 bispecific antibody including Fc (silent Fc) that lacks Fc receptor binding activity due to amino acid modification, and damages cancer cells only by ADTC activity. The amino acid sequences of VL and VH of the anti-CD123 antibody portion of XENP14045 are represented by SEQ ID NOS: 109 and 110. By using these sequences, CD123-2_mvG1_scSP34(H05') (DF) which is a bispecific antibody including VH and VL of the anti-CD123 antibody portion of XENP14045 was produced.

TABLE 7

Names and Sequences of Produced Bispecific Antibodies, etc. and Expressing Cells

| Antibody name | Anti-CD3 scFv | Recognition antigen and sequences of variable regions |
|---|---|---|
| KM2160_mvG4PE(R409K) (F) | non | Recognition antigen: CCR4 |
| KM2160_mvG1 (DF) | non | VL: SEQ ID NO: 111 |
| KM2160_mvG4PE(R409K)_scT3a (F) | scT3a | VH: SEQ ID NO: 112 |
| KM2160_mvG4PE(R409K)_scSP34(H05') (F) | scSP34(H05') | |
| KM2160_mvG4PE(R409K)_scKM14(mut1-04) (F) | scKM14(mut1-04) | |
| KM2160_mvG4PE(R409K)_scKM14(mut1-18) (F) | scKM14(mut1-18) | |
| KM2160_mvG1_scT3a (DF) | scT3a | |
| KM2160_mvG1_scSP34(H05') (DF) | scSP34(H05') | |
| KM2160_mvG1_scKM14(mut1-04) (DF) | scKM14(mut1-04) | |
| KM2160_mvG1_scKM14(mut1-18) (DF) | scKM14(mut1-18) | |
| KM2160_IgG1 (DF) | non | |
| CD123-1_mvG1 (DF) | non | Recognition antigen: CD123 |
| CD123-1_mvG4PE(R409K)_scSP34(H05') (F) | scSP34(H05') | VL: SEQ ID NO: 113 |
| CD123-1_mvG1_scSP34(H05') (DF) | scSP34(H05') | VH: SEQ ID NO: 114 |
| CD123-1_IgG1 (DF) | non | |
| CD123-2_mvG1_scSP34(H05') (DF) | scSP34(H05') | Recognition antigen: CD123<br>VL: SEQ ID NO: 109<br>VH: SEQ ID NO: 110 |

(2) Evaluation of Cellular Cytotoxicity and Cytokine Production of CD3/CCR4 Bispecific Antibodies The cellular cytotoxicity of the produced CD3/CCR4 bispecific antibodies was measured by flow cytometry using PEER cells (JCRB cell bank JCRB0830), a CCR4-positive T cell lymphoma-derived cell line. The PEER cells were previously fluorescently labeled using CellVue (registered trademark) Claret Far Red Fluorescent Cell Linker Kit (Sigma-Aldrich Co. LLC), and diluted to $2.0\times10^5$ cells/mL and added to a 96-well plate at 50 μL/well. Subsequently, each of human immunoglobulin (Japan Blood Products Organization) prepared at 4 mg/mL with RPMI medium, and PBMC derived from healthy human peripheral blood prepared at a cell density of $1\times10^6$ cells/mL was added to the above plate at 50 μL/well.

Finally, each of various bispecific antibodies prepared to a concentration four times the final concentration was added at 50 μL/well, and incubated under the condition of 37° C. and 5% $CO_2$. At 48 hours after the addition of the antibodies, the plate was centrifuged and the culture supernatant was removed, and SYTOX (registered trademark) Dead Cell Stain Reagent (Thermo Fisher Scientific, Inc.) diluted to 1/1000 with a staining buffer (the same as that used in Example 12) was added at 100 μL/well, and the plate was left to stand at room temperature for 5 to 10 minutes. After washing the cells twice with a staining buffer, the fluorescence intensities in APC and BV421 channels were measured using a flow cytometer FACS Canto II (BD Biosciences Company).

APEER cell fraction was selected by FSC and SSC, and APC(+) and BV421(−) fraction was counted for viable cells, and based on the viable cell count of no addition of the test substance, the percentage of decrease in the viable cell count by the addition of each bispecific antibody was calculated as the cellular cytotoxicity (%). In addition, the culture supernatant was collected at the same time, and the cytokine concentration was measured in accordance with the method described in Example 7. The measurement results of the cellular cytotoxicity are shown in FIGS. 36(A) to 36(C).

As shown in FIGS. 36(A) to 36(C), in KM2160 mvG4 (R409K) (F) having no effector activity, and 4D5_mvG1_scSP34(H05') (DF), which is an anti-HER2 bispecific antibody having ADCC and ADTC activity but not binding to the PEER cell line, no cellular cytotoxicity was observed. In KM2160_mvG1 (DF) having only ADCC activity and KM2160_mvG4PE(R409K)_scXX (F) [XX: T3a, SP34(H05'), KM14(mut1-04), or KM14(mut1-18)] having only ADTC activity, cellular cytotoxicity was observed, and the activity of KM2160_mvG1 (DF) tended to be higher than that of KM2160_mvG4PE(R409K)_scXX (F).

Further, KM2160_mvG1_scXX (DF) (XX: T3a, SP34 (H05'), KM14(mut1-04), or KM14(mut1-18)) having ADCC and ADTC activity exhibited cellular cytotoxicity far exceeding that of the above antibodies. KM2160_mvG1_scSP34(H05') (DF) exhibited higher cellular cytotoxicity even as compared with KM2160_IgG1 (DF), which is an IgG1-type antibody having a strong ADCC activity and binding bivalently.

The measurement results of the production of cytokines (IL-2 and IFN-γ) are shown in FIGS. 37(A) and 37(B). As shown in FIG. 37(A), in KM2160_mvG1_scXX (DF) (XX: T3a, SP34(H05'), KM14(mut1-04), or KM14(mut1-18)), which exhibited high cellular cytotoxicity above, little increase in the production of IL-2 was observed. As shown in FIG. 37(B), with respect to the production of IFN-γ, an increase was observed in KM2160_mvG1_scSP34(H05') (DF) and KM2160_mvG1_scKM14(mut1-18) (DF) only at the maximum concentration of 50 nM.

From the above, it was revealed that also the CD3/CCR4 bispecific antibodies can exhibit high cellular cytotoxicity without accompanying a significant increase in cytokine production by having both ADCC and ADTC activity in one molecule.

(3) Evaluation of Cellular Cytotoxicity and Cytokine Production of CD3/CD123 Bispecific Antibodies The cellular cytotoxicity and the cytokine production of the produced CD3/CD123 bispecific antibodies were measured by flow cytometry using MOLM13 cells (DSMZ ACC 554) and OCI-AML3 cells (DAMZ ACC 582), which are CD123-positive acute myeloid leukemia (AML)-derived cell lines, in accordance with the method described in Example 13(2). The measurement results of the cellular cytotoxicity of the molecules including CD123-1 as the variable region against MOLM13 cells are shown in FIG. 38(A), and the cytokine production is shown in FIG. 38(B).

As shown in FIG. 38 (A), no cellular cytotoxicity was observed in 4D5_mvG1_scSP34(H05') (DF) used as a negative control. The cellular cytotoxicity increased in the order of CD123-1_mvG1 (DF) and CD123-1_hIgG1 (DF), which have ADCC activity, and CD123-1_mvG4(R409K)_scSP34 (H05') (F) having ADTC activity, and further, in the CD123-1_mvG1_scSP34(H05') (DF) molecule having both ADCC and ADTC activity, the cellular cytotoxicity was the highest. Further, as shown in FIG. 38(B), no significant difference was observed among the molecules in terms of cytokine production at this time.

The measurement results of the cellular cytotoxicity of CD123-2_mvG1_scSP34(H05') (DF) including CD123-2 as the variable region and the in-house produced XENP14045 which is a comparison control against MOLM13 and OCI-AML3 cells are shown in FIGS. 39(A) and 39(B), respectively, and the cytokine production corresponding thereto is shown in FIGS. 40(A), 40(B), 40(C), and 40(D), respectively.

As shown in FIGS. 39(A) and 39(B), XENP14045 exhibited cellular cytotoxicity against both cell lines from a concentration as low as about 1/10 of the concentration of CD123-2_mvG1_scSP34(H05') (DF). Both the molecules exhibited the cellular cytotoxicity of 80% or more at the maximum. In 4D5_mvG1_scSP34(H05') (DF) used as the negative control, no cellular cytotoxicity was observed.

As shown in FIGS. 40(A) to 40(D), in the case of XENP14045, an increase in cytokine production was observed in an antibody concentration-dependent manner in both cell lines. On the other hand, in the case of CD123-2_mvG1_scSP34(H05') (DF), the production of IL-2 did not substantially change and remained low even when the antibody concentration increased, and the production of IFN-γ was also very low as compared with XENP14045, and there was no significant increase in an antibody concentration-dependent manner.

From the above, it was revealed that also the CD3/CD123 bispecific antibodies can exhibit high cellular cytotoxicity without accompanying significant cytokine production by having both ADTC and ADCC activity in one molecule. Therefore, it was revealed that the anti-CD3 bispecific antibody of the present invention can exhibit comparable cellular cytotoxicity without accompanying significant cytokine production as compared with an anti-CD3 bispecific antibody, which has strong affinity for CD3 and has only the mechanism of action of ADTC activity.

[Example 14] Designing of Anti-CD3/HER2 Bispecific Antibodies with Modified CH3 Region and Modified Anti-CD3 scFv Region It is known that in the production of bispecific antibodies, the proportion of the target molecule is increased by introducing Knobs into Holes (KIH) modification into the CH3 region thereof. In Examples 8 and 9, KIH modification was introduced into the anti-CD3/HER2 bispecific antibodies in which the Fab against the cancer antigen is bivalent, but in this Example, KIH modification was introduced into the anti-CD3/HER2 bispecific antibodies in which the Fab against the cancer antigen is monovalent.

In the anti-CD3/HER2 bispecific antibody in which the Fab against the cancer antigen is monovalent, the polypeptide 1 (VH-CH1-Fc-scFv) and the polypeptide 2 (VL-CL-Fc) are present, and therefore, a Knobs-type or Holes-type amino acid modification can be introduced into either polypeptide. Further, in the KIH modification introduced in Examples 8 and 9, an intermolecular disulfide bond is introduced between the two CH3 moieties, but the KIH modification without including a disulfide bond can also be applied to the CD3 bispecific antibodies of the present invention. In the KIH modification without including a disulfide bond, amino acid residue substitutions of S354C and T366W are added to one of the two Fc polypeptide chains, and amino acid residue substitutions of Y349C, T366S, L368A and Y407V are added to the other.

Further, anti-CD3 bispecific antibodies in which the modifications to enhance the physicochemical stability were added to scFv were produced. Specifically, a disulfide bond was introduced by modifying the amino acid on the interaction surface of VH and VL of scFv with reference to the method described in Nat. Biotechnol. 14, 1239-45, 1996. Specifically, the amino acid at position 44 (according to Kabat numbering) of VH of scFv was substituted with Cys, and the amino acid at position 100 (according to Kabat numbering) of VL was substituted with Cys. This modification is referred to as (CC) or CC modification. In addition, scFv in which the amino acid at position 44 of VH was substituted with Ser and an amino acid at position 100 of VL was substituted with Glu was produced. This modification is referred to as (SE) or SE modification.

A design example and a structural position of the amino acid modification to be introduced into the CH3 region and the anti-CD3 scFv in the anti-CD3 bispecific antibodies in which the Fab against the cancer antigen is monovalent are shown in FIG. 42. The modification shown in FIG. 42 can also be applied to the anti-CD3 bispecific antibodies in which the Fab against the cancer antigen is bivalent.

In Examples 1 to 13, a plurality of specific sequences of anti-CD3 scFv capable of enhancing the cellular cytotoxicity without accompanying significant cytokine production are shown, and further, examples of the anti-CD3 bispecific antibody having such scFv are shown. With respect to the amino acid modification to be introduced into the CH3 region and the anti-CD3 scFv region described above, they can be introduced independently of the sequence of the anti-CD3 scFv.

Further, as the scFv, not only one in which VH, a linker, and VL are bound in this order from the N-terminal side (VH-linker-VL type, also referred to as HL type), but also one in which VL, a linker, and VH are bound in this order from the N-terminal side (VL-linker-VH type, also referred to as LH type) is also known.

Therefore, the anti-CD3 scFv in the present invention is also not limited to the VH-linker-VL type produced in Examples 1 to 13, and the VL-linker-VH type can also be designed, and the amino acid modification shown in FIG. 42 can be introduced into both types.

From the above, with respect to the modifications introduced into the anti-CD3 bispecific antibody of the present invention, the modifications of the CH3 moiety, the scFv clone name, the order of VH and VL of scFv, and the amino acid modifications introduced into scFv are shown in a table (FIG. 43). With respect to scSP34(H05'), the amino acid sequence using the FR sequence shown in FIG. 26 can also be used in the same manner. Examples thereof include VH(HV3) represented by SEQ ID NO: 159, VH(HV5) represented by SEQ ID NO: 160, VL(LV8a) represented by SEQ ID NO: 165, and the like. Note that the modification in FIG. 43 can be applied also to the anti-CD3 bispecific antibody that is bivalent at the cancer antigen side.

[Example 15] Production of Anti-CD3/HER2 Bispecific Antibodies with Modified CH3 Region and Modified Anti-CD3 scFv Region, and Evaluation of Cellular Cytotoxicity and Cytokine Production (1) Production of Bispecific Antibodies The amino acid sequences of the four sets of Fc regions (KIH-1 to KIH-4) in which the KIH modification designed in Example 14 was introduced are represented by SEQ ID NOS: 147 to 154. Further, various bispecific antibodies having scFv including any of these four types of KIH modifications and/or the CC modification or the SE modification of scFv were produced according to the method described in Example 6. The produced various bispecific antibodies and the amino acid sequences of the constituent elements thereof are shown in Tables 8 and 9. The amino acid sequence of scSP34(H05'), which is the scFv of the bispecific antibody in Table 8, is represented by SEQ ID NO: 82.

Specific amino acid sequences of VH and VL of scFv into which the CC modification or the SE modification was introduced are represented by SEQ ID NOS: 155 to 191. As specific examples of the specific amino acid sequences of anti-CD3 scFv constituted by these VH and VL, the VH-linker-VL type sequences are represented by SEQ ID NOS: 192 to 205 and the VL-linker-VH type sequences are represented by SEQ ID NO: 206 to 217 (as the VL-linker-VH type sequence, sequences in which the CC modification or the SE modification is not introduced are also shown).

Further, specific examples of the anti-CD3/HER2 bispecific antibodies prepared according to the method described in Example 6 using these scFv sequences and the anti-CD3 scFv sequences thereof are shown in Table 9. In the name of the bispecific antibody, the respective constituent elements of the bispecific antibody (type of KIH modification introduced, anti-CD3 scFv clone name, the order of VH and VL of scFv, and modification introduced into scFv) are shown in order.

Specifically, for example, 4D5_mvG1(KIH-1)_scXX (YY)(ZZ) (DF) indicates that the Fab clone is 4D5, mvG1 indicates that the antibody is monovalent at the cancer antigen side and the Fc region is based on IgG1, KIH-1 indicates that the modification pattern of the Fc (CH3) moiety is KIH-1 type, scXX indicates that the anti-CD3 scFv clone is XX, and one in which (LH) is described in the (YY) portion indicates the VL-linker-VH type (one in which there is no description in this portion is the VH-linker-VL type), one in which (CC) is described in the (ZZ) portion indicates that scFv has the CC modification, and one in which (SE) is described in the (ZZ) portion indicates that scFv has the SE modification, and (DF) indicates that it does not include fucose.

In Table 10, the amino acid sequences of VH, VL, heavy chain CDRs and light chain CDRs included in various anti-CD3 scFv are represented by SEQ ID NOS. Note that Table 10 applies regardless of whether the scFv is the HL type or the LH type.

TABLE 8

Bispecific Antibodies in which KIH Modification was Introduced and Amino Acid Sequences

| Bispecific antibody | SEQ ID NO of amino acid sequence of Fc region of polypeptide 1 | SEQ ID NO of amino acid sequence of Fc region of polypeptide 2 |
|---|---|---|
| 4D5_mvG1(KIH-1)_scSP34(H05') (DF) | SEQ ID NO: 147 | SEQ ID NO: 148 |
| 4D5_mvG1(KIH-2)_scSP34(H05') (DF) | SEQ ID NO: 149 | SEQ ID NO: 150 |
| 4D5_mvG1(KIH-3)_scSP34(H05') (DF) | SEQ ID NO: 151 | SEQ ID NO: 152 |
| 4D5_mvG1(KIH-4)_scSP34(H05') (DF) | SEQ ID NO: 153 | SEQ ID NO: 154 |

TABLE 9

Names and Amino Acid Sequences of Produced Various Bispecific Antibodies

| Bispecific antibody | SEQ ID NO of amino acid sequence of anti-CD3 scFv |
|---|---|
| 4D5_mvG1(KIH-1)_scSP34(H05')(CC) (DF) | SEQ ID NO: 192 |
| 4D5_mvG1(KIH-1)_scSP34(H05'_HV3LV8a)(CC) (DF) | SEQ ID NO: 193 |
| 4D5_mvG1(KIH-1)_scSP34(H05'_HV5LV8a)(CC) (DF) | SEQ ID NO: 194 |
| 4D5_mvG1(KIH-1)_scSP34(H05')(SE) (DF) | SEQ ID NO: 195 |
| 4D5_mvG1(KIH-1)_scKM14(mut1-03)(CC) (DF) | SEQ ID NO: 196 |
| 4D5_mvG1(KIH-1)_scKM14(mut1-04)(CC) (DF) | SEQ ID NO: 197 |
| 4D5_mvG1(KIH-1)_scKM14(mut1-18)(CC) (DF) | SEQ ID NO: 198 |
| 4D5_mvG1(KIH-1)_scKM14(mut1-22)(CC) (DF) | SEQ ID NO: 199 |
| 4D5_mvG1(KIH-1)_scKM14(mut1-25)(CC) (DF) | SEQ ID NO: 200 |
| 4D5_mvG1(KIH-1)_scKM14(mut1-26)(CC) (DF) | SEQ ID NO: 201 |
| 4D5_mvG1(KIH-1)_scKM14(mut1-18)(SE) (DF) | SEQ ID NO: 202 |
| 4D5_mvG1(KIH-1)_scKM14(mut1-22)(SE) (DF) | SEQ ID NO: 203 |
| 4D5_mvG1(KIH-1)_scKM14(mut1-25)(SE) (DF) | SEQ ID NO: 204 |
| 4D5_mvG1(KIH-1)_scKM14(mut1-26)(SE) (DF) | SEQ ID NO: 205 |
| 4D5_mvG1(KIH-1)_scSP34(H05')(LH) (DF) | SEQ ID NO: 206 |
| 4D5_mvG1(KIH-1)_scSP34(H05')(LH)(CC) (DF) | SEQ ID NO: 207 |
| 4D5_mvG1(KIH-1)_scSP34(H05'_HV3LV8a)(LH) (DF) | SEQ ID NO: 208 |
| 4D5_mvG1(KIH-1)_scSP34(H05'_HV5LV8a)(LH) (DF) | SEQ ID NO: 209 |
| 4D5_mvG1(KIH-1)_scSP34(H05'_HV3LV8a)(LH)(CC) (DF) | SEQ ID NO: 210 |
| 4D5_mvG1(KIH-1)_scSP34(H05'_HV5LV8a)(LH)(CC) (DF) | SEQ ID NO: 211 |

TABLE 9-continued

| Names and Amino Acid Sequences of Produced Various Bispecific Antibodies | |
|---|---|
| Bispecific antibody | SEQ ID NO of amino acid sequence of anti-CD3 scFv |
| 4D5_mvG1(KIH-1)_scKM14(mut1-03)(LH) (DF) | SEQ ID NO: 212 |
| 4D5_mvG1(KIH-1)_scKM14(mut1-04)(LH) (DF) | SEQ ID NO: 213 |
| 4D5_mvG1(KIH-1)_scKM14(mut1-18)(LH) (DF) | SEQ ID NO: 214 |
| 4D5_mvG1(KIH-1)_scKM14(mut1-22)(LH) (DF) | SEQ ID NO: 215 |
| 4D5_mvG1(KIH-1)_scKM14(mut1-25)(LH) (DF) | SEQ ID NO: 216 |
| 4D5_mvG1(KIH-1)_scKM14(mut1-26)(LH) (DF) | SEQ ID NO: 217 |

TABLE 10

SEQ ID NOS of VH, VL, and CDR Sequences Included in Various CD3 scFv

| Name of CD3 scFv | SEQ ID NO of amino acid sequence | | | |
|---|---|---|---|---|
| | VH | VL | HCDRs 1 to 3 | LCDRs 1 to 3 |
| scSP34(H05') | 115 | 116 | 83 to 85 | 86 to 88 |
| scSP34(H05')(CC) | 155 | 157 | 83 to 85 | 86 to 88 |
| scSP34(H05')(SE) | 156 | 158 | 83 to 85 | 86 to 88 |
| scSP34(H05'_HV3LV8a) | 159 | 165 | 83 to 85 | 86 to 88 |
| scSP34(H05'_HV5LV8a) | 160 | 165 | 83 to 85 | 86 to 88 |
| scSP34(H05'_HV3LV8a)(CC) | 161 | 166 | 83 to 85 | 86 to 88 |
| scSP34(H05'_HV5LV8a)(CC) | 162 | 166 | 83 to 85 | 86 to 88 |
| scSP34(H05'_HV3LV8a)(SE) | 163 | 167 | 83 to 85 | 86 to 88 |
| scSP34(H05'_HV5LV8a)(SE) | 164 | 167 | 83 to 85 | 86 to 88 |
| scKM14(mut1-03) | 94 | 126 | 98 to 100 | 132, 96, 97 |
| scKM14(mut1-04) | 94 | 127 | 98 to 100 | 133, 96, 97 |
| scKM14(mut1-18) | 128 | 93 | 98, 134, 100 | 95 to 97 |
| scKM14(mut1-22) | 129 | 93 | 98, 135, 100 | 95 to 97 |
| scKM14(mut1-25) | 130 | 93 | 98, 136, 100 | 95 to 97 |
| scKM14(mut1-26) | 131 | 93 | 98, 137, 100 | 95 to 97 |
| scKM14(mut1-03)(CC) | 168 | 180 | 98 to 100 | 132, 96, 97 |
| scKM14(mut1-04)(CC) | 169 | 181 | 98 to 100 | 133, 96, 97 |
| scKM14(mut1-18)(CC) | 170 | 182 | 98, 134, 100 | 95 to 97 |
| scKM14(mut1-22)(CC) | 171 | 183 | 98, 135, 100 | 95 to 97 |
| scKM14(mut1-25)(CC) | 172 | 184 | 98, 136, 100 | 95 to 97 |
| scKM14(mut1-26)(CC) | 173 | 185 | 98, 137, 100 | 95 to 97 |
| scKM14(mut1-03)(SE) | 174 | 186 | 98 to 100 | 132, 96, 97 |
| scKM14(mut1-04)(SE) | 175 | 187 | 98 to 100 | 133, 96, 97 |
| scKM14(mut1-18)(SE) | 176 | 188 | 98, 134, 100 | 95 to 97 |
| scKM14(mut1-22)(SE) | 177 | 189 | 98, 135, 100 | 95 to 97 |
| scKM14(mut1-25)(SE) | 178 | 190 | 98, 136, 100 | 95 to 97 |
| scKM14(mut1-26)(SE) | 179 | 191 | 98, 137, 100 | 95 to 97 |

(2) Measurement of Affinity of Produced Bispecific Antibodies for CD3

The affinity of the produced bispecific antibodies for CD3 was measured according to the method described in Example 9 (4). The results are shown in FIG. 44. It was found that the binding activity to soluble CD3 is maintained even in a molecule in which the modifications were introduced into the Fc (CH3), a molecule in which the anti-CD3 scFv was changed to the VL-Linker-VH type, and a molecule in which the modifications were introduced into the anti-CD3 scFv. Further, as for the affinity thereof, almost all the $K_D$ values were on the order of $10^{-7}$ in the same manner as the bispecific antibodies shown in Examples 11-(2) and 12-(6), and all the $K_D$ values were $8\times10^{-8}$ or more.

(3) Cellular Cytotoxicity and Cytokine Production During Cytotoxic Assay

The cellular cytotoxicity against BT-20 cells and the cytokine production during cytotoxic assay of the produced bispecific antibodies were measured according to the method described in Example 12-(8). The BT-20 cells were prepared at a cell density of $5\times10^5$ cells/mL at seeding. The results of the cellular cytotoxicity and the cytokine production are shown in FIGS. 45A to 45D and 46A to 46F, respectively.

From FIG. 45A, the bispecific antibodies in which any of four types of KIH modifications from KIH-1 to KIH-4 was introduced into the Fc (CH3) of 4D5_mvG1_scSP34(H05') (DF) exhibited the same cellular cytotoxicity as before the modification. Therefore, it was revealed that the presence or absence of the KIH modification and its pattern do not affect the activity of the bispecific antibody in the present invention.

From FIGS. 45B to 45D, even the bispecific antibodies in which the scFv was changed to the VL-Linker-VH type and the bispecific antibodies in which the CC modification or the SE modification was introduced into scFv have higher cellular cytotoxicity than 4D5_mvG1 (DF) having no scFv, and the function of anti-CD3 scFv was maintained. Only scKM14(mut1-25) had the reduced activity due to changing to the LH type. Multiple antibodies whose activity is comparable to that of the bispecific antibodies having anti-CD3 scFv before modification (Examples 11 and 12) were obtained. In the case where the scFv was SP34(H05'), when the CC modification was introduced, the tendency that the cellular cytotoxicity is decreased was observed.

Further, from FIG. 45B, it was found that the bispecific antibody having scSP34(H05') as the anti-CD3 scFv exhibits cellular cytotoxicity comparable to that of the bispecific antibodies having scSP34(H05') (SE), scSP34(H05' HV3LV8a), or scSP34(H05' HV5LV8a). It was found that the bispecific antibody having scSP34(H05') (CC) as the scFv exhibits cellular cytotoxicity comparable to that of the bispecific antibodies having scSP34(H05' HV3LV8a) (CC) or scSP34(H05'_HV5LV8a) (CC). These bispecific antibodies exhibited similar cellular cytotoxicity even in the case of (LH) type, and therefore, it was found that the activity of the bispecific antibody is not affected by whether the scFv is the VH-Linker-VL type or the VL-Linker-VH type.

From FIGS. 46A to 46F, it was found that in the case of the bispecific antibodies in which the modification was introduced into the Fc (CH3), the bispecific antibodies in which the anti-CD3 scFv was changed to the VL-Linker-VH type, and the bispecific antibodies in which the modification was introduced into the anti-CD3 scFv, the cytokine production during cytotoxic assay is suppressed to a low level as compared with the CD3/HER2 bispecific antibody having anti-CD3 scFv with strong affinity (CD3/HER2 FabxscFv). In addition, the order of the cellular cytotoxicity of respective bispecific antibodies shown in FIGS. 45B to 45D and the order of the cytokine production in FIG. 46 corresponding thereto were almost the same.

From the above results, it was revealed that the anti-CD3 bispecific antibody of the present invention can exhibit high cellular cytotoxicity without accompanying significant cytokine production by having both an ADTC activity and an ADCC activity in one molecule when the affinity for CD3 is within an appropriate range regardless of introduction of the KIH modification into the Fc (CH3), regardless of whether the anti-CD3 scFv is the VH-Linker-VL type or the VL-Linker-VH type, and also even if the CC modification or the SE modification is introduced into the anti-CD3 scFv.

The present invention has been explained in detail with reference to specific embodiments, but it is obvious to those skilled in the art that various changes and modifications can be made without departing from the spirit and scope of the present invention. The present application is based on Japanese Patent Application filed on Feb. 14, 2020 (Patent Application No. 2020-023855), which is incorporated by reference herein in its entirety.

SEQUENCE LISTING FREE TEXT

SEQ ID NO: 1: nucleotide sequence of CH1-Hinge-Fc moiety of first polypeptide of IgG1-type anti-HER2 monovalent antibody SEQ ID NO: 2: amino acid sequence of CH1-Hinge-Fc moiety of first polypeptide of IgG1-type anti-HER2 monovalent antibody SEQ ID NO: 3: nucleotide sequence of CL-Hinge-Fc moiety of second polypeptide of IgG1-type anti-HER2 monovalent antibody SEQ ID NO: 4: amino acid sequence of CL-Hinge-Fc moiety of second polypeptide of IgG1-type anti-HER2 monovalent antibody SEQ ID NO: 5: nucleotide sequence of CH1-Hinge-Fc moiety of first polypeptide of IgG4PE(R409K)-type anti-HER2 monovalent antibody SEQ ID NO: 6: amino acid sequence of CH1-Hinge-Fc moiety of first polypeptide of IgG4PE(R409K)-type anti-HER2 monovalent antibody SEQ ID NO: 7: nucleotide sequence of CL-Hinge-Fc moiety of second polypeptide of IgG4PE(R409K)-type anti-HER2 monovalent antibody SEQ ID NO: 8: amino acid sequence of CL-Hinge-Fc moiety of second polypeptide of IgG4PE(R409K)-type anti-HER2 monovalent antibody SEQ ID NO: 9: amino acid sequence of anti-CD3 scFv (scT3a)

SEQ ID NO: 10: amino acid sequence of polypeptide 1 of DNP2_mvG4PE(R409K) (F)

SEQ ID NO: 11: amino acid sequence of polypeptide 2 of DNP2_mvG4PE(R409K) (F)

SEQ ID NO: 12: amino acid sequence of polypeptide 1 of DNP2_mvG1 (DF)

SEQ ID NO: 13: amino acid sequence of polypeptide 2 of DNP2_mvG1 (DF)

SEQ ID NO: 14: amino acid sequence of polypeptide 1 of DNP2_mvG4PE(R409K)_scT3a (F)

SEQ ID NO: 15: amino acid sequence of polypeptide 2 of DNP2_mvG4PE(R409K)_scT3a (F)

SEQ ID NO: 16: amino acid sequence of polypeptide 1 of DNP2_mvG1_scT3a (DF)

SEQ ID NO: 17: amino acid sequence of polypeptide 2 of DNP2_mvG1_scT3a (DF)

SEQ ID NO: 18: amino acid sequence of polypeptide 1 of DNP2_IgG1 (DF)

SEQ ID NO: 19: amino acid sequence of polypeptide 2 of DNP2 IgG1 (DF)

SEQ ID NO: 20: amino acid sequence of polypeptide 1 of 4D5_mvG4PE(R409K) (F)

SEQ ID NO: 21: amino acid sequence of polypeptide 2 of 4D5_mvG4PE(R409K) (F)

SEQ ID NO: 22: amino acid sequence of polypeptide 1 of 4D5_mvG1 (DF)

SEQ ID NO: 23: amino acid sequence of polypeptide 2 of 4D5_mvG1 (DF)

SEQ ID NO: 24: amino acid sequence of polypeptide 1 of 4D5_mvG4PE(R409K)_scT3a (F)

SEQ ID NO: 25: amino acid sequence of polypeptide 2 of 4D5_mvG4PE(R409K)_scT3a (F)

SEQ ID NO: 26: amino acid sequence of polypeptide 1 of 4D5_mvG1_scT3a (DF)

SEQ ID NO: 27: amino acid sequence of polypeptide 2 of 4D5_mvG1_scT3a (DF)

SEQ ID NO: 28: amino acid sequence of polypeptide 1 of 4D5_IgG1 (DF)

SEQ ID NO: 29: amino acid sequence of polypeptide 2 of 4D5_IgG1 (DF)

SEQ ID NO: 30: amino acid sequence of polypeptide 1 of DNP2_IgG4PE(R409K) (F)

SEQ ID NO: 31: amino acid sequence of polypeptide 2 of DNP2_IgG4PE(R409K) (F)

SEQ ID NO: 32: amino acid sequence of polypeptide 1 of DNP2_IgG4PE(R409K)_scT3a (F)

SEQ ID NO: 33: amino acid sequence of polypeptide 2 of DNP2_IgG4PE(R409K)_scT3a (F)

SEQ ID NO: 34: amino acid sequence of polypeptide 3 of DNP2_IgG4PE(R409K)_scT3a (F)

SEQ ID NO: 35: amino acid sequence of polypeptide 1 of DNP2_IgG1 (DF)

SEQ ID NO: 36: amino acid sequence of polypeptide 2 of DNP2_IgG1 (DF)

SEQ ID NO: 37: amino acid sequence of polypeptide 1 of DNP2_IgG1_scT3a (DF)

SEQ ID NO: 38: amino acid sequence of polypeptide 2 of DNP2_IgG1_scT3a (DF)
SEQ ID NO: 39: amino acid sequence of polypeptide 3 of DNP2_IgG1_scT3a (DF)
SEQ ID NO: 40: amino acid sequence of polypeptide 1 of 4D5_IgG4PE(R409K) (F)
SEQ ID NO: 41: amino acid sequence of polypeptide 2 of 4D5_IgG4PE(R409K) (F)
SEQ ID NO: 42: amino acid sequence of polypeptide 1 of 4D5_IgG4PE(R409K)_scT3a (F)
SEQ ID NO: 43: amino acid sequence of polypeptide 2 of 4D5_IgG4PE(R409K)_scT3a (F)
SEQ ID NO: 44: amino acid sequence of polypeptide 3 of 4D5_IgG4PE(R409K)_scT3a (F)
SEQ ID NO: 45: amino acid sequence of polypeptide 1 of 4D5_IgG1_scT3a (DF)
SEQ ID NO: 46: amino acid sequence of polypeptide 2 of 4D5_IgG1_scT3a (DF)
SEQ ID NO: 47: amino acid sequence of polypeptide 3 of 4D5_IgG1_scT3a (DF)
SEQ ID NO: 48: amino acid sequence of polypeptide 1 of 8962_IgG1 (DF)
SEQ ID NO: 49: amino acid sequence of polypeptide 2 of 8962_IgG1 (DF)
SEQ ID NO: 50: amino acid sequence of polypeptide 1 of 8962_IgG1_scT3a (DF)
SEQ ID NO: 51: amino acid sequence of polypeptide 2 of 8962_IgG1_scT3a (DF)
SEQ ID NO: 52: amino acid sequence of polypeptide 3 of 8962_IgG1_scT3a (DF)
SEQ ID NO: 53: amino acid sequence of polypeptide 1 of 4D5_mvG4PE(R409K)_scT3a (LC) (F)
SEQ ID NO: 54: amino acid sequence of polypeptide 2 of 4D5_mvG4PE(R409K)_scT3a (LC) (F)
SEQ ID NO: 55: amino acid sequence of polypeptide 1 of 4D5_mvG1_scT3a (LC) (DF)
SEQ ID NO: 56: amino acid sequence of polypeptide 2 of 4D5_mvG1_scT3a (LC) (DF)
SEQ ID NO: 57: amino acid sequence of polypeptide 1 of 4D5_scT3a_IgG1 (DF)
SEQ ID NO: 58: amino acid sequence of polypeptide 2 of 4D5_scT3a_IgG1 (DF)
SEQ ID NO: 59: amino acid sequence of polypeptide 3 of 4D5_scT3a_IgG1 (DF)
SEQ ID NO: 60: amino acid sequence of polypeptide 1 of 4D5mut_scT3a_IgG1 (DF)
SEQ ID NO: 61: amino acid sequence of polypeptide 2 of 4D5mut_scT3a_IgG1 (DF)
SEQ ID NO: 62: amino acid sequence of polypeptide 3 of 4D5mut_scT3a_IgG1 (DF)
SEQ ID NO: 63: amino acid sequence of polypeptide 1 of 4D5mut_scSP34(H05') IgG1 (DF)
SEQ ID NO: 64: amino acid sequence of polypeptide 2 of 4D5mut_scSP34(H05')_IgG1 (DF)
SEQ ID NO: 65: amino acid sequence of polypeptide 3 of 4D5mut_scSP34(H05')_IgG1 (DF)
SEQ ID NO: 66: amino acid sequence of polypeptide 1 of 4D5mut_scSP34_IgG1 (DF)
SEQ ID NO: 67: amino acid sequence of polypeptide 2 of 4D5mut_scSP34_IgG1 (DF)
SEQ ID NO: 68: amino acid sequence of polypeptide 3 of 4D5mut_scSP34_IgG1 (DF)
SEQ ID NO: 69: amino acid sequence of polypeptide 1 of 4D5mut_mvG1_scT3a (DF)
SEQ ID NO: 70: amino acid sequence of polypeptide 2 of 4D5mut_mvG1_scT3a (DF)
SEQ ID NO: 71: amino acid sequence of polypeptide 1 of DNP2_mvG1_$(scT3a)_2$ (DF)
SEQ ID NO: 72: amino acid sequence of polypeptide 2 of DNP2_mvG1_$(scT3a)_2$ (DF)
SEQ ID NO: 73: amino acid sequence of anti-CD3 scFv (scI2C)
SEQ ID NO: 74: nucleotide sequence of anti-CD3 scFv (scSP34)
SEQ ID NO: 75: amino acid sequence of anti-CD3 scFv (scSP34)
SEQ ID NO: 76: amino acid sequence of CDR H1 of anti-CD3 scFv (scSP34)
SEQ ID NO: 77: amino acid sequence of CDR H2 of anti-CD3 scFv (scSP34)
SEQ ID NO: 78: amino acid sequence of CDR H3 of anti-CD3 scFv (scSP34)
SEQ ID NO: 79: amino acid sequence of CDR L1 of anti-CD3 scFv (scSP34)
SEQ ID NO: 80: amino acid sequence of CDR L2 of anti-CD3 scFv (scSP34)
SEQ ID NO: 81: amino acid sequence of CDR L3 of anti-CD3 scFv (scSP34)
SEQ ID NO: 82: amino acid sequence of anti-CD3 scFv (scSP34(H05'))
SEQ ID NO: 83: amino acid sequence of CDR H1 of anti-CD3 scFv (scSP34(H05'))
SEQ ID NO: 84: amino acid sequence of CDR H2 of anti-CD3 scFv (scSP34(H05'))
SEQ ID NO: 85: amino acid sequence of CDR H3 of anti-CD3 scFv (scSP34(H05'))
SEQ ID NO: 86: amino acid sequence of CDR L1 of anti-CD3 scFv (scSP34(H05'))
SEQ ID NO: 87: amino acid sequence of CDR L2 of anti-CD3 scFv (scSP34(H05'))
SEQ ID NO: 88: amino acid sequence of CDR L3 of anti-CD3 scFv (scSP34(H05'))
SEQ ID NO: 89: nucleotide sequence of primer for antibody gene cloning (VL)
SEQ ID NO: 90: nucleotide sequence of primer for antibody gene cloning (VH)
SEQ ID NO: 91: nucleotide sequence of VL of anti-CD3 antibody KM14
SEQ ID NO: 92: nucleotide sequence of VH of anti-CD3 antibody KM14
SEQ ID NO: 93: amino acid sequence of VL of anti-CD3 antibody KM14
SEQ ID NO: 94: amino acid sequence of VH of anti-CD3 antibody KM14
SEQ ID NO: 95: amino acid sequence of CDR L1 of anti-CD3 antibody KM14
SEQ ID NO: 96: amino acid sequence of CDR L2 of anti-CD3 antibody KM14
SEQ ID NO: 97: amino acid sequence of CDR L3 of anti-CD3 antibody KM14
SEQ ID NO: 98: amino acid sequence of CDR H1 of anti-CD3 antibody KM14
SEQ ID NO: 99: amino acid sequence of CDR H2 of anti-CD3 antibody KM14
SEQ ID NO: 100: amino acid sequence of CDR H3 of anti-CD3 antibody KM14
SEQ ID NO: 101: nucleotide sequence of anti-CD3 scFv (scKM14)
SEQ ID NO: 102: amino acid sequence of anti-CD3 scFv (scKM14)
SEQ ID NO: 103: amino acid sequence of anti-CD3 scFv (scKM14(mut1-03))

SEQ ID NO: 104: amino acid sequence of anti-CD3 scFv (scKM14(mut1-04))
SEQ ID NO: 105: amino acid sequence of anti-CD3 scFv (scKM14(mut1-18))
SEQ ID NO: 106: amino acid sequence of anti-CD3 scFv (scKM14(mut1-22))
SEQ ID NO: 107: amino acid sequence of anti-CD3 scFv (scKM14(mut1-25))
SEQ ID NO: 108: amino acid sequence of anti-CD3 scFv (scKM14(mut1-26))
SEQ ID NO: 109: amino acid sequence of VL of XENP14045 anti-CD123 antibody
SEQ ID NO: 110: amino acid sequence of VH of XENP14045 anti-CD123 antibody
SEQ ID NO: 111: amino acid sequence of VL of KM2160 anti-CCR4 antibody
SEQ ID NO: 112: amino acid sequence of VH of KM2160 anti-CCR4 antibody
SEQ ID NO: 113: amino acid sequence of VL of anti-CD123 antibody (CD123-1)
SEQ ID NO: 114: amino acid sequence of VH of anti-CD123 antibody (CD123-1)
SEQ ID NO: 115: amino acid sequence of VH of SP34 (H05')
SEQ ID NO: 116: amino acid sequence of VL of SP34 (H05')
SEQ ID NO: 117: amino acid sequence of anti-CD3 scFv (scSP34(H04'))
SEQ ID NO: 118: amino acid sequence of CDR H1 of anti-CD3 scFv (scSP34(H04'))
SEQ ID NO: 119: amino acid sequence of CDR H2 of anti-CD3 scFv (scSP34(H04'))
SEQ ID NO: 120: amino acid sequence of CDR H3 of anti-CD3 scFv (scSP34(H04'))
SEQ ID NO: 121: amino acid sequence of CDR L1 of anti-CD3 scFv (scSP34(H04'))
SEQ ID NO: 122: amino acid sequence of CDR L2 of anti-CD3 scFv (scSP34(H04'))
SEQ ID NO: 123: amino acid sequence of CDR L3 of anti-CD3 scFv (scSP34(H04'))
SEQ ID NO: 124: amino acid sequence of VH of SP34 (H04')
SEQ ID NO: 125: amino acid sequence of VL of SP34 (H04')
SEQ ID NO: 126: amino acid sequence of VL of mut1-03
SEQ ID NO: 127: amino acid sequence of VL of mut1-04
SEQ ID NO: 128: amino acid sequence of VH of mut1-18
SEQ ID NO: 129: amino acid sequence of VH of mut1-22
SEQ ID NO: 130: amino acid sequence of VH of mut1-25
SEQ ID NO: 131: amino acid sequence of VH of mut1-26
SEQ ID NO: 132: amino acid sequence of CDR L1 of mut1-03
SEQ ID NO: 133: amino acid sequence of CDR L1 of mut1-04
SEQ ID NO: 134: amino acid sequence of CDR H2 of mut1-18
SEQ ID NO: 135: amino acid sequence of CDR H2 of mut1-22
SEQ ID NO: 136: amino acid sequence of CDR H2 of mut1-25
SEQ ID NO: 137: amino acid sequence of CDR H2 of mut1-26
SEQ ID NO: 138: amino acid sequence of human CD3 protein
SEQ ID NO: 139: amino acid sequence of monkey CD3 protein
SEQ ID NO: 140: amino acid sequence of extracellular domain of human CD3 protein
SEQ ID NO: 141: nucleotide sequence of human CD3 protein
SEQ ID NO: 142: nucleotide sequence of monkey CD3 protein
SEQ ID NO: 143: amino acid sequence of peptide linker
SEQ ID NO: 144: amino acid sequence of peptide linker
SEQ ID NO: 145: amino acid sequence of peptide linker
SEQ ID NO: 146: amino acid sequence of N-terminal non-acetylated peptide of human CD3F
SEQ ID NO: 147: amino acid sequence of Knobs into Holes pattern 1 (KIH-1) of Fc moiety
SEQ ID NO: 148: amino acid sequence of Knobs into Holes pattern 1 (KIH-1) of Fc moiety
SEQ ID NO: 149: amino acid sequence of Knobs into Holes pattern 2 (KIH-2) of Fc moiety
SEQ ID NO: 150: amino acid sequence of Knobs into Holes pattern 2 (KIH-2) of Fc moiety
SEQ ID NO: 151: amino acid sequence of Knobs into Holes pattern 3 (KIH-3) of Fc moiety
SEQ ID NO: 152: amino acid sequence of Knobs into Holes pattern 3 (KIH-3) of Fc moiety
SEQ ID NO: 153: amino acid sequence of Knobs into Holes pattern 4 (KIH-4) of Fc moiety
SEQ ID NO: 154: amino acid sequence of Knobs into Holes pattern 4 (KIH-4) of Fc moiety
SEQ ID NO: 155: amino acid sequence of CC-modified VH of scSP34(H05')
SEQ ID NO: 156: amino acid sequence of SE-modified VH of scSP34(H05')
SEQ ID NO: 157: amino acid sequence of CC-modified VL of scSP34(H05')
SEQ ID NO: 158: amino acid sequence of SE-modified VL of scSP34(H05')
SEQ ID NO: 159: amino acid sequence of VH(HV3) of humanized scSP34(H05')
SEQ ID NO: 160: amino acid sequence of VH(HV5) of humanized scSP34(H05')
SEQ ID NO: 161: amino acid sequence of CC-modified VH(HV3) of humanized scSP34(H05')
SEQ ID NO: 162: amino acid sequence of CC-modified VH(HV5) of humanized scSP34(H05')
SEQ ID NO: 163: amino acid sequence of SE-modified VH(HV3) of humanized scSP34(H05')
SEQ ID NO: 164: amino acid sequence of SE-modified VH(HV5) of humanized scSP34(H05')
SEQ ID NO: 165: amino acid sequence of VL(LV8a) of humanized scSP34(H05')
SEQ ID NO: 166: amino acid sequence of CC-modified VL(LV8a) of humanized scSP34(H05')
SEQ ID NO: 167: amino acid sequence of SE-modified VL(LV8a) of humanized scSP34(H05')
SEQ ID NO: 168: amino acid sequence of CC-modified VH of scKM14(mut1-03)
SEQ ID NO: 169: amino acid sequence of CC-modified VH of scKM14(mut1-04)
SEQ ID NO: 170: amino acid sequence of CC-modified VH of scKM14(mut1-18)
SEQ ID NO: 171: amino acid sequence of CC-modified VH of scKM14(mut1-22)
SEQ ID NO: 172: amino acid sequence of CC-modified VH of scKM14(mut1-25)
SEQ ID NO: 173: amino acid sequence of CC-modified VH of scKM14(mut1-26)
SEQ ID NO: 174: amino acid sequence of SE-modified VH of scKM14(mut1-03)

SEQ ID NO: 175: amino acid sequence of SE-modified VH of scKM14(mut1-04)

SEQ ID NO: 176: amino acid sequence of SE-modified VH of scKM14(mut1-18)

SEQ ID NO: 177: amino acid sequence of SE-modified VH of scKM14(mut1-22)

SEQ ID NO: 178: amino acid sequence of SE-modified VH of scKM14(mut1-25)

SEQ ID NO: 179: amino acid sequence of SE-modified VH of scKM14(mut1-26)

SEQ ID NO: 180: amino acid sequence of CC-modified VL of scKM14(mut1-03)

SEQ ID NO: 181: amino acid sequence of CC-modified VL of scKM14(mut1-04)

SEQ ID NO: 182: amino acid sequence of CC-modified VL of scKM14(mut1-18)

SEQ ID NO: 183: amino acid sequence of CC-modified VL of scKM14(mut1-22)

SEQ ID NO: 184: amino acid sequence of CC-modified VL of scKM14(mut1-25)

SEQ ID NO: 185: amino acid sequence of CC-modified VL of scKM14(mut1-26)

SEQ ID NO: 186: amino acid sequence of SE-modified VL of scKM14(mut1-03)

SEQ ID NO: 187: amino acid sequence of SE-modified VL of scKM14(mut1-04)

SEQ ID NO: 188: amino acid sequence of SE-modified VL of scKM14(mut1-18)

SEQ ID NO: 189: amino acid sequence of SE-modified VL of scKM14(mut1-22)

SEQ ID NO: 190: amino acid sequence of SE-modified VL of scKM14(mut1-25)

SEQ ID NO: 191: amino acid sequence of SE-modified VL of scKM14(mut1-26)

SEQ ID NO: 192: full-length amino acid sequence of scSP34(H05')CC-modified type scFv SEQ ID NO: 193: full-length amino acid sequence of humanized scSP34(H05'_HV3LV8a)_CC-modified type scFv SEQ ID NO: 194: full-length amino acid sequence of humanized scSP34(H05'_HV5LV8a)_CC-modified type scFv SEQ ID NO: 195: full-length amino acid sequence of scSP34(H05')_SE-modified type scFv SEQ ID NO: 196: full-length amino acid sequence of scKM14(mut1-03)_CC-modified type scFv SEQ ID NO: 197: full-length amino acid sequence of scKM14(mut1-04)_CC-modified type scFv SEQ ID NO: 198: full-length amino acid sequence of scKM14(mut1-18)_CC-modified type scFv SEQ ID NO: 199: full-length amino acid sequence of scKM14(mut1-22)_CC-modified type scFv SEQ ID NO: 200: full-length amino acid sequence of scKM14(mut1-25)_CC-modified type scFv SEQ ID NO: 201: full-length amino acid sequence of scKM14(mut1-26)_CC-modified type scFv SEQ ID NO: 202: full-length amino acid sequence of scKM14(mut1-18)_SE-modified type scFv SEQ ID NO: 203: full-length amino acid sequence of scKM14(mut1-22)_SE-modified type scFv SEQ ID NO: 204: full-length amino acid sequence of scKM14(mut1-25)_SE-modified type scFv SEQ ID NO: 205: full-length amino acid sequence of scKM14(mut1-26)_SE-modified type scFv SEQ ID NO: 206: full-length amino acid sequence of scSP34(H05')_LH-type scFv SEQ ID NO: 207: full-length amino acid sequence of scSP34(H05')_CC-modified LH-type scFv SEQ ID NO: 208: full-length amino acid sequence of humanized scSP34(H05' HV3LV8a)_LH-type scFv SEQ ID NO: 209: full-length amino acid sequence of humanized scSP34(H05'_HV5LV8a)_LH-type scFv SEQ ID NO: 210: full-length amino acid sequence of humanized scSP34(H05'_HV3LV8a)_CC-modified LH-type scFv SEQ ID NO: 211: full-length amino acid sequence of humanized scSP34(H05'_HV5LV8a)_CC-modified LH-type scFv SEQ ID NO: 212: full-length amino acid sequence of scKM14(mut1-03)_LH-type scFv SEQ ID NO: 213: full-length amino acid sequence of scKM14(mut1-04)_LH-type scFv SEQ ID NO: 214: full-length amino acid sequence of scKM14(mut1-18)_LH-type scFv SEQ ID NO: 215: full-length amino acid sequence of scKM14(mut1-22)_LH-type scFv SEQ ID NO: 216: full-length amino acid sequence of scKM14(mut1-25)_LH-type scFv SEQ ID NO: 217: full-length amino acid sequence of scKM14(mut1-26)_LH-type scFv

The invention claimed is:

1. An anti-CD3 bispecific antibody or a bispecific antibody fragment thereof, comprising:

an Fc region having a binding ability to an Fc receptor and one CD3 binding domain with reduced affinity for CD3 bound to the C-terminal side of the Fc region, and further comprising: a disease-related antigen binding domain, wherein the amino acid sequences of HCDRs 1 to 3 and LCDRs 1 to 3 of the CD3 binding domain are any one selected from the following (a) to (h):

(a) HCDRs 1 to 3 comprising the amino acid sequences represented by SEQ ID NOS: 118 to 120, respectively, and LCDRs 1 to 3 comprising the amino acid sequences represented by SEQ ID NOS: 121 to 123, respectively;

(b) HCDRs 1 to 3 comprising the amino acid sequences represented by SEQ ID NOS: 83 to 85, respectively, and LCDRs 1 to 3 comprising the amino acid sequences represented by SEQ ID NOS: 86 to 88, respectively;

(c) HCDRs 1 to 3 comprising the amino acid sequences represented by SEQ ID NOS: 98 to 100, respectively, and LCDRs 1 to 3 containing the amino acid sequences represented by SEQ ID NOS: 132, 96, and 97, respectively;

(d) HCDRs 1 to 3 comprising the amino acid sequences represented by SEQ ID NOS: 98 to 100, respectively, and LCDRs 1 to 3 comprising the amino acid sequences represented by SEQ ID NOS: 133, 96, and 97, respectively;

(e) HCDRs 1 to 3 comprising the amino acid sequences represented by SEQ ID NOS: 98, 134, and 100, respectively, and LCDRs 1 to 3 comprising the amino acid sequences represented by SEQ ID NOS: 95 to 97, respectively;

(f) HCDRs 1 to 3 comprising the amino acid sequences represented by SEQ ID NOS: 98, 135, and 100, respectively, and LCDRs 1 to 3 comprising the amino acid sequences represented by SEQ ID NOS: 95 to 97, respectively;

(g) HCDRs 1 to 3 comprising the amino acid sequences represented by SEQ ID NOS: 98, 136, and 100, respectively, and LCDRs 1 to 3 comprising the amino acid sequences represented by SEQ ID NOS: 95 to 97, respectively; and (h) HCDRs 1 to 3 comprising the amino acid sequences represented by SEQ ID NOS: 98, 137, and 100, respectively, and LCDRs 1 to 3 comprising the amino acid sequences represented by SEQ ID NOS: 95 to 97, respectively.

2. An anti-CD3 bispecific antibody or a bispecific antibody fragment thereof, comprising:

an Fc region having a binding ability to an Fc receptor and one CD3 binding domain bound to the C-terminal side of the Fc region, and further comprising a disease-related antigen binding domain, wherein in the presence of CD3-positive T cells and disease-related antigen-positive cells, an ability to induce cytokine production is reduced as compared with an anti-CD3 bispecific antibody using an anti-CD3 monoclonal antibody SP34, wherein the amino acid sequences of HCDRs 1 to 3 and LCDRs 1 to 3 of the CD3 binding domain are any one selected from the following (a) to (h):

(a) HCDRs 1 to 3 comprising the amino acid sequences represented by SEQ ID NOS: 118 to 120, respectively, and LCDRs 1 to 3 comprising the amino acid sequences represented by SEQ ID NOS: 121 to 123, respectively;

(b) HCDRs 1 to 3 comprising the amino acid sequences represented by SEQ ID NOS: 83 to 85, respectively, and LCDRs 1 to 3 comprising the amino acid sequences represented by SEQ ID NOS: 86 to 88, respectively;

(c) HCDRs 1 to 3 comprising the amino acid sequences represented by SEQ ID NOS: 98 to 100, respectively, and LCDRs 1 to 3 containing the amino acid sequences represented by SEQ ID NOS: 132, 96, and 97, respectively;

(d) HCDRs 1 to 3 comprising the amino acid sequences represented by SEQ ID NOS: 98 to 100, respectively, and LCDRs 1 to 3 comprising the amino acid sequences represented by SEQ ID NOS: 133, 96, and 97, respectively;

(e) HCDRs 1 to 3 comprising the amino acid sequences represented by SEQ ID NOS: 98, 134, and 100, respectively, and LCDRs 1 to 3 comprising the amino acid sequences represented by SEQ ID NOS: 95 to 97, respectively;

(f) HCDRs 1 to 3 comprising the amino acid sequences represented by SEQ ID NOS: 98, 135, and 100, respectively, and LCDRs 1 to 3 comprising the amino acid sequences represented by SEQ ID NOS: 95 to 97, respectively;

(g) HCDRs 1 to 3 comprising the amino acid sequences represented by SEQ ID NOS: 98, 136, and 100, respectively, and LCDRs 1 to 3 comprising the amino acid sequences represented by SEQ ID NOS: 95 to 97, respectively; and (h) HCDRs 1 to 3 comprising the amino acid sequences represented by SEQ ID NOS: 98, 137, and 100, respectively, and LCDRs 1 to 3 comprising the amino acid sequences represented by SEQ ID NOS: 95 to 97, respectively.

3. The anti-CD3 bispecific antibody or the bispecific antibody fragment thereof according to claim 1, wherein the dissociation constant ($K_D$) of the CD3 binding domain for CD3 is $6\times10^{-8}$ or more.

4. The anti-CD3 bispecific antibody or the bispecific antibody fragment thereof according to claim 1, wherein the dissociation constant of the CD3 binding domain for CD3 is larger than that of an anti-CD3 monoclonal antibody SP34 or KM14 serving as a comparison control.

5. The anti-CD3 bispecific antibody or the bispecific antibody fragment thereof according to claim 1, wherein the amino acid sequence of the CD3 binding domain has 90% or more homology with the amino acid sequence of the CD3 binding domain of an anti-CD3 monoclonal antibody SP34 or KM14 serving as a reference, and the affinity for CD3 is reduced by 10% or more as compared with that of the anti-CD3 monoclonal antibody SP34 or KM14.

6. The anti-CD3 bispecific antibody or the bispecific antibody fragment thereof according to claim 1, which comprises one or two disease-related antigen binding domains.

7. The anti-CD3 bispecific antibody or the bispecific antibody fragment thereof according to claim 1, wherein each of the CD3 binding domain and the disease-related antigen binding domain is any one selected from scFv, Fab, and VHH.

8. The anti-CD3 bispecific antibody or the bispecific antibody fragment thereof according to claim 1, wherein the CD3 binding domain and/or the disease-related antigen binding domain is bound to the Fc region through a linker.

9. The anti-CD3 bispecific antibody or the bispecific antibody fragment thereof according to claim 1, wherein the CD3 binding domain comprises a heavy chain variable region (abbreviated as VH) comprising complementarity determining regions (abbreviated as CDRs) 1 to 3 of an antibody heavy chain and a light chain variable region (abbreviated as VL) comprising CDRs 1 to 3 of an antibody light chain.

10. The anti-CD3 bispecific antibody or the bispecific antibody fragment thereof according to claim 1, wherein the CD3 binding domain is scFv.

11. The anti-CD3 bispecific antibody or the bispecific antibody fragment thereof according to claim 1, wherein the amino acid sequences of VH and VL of the CD3 binding domain are any one selected from the following (aa) to (rr):

(aa) VH comprising the amino acid sequence represented by SEQ ID NO: 124 and VL comprising the amino acid sequence represented by SEQ ID NO: 125;

(bb) VH comprising the amino acid sequence represented by SEQ ID NO: 115 and VL comprising the amino acid sequence represented by SEQ ID NO: 116;

(cc) VH comprising the amino acid sequence represented by SEQ ID NO: 94 and VL comprising the amino acid sequence represented by SEQ ID NO: 126;

(dd) VH comprising the amino acid sequence represented by SEQ ID NO: 94 and VL comprising the amino acid sequence represented by SEQ ID NO: 127;

(ee) VH comprising the amino acid sequence represented by SEQ ID NO: 128 and VL comprising the amino acid sequence represented by SEQ ID NO: 93;

(ff) VH comprising the amino acid sequence represented by SEQ ID NO: 129 and VL comprising the amino acid sequence represented by SEQ ID NO: 93;

(gg) VH comprising the amino acid sequence represented by SEQ ID NO: 130 and VL comprising the amino acid sequence represented by SEQ ID NO: 93;

(hh) VH comprising the amino acid sequence represented by SEQ ID NO: 131 and VL comprising the amino acid sequence represented by SEQ ID NO: 93;

(ii) VH comprising the amino acid sequence represented by SEQ ID NO: 159 and VL comprising the amino acid sequence represented by SEQ ID NO: 165;

(jj) VH comprising the amino acid sequence represented by SEQ ID NO: 160 and VL comprising the amino acid sequence represented by SEQ ID NO: 165;

(kk) VH comprising the amino acid sequence represented by SEQ ID NO: 161 and VL comprising the amino acid sequence represented by SEQ ID NO: 166;

(ll) VH comprising the amino acid sequence represented by SEQ ID NO: 162 and VL comprising the amino acid sequence represented by SEQ ID NO: 166;

(mm) VH comprising the amino acid sequence represented by SEQ ID NO: 168 and VL comprising the amino acid sequence represented by SEQ ID NO: 180;

(nn) VH comprising the amino acid sequence represented by SEQ ID NO: 169 and VL comprising the amino acid sequence represented by SEQ ID NO: 181;

(oo) VH comprising the amino acid sequence represented by SEQ ID NO: 170 and VL comprising the amino acid sequence represented by SEQ ID NO: 182;

(pp) VH comprising the amino acid sequence represented by SEQ ID NO: 171 and VL comprising the amino acid sequence represented by SEQ ID NO: 183;

(qq) VH comprising the amino acid sequence represented by SEQ ID NO: 172 and VL comprising the amino acid sequence represented by SEQ ID NO: 184; and (rr) VH comprising the amino acid sequence represented by SEQ ID NO: 173 and VL comprising the amino acid sequence represented by SEQ ID NO: 185.

12. The anti-CD3 bispecific antibody or the bispecific antibody fragment thereof according to claim 1, wherein the Fc region is an Fc region having an enhanced binding activity to an Fc receptor.

13. The anti-CD3 bispecific antibody or the bispecific antibody fragment thereof according to claim 12, wherein the Fc region having an enhanced binding activity to an Fc receptor is an Fc region comprising an amino acid residue modification and/or a sugar chain modification.

14. The anti-CD3 bispecific antibody or the bispecific antibody fragment thereof according to claim 12, wherein the Fc region having an enhanced binding activity to an Fc receptor is an Fc region comprising both an amino acid residue modification and a sugar chain modification.

15. The anti-CD3 bispecific antibody or the bispecific antibody fragment thereof according to claim 13, wherein the amino acid residue modification is an amino acid residue modification including at least one amino acid residue modification for enhancing the binding activity to an Fc receptor.

16. The anti-CD3 bispecific antibody or the bispecific antibody fragment thereof according to claim 13, wherein the sugar chain modification is a sugar chain modification in which fucose that is α-1,6-linked to N-acetylglucosamine at the reducing end of an N-linked sugar chain that binds to Asn at position 297 according to EU numbering of the Fc region is deleted.

17. The anti-CD3 bispecific antibody or the bispecific antibody fragment thereof according to claim 1, wherein two Fabs are included as the disease-related antigen binding domains, and the C terminus of the heavy chain (VH-CH1) of each of the Fabs is bound to the Fc region directly or through a linker.

18. The anti-CD3 bispecific antibody or the bispecific antibody fragment thereof according to claim 1, wherein one Fab is included as the disease-related antigen binding domain, and the C termini of the heavy chain (VH-CH1) and the light chain (VL-CL) of the Fab are bound to the Fc region directly or through a linker.

19. The anti-CD3 bispecific antibody or the bispecific antibody fragment thereof according to claim 1, wherein one Fab is included as the disease-related antigen binding domain, and the CD3 binding domain is bound to an Fc chain at a side bound to the heavy chain (VH-CH1) of the Fab directly or through a linker.

20. The anti-CD3 bispecific antibody or the bispecific antibody fragment thereof according to claim 1, wherein one Fab is included as the disease-related antigen binding domain, and the CD3 binding domain is bound to an Fc chain at a side bound to the light chain (VL-CL) of the Fab directly or through a linker.

21. The anti-CD3 bispecific antibody or the bispecific antibody fragment thereof according to claim 17, wherein the linker is a hinge or a variant thereof.

* * * * *

SEQUENCE LISTING

```
<160> NUMBER OF SEQ ID NOS: 270

<210> SEQ ID NO 1
<211> LENGTH: 990
<212> TYPE: DNA
<213> ORGANISM: Artificial Sequence
<220> FEATURE:
<223> OTHER INFORMATION: description of the artificial sequence: the
      nucleotide sequence of CH1-Hinge-Fc portion of IgG1 type anti-HER2
      monovalent antibody first polypeptide

<400> SEQUENCE: 1

gctagcacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240
```

tacatctgca acgtgaatca caagcccagc aacaccaagg tggacaagaa agttgagccc 300
aaatctagcg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720
ctgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 2
<211> LENGTH: 330
<212> TYPE: PRT
<213> ORGANISM: Artificial Sequence
<220> FEATURE:
<223> OTHER INFORMATION: description of the artificial sequence: the amino acid sequence of CH1-Hinge-Fc part of IgG1-type anti-HER2 monovalent antibody first polypeptide

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 3
<211> LENGTH: 1002
<212> TYPE: DNA
<213> ORGANISM: Artificial Sequence
<220> FEATURE:
<223> OTHER INFORMATION: description of the artificial sequence: the
      nucleotide sequence of CL-Hinge-Fc part of IgG1 type anti-HER2
      monovalent antibody second polypeptide

<400> SEQUENCE: 3

cgtacggtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagctcgcc cgtcacaaag     300

agcttcaaca ggggagagag cgacaaaact cacacatgcc caccgtgccc agcacctgaa     360

ctcctggggg gaccgtcagt cttcctcttc cccccaaaac ccaaggacac cctcatgatc     420

tcccggaccc ctgaggtcac atgcgtggtg gtggacgtga gccacgaaga ccctgaggtc     480

aagttcaact ggtacgtgga cggcgtggag gtgcataatg ccaagacaaa gccgcgggag     540

gagcagtaca acagcacgta ccgtgtggtc agcgtcctca ccgtcctgca ccaggactgg     600

ctgaatggca aggagtacaa gtgcaaggtc tccaacaaag ccctcccagc ccccatcgag     660

aaaaccatct ccaaagccaa agggcagccc cgagaaccac aggtgtacac cctgccccca     720

tcccgggatg agctgaccaa gaaccaggtc agcctgacct gcctggtcaa aggcttctat     780

cccagcgaca tcgccgtgga gtgggagagc aatgggcagc cggagaacaa ctacaagacc     840

acgcctcccg tgctggactc cgacggctcc ttcttcctct acagcaagct caccgtggac     900

aagagcaggt ggcagcaggg gaacgtcttc tcatgctccg tgatgcatga ggctctgcac     960

aaccgcttca cgcagaagag cctctccctg tctccgggta aa                       1002


<210> SEQ ID NO 4
<211> LENGTH: 334
<212> TYPE: PRT
<213> ORGANISM: Artificial Sequence
<220> FEATURE:
<223> OTHER INFORMATION: description of the artificial sequence: the
      amino acid sequence of CL-Hinge-Fc part of IgG1 type anti-HER2
      monovalent antibody second polypeptide

<400> SEQUENCE: 4
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn Arg Phe Thr Gln Lys Ser Leu Ser Leu Ser Pro Gly Lys
                325                 330
```

<210> SEQ ID NO 5
<211> LENGTH: 981
<212> TYPE: DNA
<213> ORGANISM: Artificial Sequence
<220> FEATURE:
<223> OTHER INFORMATION: description of the artificial sequence: the nucleotide sequence of the CH1-Hinge-Fc portion of the first polypeptide of IgG4PE (R409K) type anti-HER2 monovalent antibody

<400> SEQUENCE: 5

```
gctagcacca aggggccatc cgtcttcccc ctggcgccct cctccaagag cacctccgag      60

agcacagccg ccctgggctg cctggtcaag gactacttcc ccgaaccggt gacggtgtcg     120
```

```
tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc accatgccca gcacctgagt tcgagggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaagcta accgtggaca agagcaggtg gcaggagggg    900

aatgtcttct catgctccgt gatgcatgag gctctgcaca accactacac acagaagagc    960

ctctccctgt ctctgggtaa a                                              981
```

<210> SEQ ID NO 6
<211> LENGTH: 327
<212> TYPE: PRT
<213> ORGANISM: Artificial Sequence
<220> FEATURE:
<223> OTHER INFORMATION: description of the artificial sequence: the amino acid sequence of CH1-Hinge-Fc portion of IgG4PE (R409K) type anti-HER2 monovalent antibody first polypeptide

<400> SEQUENCE: 6

```
Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 7
<211> LENGTH: 1008
<212> TYPE: DNA
<213> ORGANISM: Artificial Sequence
<220> FEATURE:
<223> OTHER INFORMATION: description of the artificial sequence: the nucleotide sequence of CL-Hinge-Fc part of IgG4PE (R409K) type anti-HER2 monovalent antibody second polypeptide

<400> SEQUENCE: 7

```
cgtacggtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagag cgagtccaaa tatggtcccc catgcccacc atgcccagca    360

cctgagttcg aggggggacc atcagtcttc ctgttccccc caaaacccaa ggacactctc    420

atgatctccc ggacccctga ggtcacgtgc gtggtggtgg acgtgagcca ggaagacccc    480

gaggtccagt tcaactggta cgtggatggc gtggaggtgc ataatgccaa gacaaagccg    540

cgggaggagc agttcaacag cacgtaccgt gtggtcagcg tcctcaccgt cctgcaccag    600

gactggctga acggcaagga gtacaagtgc aaggtctcca acaaaggcct cccgtcctcc    660

atcgagaaaa ccatctccaa agccaaaggg cagccccgag agccacaggt gtacaccctg    720

cccccatccc aggaggagat gaccaagaac caggtcagcc tgacctgcct ggtcaaaggc    780

ttctacccca gcgacatcgc cgtggagtgg gagagcaatg ggcagccgga gaacaactac    840

aagaccacgc ctcccgtgct ggactccgac ggctccttct tcctctacag caagctaacc    900

gtggacaaga gcaggtggca ggaggggaat gtcttctcat gctccgtgat gcatgaggct    960

ctgcacaacc gcttcacaca gaagagcctc tccctgtctc tgggtaaa                1008
```

<210> SEQ ID NO 8
<211> LENGTH: 336
<212> TYPE: PRT
<213> ORGANISM: Artificial Sequence
<220> FEATURE:

<223> OTHER INFORMATION: description of the artificial sequence: the
      amino acid sequence of CL-Hinge-Fc part of IgG4PE (R409K) type
      anti-HER2 monovalent antibody second polypeptide

<400> SEQUENCE: 8

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser Glu Ser Lys Tyr Gly
            100                 105                 110

Pro Pro Cys Pro Pro Cys Pro Ala Pro Glu Phe Glu Gly Gly Pro Ser
        115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser Gln Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Tyr Arg Val Val
            180                 185                 190

Ser Val Leu Thr Val Leu His Gln Asp Trp Leu Asn Gly Lys Glu Tyr
        195                 200                 205

Lys Cys Lys Val Ser Asn Lys Gly Leu Pro Ser Ser Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Gln Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
        275                 280                 285

Ser Asp Gly Ser Phe Phe Leu Tyr Ser Lys Leu Thr Val Asp Lys Ser
    290                 295                 300

Arg Trp Gln Glu Gly Asn Val Phe Ser Cys Ser Val Met His Glu Ala
305                 310                 315                 320

Leu His Asn Arg Phe Thr Gln Lys Ser Leu Ser Leu Ser Leu Gly Lys
                325                 330                 335
```

<210> SEQ ID NO 9
<211> LENGTH: 243
<212> TYPE: PRT
<213> ORGANISM: Artificial Sequence
<220> FEATURE:
<223> OTHER INFORMATION: description of the artificial sequence: the
      amino acid sequence of anti-CD3 scFv (scT3a)

<400> SEQUENCE: 9

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys


<210> SEQ ID NO 10
<211> LENGTH: 446
<212> TYPE: PRT
<213> ORGANISM: Artificial Sequence
<220> FEATURE:
<223> OTHER INFORMATION: description of the artificial sequence: the
      amino acid sequence of DNP2_mvG4PE (R409K) (F) Polypeptide 1

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110
```

Thr Leu Val Thr Val Ser Ser Ala Ser Thr Lys Gly Pro Ser Val Phe
115 120 125

Pro Leu Ala Pro Ser Ser Lys Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Lys Thr Tyr Thr Cys Asn Val Asp His Lys Pro
195 200 205

Ser Asn Thr Lys Val Asp Lys Arg Val Glu Ser Lys Tyr Gly Pro Pro
210 215 220

Cys Pro Pro Cys Pro Ala Pro Glu Phe Glu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Gln Glu Asp Pro Glu Val
260 265 270

Gln Phe Asn Trp Tyr Val Asp Gly Val Glu Val His Asn Ala Lys Thr
275 280 285

Lys Pro Arg Glu Glu Gln Phe Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Gly Leu Pro Ser Ser Ile Glu Lys Thr Ile Ser
325 330 335

Lys Ala Lys Gly Gln Pro Arg Glu Pro Gln Val Tyr Thr Leu Pro Pro
340 345 350

Ser Gln Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Glu Gly Asn Val Phe Ser Cys Ser Val Met His Glu Ala Leu His
420 425 430

Asn His Tyr Thr Gln Lys Ser Leu Ser Leu Ser Leu Gly Lys
435 440 445

<210> SEQ ID NO 11
<211> LENGTH: 443
<212> TYPE: PRT
<213> ORGANISM: Artificial Sequence
<220> FEATURE:
<223> OTHER INFORMATION: description of the artificial sequence: the amino acid sequence of DNP2_mvG4PE (R409K) (F) Polypeptide 2

<400> SEQUENCE: 11

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp

```
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Glu Ser Lys Tyr Gly Pro Pro Cys Pro Pro
    210                 215                 220

Cys Pro Ala Pro Glu Phe Glu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn Arg Phe
            420                 425                 430

Thr Gln Lys Ser Leu Ser Leu Ser Leu Gly Lys
        435                 440
```

<210> SEQ ID NO 12
<211> LENGTH: 449
<212> TYPE: PRT
<213> ORGANISM: Artificial Sequence
<220> FEATURE:
<223> OTHER INFORMATION: description of the artificial sequence: the amino acid sequence of DNP2_mvG1 (DF) polypeptide 1

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr 355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 13
<211> LENGTH: 441
<212> TYPE: PRT
<213> ORGANISM: Artificial Sequence
<220> FEATURE:
<223> OTHER INFORMATION: description of the artificial sequence: the amino acid sequence of DNP2_mvG1 (DF) polypeptide 2

<400> SEQUENCE: 13

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Ser Asp Lys Thr His Thr Cys Pro Pro Cys Pro
210 215 220

Ala Pro Glu Leu Leu Gly Gly Pro Ser Val Phe Leu Phe Pro Pro Lys
225 230 235 240

Pro Lys Asp Thr Leu Met Ile Ser Arg Thr Pro Glu Val Thr Cys Val
245 250 255

Val Val Asp Val Ser His Glu Asp Pro Glu Val Lys Phe Asn Trp Tyr 260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly Lys
        435                 440

<210> SEQ ID NO 14
<211> LENGTH: 704
<212> TYPE: PRT
<213> ORGANISM: Artificial Sequence
<220> FEATURE:
<223> OTHER INFORMATION: description of the artificial sequence: the
      amino acid sequence of DNP2_mvG4PE (R409K) _scT3a (F) polypeptide
      1

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

```
Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ser Gly
        435                 440                 445

Gly Gly Gly Ser Gly Gly Gly Gly Ser Gly Gly Gly Gly Asp Ile Lys
    450                 455                 460

Leu Gln Gln Ser Gly Ala Glu Leu Ala Arg Pro Gly Ala Ser Val Lys
465                 470                 475                 480

Met Ser Cys Lys Thr Ser Gly Tyr Thr Phe Thr Arg Tyr Thr Met His
                485                 490                 495

Trp Val Lys Gln Arg Pro Gly Gln Gly Leu Glu Trp Ile Gly Tyr Ile
            500                 505                 510

Asn Pro Ser Arg Gly Tyr Thr Asn Tyr Asn Gln Lys Phe Lys Asp Lys
        515                 520                 525

Ala Thr Leu Thr Thr Asp Lys Ser Ser Ser Thr Ala Tyr Met Gln Leu
    530                 535                 540

Ser Ser Leu Thr Ser Glu Asp Ser Ala Val Tyr Tyr Cys Ala Arg Tyr
545                 550                 555                 560

Tyr Asp Asp His Tyr Cys Leu Asp Tyr Trp Gly Gln Gly Thr Thr Leu
                565                 570                 575

Thr Val Ser Ser Val Glu Gly Gly Ser Gly Gly Ser Gly Gly Ser Gly
            580                 585                 590
```

```
Gly Ser Gly Gly Val Asp Asp Ile Gln Leu Thr Gln Ser Pro Ala Ile
        595                 600                 605

Met Ser Ala Ser Pro Gly Glu Lys Val Thr Met Thr Cys Arg Ala Ser
    610                 615                 620

Ser Ser Val Ser Tyr Met Asn Trp Tyr Gln Gln Lys Ser Gly Thr Ser
625                 630                 635                 640

Pro Lys Arg Trp Ile Tyr Asp Thr Ser Lys Val Ala Ser Gly Val Pro
                645                 650                 655

Tyr Arg Phe Ser Gly Ser Gly Ser Gly Thr Ser Tyr Ser Leu Thr Ile
            660                 665                 670

Ser Ser Met Glu Ala Glu Asp Ala Ala Thr Tyr Tyr Cys Gln Gln Trp
        675                 680                 685

Ser Ser Asn Pro Leu Thr Phe Gly Ala Gly Thr Lys Leu Glu Leu Lys
    690                 695                 700


<210> SEQ ID NO 15
<211> LENGTH: 443
<212> TYPE: PRT
<213> ORGANISM: Artificial Sequence
<220> FEATURE:
<223> OTHER INFORMATION: description of the artificial sequence: the
      amino acid sequence of DNP2_mvG4PE (R409K) _scT3a (F) polypeptide
      2

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Glu Ser Lys Tyr Gly Pro Pro Cys Pro Pro
    210                 215                 220

Cys Pro Ala Pro Glu Phe Glu Gly Gly Pro Ser Val Phe Leu Phe Pro
225                 230                 235                 240

Pro Lys Pro Lys Asp Thr Leu Met Ile Ser Arg Thr Pro Glu Val Thr
```

```
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn Arg Phe
            420                 425                 430

Thr Gln Lys Ser Leu Ser Leu Ser Leu Gly Lys
        435                 440


<210> SEQ ID NO 16
<211> LENGTH: 707
<212> TYPE: PRT
<213> ORGANISM: Artificial Sequence
<220> FEATURE:
<223> OTHER INFORMATION: description of the artificial sequence: the
      amino acid sequence of DNP2_mvG1_scT3a (DF) polypeptide 1

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

-continued

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Ser Gly Gly Gly Gly Ser Gly Gly Gly Gly Ser Gly Gly Gly Gly
    450                 455                 460

Asp Ile Lys Leu Gln Gln Ser Gly Ala Glu Leu Ala Arg Pro Gly Ala
465                 470                 475                 480

Ser Val Lys Met Ser Cys Lys Thr Ser Gly Tyr Thr Phe Thr Arg Tyr
                485                 490                 495

Thr Met His Trp Val Lys Gln Arg Pro Gly Gln Gly Leu Glu Trp Ile
            500                 505                 510

Gly Tyr Ile Asn Pro Ser Arg Gly Tyr Thr Asn Tyr Asn Gln Lys Phe
        515                 520                 525

Lys Asp Lys Ala Thr Leu Thr Thr Asp Lys Ser Ser Ser Thr Ala Tyr
    530                 535                 540

Met Gln Leu Ser Ser Leu Thr Ser Glu Asp Ser Ala Val Tyr Tyr Cys
545                 550                 555                 560

Ala Arg Tyr Tyr Asp Asp His Tyr Cys Leu Asp Tyr Trp Gly Gln Gly
                565                 570                 575

Thr Thr Leu Thr Val Ser Ser Val Glu Gly Gly Ser Gly Gly Ser Gly
```

580 585 590

Gly Ser Gly Gly Ser Gly Gly Val Asp Asp Ile Gln Leu Thr Gln Ser
595 600 605

Pro Ala Ile Met Ser Ala Ser Pro Gly Glu Lys Val Thr Met Thr Cys
610 615 620

Arg Ala Ser Ser Ser Val Ser Tyr Met Asn Trp Tyr Gln Gln Lys Ser
625 630 635 640

Gly Thr Ser Pro Lys Arg Trp Ile Tyr Asp Thr Ser Lys Val Ala Ser
645 650 655

Gly Val Pro Tyr Arg Phe Ser Gly Ser Gly Ser Gly Thr Ser Tyr Ser
660 665 670

Leu Thr Ile Ser Ser Met Glu Ala Glu Asp Ala Ala Thr Tyr Tyr Cys
675 680 685

Gln Gln Trp Ser Ser Asn Pro Leu Thr Phe Gly Ala Gly Thr Lys Leu
690 695 700

Glu Leu Lys
705

<210> SEQ ID NO 17
<211> LENGTH: 441
<212> TYPE: PRT
<213> ORGANISM: Artificial Sequence
<220> FEATURE:
<223> OTHER INFORMATION: description of the artificial sequence: the amino acid sequence of DNP2_mvG1_scT3a (DF) polypeptide 2

<400> SEQUENCE: 17

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Ser Asp Lys Thr His Thr Cys Pro Pro Cys Pro
210 215 220

```
Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly Lys
        435                 440


<210> SEQ ID NO 18
<211> LENGTH: 449
<212> TYPE: PRT
<213> ORGANISM: Artificial Sequence
<220> FEATURE:
<223> OTHER INFORMATION: description of the artificial sequence: the
      amino acid sequence of DNP2_IgG1 (DF) polypeptide 1

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 19
<211> LENGTH: 214
<212> TYPE: PRT
<213> ORGANISM: Artificial Sequence
<220> FEATURE:
<223> OTHER INFORMATION: description of the artificial sequence: the
      amino acid sequence of DNP2_IgG1 (DF) polypeptide 2

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 20
<211> LENGTH: 447
<212> TYPE: PRT
<213> ORGANISM: Artificial Sequence
<220> FEATURE:
<223> OTHER INFORMATION: description of the artificial sequence: the
      amino acid sequence of 4D5_mvG4PE (R409K) (F) Polypeptide 1

<400> SEQUENCE: 20
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 21
<211> LENGTH: 443
<212> TYPE: PRT
<213> ORGANISM: Artificial Sequence
<220> FEATURE:
<223> OTHER INFORMATION: description of the artificial sequence: the
      amino acid sequence of 4D5_mvG4PE (R409K) (F) Polypeptide 2

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Glu Ser Lys Tyr Gly Pro Pro Cys Pro Pro
    210                 215                 220

Cys Pro Ala Pro Glu Phe Glu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn Arg Phe
            420                 425                 430

Thr Gln Lys Ser Leu Ser Leu Ser Leu Gly Lys
        435                 440
```

<210> SEQ ID NO 22
<211> LENGTH: 450
<212> TYPE: PRT
<213> ORGANISM: Artificial Sequence
<220> FEATURE:
<223> OTHER INFORMATION: description of the artificial sequence: the amino acid sequence of 4D5_mvG1 (DF) polypeptide 1

<400> SEQUENCE: 22

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Ser Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445

Gly Lys
    450


<210> SEQ ID NO 23
<211> LENGTH: 441
<212> TYPE: PRT
<213> ORGANISM: Artificial Sequence
<220> FEATURE:
<223> OTHER INFORMATION: description of the artificial sequence: the
      amino acid sequence of 4D5_mvG1 (DF) polypeptide 2

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335
```

Pro Arg Glu Pro Gln Val Tyr Thr Leu Pro Pro Ser Arg Asp Glu Leu
340 345 350

Thr Lys Asn Gln Val Ser Leu Thr Cys Leu Val Lys Gly Phe Tyr Pro
355 360 365

Ser Asp Ile Ala Val Glu Trp Glu Ser Asn Gly Gln Pro Glu Asn Asn
370 375 380

Tyr Lys Thr Thr Pro Pro Val Leu Asp Ser Asp Gly Ser Phe Phe Leu
385 390 395 400

Tyr Ser Lys Leu Thr Val Asp Lys Ser Arg Trp Gln Gln Gly Asn Val
405 410 415

Phe Ser Cys Ser Val Met His Glu Ala Leu His Asn Arg Phe Thr Gln
420 425 430

Lys Ser Leu Ser Leu Ser Pro Gly Lys
435 440

<210> SEQ ID NO 24
<211> LENGTH: 705
<212> TYPE: PRT
<213> ORGANISM: Artificial Sequence
<220> FEATURE:
<223> OTHER INFORMATION: description of the artificial sequence: the amino acid sequence of 4D5_mvG4PE (R409K) _scT3a (F) polypeptide 1

<400> SEQUENCE: 24

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Glu Gly Gly Pro Ser Val
225 230 235 240

Phe Leu Phe Pro Pro Lys Pro Lys Asp Thr Leu Met Ile Ser Arg Thr

```
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ser
        435                 440                 445

Gly Gly Gly Gly Ser Gly Gly Gly Gly Ser Gly Gly Gly Gly Asp Ile
    450                 455                 460

Lys Leu Gln Gln Ser Gly Ala Glu Leu Ala Arg Pro Gly Ala Ser Val
465                 470                 475                 480

Lys Met Ser Cys Lys Thr Ser Gly Tyr Thr Phe Thr Arg Tyr Thr Met
                485                 490                 495

His Trp Val Lys Gln Arg Pro Gly Gln Gly Leu Glu Trp Ile Gly Tyr
            500                 505                 510

Ile Asn Pro Ser Arg Gly Tyr Thr Asn Tyr Asn Gln Lys Phe Lys Asp
        515                 520                 525

Lys Ala Thr Leu Thr Thr Asp Lys Ser Ser Ser Thr Ala Tyr Met Gln
    530                 535                 540

Leu Ser Ser Leu Thr Ser Glu Asp Ser Ala Val Tyr Tyr Cys Ala Arg
545                 550                 555                 560

Tyr Tyr Asp Asp His Tyr Cys Leu Asp Tyr Trp Gly Gln Gly Thr Thr
                565                 570                 575

Leu Thr Val Ser Ser Val Glu Gly Gly Ser Gly Gly Ser Gly Gly Ser
            580                 585                 590

Gly Gly Ser Gly Gly Val Asp Asp Ile Gln Leu Thr Gln Ser Pro Ala
        595                 600                 605

Ile Met Ser Ala Ser Pro Gly Glu Lys Val Thr Met Thr Cys Arg Ala
    610                 615                 620

Ser Ser Ser Val Ser Tyr Met Asn Trp Tyr Gln Gln Lys Ser Gly Thr
625                 630                 635                 640

Ser Pro Lys Arg Trp Ile Tyr Asp Thr Ser Lys Val Ala Ser Gly Val
                645                 650                 655

Pro Tyr Arg Phe Ser Gly Ser Gly Ser Gly Thr Ser Tyr Ser Leu Thr
            660                 665                 670
```

Ile Ser Ser Met Glu Ala Glu Asp Ala Ala Thr Tyr Tyr Cys Gln Gln
        675                 680                 685

Trp Ser Ser Asn Pro Leu Thr Phe Gly Ala Gly Thr Lys Leu Glu Leu
    690                 695                 700

Lys
705

<210> SEQ ID NO 25
<211> LENGTH: 443
<212> TYPE: PRT
<213> ORGANISM: Artificial Sequence
<220> FEATURE:
<223> OTHER INFORMATION: description of the artificial sequence: the
      amino acid sequence of 4D5_mvG4PE (R409K) _scT3a (F) polypeptide 2

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Glu Ser Lys Tyr Gly Pro Pro Cys Pro Pro
    210                 215                 220

Cys Pro Ala Pro Glu Phe Glu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser 305 310 315 320

Asn Lys Gly Leu Pro Ser Ser Ile Glu Lys Thr Ile Ser Lys Ala Lys
325 330 335

Gly Gln Pro Arg Glu Pro Gln Val Tyr Thr Leu Pro Pro Ser Gln Glu
340 345 350

Glu Met Thr Lys Asn Gln Val Ser Leu Thr Cys Leu Val Lys Gly Phe
355 360 365

Tyr Pro Ser Asp Ile Ala Val Glu Trp Glu Ser Asn Gly Gln Pro Glu
370 375 380

Asn Asn Tyr Lys Thr Thr Pro Pro Val Leu Asp Ser Asp Gly Ser Phe
385 390 395 400

Phe Leu Tyr Ser Lys Leu Thr Val Asp Lys Ser Arg Trp Gln Glu Gly
405 410 415

Asn Val Phe Ser Cys Ser Val Met His Glu Ala Leu His Asn Arg Phe
420 425 430

Thr Gln Lys Ser Leu Ser Leu Ser Leu Gly Lys
435 440

<210> SEQ ID NO 26
<211> LENGTH: 708
<212> TYPE: PRT
<213> ORGANISM: Artificial Sequence
<220> FEATURE:
<223> OTHER INFORMATION: description of the artificial sequence: the amino acid sequence of 4D5_mvG1_scT3a (DF) polypeptide 1

<400> SEQUENCE: 26

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Ser Asp
210 215 220

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Gly Gly Gly Ser Gly Gly Gly Gly Ser Gly Gly Gly
    450                 455                 460

Gly Asp Ile Lys Leu Gln Gln Ser Gly Ala Glu Leu Ala Arg Pro Gly
465                 470                 475                 480

Ala Ser Val Lys Met Ser Cys Lys Thr Ser Gly Tyr Thr Phe Thr Arg
                485                 490                 495

Tyr Thr Met His Trp Val Lys Gln Arg Pro Gly Gln Gly Leu Glu Trp
            500                 505                 510

Ile Gly Tyr Ile Asn Pro Ser Arg Gly Tyr Thr Asn Tyr Asn Gln Lys
        515                 520                 525

Phe Lys Asp Lys Ala Thr Leu Thr Thr Asp Lys Ser Ser Ser Thr Ala
    530                 535                 540

Tyr Met Gln Leu Ser Ser Leu Thr Ser Glu Asp Ser Ala Val Tyr Tyr
545                 550                 555                 560

Cys Ala Arg Tyr Tyr Asp Asp His Tyr Cys Leu Asp Tyr Trp Gly Gln
                565                 570                 575

Gly Thr Thr Leu Thr Val Ser Ser Val Glu Gly Gly Ser Gly Gly Ser
            580                 585                 590

Gly Gly Ser Gly Gly Ser Gly Gly Val Asp Asp Ile Gln Leu Thr Gln
        595                 600                 605

Ser Pro Ala Ile Met Ser Ala Ser Pro Gly Glu Lys Val Thr Met Thr
    610                 615                 620

Cys Arg Ala Ser Ser Ser Val Ser Tyr Met Asn Trp Tyr Gln Gln Lys
625                 630                 635                 640

Ser Gly Thr Ser Pro Lys Arg Trp Ile Tyr Asp Thr Ser Lys Val Ala
```

```
                645                 650                 655

Ser Gly Val Pro Tyr Arg Phe Ser Gly Ser Gly Ser Gly Thr Ser Tyr
            660                 665                 670

Ser Leu Thr Ile Ser Ser Met Glu Ala Glu Asp Ala Ala Thr Tyr Tyr
        675                 680                 685

Cys Gln Gln Trp Ser Ser Asn Pro Leu Thr Phe Gly Ala Gly Thr Lys
    690                 695                 700

Leu Glu Leu Lys
705


<210> SEQ ID NO 27
<211> LENGTH: 441
<212> TYPE: PRT
<213> ORGANISM: Artificial Sequence
<220> FEATURE:
<223> OTHER INFORMATION: description of the artificial sequence: the
      amino acid sequence of 4D5_mvG1_scT3a (DF) polypeptide 2

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285
```

```
Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly Lys
        435                 440


<210> SEQ ID NO 28
<211> LENGTH: 450
<212> TYPE: PRT
<213> ORGANISM: Artificial Sequence
<220> FEATURE:
<223> OTHER INFORMATION: description of the artificial sequence: the
      amino acid sequence of 4D5_IgG1 (DF) polypeptide 1

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 29
<211> LENGTH: 214
<212> TYPE: PRT
<213> ORGANISM: Artificial Sequence
<220> FEATURE:
<223> OTHER INFORMATION: description of the artificial sequence: the
      amino acid sequence of 4D5_IgG1 (DF) polypeptide 2

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 30
<211> LENGTH: 446
<212> TYPE: PRT
<213> ORGANISM: Artificial Sequence
<220> FEATURE:
<223> OTHER INFORMATION: description of the artificial sequence: the
      amino acid sequence of DNP2_IgG4PE (R409K) (F) Polypeptide 1

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 31
<211> LENGTH: 214
<212> TYPE: PRT
<213> ORGANISM: Artificial Sequence
<220> FEATURE:
<223> OTHER INFORMATION: description of the artificial sequence: the
      amino acid sequence of DNP2_IgG4PE (R409K) (F) Polypeptide 2

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 704
<212> TYPE: PRT
<213> ORGANISM: Artificial Sequence
<220> FEATURE:
<223> OTHER INFORMATION: description of the artificial sequence: the amino acid sequence of DNP2_IgG4PE (R409K) _scT3a (F) polypeptide 1

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

```
Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Cys Thr Leu Pro Pro
            340                 345                 350

Ser Gln Glu Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn Arg Phe Thr Gln Lys Ser Leu Ser Leu Ser Leu Gly Lys Ser Gly
        435                 440                 445

Gly Gly Gly Ser Gly Gly Gly Gly Ser Gly Gly Gly Gly Asp Ile Lys
    450                 455                 460

Leu Gln Gln Ser Gly Ala Glu Leu Ala Arg Pro Gly Ala Ser Val Lys
465                 470                 475                 480

Met Ser Cys Lys Thr Ser Gly Tyr Thr Phe Thr Arg Tyr Thr Met His
                485                 490                 495

Trp Val Lys Gln Arg Pro Gly Gln Gly Leu Glu Trp Ile Gly Tyr Ile
            500                 505                 510

Asn Pro Ser Arg Gly Tyr Thr Asn Tyr Asn Gln Lys Phe Lys Asp Lys
        515                 520                 525

Ala Thr Leu Thr Thr Asp Lys Ser Ser Ser Thr Ala Tyr Met Gln Leu
    530                 535                 540

Ser Ser Leu Thr Ser Glu Asp Ser Ala Val Tyr Tyr Cys Ala Arg Tyr
545                 550                 555                 560

Tyr Asp Asp His Tyr Cys Leu Asp Tyr Trp Gly Gln Gly Thr Thr Leu
                565                 570                 575

Thr Val Ser Ser Val Glu Gly Gly Ser Gly Gly Ser Gly Gly Ser Gly
            580                 585                 590

Gly Ser Gly Gly Val Asp Asp Ile Gln Leu Thr Gln Ser Pro Ala Ile
        595                 600                 605

Met Ser Ala Ser Pro Gly Glu Lys Val Thr Met Thr Cys Arg Ala Ser
    610                 615                 620

Ser Ser Val Ser Tyr Met Asn Trp Tyr Gln Gln Lys Ser Gly Thr Ser
625                 630                 635                 640

Pro Lys Arg Trp Ile Tyr Asp Thr Ser Lys Val Ala Ser Gly Val Pro
                645                 650                 655

Tyr Arg Phe Ser Gly Ser Gly Ser Gly Thr Ser Tyr Ser Leu Thr Ile
            660                 665                 670

Ser Ser Met Glu Ala Glu Asp Ala Ala Thr Tyr Tyr Cys Gln Gln Trp
        675                 680                 685

Ser Ser Asn Pro Leu Thr Phe Gly Ala Gly Thr Lys Leu Glu Leu Lys
    690                 695                 700
```

<210> SEQ ID NO 33
<211> LENGTH: 446
<212> TYPE: PRT
<213> ORGANISM: Artificial Sequence
<220> FEATURE:
<223> OTHER INFORMATION: description of the artificial sequence: the amino acid sequence of DNP2_IgG4PE (R409K) _scT3a (F) polypeptide 2

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Gln Glu Glu Met Thr Lys Asn Gln Val Ser Leu Trp Cys Leu Val
        355                 360                 365

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 34
<211> LENGTH: 214
<212> TYPE: PRT
<213> ORGANISM: Artificial Sequence
<220> FEATURE:
<223> OTHER INFORMATION: description of the artificial sequence: the
      amino acid sequence of DNP2_IgG4PE (R409K) _scT3a (F) polypeptide
      3

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 35
<211> LENGTH: 449
<212> TYPE: PRT
<213> ORGANISM: Artificial Sequence
<220> FEATURE:
<223> OTHER INFORMATION: description of the artificial sequence: the
      amino acid sequence of DNP2_IgG1 (DF) polypeptide 1
```

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 36
<211> LENGTH: 214
<212> TYPE: PRT
<213> ORGANISM: Artificial Sequence
<220> FEATURE:
<223> OTHER INFORMATION: description of the artificial sequence: the amino acid sequence of DNP2_IgG1 (DF) polypeptide 2

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 707
<212> TYPE: PRT
<213> ORGANISM: Artificial Sequence
<220> FEATURE:
<223> OTHER INFORMATION: description of the artificial sequence: the amino acid sequence of DNP2_IgG1_scT3a (DF) polypeptide 1

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
        435                 440                 445

Lys Ser Gly Gly Gly Gly Ser Gly Gly Gly Gly Ser Gly Gly Gly Gly
```

```
    450                 455                 460

Asp Ile Lys Leu Gln Gln Ser Gly Ala Glu Leu Ala Arg Pro Gly Ala
465                 470                 475                 480

Ser Val Lys Met Ser Cys Lys Thr Ser Gly Tyr Thr Phe Thr Arg Tyr
                485                 490                 495

Thr Met His Trp Val Lys Gln Arg Pro Gly Gln Gly Leu Glu Trp Ile
            500                 505                 510

Gly Tyr Ile Asn Pro Ser Arg Gly Tyr Thr Asn Tyr Asn Gln Lys Phe
        515                 520                 525

Lys Asp Lys Ala Thr Leu Thr Thr Asp Lys Ser Ser Ser Thr Ala Tyr
    530                 535                 540

Met Gln Leu Ser Ser Leu Thr Ser Glu Asp Ser Ala Val Tyr Tyr Cys
545                 550                 555                 560

Ala Arg Tyr Tyr Asp Asp His Tyr Cys Leu Asp Tyr Trp Gly Gln Gly
                565                 570                 575

Thr Thr Leu Thr Val Ser Ser Val Glu Gly Gly Ser Gly Gly Ser Gly
            580                 585                 590

Gly Ser Gly Gly Ser Gly Gly Val Asp Asp Ile Gln Leu Thr Gln Ser
        595                 600                 605

Pro Ala Ile Met Ser Ala Ser Pro Gly Glu Lys Val Thr Met Thr Cys
    610                 615                 620

Arg Ala Ser Ser Ser Val Ser Tyr Met Asn Trp Tyr Gln Gln Lys Ser
625                 630                 635                 640

Gly Thr Ser Pro Lys Arg Trp Ile Tyr Asp Thr Ser Lys Val Ala Ser
                645                 650                 655

Gly Val Pro Tyr Arg Phe Ser Gly Ser Gly Ser Gly Thr Ser Tyr Ser
            660                 665                 670

Leu Thr Ile Ser Ser Met Glu Ala Glu Asp Ala Ala Thr Tyr Tyr Cys
        675                 680                 685

Gln Gln Trp Ser Ser Asn Pro Leu Thr Phe Gly Ala Gly Thr Lys Leu
    690                 695                 700

Glu Leu Lys
705


<210> SEQ ID NO 38
<211> LENGTH: 449
<212> TYPE: PRT
<213> ORGANISM: Artificial Sequence
<220> FEATURE:
<223> OTHER INFORMATION: description of the artificial sequence: the
      amino acid sequence of DNP2_IgG1_scT3a (DF) polypeptide 2

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 39
<211> LENGTH: 214
<212> TYPE: PRT
<213> ORGANISM: Artificial Sequence
<220> FEATURE:
<223> OTHER INFORMATION: description of the artificial sequence: the
      amino acid sequence of DNP2_IgG1_scT3a (DF) polypeptide 3

<400> SEQUENCE: 39
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 40
<211> LENGTH: 447
<212> TYPE: PRT
<213> ORGANISM: Artificial Sequence
<220> FEATURE:
<223> OTHER INFORMATION: description of the artificial sequence: the
      amino acid sequence of 4D5_IgG4PE (R409K) (F) Polypeptide 1

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Glu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 41
<211> LENGTH: 214
<212> TYPE: PRT
<213> ORGANISM: Artificial Sequence
<220> FEATURE:
<223> OTHER INFORMATION: description of the artificial sequence: the amino acid sequence of 4D5_IgG4PE (R409K) (F) Polypeptide 2

<400> SEQUENCE: 41

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly

```
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 42
<211> LENGTH: 705
<212> TYPE: PRT
<213> ORGANISM: Artificial Sequence
<220> FEATURE:
<223> OTHER INFORMATION: description of the artificial sequence: the
      amino acid sequence of 4D5_IgG4PE (R409K) _scT3a (F) polypeptide 1

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Cys Thr Leu Pro
            340                 345                 350

Pro Ser Gln Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn Arg Phe Thr Gln Lys Ser Leu Ser Leu Ser Leu Gly Lys Ser
        435                 440                 445

Gly Gly Gly Gly Ser Gly Gly Gly Gly Ser Gly Gly Gly Gly Asp Ile
    450                 455                 460

Lys Leu Gln Gln Ser Gly Ala Glu Leu Ala Arg Pro Gly Ala Ser Val
465                 470                 475                 480

Lys Met Ser Cys Lys Thr Ser Gly Tyr Thr Phe Thr Arg Tyr Thr Met
                485                 490                 495

His Trp Val Lys Gln Arg Pro Gly Gln Gly Leu Glu Trp Ile Gly Tyr
            500                 505                 510

Ile Asn Pro Ser Arg Gly Tyr Thr Asn Tyr Asn Gln Lys Phe Lys Asp
        515                 520                 525

Lys Ala Thr Leu Thr Thr Asp Lys Ser Ser Ser Thr Ala Tyr Met Gln
    530                 535                 540

Leu Ser Ser Leu Thr Ser Glu Asp Ser Ala Val Tyr Tyr Cys Ala Arg
545                 550                 555                 560

Tyr Tyr Asp Asp His Tyr Cys Leu Asp Tyr Trp Gly Gln Gly Thr Thr
                565                 570                 575

Leu Thr Val Ser Ser Val Glu Gly Gly Ser Gly Gly Ser Gly Gly Ser
            580                 585                 590

Gly Gly Ser Gly Gly Val Asp Asp Ile Gln Leu Thr Gln Ser Pro Ala
        595                 600                 605

Ile Met Ser Ala Ser Pro Gly Glu Lys Val Thr Met Thr Cys Arg Ala
```

```
    610                 615                 620

Ser Ser Ser Val Ser Tyr Met Asn Trp Tyr Gln Gln Lys Ser Gly Thr
625                 630                 635                 640

Ser Pro Lys Arg Trp Ile Tyr Asp Thr Ser Lys Val Ala Ser Gly Val
                645                 650                 655

Pro Tyr Arg Phe Ser Gly Ser Gly Ser Gly Thr Ser Tyr Ser Leu Thr
            660                 665                 670

Ile Ser Ser Met Glu Ala Glu Asp Ala Ala Thr Tyr Tyr Cys Gln Gln
        675                 680                 685

Trp Ser Ser Asn Pro Leu Thr Phe Gly Ala Gly Thr Lys Leu Glu Leu
    690                 695                 700

Lys
705


<210> SEQ ID NO 43
<211> LENGTH: 447
<212> TYPE: PRT
<213> ORGANISM: Artificial Sequence
<220> FEATURE:
<223> OTHER INFORMATION: description of the artificial sequence: the
      amino acid sequence of 4D5_IgG4PE (R409K) _scT3a (F) polypeptide 2

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 44
<211> LENGTH: 214
<212> TYPE: PRT
<213> ORGANISM: Artificial Sequence
<220> FEATURE:
<223> OTHER INFORMATION: description of the artificial sequence: the amino acid sequence of 4D5_IgG4PE (R409K) _scT3a (F) Polypeptide 3

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 45
<211> LENGTH: 708
<212> TYPE: PRT
<213> ORGANISM: Artificial Sequence
<220> FEATURE:
<223> OTHER INFORMATION: description of the artificial sequence: the amino acid sequence of 4D5_IgG1_scT3a (DF) polypeptide 1

<400> SEQUENCE: 45

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys

```
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys Ser Gly Gly Gly Gly Ser Gly Gly Gly Gly Ser Gly Gly Gly
    450                 455                 460

Gly Asp Ile Lys Leu Gln Gln Ser Gly Ala Glu Leu Ala Arg Pro Gly
465                 470                 475                 480

Ala Ser Val Lys Met Ser Cys Lys Thr Ser Gly Tyr Thr Phe Thr Arg
                485                 490                 495

Tyr Thr Met His Trp Val Lys Gln Arg Pro Gly Gln Gly Leu Glu Trp
            500                 505                 510

Ile Gly Tyr Ile Asn Pro Ser Arg Gly Tyr Thr Asn Tyr Asn Gln Lys
        515                 520                 525

Phe Lys Asp Lys Ala Thr Leu Thr Thr Asp Lys Ser Ser Ser Thr Ala
    530                 535                 540

Tyr Met Gln Leu Ser Ser Leu Thr Ser Glu Asp Ser Ala Val Tyr Tyr
545                 550                 555                 560

Cys Ala Arg Tyr Tyr Asp Asp His Tyr Cys Leu Asp Tyr Trp Gly Gln
                565                 570                 575

Gly Thr Thr Leu Thr Val Ser Ser Val Glu Gly Gly Ser Gly Gly Ser
            580                 585                 590

Gly Gly Ser Gly Gly Ser Gly Gly Val Asp Asp Ile Gln Leu Thr Gln
        595                 600                 605

Ser Pro Ala Ile Met Ser Ala Ser Pro Gly Glu Lys Val Thr Met Thr
    610                 615                 620

Cys Arg Ala Ser Ser Ser Val Ser Tyr Met Asn Trp Tyr Gln Gln Lys
625                 630                 635                 640

Ser Gly Thr Ser Pro Lys Arg Trp Ile Tyr Asp Thr Ser Lys Val Ala
                645                 650                 655

Ser Gly Val Pro Tyr Arg Phe Ser Gly Ser Gly Ser Gly Thr Ser Tyr
            660                 665                 670

Ser Leu Thr Ile Ser Ser Met Glu Ala Glu Asp Ala Ala Thr Tyr Tyr
        675                 680                 685

Cys Gln Gln Trp Ser Ser Asn Pro Leu Thr Phe Gly Ala Gly Thr Lys
    690                 695                 700

Leu Glu Leu Lys
705
```

<210> SEQ ID NO 46

```
<211> LENGTH: 450
<212> TYPE: PRT
<213> ORGANISM: Artificial Sequence
<220> FEATURE:
<223> OTHER INFORMATION: description of the artificial sequence: the
      amino acid sequence of 4D5_IgG1_scT3a (DF) polypeptide 2

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
```

```
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 47
<211> LENGTH: 214
<212> TYPE: PRT
<213> ORGANISM: Artificial Sequence
<220> FEATURE:
<223> OTHER INFORMATION: description of the artificial sequence: the
      amino acid sequence of 4D5_IgG1_scT3a (DF) polypeptide 3

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 48
<211> LENGTH: 450
<212> TYPE: PRT
<213> ORGANISM: Artificial Sequence
<220> FEATURE:
<223> OTHER INFORMATION: description of the artificial sequence: the
      amino acid sequence of 8962_IgG1 (DF) polypeptide 1
```

<400> SEQUENCE: 48

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Lys Gln Ser Pro Gly Gln Gly Leu Glu Trp Met
        35                  40                  45

Gly Tyr Ile Tyr Pro Asn Asn Gly Gly Thr Gly Tyr Asn Gln Lys Phe
    50                  55                  60

Lys Ser Lys Val Thr Ile Thr Val Asp Thr Ser Thr Ser Thr Ala Tyr
65                  70                  75                  80

Met Glu Leu His Ser Leu Arg Ser Glu Asp Thr Ala Val Tyr Tyr Cys
                85                  90                  95

Ala Thr Tyr Gly His Tyr Tyr Gly Tyr Met Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 49
<211> LENGTH: 213
<212> TYPE: PRT
<213> ORGANISM: Artificial Sequence
<220> FEATURE:
<223> OTHER INFORMATION: description of the artificial sequence: the amino acid sequence of 8962_IgG1 (DF) polypeptide 2

<400> SEQUENCE: 49

Asp Ile Gln Leu Thr Gln Ser Pro Ser Ser Leu Ser Ala Ser Pro Gly
1 5 10 15

Asp Arg Val Thr Ile Thr Cys Ser Ala Ser Ser Ser Val Ser Tyr Met
20 25 30

His Trp Phe Gln Gln Lys Pro Gly Lys Ala Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Leu Gln Pro Glu
65 70 75 80

Asp Ile Ala Thr Tyr Tyr Cys Gln Gln Arg Ser Ser Tyr Pro Tyr Thr
85 90 95

Phe Gly Gly Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 50
<211> LENGTH: 708
<212> TYPE: PRT
<213> ORGANISM: Artificial Sequence
<220> FEATURE:
<223> OTHER INFORMATION: description of the artificial sequence: the amino acid sequence of 8962_IgG1_scT3a (DF) polypeptide 1

<400> SEQUENCE: 50

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

```
Asn Met Asp Trp Val Lys Gln Ser Pro Gly Gln Gly Leu Glu Trp Met
        35                  40                  45

Gly Tyr Ile Tyr Pro Asn Asn Gly Gly Thr Gly Tyr Asn Gln Lys Phe
    50                  55                  60

Lys Ser Lys Val Thr Ile Thr Val Asp Thr Ser Thr Ser Thr Ala Tyr
65                  70                  75                  80

Met Glu Leu His Ser Leu Arg Ser Glu Asp Thr Ala Val Tyr Tyr Cys
                85                  90                  95

Ala Thr Tyr Gly His Tyr Tyr Gly Tyr Met Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445
```

Gly Lys Ser Gly Gly Gly Gly Ser Gly Gly Gly Gly Ser Gly Gly Gly
    450                 455                 460

Gly Asp Ile Lys Leu Gln Gln Ser Gly Ala Glu Leu Ala Arg Pro Gly
465                 470                 475                 480

Ala Ser Val Lys Met Ser Cys Lys Thr Ser Gly Tyr Thr Phe Thr Arg
                485                 490                 495

Tyr Thr Met His Trp Val Lys Gln Arg Pro Gly Gln Gly Leu Glu Trp
            500                 505                 510

Ile Gly Tyr Ile Asn Pro Ser Arg Gly Tyr Thr Asn Tyr Asn Gln Lys
        515                 520                 525

Phe Lys Asp Lys Ala Thr Leu Thr Thr Asp Lys Ser Ser Ser Thr Ala
    530                 535                 540

Tyr Met Gln Leu Ser Ser Leu Thr Ser Glu Asp Ser Ala Val Tyr Tyr
545                 550                 555                 560

Cys Ala Arg Tyr Tyr Asp Asp His Tyr Cys Leu Asp Tyr Trp Gly Gln
                565                 570                 575

Gly Thr Thr Leu Thr Val Ser Ser Val Glu Gly Gly Ser Gly Gly Ser
            580                 585                 590

Gly Gly Ser Gly Gly Ser Gly Gly Val Asp Asp Ile Gln Leu Thr Gln
        595                 600                 605

Ser Pro Ala Ile Met Ser Ala Ser Pro Gly Glu Lys Val Thr Met Thr
    610                 615                 620

Cys Arg Ala Ser Ser Ser Val Ser Tyr Met Asn Trp Tyr Gln Gln Lys
625                 630                 635                 640

Ser Gly Thr Ser Pro Lys Arg Trp Ile Tyr Asp Thr Ser Lys Val Ala
                645                 650                 655

Ser Gly Val Pro Tyr Arg Phe Ser Gly Ser Gly Ser Gly Thr Ser Tyr
            660                 665                 670

Ser Leu Thr Ile Ser Ser Met Glu Ala Glu Asp Ala Ala Thr Tyr Tyr
        675                 680                 685

Cys Gln Gln Trp Ser Ser Asn Pro Leu Thr Phe Gly Ala Gly Thr Lys
    690                 695                 700

Leu Glu Leu Lys
705

<210> SEQ ID NO 51
<211> LENGTH: 450
<212> TYPE: PRT
<213> ORGANISM: Artificial Sequence
<220> FEATURE:
<223> OTHER INFORMATION: description of the artificial sequence: the amino acid sequence of 8962_IgG1_scT3a (DF) polypeptide 2

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Lys Gln Ser Pro Gly Gln Gly Leu Glu Trp Met
        35                  40                  45

Gly Tyr Ile Tyr Pro Asn Asn Gly Gly Thr Gly Tyr Asn Gln Lys Phe
    50                  55                  60

Lys Ser Lys Val Thr Ile Thr Val Asp Thr Ser Thr Ser Thr Ala Tyr
65                  70                  75                  80

Met Glu Leu His Ser Leu Arg Ser Glu Asp Thr Ala Val Tyr Tyr Cys
                85                  90                  95

```
Ala Thr Tyr Gly His Tyr Tyr Gly Tyr Met Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 52
<211> LENGTH: 213
<212> TYPE: PRT
<213> ORGANISM: Artificial Sequence
<220> FEATURE:
<223> OTHER INFORMATION: description of the artificial sequence: the amino acid sequence of 8962_IgG1_scT3a (DF) polypeptide 3

<400> SEQUENCE: 52

Asp Ile Gln Leu Thr Gln Ser Pro Ser Ser Leu Ser Ala Ser Pro Gly
1 5 10 15

Asp Arg Val Thr Ile Thr Cys Ser Ala Ser Ser Ser Val Ser Tyr Met
20 25 30

His Trp Phe Gln Gln Lys Pro Gly Lys Ala Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Leu Gln Pro Glu
65 70 75 80

Asp Ile Ala Thr Tyr Tyr Cys Gln Gln Arg Ser Ser Tyr Pro Tyr Thr
85 90 95

Phe Gly Gly Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 53
<211> LENGTH: 447
<212> TYPE: PRT
<213> ORGANISM: Artificial Sequence
<220> FEATURE:
<223> OTHER INFORMATION: description of the artificial sequence: the amino acid sequence of 4D5_mvG4PE (R409K) _scT3a (LC) (F) Polypeptide 1

<400> SEQUENCE: 53

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 54
<211> LENGTH: 701
<212> TYPE: PRT
<213> ORGANISM: Artificial Sequence
<220> FEATURE:
<223> OTHER INFORMATION: description of the artificial sequence: the
      amino acid sequence of 4D5_mvG4PE (R409K) _scT3a (LC) (F)
      Polypeptide 2

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Glu Ser Lys Tyr Gly Pro Pro Cys Pro Pro
    210                 215                 220

Cys Pro Ala Pro Glu Phe Glu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn Arg Phe
            420                 425                 430

Thr Gln Lys Ser Leu Ser Leu Ser Leu Gly Lys Ser Gly Gly Gly Gly
        435                 440                 445

Ser Gly Gly Gly Gly Ser Gly Gly Gly Gly Asp Ile Lys Leu Gln Gln
```

```
    450                 455                 460

Ser Gly Ala Glu Leu Ala Arg Pro Gly Ala Ser Val Lys Met Ser Cys
465                 470                 475                 480

Lys Thr Ser Gly Tyr Thr Phe Thr Arg Tyr Thr Met His Trp Val Lys
                485                 490                 495

Gln Arg Pro Gly Gln Gly Leu Glu Trp Ile Gly Tyr Ile Asn Pro Ser
            500                 505                 510

Arg Gly Tyr Thr Asn Tyr Asn Gln Lys Phe Lys Asp Lys Ala Thr Leu
        515                 520                 525

Thr Thr Asp Lys Ser Ser Ser Thr Ala Tyr Met Gln Leu Ser Ser Leu
    530                 535                 540

Thr Ser Glu Asp Ser Ala Val Tyr Tyr Cys Ala Arg Tyr Tyr Asp Asp
545                 550                 555                 560

His Tyr Cys Leu Asp Tyr Trp Gly Gln Gly Thr Thr Leu Thr Val Ser
                565                 570                 575

Ser Val Glu Gly Gly Ser Gly Gly Ser Gly Gly Ser Gly Gly Ser Gly
            580                 585                 590

Gly Val Asp Asp Ile Gln Leu Thr Gln Ser Pro Ala Ile Met Ser Ala
        595                 600                 605

Ser Pro Gly Glu Lys Val Thr Met Thr Cys Arg Ala Ser Ser Ser Val
    610                 615                 620

Ser Tyr Met Asn Trp Tyr Gln Gln Lys Ser Gly Thr Ser Pro Lys Arg
625                 630                 635                 640

Trp Ile Tyr Asp Thr Ser Lys Val Ala Ser Gly Val Pro Tyr Arg Phe
                645                 650                 655

Ser Gly Ser Gly Ser Gly Thr Ser Tyr Ser Leu Thr Ile Ser Ser Met
            660                 665                 670

Glu Ala Glu Asp Ala Ala Thr Tyr Tyr Cys Gln Gln Trp Ser Ser Asn
        675                 680                 685

Pro Leu Thr Phe Gly Ala Gly Thr Lys Leu Glu Leu Lys
    690                 695                 700


<210> SEQ ID NO 55
<211> LENGTH: 450
<212> TYPE: PRT
<213> ORGANISM: Artificial Sequence
<220> FEATURE:
<223> OTHER INFORMATION: description of the artificial sequence: the
      amino acid sequence of 4D5_mvG1_scT3a (LC) (DF) polypeptide 1

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Ser Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 56
<211> LENGTH: 699
<212> TYPE: PRT
<213> ORGANISM: Artificial Sequence
<220> FEATURE:
<223> OTHER INFORMATION: description of the artificial sequence: the
      amino acid sequence of 4D5_mvG1_scT3a (LC) (DF) polypeptide 2

<400> SEQUENCE: 56

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430
```

Lys Ser Leu Ser Leu Ser Pro Gly Lys Ser Gly Gly Gly Gly Ser Gly
435 440 445

Gly Gly Gly Ser Gly Gly Gly Gly Asp Ile Lys Leu Gln Gln Ser Gly
450 455 460

Ala Glu Leu Ala Arg Pro Gly Ala Ser Val Lys Met Ser Cys Lys Thr
465 470 475 480

Ser Gly Tyr Thr Phe Thr Arg Tyr Thr Met His Trp Val Lys Gln Arg
485 490 495

Pro Gly Gln Gly Leu Glu Trp Ile Gly Tyr Ile Asn Pro Ser Arg Gly
500 505 510

Tyr Thr Asn Tyr Asn Gln Lys Phe Lys Asp Lys Ala Thr Leu Thr Thr
515 520 525

Asp Lys Ser Ser Ser Thr Ala Tyr Met Gln Leu Ser Ser Leu Thr Ser
530 535 540

Glu Asp Ser Ala Val Tyr Tyr Cys Ala Arg Tyr Tyr Asp Asp His Tyr
545 550 555 560

Cys Leu Asp Tyr Trp Gly Gln Gly Thr Thr Leu Thr Val Ser Ser Val
565 570 575

Glu Gly Gly Ser Gly Gly Ser Gly Gly Ser Gly Gly Ser Gly Gly Val
580 585 590

Asp Asp Ile Gln Leu Thr Gln Ser Pro Ala Ile Met Ser Ala Ser Pro
595 600 605

Gly Glu Lys Val Thr Met Thr Cys Arg Ala Ser Ser Ser Val Ser Tyr
610 615 620

Met Asn Trp Tyr Gln Gln Lys Ser Gly Thr Ser Pro Lys Arg Trp Ile
625 630 635 640

Tyr Asp Thr Ser Lys Val Ala Ser Gly Val Pro Tyr Arg Phe Ser Gly
645 650 655

Ser Gly Ser Gly Thr Ser Tyr Ser Leu Thr Ile Ser Ser Met Glu Ala
660 665 670

Glu Asp Ala Ala Thr Tyr Tyr Cys Gln Gln Trp Ser Ser Asn Pro Leu
675 680 685

Thr Phe Gly Ala Gly Thr Lys Leu Glu Leu Lys
690 695

<210> SEQ ID NO 57
<211> LENGTH: 472
<212> TYPE: PRT
<213> ORGANISM: Artificial Sequence
<220> FEATURE:
<223> OTHER INFORMATION: description of the artificial sequence: the amino acid sequence of 4D5_scT3a_IgG1 (DF) polypeptide 1 amino acid sequence

<400> SEQUENCE: 57

Asp Ile Lys Leu Gln Gln Ser Gly Ala Glu Leu Ala Arg Pro Gly Ala
1 5 10 15

Ser Val Lys Met Ser Cys Lys Thr Ser Gly Tyr Thr Phe Thr Arg Tyr
20 25 30

Thr Met His Trp Val Lys Gln Arg Pro Gly Gln Gly Leu Glu Trp Ile
35 40 45

Gly Tyr Ile Asn Pro Ser Arg Gly Tyr Thr Asn Tyr Asn Gln Lys Phe
50 55 60

Lys Asp Lys Ala Thr Leu Thr Thr Asp Lys Ser Ser Ser Thr Ala Tyr
65 70 75 80

Met Gln Leu Ser Ser Leu Thr Ser Glu Asp Ser Ala Val Tyr Tyr Cys

```
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Thr Lys Tyr Gly Pro Pro Cys Pro Pro Cys Pro Ala
                245                 250                 255

Pro Glu Phe Glu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Cys Thr Leu Pro Pro Ser Gln Glu Glu Met Thr
    370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430

Ser Lys Leu Thr Val Asp Lys Ser Arg Trp Gln Glu Gly Asn Val Phe
        435                 440                 445

Ser Cys Ser Val Met His Glu Ala Leu His Asn Arg Phe Thr Gln Lys
    450                 455                 460

Ser Leu Ser Leu Ser Leu Gly Lys
465                 470
```

<210> SEQ ID NO 58
<211> LENGTH: 450
<212> TYPE: PRT
<213> ORGANISM: Artificial Sequence
<220> FEATURE:
<223> OTHER INFORMATION: description of the artificial sequence: the
amino acid sequence of 4D5_scT3a_IgG1 (DF) polypeptide 2

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 59
<211> LENGTH: 214
<212> TYPE: PRT
<213> ORGANISM: Artificial Sequence
<220> FEATURE:
<223> OTHER INFORMATION: description of the artificial sequence: the amino acid sequence of 4D5_scT3a_IgG1 (DF) polypeptide 3

<400> SEQUENCE: 59

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 60
<211> LENGTH: 472
<212> TYPE: PRT
<213> ORGANISM: Artificial Sequence
<220> FEATURE:
<223> OTHER INFORMATION: description of the artificial sequence: the amino acid sequence of 4D5mut_scT3a_IgG1 (DF) polypeptide 1

<400> SEQUENCE: 60

Asp Ile Lys Leu Gln Gln Ser Gly Ala Glu Leu Ala Arg Pro Gly Ala

-continued

```
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Thr Lys Tyr Gly Pro Pro Cys Pro Pro Cys Pro Ala
                245                 250                 255

Pro Glu Phe Glu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Cys Thr Leu Pro Pro Ser Gln Glu Glu Met Thr
    370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430
```

Ser Lys Leu Thr Val Asp Lys Ser Arg Trp Gln Glu Gly Asn Val Phe
435 440 445

Ser Cys Ser Val Met His Glu Ala Leu His Asn Arg Phe Thr Gln Lys
450 455 460

Ser Leu Ser Leu Ser Leu Gly Lys
465 470

<210> SEQ ID NO 61
<211> LENGTH: 450
<212> TYPE: PRT
<213> ORGANISM: Artificial Sequence
<220> FEATURE:
<223> OTHER INFORMATION: description of the artificial sequence: the amino acid sequence of 4D5mut_scT3a_IgG1 (DF) polypeptide 2

<400> SEQUENCE: 61

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Ala Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Ala Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys

```
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 62
<211> LENGTH: 214
<212> TYPE: PRT
<213> ORGANISM: Artificial Sequence
<220> FEATURE:
<223> OTHER INFORMATION: description of the artificial sequence: the
      amino acid sequence of 4D5mut_scT3a_IgG1 (DF) polypeptide 3

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 63
<211> LENGTH: 478
<212> TYPE: PRT
<213> ORGANISM: Artificial Sequence
<220> FEATURE:
<223> OTHER INFORMATION: description of the artificial sequence: the
      amino acid sequence of 4D5mut_scSP34 (H05) _ IgG1 (DF) polypeptide
      1

<400> SEQUENCE: 63

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
        195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Glu Asn Leu Trp Val Phe
225                 230                 235                 240

Gly Gly Gly Thr Lys Leu Thr Val Leu Gly Thr Lys Tyr Gly Pro Pro
                245                 250                 255

Cys Pro Pro Cys Pro Ala Pro Glu Phe Glu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Asn Gly Lys Glu Tyr Lys Cys
```

340 345 350

Lys Val Ser Asn Lys Gly Leu Pro Ser Ser Ile Glu Lys Thr Ile Ser
355 360 365

Lys Ala Lys Gly Gln Pro Arg Glu Pro Gln Val Cys Thr Leu Pro Pro
370 375 380

Ser Gln Glu Glu Met Thr Lys Asn Gln Val Ser Leu Ser Cys Ala Val
385 390 395 400

Lys Gly Phe Tyr Pro Ser Asp Ile Ala Val Glu Trp Glu Ser Asn Gly
405 410 415

Gln Pro Glu Asn Asn Tyr Lys Thr Thr Pro Pro Val Leu Asp Ser Asp
420 425 430

Gly Ser Phe Phe Leu Val Ser Lys Leu Thr Val Asp Lys Ser Arg Trp
435 440 445

Gln Glu Gly Asn Val Phe Ser Cys Ser Val Met His Glu Ala Leu His
450 455 460

Asn Arg Phe Thr Gln Lys Ser Leu Ser Leu Ser Leu Gly Lys
465 470 475

<210> SEQ ID NO 64
<211> LENGTH: 450
<212> TYPE: PRT
<213> ORGANISM: Artificial Sequence
<220> FEATURE:
<223> OTHER INFORMATION: description of the artificial sequence: the amino acid sequence of 4D5mut_scSP34 (H05) _ IgG1 (DF) polypeptide 2

<400> SEQUENCE: 64

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Ala Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Ala Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Cys Arg Asp Glu Leu Thr Lys Asn Gln Val Ser Leu
355 360 365

Trp Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 65
<211> LENGTH: 214
<212> TYPE: PRT
<213> ORGANISM: Artificial Sequence
<220> FEATURE:
<223> OTHER INFORMATION: description of the artificial sequence: the amino acid sequence of 4D5mut_scSP34 (H05) _ IgG1 (DF) polypeptide 3

<400> SEQUENCE: 65

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 66
<211> LENGTH: 478
<212> TYPE: PRT
<213> ORGANISM: Artificial Sequence
<220> FEATURE:
<223> OTHER INFORMATION: description of the artificial sequence: the amino acid sequence of 4D5mut_scSP34_IgG1 (DF) polypeptide 1

<400> SEQUENCE: 66

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
        195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Ser Asn Leu Trp Val Phe
225                 230                 235                 240

Gly Gly Gly Thr Lys Leu Thr Val Leu Gly Thr Lys Tyr Gly Pro Pro
                245                 250                 255
```

```
Cys Pro Pro Cys Pro Ala Pro Glu Phe Glu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Gly Leu Pro Ser Ser Ile Glu Lys Thr Ile Ser
        355                 360                 365

Lys Ala Lys Gly Gln Pro Arg Glu Pro Gln Val Cys Thr Leu Pro Pro
    370                 375                 380

Ser Gln Glu Glu Met Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
        435                 440                 445

Gln Glu Gly Asn Val Phe Ser Cys Ser Val Met His Glu Ala Leu His
    450                 455                 460

Asn Arg Phe Thr Gln Lys Ser Leu Ser Leu Ser Leu Gly Lys
465                 470                 475


<210> SEQ ID NO 67
<211> LENGTH: 450
<212> TYPE: PRT
<213> ORGANISM: Artificial Sequence
<220> FEATURE:
<223> OTHER INFORMATION: description of the artificial sequence: the
      amino acid sequence of 4D5mut_scSP34_IgG1 (DF) polypeptide 2

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Ala Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Ala Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

```
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 68
<211> LENGTH: 214
<212> TYPE: PRT
<213> ORGANISM: Artificial Sequence
<220> FEATURE:
<223> OTHER INFORMATION: description of the artificial sequence: the
      amino acid sequence of 4D5mut_scSP34_IgG1 (DF) polypeptide 3

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 69
<211> LENGTH: 708
<212> TYPE: PRT
<213> ORGANISM: Artificial Sequence
<220> FEATURE:
<223> OTHER INFORMATION: description of the artificial sequence: the amino acid sequence of 4D5mut_mvG1_scT3a (DF) polypeptide 1

<400> SEQUENCE: 69

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Ala Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Ala Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Ser Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Gly Gly Gly Gly Ser Gly Gly Gly Gly Ser Gly Gly Gly
    450                 455                 460

Gly Asp Ile Lys Leu Gln Gln Ser Gly Ala Glu Leu Ala Arg Pro Gly
465                 470                 475                 480

Ala Ser Val Lys Met Ser Cys Lys Thr Ser Gly Tyr Thr Phe Thr Arg
                485                 490                 495

Tyr Thr Met His Trp Val Lys Gln Arg Pro Gly Gln Gly Leu Glu Trp
            500                 505                 510

Ile Gly Tyr Ile Asn Pro Ser Arg Gly Tyr Thr Asn Tyr Asn Gln Lys
        515                 520                 525

Phe Lys Asp Lys Ala Thr Leu Thr Thr Asp Lys Ser Ser Ser Thr Ala
    530                 535                 540

Tyr Met Gln Leu Ser Ser Leu Thr Ser Glu Asp Ser Ala Val Tyr Tyr
545                 550                 555                 560

Cys Ala Arg Tyr Tyr Asp Asp His Tyr Cys Leu Asp Tyr Trp Gly Gln
                565                 570                 575

Gly Thr Thr Leu Thr Val Ser Ser Val Glu Gly Gly Ser Gly Gly Ser
            580                 585                 590
```

```
Gly Gly Ser Gly Gly Ser Gly Gly Val Asp Asp Ile Gln Leu Thr Gln
        595                 600                 605

Ser Pro Ala Ile Met Ser Ala Ser Pro Gly Glu Lys Val Thr Met Thr
    610                 615                 620

Cys Arg Ala Ser Ser Ser Val Ser Tyr Met Asn Trp Tyr Gln Gln Lys
625                 630                 635                 640

Ser Gly Thr Ser Pro Lys Arg Trp Ile Tyr Asp Thr Ser Lys Val Ala
                645                 650                 655

Ser Gly Val Pro Tyr Arg Phe Ser Gly Ser Gly Ser Gly Thr Ser Tyr
            660                 665                 670

Ser Leu Thr Ile Ser Ser Met Glu Ala Glu Asp Ala Ala Thr Tyr Tyr
        675                 680                 685

Cys Gln Gln Trp Ser Ser Asn Pro Leu Thr Phe Gly Ala Gly Thr Lys
    690                 695                 700

Leu Glu Leu Lys
705


<210> SEQ ID NO 70
<211> LENGTH: 441
<212> TYPE: PRT
<213> ORGANISM: Artificial Sequence
<220> FEATURE:
<223> OTHER INFORMATION: description of the artificial sequence: the
      amino acid sequence of 4D5mut_mvG1_scT3a (DF) polypeptide 2

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240
```

```
Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly Lys
        435                 440
```

<210> SEQ ID NO 71
<211> LENGTH: 707
<212> TYPE: PRT
<213> ORGANISM: Artificial Sequence
<220> FEATURE:
<223> OTHER INFORMATION: description of the artificial sequence: the amino acid sequence of DNP2_mvG1_ (scT3a) 2 (DF) polypeptide 1

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Ser Ser Ser Trp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Ser Gly Gly Gly Gly Ser Gly Gly Gly Gly Ser Gly Gly Gly Gly
    450                 455                 460

Asp Ile Lys Leu Gln Gln Ser Gly Ala Glu Leu Ala Arg Pro Gly Ala
465                 470                 475                 480

Ser Val Lys Met Ser Cys Lys Thr Ser Gly Tyr Thr Phe Thr Arg Tyr
                485                 490                 495

Thr Met His Trp Val Lys Gln Arg Pro Gly Gln Gly Leu Glu Trp Ile
            500                 505                 510

Gly Tyr Ile Asn Pro Ser Arg Gly Tyr Thr Asn Tyr Asn Gln Lys Phe
        515                 520                 525

Lys Asp Lys Ala Thr Leu Thr Thr Asp Lys Ser Ser Ser Thr Ala Tyr
    530                 535                 540

Met Gln Leu Ser Ser Leu Thr Ser Glu Asp Ser Ala Val Tyr Tyr Cys
545                 550                 555                 560

Ala Arg Tyr Tyr Asp Asp His Tyr Cys Leu Asp Tyr Trp Gly Gln Gly
                565                 570                 575
```

Thr Thr Leu Thr Val Ser Ser Val Glu Gly Gly Ser Gly Gly Ser Gly
580 585 590

Gly Ser Gly Gly Ser Gly Gly Val Asp Asp Ile Gln Leu Thr Gln Ser
595 600 605

Pro Ala Ile Met Ser Ala Ser Pro Gly Glu Lys Val Thr Met Thr Cys
610 615 620

Arg Ala Ser Ser Ser Val Ser Tyr Met Asn Trp Tyr Gln Gln Lys Ser
625 630 635 640

Gly Thr Ser Pro Lys Arg Trp Ile Tyr Asp Thr Ser Lys Val Ala Ser
645 650 655

Gly Val Pro Tyr Arg Phe Ser Gly Ser Gly Ser Gly Thr Ser Tyr Ser
660 665 670

Leu Thr Ile Ser Ser Met Glu Ala Glu Asp Ala Ala Thr Tyr Tyr Cys
675 680 685

Gln Gln Trp Ser Ser Asn Pro Leu Thr Phe Gly Ala Gly Thr Lys Leu
690 695 700

Glu Leu Lys
705

<210> SEQ ID NO 72
<211> LENGTH: 699
<212> TYPE: PRT
<213> ORGANISM: Artificial Sequence
<220> FEATURE:
<223> OTHER INFORMATION: description of the artificial sequence: the amino acid sequence of DNP2_mvG1_ (scT3a) 2 (DF) polypeptide 2

<400> SEQUENCE: 72

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Ser Asp Lys Thr His Thr Cys Pro Pro Cys Pro

```
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
            420                 425                 430

Lys Ser Leu Ser Leu Ser Pro Gly Lys Ser Gly Gly Gly Gly Ser Gly
        435                 440                 445

Gly Gly Gly Ser Gly Gly Gly Gly Asp Ile Lys Leu Gln Gln Ser Gly
    450                 455                 460

Ala Glu Leu Ala Arg Pro Gly Ala Ser Val Lys Met Ser Cys Lys Thr
465                 470                 475                 480

Ser Gly Tyr Thr Phe Thr Arg Tyr Thr Met His Trp Val Lys Gln Arg
                485                 490                 495

Pro Gly Gln Gly Leu Glu Trp Ile Gly Tyr Ile Asn Pro Ser Arg Gly
            500                 505                 510

Tyr Thr Asn Tyr Asn Gln Lys Phe Lys Asp Lys Ala Thr Leu Thr Thr
        515                 520                 525

Asp Lys Ser Ser Ser Thr Ala Tyr Met Gln Leu Ser Ser Leu Thr Ser
    530                 535                 540

Glu Asp Ser Ala Val Tyr Tyr Cys Ala Arg Tyr Tyr Asp Asp His Tyr
545                 550                 555                 560

Cys Leu Asp Tyr Trp Gly Gln Gly Thr Thr Leu Thr Val Ser Ser Val
                565                 570                 575

Glu Gly Gly Ser Gly Gly Ser Gly Gly Ser Gly Gly Ser Gly Gly Val
            580                 585                 590

Asp Asp Ile Gln Leu Thr Gln Ser Pro Ala Ile Met Ser Ala Ser Pro
        595                 600                 605

Gly Glu Lys Val Thr Met Thr Cys Arg Ala Ser Ser Ser Val Ser Tyr
    610                 615                 620

Met Asn Trp Tyr Gln Gln Lys Ser Gly Thr Ser Pro Lys Arg Trp Ile
625                 630                 635                 640
```

```
Tyr Asp Thr Ser Lys Val Ala Ser Gly Val Pro Tyr Arg Phe Ser Gly
                645                 650                 655

Ser Gly Ser Gly Thr Ser Tyr Ser Leu Thr Ile Ser Ser Met Glu Ala
            660                 665                 670

Glu Asp Ala Ala Thr Tyr Tyr Cys Gln Gln Trp Ser Ser Asn Pro Leu
        675                 680                 685

Thr Phe Gly Ala Gly Thr Lys Leu Glu Leu Lys
    690                 695
```

<210> SEQ ID NO 73
<211> LENGTH: 249
<212> TYPE: PRT
<213> ORGANISM: Artificial Sequence
<220> FEATURE:
<223> OTHER INFORMATION: description of the artificial sequence: the amino acid sequence of Anti-CD3 scFv (scI2C)

<400> SEQUENCE: 73

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Leu Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

<210> SEQ ID NO 74
<211> LENGTH: 747
<212> TYPE: DNA
<213> ORGANISM: Artificial Sequence
<220> FEATURE:
<223> OTHER INFORMATION: description of the artificial sequence: the nucleotide sequence of anti-CD3 scFv (scSP34)

<400> SEQUENCE: 74
gaagtccagc ttgtggagtc tggtggcggc ttggttcaac ctaagggctc attgaagctg 60
tcctgtgctg ccagcggttt caccttcaac acatacgcta tgaattgggt acggcaggct 120
cctggcaaag gtttggaatg ggttgccagg atacggtcta aatacaacaa ttacgctacc 180
tactacgctg atagtgtcaa ggatcgcttc accataagcc gcgatgacag tcaaagcata 240
ctttaccttc aaatgaacaa cctcaaaaca gaggatactg caatgtacta ctgcgtgaga 300
cacggcaact ttggaaacag ctacgtctcc tggtttgcat attgggggca ggggaccctg 360
gtgactgtgt caagtggagg tggtgggagt ggagggggag gttcaggcgg tggagggagt 420
caagccgtcg ttacacaaga atctgccctc accaccagcc caggcgagac agttacactt 480
acttgccgca gttcaactgg ggcagttacc acttctaatt atgctaactg ggtgcaggag 540
aaaccagacc atctttttac tggtctgatt ggaggtacaa ataaacgggc tcctggggta 600
cccgccagat tcagtggtag tcttatcggc gataaagctg ctctgaccat caccggtgcc 660
caaactgaag acgaagcaat atatttttgc gctctgtggt acagtaatct ctgggtattt 720
ggtggcggga ccaaacttac cgtattg 747

<210> SEQ ID NO 75
<211> LENGTH: 249
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34)

<400> SEQUENCE: 75

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Gln Ser Ile
65 70 75 80

Leu Tyr Leu Gln Met Asn Asn Leu Lys Thr Glu Asp Thr Ala Met Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser Gly Gly Gly
115 120 125

Gly Ser Gly Gly Gly Gly Ser Gly Gly Gly Gly Ser Gln Ala Val Val
130 135 140

Thr Gln Glu Ser Ala Leu Thr Thr Ser Pro Gly Glu Thr Val Thr Leu
145 150 155 160

Thr Cys Arg Ser Ser Thr Gly Ala Val Thr Thr Ser Asn Tyr Ala Asn
165 170 175

Trp Val Gln Glu Lys Pro Asp His Leu Phe Thr Gly Leu Ile Gly Gly
180 185 190

Thr Asn Lys Arg Ala Pro Gly Val Pro Ala Arg Phe Ser Gly Ser Leu
195 200 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Ser Asn Leu Trp Val Phe
225                 230                 235                 240

Gly Gly Gly Thr Lys Leu Thr Val Leu
                245

<210> SEQ ID NO 76
<211> LENGTH: 5
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34) CDR H1

<400> SEQUENCE: 76

Thr Tyr Ala Met Asn
1               5

<210> SEQ ID NO 77
<211> LENGTH: 19
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34) CDR H2

<400> SEQUENCE: 77

Arg Ile Arg Ser Lys Tyr Asn Asn Tyr Ala Thr Tyr Tyr Ala Asp Ser
1               5                   10                  15

Val Lys Asp

<210> SEQ ID NO 78
<211> LENGTH: 14
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34) CDR H3

<400> SEQUENCE: 78

His Gly Asn Phe Gly Asn Ser Tyr Val Ser Trp Phe Ala Tyr
1               5                   10

<210> SEQ ID NO 79
<211> LENGTH: 14
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34) CDR L1

<400> SEQUENCE: 79

Arg Ser Ser Thr Gly Ala Val Thr Thr Ser Asn Tyr Ala Asn
1               5                   10

<210> SEQ ID NO 80
<211> LENGTH: 7
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34) CDR L2

<400> SEQUENCE: 80

```
Gly Thr Asn Lys Arg Ala Pro
1               5


<210> SEQ ID NO 81
<211> LENGTH: 9
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34) CDR L3

<400> SEQUENCE: 81

Ala Leu Trp Tyr Ser Asn Leu Trp Val
1               5


<210> SEQ ID NO 82
<211> LENGTH: 249
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34 (H05))

<400> SEQUENCE: 82

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
        195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Glu Asn Leu Trp Val Phe
225                 230                 235                 240

Gly Gly Gly Thr Lys Leu Thr Val Leu
                245


<210> SEQ ID NO 83
<211> LENGTH: 5
```

<212> TYPE: PRT
<213> ORGANISM: Artificial Sequence
<220> FEATURE:
<223> OTHER INFORMATION: description of the artificial sequence: the amino acid sequence of anti-CD3 scFv (scSP34 (H05)) CDR H1

<400> SEQUENCE: 83

Thr Tyr Ala Met Asn
1 5

<210> SEQ ID NO 84
<211> LENGTH: 19
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34 (H05)) CDR H2

<400> SEQUENCE: 84

Arg Ile Arg Ser Lys Tyr Asn Asn Tyr Ala Thr Tyr Tyr Ala Asp Ser
1 5 10 15

Val Lys Asp

<210> SEQ ID NO 85
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34 (H05)) CDR H3

<400> SEQUENCE: 85

His Gly Asn Phe Gly Asn Ser Asp Val Ser Trp Phe Ala Tyr
1 5 10

<210> SEQ ID NO 86
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34 (H05)) CDR L1

<400> SEQUENCE: 86

Arg Ser Ser Thr Gly Ala Val Thr Thr Ser Asn Tyr Ala Asn
1 5 10

<210> SEQ ID NO 87
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34 (H05)) CDR L2

<400> SEQUENCE: 87

Gly Thr Asn Lys Arg Ala Pro
1 5

<210> SEQ ID NO 88
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34 (H05)) CDR L3

<400> SEQUENCE: 88

```
Ala Leu Trp Tyr Glu Asn Leu Trp Val
1               5


<210> SEQ ID NO 89
<211> LENGTH: 26
<212> TYPE: DNA
<213> ORGANISM: Artificial Sequence
<220> FEATURE:
<223> OTHER INFORMATION: description of the artificial sequence: the
      nucleotide sequence of primer for antibody gene cloning (VL)

<400> SEQUENCE: 89

gttgaagctc tttgtgacgg gcgagc                                          26


<210> SEQ ID NO 90
<211> LENGTH: 28
<212> TYPE: DNA
<213> ORGANISM: Artificial Sequence
<220> FEATURE:
<223> OTHER INFORMATION: description of the artificial sequence: the
      nucleotide sequence of primer for antibody gene cloning (VH)

<400> SEQUENCE: 90

gcctgagttc cacgacaccg tcaccggt                                        28


<210> SEQ ID NO 91
<211> LENGTH: 321
<212> TYPE: DNA
<213> ORGANISM: Artificial Sequence
<220> FEATURE:
<223> OTHER INFORMATION: description of the artificial sequence: the
      nucleotide sequence of anti-CD3 antibody KM14 VL

<400> SEQUENCE: 91

gccatccagt tgacccagtc tccatcctcc ctgtctgcat ctgtaggaga cagagtcacc      60

atcacttgcc gggcaagtca gggcattagc agtgctttag cctggtatca gcagaaacca     120

gggaaagccc ctaacctcct gatctatgat gcctccagtt tggaaagtgg ggtcccatca     180

aggttcagcg gcagtggatc tgggacagat ttcactctca ccatcagcag cctgcagcct     240

gaagattttg caacttatta ctgtcaacag tttaatagtt accctcggac gttcggccaa     300

gggaccaagg tggaaatcaa a                                              321


<210> SEQ ID NO 92
<211> LENGTH: 372
<212> TYPE: DNA
<213> ORGANISM: Artificial Sequence
<220> FEATURE:
<223> OTHER INFORMATION: description of the artificial sequence: the
      nucleotide sequence of anti-CD3 antibody KM14 VH

<400> SEQUENCE: 92

caggtgcaac tggtggagtc tgggggaggc gtggtccagc ctgggaggtc cctgagactc      60

tcctgtgaag cgtctggatt caccttcagt agccatggca tgcactgggt ccgccaggct     120

ccaggcaagg ggctggagtg ggtggcatct atatggtatg atggaagtaa gaaatactat     180

gcagactccg tgaagggccg attcaccatc tccagagaca attctaagaa cacgctggat     240

ctgcaaatga acagcctgag agccgaggac acggctgtgt attactgtgc gaaaaccctg     300

tattactatg gttcggagag ggcgcacggt ttggacgtct ggggccaagg gaccacggtc     360

accgtctcct ca                                                        372
```

<210> SEQ ID NO 93
<211> LENGTH: 107
<212> TYPE: PRT
<213> ORGANISM: Artificial Sequence
<220> FEATURE:
<223> OTHER INFORMATION: description of the artificial sequence: the amino acid sequence of anti-CD3 antibody KM14 VL

<400> SEQUENCE: 93

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105
```

<210> SEQ ID NO 94
<211> LENGTH: 124
<212> TYPE: PRT
<213> ORGANISM: Artificial Sequence
<220> FEATURE:
<223> OTHER INFORMATION: description of the artificial sequence: the amino acid sequence of anti-CD3 antibody KM14 VH

<400> SEQUENCE: 94

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120
```

<210> SEQ ID NO 95
<211> LENGTH: 11
<212> TYPE: PRT
<213> ORGANISM: Artificial Sequence
<220> FEATURE:
<223> OTHER INFORMATION: description of the artificial sequence: the amino acid sequence of anti-CD3 antibody KM14 CDR L1

<400> SEQUENCE: 95

```
Arg Ala Ser Gln Gly Ile Ser Ser Ala Leu Ala
1               5                   10
```

<210> SEQ ID NO 96
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 antibody KM14 CDR L2

<400> SEQUENCE: 96

Asp Ala Ser Ser Leu Glu Ser
1               5

<210> SEQ ID NO 97
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 antibody KM14 CDR L3

<400> SEQUENCE: 97

Gln Gln Phe Asn Ser Tyr Pro Arg Thr
1               5

<210> SEQ ID NO 98
<211> LENGTH: 5
<212> TYPE: PRT
<213> ORGANISM: Artificial Sequence
<220> FEATURE:
<223> OTHER INFORMATION: description of the artificial sequence: the amino acid sequence of anti-CD3 antibody KM14 CDR H1

<400> SEQUENCE: 98

Ser His Gly Met His
1               5

<210> SEQ ID NO 99
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody KM14 CDR H2

<400> SEQUENCE: 99

Ser Ile Trp Tyr Asp Gly Ser Lys Lys Tyr Tyr Ala Asp Ser Val Lys
1               5                   10                  15

Gly

<210> SEQ ID NO 100
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody KM14 CDR H3

<400> SEQUENCE: 100

Thr Leu Tyr Tyr Tyr Gly Ser Glu Arg Ala His Gly Leu Asp Val
1               5                   10                  15

<210> SEQ ID NO 101
<211> LENGTH: 738
<212> TYPE: DNA
<213> ORGANISM: Artificial Sequence
<220> FEATURE:

<223> OTHER INFORMATION: description of the artificial sequence: the
nucleotide sequence of anti-CD3 scFv (scKM14)

<400> SEQUENCE: 101
caggtgcaac tggtggagtc tgggggaggc gtggtccagc ctgggaggtc cctgagactc 60
tcctgtgaag cgtctggatt caccttcagt agccatggca tgcactgggt ccgccaggct 120
ccaggcaagg ggctggagtg ggtggcatct atatggtatg atggaagtaa gaaatactat 180
gcagactccg tgaagggccg attcaccatc tccagagaca attctaagaa cacgctggat 240
ctgcaaatga acagcctgag agccgaggac acggctgtgt attactgtgc gaaaaccctg 300
tattactatg gttcggagag ggcgcacggt ttggacgtct ggggccaagg gaccacggtc 360
accgtctcct caggaggtgg tgggagtgga gggggaggtt caggcggtgg agggagtgcc 420
atccagttga cccagtctcc atcctccctg tctgcatctg taggagacag agtcaccatc 480
acttgccggg caagtcaggg cattagcagt gctttagcct ggtatcagca gaaaccaggg 540
aaagccccta acctcctgat ctatgatgcc tccagtttgg aaagtggggt cccatcaagg 600
ttcagcggca gtggatctgg gacagatttc actctcacca tcagcagcct gcagcctgaa 660
gattttgcaa cttattactg tcaacagttt aatagttacc ctcggacgtt cggccaaggg 720
accaaggtgg aaatcaaa 738

<210> SEQ ID NO 102
<211> LENGTH: 246
<212> TYPE: PRT
<213> ORGANISM: Artificial Sequence
<220> FEATURE:
<223> OTHER INFORMATION: description of the artificial sequence: the
amino acid sequence of anti-CD3 scFv (scKM14)

<400> SEQUENCE: 102

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Gly Leu Glu Trp Val
35 40 45

Ala Ser Ile Trp Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser Gly Gly Gly Gly
115 120 125

Ser Gly Gly Gly Gly Ser Gly Gly Gly Gly Ser Ala Ile Gln Leu Thr
130 135 140

Gln Ser Pro Ser Ser Leu Ser Ala Ser Val Gly Asp Arg Val Thr Ile
145 150 155 160

Thr Cys Arg Ala Ser Gln Gly Ile Ser Ser Ala Leu Ala Trp Tyr Gln
165 170 175

Gln Lys Pro Gly Lys Ala Pro Asn Leu Leu Ile Tyr Asp Ala Ser Ser
180 185 190

Leu Glu Ser Gly Val Pro Ser Arg Phe Ser Gly Ser Gly Ser Gly Thr

```
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Gln Gly
225                 230                 235                 240

Thr Lys Val Glu Ile Lys
                245
```

<210> SEQ ID NO 103
<211> LENGTH: 246
<212> TYPE: PRT
<213> ORGANISM: Artificial Sequence
<220> FEATURE:
<223> OTHER INFORMATION: description of the artificial sequence: the amino acid sequence of anti-CD3 scFv (scKM14 (mut1-03))

<400> SEQUENCE: 103

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Arg Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Gln Gly
225                 230                 235                 240

Thr Lys Val Glu Ile Lys
                245
```

<210> SEQ ID NO 104
<211> LENGTH: 246
<212> TYPE: PRT
<213> ORGANISM: Artificial Sequence
<220> FEATURE:
<223> OTHER INFORMATION: description of the artificial sequence: the amino acid sequence of anti-CD3 scFv (scKM14 (mut1-04))

<400> SEQUENCE: 104

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Gln Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Gln Gly
225                 230                 235                 240

Thr Lys Val Glu Ile Lys
                245
```

<210> SEQ ID NO 105
<211> LENGTH: 246
<212> TYPE: PRT
<213> ORGANISM: Artificial Sequence
<220> FEATURE:
<223> OTHER INFORMATION: description of the artificial sequence: the amino acid sequence of anti-CD3 scFv (scKM14 (mut1-18))

<400> SEQUENCE: 105

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Glu Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95
```

```
Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Gln Gly
225                 230                 235                 240

Thr Lys Val Glu Ile Lys
                245


<210> SEQ ID NO 106
<211> LENGTH: 246
<212> TYPE: PRT
<213> ORGANISM: Artificial Sequence
<220> FEATURE:
<223> OTHER INFORMATION: description of the artificial sequence: the
      amino acid sequence of anti-CD3 scFv (scKM14 (mut1-22))

<400> SEQUENCE: 106

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Val Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205
```

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Gln Gly
225                 230                 235                 240

Thr Lys Val Glu Ile Lys
                245

<210> SEQ ID NO 107
<211> LENGTH: 246
<212> TYPE: PRT
<213> ORGANISM: Artificial Sequence
<220> FEATURE:
<223> OTHER INFORMATION: description of the artificial sequence: the
      amino acid sequence of anti-CD3 scFv (scKM14 (mut1-25))

<400> SEQUENCE: 107

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Lys Lys Asp Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Gln Gly
225                 230                 235                 240

Thr Lys Val Glu Ile Lys
                245

<210> SEQ ID NO 108
<211> LENGTH: 246
<212> TYPE: PRT
<213> ORGANISM: Artificial Sequence
<220> FEATURE:
<223> OTHER INFORMATION: description of the artificial sequence: the
      amino acid sequence of anti-CD3 scFv (scKM14 (mut1-26))

<400> SEQUENCE: 108

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Lys Lys Ser Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Gln Gly
225                 230                 235                 240

Thr Lys Val Glu Ile Lys
                245


<210> SEQ ID NO 109
<211> LENGTH: 113
<212> TYPE: PRT
<213> ORGANISM: Artificial Sequence
<220> FEATURE:
<223> OTHER INFORMATION: description of the artificial sequence: the
      amino acid sequence of XENP14045 anti-CD123 antibody VL

<400> SEQUENCE: 109

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Thr
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gly Gly Thr Lys Leu Glu Ile
```

```
            100                 105                 110

Lys


<210> SEQ ID NO 110
<211> LENGTH: 120
<212> TYPE: PRT
<213> ORGANISM: Artificial Sequence
<220> FEATURE:
<223> OTHER INFORMATION: description of the artificial sequence: the
      amino acid sequence of XENP14045 Anti-CD123 antibody VH

<400> SEQUENCE: 110

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Met
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 111
<211> LENGTH: 112
<212> TYPE: PRT
<213> ORGANISM: Artificial Sequence
<220> FEATURE:
<223> OTHER INFORMATION: description of the artificial sequence: the
      amino acid sequence of KM2160 anti-CCR4 antibody VL

<400> SEQUENCE: 111

Asp Val Leu Met Thr Gln Thr Pro Leu Ser Leu Pro Val Ser Leu Gly
1               5                   10                  15

Asp Gln Ala Ser Ile Ser Cys Arg Ser Ser Arg Asn Ile Val His Ile
            20                  25                  30

Asn Gly Asp Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Leu Leu Pro Trp Thr Phe Gly Gly Gly Thr Arg Leu Glu Ile Arg
            100                 105                 110


<210> SEQ ID NO 112
<211> LENGTH: 119
<212> TYPE: PRT
<213> ORGANISM: Artificial Sequence
<220> FEATURE:
<223> OTHER INFORMATION: description of the artificial sequence: the
      amino acid sequence of KM2160 Anti-CCR4 antibody VH
```

<400> SEQUENCE: 112

Glu Val Gln Leu Val Glu Ser Gly Gly Asp Leu Met Lys Pro Gly Gly
1               5                   10                  15

Ser Leu Lys Ile Ser Cys Ala Ala Ser Gly Phe Ile Phe Ser Asn Tyr
            20                  25                  30

Gly Met Ser Trp Val Arg Gln Thr Pro Asp Met Arg Leu Glu Trp Val
        35                  40                  45

Ala Thr Ile Ser Ser Ala Ser Thr Tyr Ser Tyr Tyr Pro Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ser Glu Asp Thr Gly Ile Tyr Tyr Cys
                85                  90                  95

Gly Arg His Ser Asp Gly Asn Phe Ala Phe Gly Tyr Trp Gly Arg Gly
            100                 105                 110

Thr Leu Val Thr Val Ser Ala
        115

<210> SEQ ID NO 113
<211> LENGTH: 107
<212> TYPE: PRT
<213> ORGANISM: Artificial Sequence
<220> FEATURE:
<223> OTHER INFORMATION: description of the artificial sequence: the amino acid sequence of anti-CD123 antibody (CD123-1) VL

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 114
<211> LENGTH: 119
<212> TYPE: PRT
<213> ORGANISM: Artificial Sequence
<220> FEATURE:
<223> OTHER INFORMATION: description of the artificial sequence: the amino acid sequence of anti-CD123 antibody (CD123-1) VH

<400> SEQUENCE: 114

Gln Val Gln Leu Val Gln Ser Gly Ala Glu Val Lys Lys Pro Gly Ser
1               5                   10                  15

Ser Val Lys Val Ser Cys Met Ala Ser Gly Gly Thr Val Ser Ser Tyr
            20                  25                  30

Ala Ile Ser Trp Val Arg Gln Ala Pro Gly Gln Gly Leu Glu Trp Met
        35                  40                  45

```
Gly Glu Ile Ile Pro Ile Phe Gly Ile Val Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Glu Thr Ala Val Ala Gly Ile Leu Gly Tyr Trp Gly Gln Gly
            100                 105                 110

Thr Leu Val Thr Val Ser Ser
        115


<210> SEQ ID NO 115
<211> LENGTH: 125
<212> TYPE: PRT
<213> ORGANISM: Artificial Sequence
<220> FEATURE:
<223> OTHER INFORMATION: description of the artificial sequence: the
      amino acid sequence of SP34(H05) VH

<400> SEQUENCE: 115

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125


<210> SEQ ID NO 116
<211> LENGTH: 109
<212> TYPE: PRT
<213> ORGANISM: Artificial Sequence
<220> FEATURE:
<223> OTHER INFORMATION: description of the artificial sequence: the
      amino acid sequence of SP34(H05) VL

<400> SEQUENCE: 116

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Glu Asn
                85                  90                  95
```

```
Leu Trp Val Phe Gly Gly Gly Thr Lys Leu Thr Val Leu
            100                 105


<210> SEQ ID NO 117
<211> LENGTH: 249
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34(H04))

<400> SEQUENCE: 117

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Glu Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
        195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Glu Asn Leu Trp Val Phe
225                 230                 235                 240

Gly Gly Gly Thr Lys Leu Thr Val Leu
                245


<210> SEQ ID NO 118
<211> LENGTH: 5
<212> TYPE: PRT
<213> ORGANISM: Artificial Sequence
<220> FEATURE:
<223> OTHER INFORMATION: description of the artificial sequence: the
      amino acid sequence of anti-CD3 scFv (scSP34(H04)) CDR H1

<400> SEQUENCE: 118

Thr Tyr Ala Met Asn
1               5


<210> SEQ ID NO 119
<211> LENGTH: 19
```

<212> TYPE: PRT
<213> ORGANISM: Artificial Sequence
<220> FEATURE:
<223> OTHER INFORMATION: description of the artificial sequence: the amino acid sequence of anti-CD3 scFv (scSP34(H04')) CDR H2

<400> SEQUENCE: 119

Arg Ile Arg Ser Lys Tyr Asn Asn Tyr Ala Thr Tyr Tyr Ala Asp Ser
1 5 10 15

Val Lys Asp

<210> SEQ ID NO 120
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34(H04)) CDR H3

<400> SEQUENCE: 120

His Gly Asn Phe Gly Asn Glu Tyr Val Ser Trp Phe Ala Tyr
1 5 10

<210> SEQ ID NO 121
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34(H04)) CDR L1

<400> SEQUENCE: 121

Arg Ser Ser Thr Gly Ala Val Thr Thr Ser Asn Tyr Ala Asn
1 5 10

<210> SEQ ID NO 122
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34(H04)) CDR L2

<400> SEQUENCE: 122

Gly Thr Asn Lys Arg Ala Pro
1 5

<210> SEQ ID NO 123
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 scFv (scSP34(H04)) CDR L3

<400> SEQUENCE: 123

Ala Leu Trp Tyr Glu Asn Leu Trp Val
1 5

<210> SEQ ID NO 124
<211> LENGTH: 125
<212> TYPE: PRT
<213> ORGANISM: Artificial Sequence
<220> FEATURE:
<223> OTHER INFORMATION: description of the artificial sequence: the amino acid sequence of SP34(H04) VH

<400> SEQUENCE: 124

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Glu Tyr Val Ser Trp Phe
            100                 105                 110

Ala Tyr Trp Gly Gln Gly Thr Leu Val Thr Val Ser Ser
        115                 120                 125


<210> SEQ ID NO 125
<211> LENGTH: 109
<212> TYPE: PRT
<213> ORGANISM: Artificial Sequence
<220> FEATURE:
<223> OTHER INFORMATION: description of the artificial sequence: the
      amino acid sequence of SP34(H04) VL

<400> SEQUENCE: 125

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Glu Asn
                85                  90                  95

Leu Trp Val Phe Gly Gly Gly Thr Lys Leu Thr Val Leu
            100                 105


<210> SEQ ID NO 126
<211> LENGTH: 107
<212> TYPE: PRT
<213> ORGANISM: Artificial Sequence
<220> FEATURE:
<223> OTHER INFORMATION: description of the artificial sequence: the
      amino acid sequence of mut1-03 VL

<400> SEQUENCE: 126

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Arg Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60
```

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Arg
85 90 95

Thr Phe Gly Gln Gly Thr Lys Val Glu Ile Lys
100 105

<210> SEQ ID NO 127
<211> LENGTH: 107
<212> TYPE: PRT
<213> ORGANISM: Artificial Sequence
<220> FEATURE:
<223> OTHER INFORMATION: description of the artificial sequence: the amino acid sequence of mut1-04 VL

<400> SEQUENCE: 127

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Gln Ser Ser Ala
20 25 30

Leu Ala Trp Tyr Gln Gln Lys Pro Gly Lys Ala Pro Asn Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Arg
85 90 95

Thr Phe Gly Gln Gly Thr Lys Val Glu Ile Lys
100 105

<210> SEQ ID NO 128
<211> LENGTH: 124
<212> TYPE: PRT
<213> ORGANISM: Artificial Sequence
<220> FEATURE:
<223> OTHER INFORMATION: description of the artificial sequence: the amino acid sequence of mut1-18 VH

<400> SEQUENCE: 128

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Gly Leu Glu Trp Val
35 40 45

Ala Ser Ile Trp Tyr Glu Gly Ser Lys Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser
115 120

<210> SEQ ID NO 129

<211> LENGTH: 124
<212> TYPE: PRT
<213> ORGANISM: Artificial Sequence
<220> FEATURE:
<223> OTHER INFORMATION: description of the artificial sequence: the amino acid sequence of mut1-22 VH

<400> SEQUENCE: 129

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Val Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120
```

<210> SEQ ID NO 130
<211> LENGTH: 124
<212> TYPE: PRT
<213> ORGANISM: Artificial Sequence
<220> FEATURE:
<223> OTHER INFORMATION: description of the artificial sequence: the amino acid sequence of mut1-25 VH

<400> SEQUENCE: 130

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Ser Ile Trp Tyr Asp Gly Ser Lys Lys Asp Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120
```

<210> SEQ ID NO 131
<211> LENGTH: 124
<212> TYPE: PRT
<213> ORGANISM: Artificial Sequence
<220> FEATURE:
<223> OTHER INFORMATION: description of the artificial sequence: the amino acid sequence of mut1-26 VH

<400> SEQUENCE: 131

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Gly Leu Glu Trp Val
35 40 45

Ala Ser Ile Trp Tyr Asp Gly Ser Lys Lys Ser Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser
115 120

<210> SEQ ID NO 132
<211> LENGTH: 11
<212> TYPE: PRT
<213> ORGANISM: Artificial Sequence
<220> FEATURE:
<223> OTHER INFORMATION: description of the artificial sequence: the amino acid sequence of mut1-03 CDR L1

<400> SEQUENCE: 132

Arg Ala Ser Gln Gly Arg Ser Ser Ala Leu Ala
1 5 10

<210> SEQ ID NO 133
<211> LENGTH: 11
<212> TYPE: PRT
<213> ORGANISM: Artificial Sequence
<220> FEATURE:
<223> OTHER INFORMATION: description of the artificial sequence: the amino acid sequence of mut1-04 CDR L1

<400> SEQUENCE: 133

Arg Ala Ser Gln Gly Gln Ser Ser Ala Leu Ala
1 5 10

<210> SEQ ID NO 134
<211> LENGTH: 17
<212> TYPE: PRT
<213> ORGANISM: Artificial Sequence
<220> FEATURE:
<223> OTHER INFORMATION: description of the artificial sequence: the amino acid sequence of mut1-18 CDR H2

<400> SEQUENCE: 134

Ser Ile Trp Tyr Glu Gly Ser Lys Lys Tyr Tyr Ala Asp Ser Val Lys
1 5 10 15

Gly

<210> SEQ ID NO 135
<211> LENGTH: 17
<212> TYPE: PRT
<213> ORGANISM: Artificial Sequence
<220> FEATURE:
<223> OTHER INFORMATION: description of the artificial sequence: the amino acid sequence of mut1-22 CDR H2

<400> SEQUENCE: 135

```
Ser Ile Trp Tyr Asp Gly Ser Val Lys Tyr Tyr Ala Asp Ser Val Lys
1               5                   10                  15

Gly


<210> SEQ ID NO 136
<211> LENGTH: 17
<212> TYPE: PRT
<213> ORGANISM: Artificial Sequence
<220> FEATURE:
<223> OTHER INFORMATION: description of the artificial sequence: the
      amino acid sequence of mut1-25 CDR H2

<400> SEQUENCE: 136

Ser Ile Trp Tyr Asp Gly Ser Lys Lys Asp Tyr Ala Asp Ser Val Lys
1               5                   10                  15

Gly


<210> SEQ ID NO 137
<211> LENGTH: 17
<212> TYPE: PRT
<213> ORGANISM: Artificial Sequence
<220> FEATURE:
<223> OTHER INFORMATION: description of the artificial sequence: the
      amino acid sequence of mut1-26 CDR H2

<400> SEQUENCE: 137

Ser Ile Trp Tyr Asp Gly Ser Lys Lys Ser Tyr Ala Asp Ser Val Lys
1               5                   10                  15

Gly


<210> SEQ ID NO 138
<211> LENGTH: 186
<212> TYPE: PRT
<213> ORGANISM: Homo sapiens

<400> SEQUENCE: 138

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125

Tyr Trp Ser Lys Asn Arg Lys Ala Lys Ala Lys Pro Val Thr Arg Gly
    130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
```

180 185

<210> SEQ ID NO 139
<211> LENGTH: 177
<212> TYPE: PRT
<213> ORGANISM: Macaca fascicularis

<400> SEQUENCE: 139

Gln Asp Gly Asn Glu Glu Met Gly Ser Ile Thr Gln Thr Pro Tyr Gln
1 5 10 15

Val Ser Ile Ser Gly Thr Thr Val Ile Leu Thr Cys Ser Gln His Leu
20 25 30

Gly Ser Glu Ala Gln Trp Gln His Asn Gly Lys Asn Lys Glu Asp Ser
35 40 45

Gly Asp Arg Leu Phe Leu Pro Glu Phe Ser Glu Met Glu Gln Ser Gly
50 55 60

Tyr Tyr Val Cys Tyr Pro Arg Gly Ser Asn Pro Glu Asp Ala Ser His
65 70 75 80

His Leu Tyr Leu Lys Ala Arg Val Cys Glu Asn Cys Met Glu Met Asp
85 90 95

Val Met Ala Val Ala Thr Ile Val Ile Val Asp Ile Cys Ile Thr Leu
100 105 110

Gly Leu Leu Leu Leu Val Tyr Tyr Trp Ser Lys Asn Arg Lys Ala Lys
115 120 125

Ala Lys Pro Val Thr Arg Gly Ala Gly Ala Gly Gly Arg Gln Arg Gly
130 135 140

Gln Asn Lys Glu Arg Pro Pro Pro Val Pro Asn Pro Asp Tyr Glu Pro
145 150 155 160

Ile Arg Lys Gly Gln Gln Asp Leu Tyr Ser Gly Leu Asn Gln Arg Arg
165 170 175

Ile

<210> SEQ ID NO 140
<211> LENGTH: 105
<212> TYPE: PRT
<213> ORGANISM: Homo sapiens

<400> SEQUENCE: 140

Gln Asp Gly Asn Glu Glu Met Gly Gly Ile Thr Gln Thr Pro Tyr Lys
1 5 10 15

Val Ser Ile Ser Gly Thr Thr Val Ile Leu Thr Cys Pro Gln Tyr Pro
20 25 30

Gly Ser Glu Ile Leu Trp Gln His Asn Asp Lys Asn Ile Gly Gly Asp
35 40 45

Glu Asp Asp Lys Asn Ile Gly Ser Asp Glu Asp His Leu Ser Leu Lys
50 55 60

Glu Phe Ser Glu Leu Glu Gln Ser Gly Tyr Tyr Val Cys Tyr Pro Arg
65 70 75 80

Gly Ser Lys Pro Glu Asp Ala Asn Phe Tyr Leu Tyr Leu Arg Ala Arg
85 90 95

Val Cys Glu Asn Cys Met Glu Met Asp
100 105

<210> SEQ ID NO 141
<211> LENGTH: 561
<212> TYPE: DNA
<213> ORGANISM: Homo sapiens

<400> SEQUENCE: 141
caagatggta atgaagaaat gggtggtatt acacagacac catataaagt ctccatctct 60
ggaaccacag taatattgac atgccctcag tatcctggat ctgaaatact atggcaacac 120
aatgataaaa acataggcgg tgatgaggat gataaaaaca taggcagtga tgaggatcac 180
ctgtcactga aggaattttc agaattggag caaagtggtt attatgtctg ctaccccaga 240
ggaagcaaac cagaagatgc gaacttttat ctctacctga gggcaagagt gtgtgagaac 300
tgcatggaga tggatgtgat gtcggtggcc acaattgtca tagtggacat ctgcatcact 360
gggggcttgc tgctgctggt ttactactgg agcaagaata gaaaggccaa ggccaagcct 420
gtgacacgag gagcgggtgc tggcggcagg caaaggggac aaaacaagga gaggccacca 480
cctgttccca acccagacta tgagcccatc cggaaaggcc agcgggacct gtattctggc 540
ctgaatcaga gacgcatctg a 561

<210> SEQ ID NO 142
<211> LENGTH: 534
<212> TYPE: DNA
<213> ORGANISM: Macaca fascicularis

<400> SEQUENCE: 142
caagatggta atgaagaaat gggtagtatt acacagacac catatcaagt ctccatctct 60
ggaaccacag taatactgac atgctctcag catcttggat ctgaagcaca atggcaacac 120
aatggtaaaa acaaaggaga ttctggggat caactgtttc tgccggaatt ttcagaaatg 180
gagcaaagtg gttattatgt ctgctacccc agaggaagca atccagagga cgcgagccat 240
catctctacc tgaaggcaag agtgtgtgag aactgcatgg agatggatgt gatggcggtg 300
gccacaattg tcatagtgga catctgcatc actctgggct tgctgctgct ggtttactac 360
tggagcaaga atagaaaggc caaggccaag cctgtgacac gaggagcagg tgctggcggc 420
aggcaaaggg gacaaaacaa ggagaggcca ccacctgttc ccaacccaga ctatgagccc 480
atccggaaag gccagcagga tctgtattct ggcctgaatc agagacgcat ctga 534

<210> SEQ ID NO 143
<211> LENGTH: 5
<212> TYPE: PRT
<213> ORGANISM: Artificial Sequence
<220> FEATURE:
<223> OTHER INFORMATION: description of the artificial sequence: the amino acid sequence of peptide linker

<400> SEQUENCE: 143

Ser Gly Gly Gly Gly
1 5

<210> SEQ ID NO 144
<211> LENGTH: 5
<212> TYPE: PRT
<213> ORGANISM: Artificial Sequence
<220> FEATURE:
<223> OTHER INFORMATION: description of the artificial sequence: the amino acid sequence of peptide linker

<400> SEQUENCE: 144

Glu Ala Ala Ala Lys
1 5

<210> SEQ ID NO 145

<211> LENGTH: 5
<212> TYPE: PRT
<213> ORGANISM: Artificial Sequence
<220> FEATURE:
<223> OTHER INFORMATION: description of the artificial sequence: the amino acid sequence of peptide linker

<400> SEQUENCE: 145

Pro Ala Pro Ala Pro
1 5

<210> SEQ ID NO 146
<211> LENGTH: 28
<212> TYPE: PRT
<213> ORGANISM: Artificial Sequence
<220> FEATURE:
<223> OTHER INFORMATION: description of the artificial sequence: the amino acid sequence of N-terminal non-acetylated peptide of human CD3

<400> SEQUENCE: 146

Gln Asp Gly Asn Glu Glu Met Gly Gly Ile Thr Gln Thr Pro Tyr Lys
1 5 10 15

Val Ser Ile Ser Gly Thr Thr Val Ile Leu Thr Cys
20 25

<210> SEQ ID NO 147
<211> LENGTH: 217
<212> TYPE: PRT
<213> ORGANISM: Artificial Sequence
<220> FEATURE:
<223> OTHER INFORMATION: description of the artificial sequence: the amino acid sequence of Fc(KIH-1)_Knobs_AA

<400> SEQUENCE: 147

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Cys Arg Asp Glu Leu
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

```
Lys Ser Leu Ser Leu Ser Pro Gly Lys
    210                 215


<210> SEQ ID NO 148
<211> LENGTH: 217
<212> TYPE: PRT
<213> ORGANISM: Artificial Sequence
<220> FEATURE:
<223> OTHER INFORMATION: description of the artificial sequence: the
      amino acid sequence of Fc(KIH-1)_Holes_AA

<400> SEQUENCE: 148

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215


<210> SEQ ID NO 149
<211> LENGTH: 217
<212> TYPE: PRT
<213> ORGANISM: Artificial Sequence
<220> FEATURE:
<223> OTHER INFORMATION: description of the artificial sequence: the
      amino acid sequence of Fc(KIH-2)_Holes_AA

<400> SEQUENCE: 149

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 150
<211> LENGTH: 217
<212> TYPE: PRT
<213> ORGANISM: Artificial Sequence
<220> FEATURE:
<223> OTHER INFORMATION: description of the artificial sequence: the
      amino acid sequence of Fc(KIH-2)_Knobs_AA

<400> SEQUENCE: 150

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn Arg Phe Thr Gln
```

```
        195                 200                 205

Lys Ser Leu Ser Leu Ser Pro Gly Lys
    210                 215


<210> SEQ ID NO 151
<211> LENGTH: 217
<212> TYPE: PRT
<213> ORGANISM: Artificial Sequence
<220> FEATURE:
<223> OTHER INFORMATION: description of the artificial sequence: the
      amino acid sequence of Fc(KIH-3)_Knobs_AA

<400> SEQUENCE: 151

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 152
<211> LENGTH: 217
<212> TYPE: PRT
<213> ORGANISM: Artificial Sequence
<220> FEATURE:
<223> OTHER INFORMATION: description of the artificial sequence: the
      amino acid sequence of Fc(KIH-3)_Holes_AA

<400> SEQUENCE: 152

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
```

```
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215


<210> SEQ ID NO 153
<211> LENGTH: 217
<212> TYPE: PRT
<213> ORGANISM: Artificial Sequence
<220> FEATURE:
<223> OTHER INFORMATION: description of the artificial sequence: the
      amino acid sequence of Fc(KIH-4)_Holes_AA

<400> SEQUENCE: 153

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 154
<211> LENGTH: 217
<212> TYPE: PRT
<213> ORGANISM: Artificial Sequence
<220> FEATURE:
<223> OTHER INFORMATION: description of the artificial sequence: the
      amino acid sequence of Fc(KIH-4)_Knobs_AA

<400> SEQUENCE: 154

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215


<210> SEQ ID NO 155
<211> LENGTH: 125
<212> TYPE: PRT
<213> ORGANISM: Artificial Sequence
<220> FEATURE:
<223> OTHER INFORMATION: description of the artificial sequence: the
      amino acid sequence of scSP34(H05)_VH(44C)_AA

<400> SEQUENCE: 155

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45
```

```
Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125


<210> SEQ ID NO 156
<211> LENGTH: 125
<212> TYPE: PRT
<213> ORGANISM: Artificial Sequence
<220> FEATURE:
<223> OTHER INFORMATION: description of the artificial sequence: the
      amino acid sequence of scSP34(H05)_VH(44S)_AA

<400> SEQUENCE: 156

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Ser Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125


<210> SEQ ID NO 157
<211> LENGTH: 109
<212> TYPE: PRT
<213> ORGANISM: Artificial Sequence
<220> FEATURE:
<223> OTHER INFORMATION: description of the artificial sequence: the
      amino acid sequence of scSP34(H05)_VL(100C)_AA

<400> SEQUENCE: 157

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Glu Asn
                85                  90                  95
```

Leu Trp Val Phe Gly Cys Gly Thr Lys Leu Thr Val Leu
100 105

<210> SEQ ID NO 158
<211> LENGTH: 109
<212> TYPE: PRT
<213> ORGANISM: Artificial Sequence
<220> FEATURE:
<223> OTHER INFORMATION: description of the artificial sequence: the amino acid sequence of scSP34(H05)_VL(100E)_AA

<400> SEQUENCE: 158

Gln Ala Val Val Thr Gln Glu Ser Ala Leu Thr Thr Ser Pro Gly Glu
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Asp His Leu Phe Thr Gly
35 40 45

Leu Ile Gly Gly Thr Asn Lys Arg Ala Pro Gly Val Pro Ala Arg Phe
50 55 60

Ser Gly Ser Leu Ile Gly Asp Lys Ala Ala Leu Thr Ile Thr Gly Ala
65 70 75 80

Gln Thr Glu Asp Glu Ala Ile Tyr Phe Cys Ala Leu Trp Tyr Glu Asn
85 90 95

Leu Trp Val Phe Gly Glu Gly Thr Lys Leu Thr Val Leu
100 105

<210> SEQ ID NO 159
<211> LENGTH: 125
<212> TYPE: PRT
<213> ORGANISM: Artificial Sequence
<220> FEATURE:
<223> OTHER INFORMATION: description of the artificial sequence: the amino acid sequence of scSP34(H05)_VH(HV3)_AA

<400> SEQUENCE: 159

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Val Arg His Gly Asn Phe Gly Asn Ser Asp Val Ser Trp Phe
100 105 110

Ala Tyr Trp Gly Gln Gly Thr Leu Val Thr Val Ser Ser
115 120 125

<210> SEQ ID NO 160
<211> LENGTH: 125
<212> TYPE: PRT
<213> ORGANISM: Artificial Sequence
<220> FEATURE:
<223> OTHER INFORMATION: description of the artificial sequence: the amino acid sequence of scSP34(H05)_VH(HV5)_AA

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125

<210> SEQ ID NO 161
<211> LENGTH: 125
<212> TYPE: PRT
<213> ORGANISM: Artificial Sequence
<220> FEATURE:
<223> OTHER INFORMATION: description of the artificial sequence: the amino acid sequence of scSP34(H05)_VH(HV3)(44C)_AA

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125

<210> SEQ ID NO 162
<211> LENGTH: 125
<212> TYPE: PRT
<213> ORGANISM: Artificial Sequence
<220> FEATURE:
<223> OTHER INFORMATION: description of the artificial sequence: the amino acid sequence of scSP34(H05)_VH(HV5)(44C)_AA

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val

```
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125


<210> SEQ ID NO 163
<211> LENGTH: 125
<212> TYPE: PRT
<213> ORGANISM: Artificial Sequence
<220> FEATURE:
<223> OTHER INFORMATION: description of the artificial sequence: the
      amino acid sequence of scSP34(H05)_VH(HV3)(44S)_AA

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Ser Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125


<210> SEQ ID NO 164
<211> LENGTH: 125
<212> TYPE: PRT
<213> ORGANISM: Artificial Sequence
<220> FEATURE:
<223> OTHER INFORMATION: description of the artificial sequence: the
      amino acid sequence of scSP34(H05)_VH(HV5)(44S)_AA

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Ser Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Met Tyr
```

```
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser
        115                 120                 125


<210> SEQ ID NO 165
<211> LENGTH: 109
<212> TYPE: PRT
<213> ORGANISM: Artificial Sequence
<220> FEATURE:
<223> OTHER INFORMATION: description of the artificial sequence: the
      amino acid sequence of scSP34(H05)_VL(LV8a)_AA

<400> SEQUENCE: 165

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Thr Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Ile Tyr Phe Cys Ala Leu Trp Tyr Glu Asn
                85                  90                  95

Leu Trp Val Phe Gly Gly Gly Thr Lys Leu Thr Val Leu
            100                 105


<210> SEQ ID NO 166
<211> LENGTH: 109
<212> TYPE: PRT
<213> ORGANISM: Artificial Sequence
<220> FEATURE:
<223> OTHER INFORMATION: description of the artificial sequence: the
      amino acid sequence of scSP34(H05)_VL(LV8a)(100C)_AA

<400> SEQUENCE: 166

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Thr Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Ile Tyr Phe Cys Ala Leu Trp Tyr Glu Asn
                85                  90                  95

Leu Trp Val Phe Gly Cys Gly Thr Lys Leu Thr Val Leu
            100                 105


<210> SEQ ID NO 167
<211> LENGTH: 109
<212> TYPE: PRT
<213> ORGANISM: Artificial Sequence
<220> FEATURE:
<223> OTHER INFORMATION: description of the artificial sequence: the
```

amino acid sequence of scSP34(H05)_VL(LV8a)(100E)_AA

<400> SEQUENCE: 167

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Thr Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Ile Tyr Phe Cys Ala Leu Trp Tyr Glu Asn
                85                  90                  95

Leu Trp Val Phe Gly Glu Gly Thr Lys Leu Thr Val Leu
            100                 105
```

<210> SEQ ID NO 168
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-03)_VH(44C)_AA

<400> SEQUENCE: 168

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120
```

<210> SEQ ID NO 169
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-04)_VH(44C)_AA

<400> SEQUENCE: 169

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45
```

Ala Ser Ile Trp Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser
115 120

<210> SEQ ID NO 170
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-18)_VH(44C)_AA

<400> SEQUENCE: 170

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Cys Leu Glu Trp Val
35 40 45

Ala Ser Ile Trp Tyr Glu Gly Ser Lys Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser
115 120

<210> SEQ ID NO 171
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-22)_VH(44C)_AA

<400> SEQUENCE: 171

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Cys Leu Glu Trp Val
35 40 45

Ala Ser Ile Trp Tyr Asp Gly Ser Val Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

```
Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120


<210> SEQ ID NO 172
<211> LENGTH: 124
<212> TYPE: PRT
<213> ORGANISM: Artificial Sequence
<220> FEATURE:
<223> OTHER INFORMATION: description of the artificial sequence: the
      amino acid sequence of scKM14(mut1-25)_VH(44C)_AA

<400> SEQUENCE: 172

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Lys Lys Asp Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120


<210> SEQ ID NO 173
<211> LENGTH: 124
<212> TYPE: PRT
<213> ORGANISM: Artificial Sequence
<220> FEATURE:
<223> OTHER INFORMATION: description of the artificial sequence: the
      amino acid sequence of scKM14(mut1-26)_VH(44C)_AA

<400> SEQUENCE: 173

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Lys Lys Ser Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120


<210> SEQ ID NO 174
```

<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-03)_VH(44S)_AA

<400> SEQUENCE: 174

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Ser Leu Glu Trp Val
35 40 45

Ala Ser Ile Trp Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser
115 120

<210> SEQ ID NO 175
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-04)_VH(44S)_AA

<400> SEQUENCE: 175

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Ser Leu Glu Trp Val
35 40 45

Ala Ser Ile Trp Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser
115 120

<210> SEQ ID NO 176
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-18)_VH(44S)_AA

<400> SEQUENCE: 176

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Ser Leu Glu Trp Val
        35                  40                  45

Ala Ser Ile Trp Tyr Glu Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120
```

<210> SEQ ID NO 177
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-22)_VH(44S)_AA

<400> SEQUENCE: 177

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Ser Leu Glu Trp Val
        35                  40                  45

Ala Ser Ile Trp Tyr Asp Gly Ser Val Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120
```

<210> SEQ ID NO 178
<211> LENGTH: 124
<212> TYPE: PRT
<213> ORGANISM: Artificial Sequence
<220> FEATURE:
<223> OTHER INFORMATION: description of the artificial sequence: the amino acid sequence of scKM14(mut1-25)_VH(44S)_AA

<400> SEQUENCE: 178

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Ser Leu Glu Trp Val
        35                  40                  45
```

```
Ala Ser Ile Trp Tyr Asp Gly Ser Lys Lys Asp Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120


<210> SEQ ID NO 179
<211> LENGTH: 124
<212> TYPE: PRT
<213> ORGANISM: Artificial Sequence
<220> FEATURE:
<223> OTHER INFORMATION: description of the artificial sequence: the
      amino acid sequence of scKM14(mut1-26)_VH(44S)_AA

<400> SEQUENCE: 179

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Ser Leu Glu Trp Val
        35                  40                  45

Ala Ser Ile Trp Tyr Asp Gly Ser Lys Lys Ser Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser
        115                 120


<210> SEQ ID NO 180
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-03)_VL(100C)_AA

<400> SEQUENCE: 180

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Arg Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95
```

```
Thr Phe Gly Cys Gly Thr Lys Val Glu Ile Lys
            100                 105


<210> SEQ ID NO 181
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-04)_VL(100C)_AA

<400> SEQUENCE: 181

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Gln Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Cys Gly Thr Lys Val Glu Ile Lys
            100                 105


<210> SEQ ID NO 182
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-18)_VL(100C)_AA

<400> SEQUENCE: 182

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Cys Gly Thr Lys Val Glu Ile Lys
            100                 105


<210> SEQ ID NO 183
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-22)_VL(100C)_AA

<400> SEQUENCE: 183

Ala Ile Gln Leu Thr Gln Ser Pro Ser Ser Leu Ser Ala Ser Val Gly
```

```
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Cys Gly Thr Lys Val Glu Ile Lys
            100                 105


<210> SEQ ID NO 184
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-25)_VL(100C)_AA

<400> SEQUENCE: 184

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Cys Gly Thr Lys Val Glu Ile Lys
            100                 105


<210> SEQ ID NO 185
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-26)_VL(100C)_AA

<400> SEQUENCE: 185

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
```

```
                85                  90                  95

Thr Phe Gly Cys Gly Thr Lys Val Glu Ile Lys
            100                 105


<210> SEQ ID NO 186
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-03)_VL(100E)_AA

<400> SEQUENCE: 186

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Arg Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Glu Gly Thr Lys Val Glu Ile Lys
            100                 105


<210> SEQ ID NO 187
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-04)_VL(100E)_AA

<400> SEQUENCE: 187

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Gln Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Glu Gly Thr Lys Val Glu Ile Lys
            100                 105


<210> SEQ ID NO 188
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-18)_VL(100E)_AA

<400> SEQUENCE: 188
```

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Glu Gly Thr Lys Val Glu Ile Lys
            100                 105


<210> SEQ ID NO 189
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-22)_VL(100E)_AA

<400> SEQUENCE: 189

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Glu Gly Thr Lys Val Glu Ile Lys
            100                 105


<210> SEQ ID NO 190
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-25)_VL(100E)_AA

<400> SEQUENCE: 190

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Phe Asn Ser Tyr Pro Arg
                85                  90                  95

Thr Phe Gly Glu Gly Thr Lys Val Glu Ile Lys
            100                 105


<210> SEQ ID NO 191
<211> LENGTH: 107
<212> TYPE: PRT
<213> ORGANISM: Artificial Sequence
<220> FEATURE:
<223> OTHER INFORMATION: description of the artificial sequence: the
      amino acid sequence of scKM14(mut1-26)_VL(100E)_AA

<400> SEQUENCE: 191

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Glu Gly Thr Lys Val Glu Ile Lys
            100                 105


<210> SEQ ID NO 192
<211> LENGTH: 249
<212> TYPE: PRT
<213> ORGANISM: Artificial Sequence
<220> FEATURE:
<223> OTHER INFORMATION: description of the artificial sequence: the
      amino acid sequence of scSP34(H05)_scFv(CC)_AA

<400> SEQUENCE: 192

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160
```

Thr Cys Arg Ser Ser Thr Gly Ala Val Thr Thr Ser Asn Tyr Ala Asn
165 170 175

Trp Val Gln Glu Lys Pro Asp His Leu Phe Thr Gly Leu Ile Gly Gly
180 185 190

Thr Asn Lys Arg Ala Pro Gly Val Pro Ala Arg Phe Ser Gly Ser Leu
195 200 205

Ile Gly Asp Lys Ala Ala Leu Thr Ile Thr Gly Ala Gln Thr Glu Asp
210 215 220

Glu Ala Ile Tyr Phe Cys Ala Leu Trp Tyr Glu Asn Leu Trp Val Phe
225 230 235 240

Gly Cys Gly Thr Lys Leu Thr Val Leu
245

<210> SEQ ID NO 193
<211> LENGTH: 249
<212> TYPE: PRT
<213> ORGANISM: Artificial Sequence
<220> FEATURE:
<223> OTHER INFORMATION: description of the artificial sequence: the amino acid sequence of scSP34(H05_HV3LV8a)_scFv(CC)_AA

<400> SEQUENCE: 193

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Cys Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Val Arg His Gly Asn Phe Gly Asn Ser Asp Val Ser Trp Phe
100 105 110

Ala Tyr Trp Gly Gln Gly Thr Leu Val Thr Val Ser Ser Gly Gly Gly
115 120 125

Gly Ser Gly Gly Gly Gly Ser Gly Gly Gly Gly Ser Gln Ala Val Val
130 135 140

Thr Gln Glu Pro Ser Leu Thr Val Ser Pro Gly Gly Thr Val Thr Leu
145 150 155 160

Thr Cys Arg Ser Ser Thr Gly Ala Val Thr Thr Ser Asn Tyr Ala Asn
165 170 175

Trp Val Gln Gln Lys Pro Gly Gln Ala Phe Thr Gly Leu Ile Gly Gly
180 185 190

Thr Asn Lys Arg Ala Pro Gly Val Pro Ala Arg Phe Ser Gly Ser Leu
195 200 205

Leu Gly Gly Lys Ala Ala Leu Thr Leu Ser Gly Ala Gln Pro Glu Asp
210 215 220

Glu Ala Ile Tyr Phe Cys Ala Leu Trp Tyr Glu Asn Leu Trp Val Phe
225 230 235 240

Gly Cys Gly Thr Lys Leu Thr Val Leu
245

<210> SEQ ID NO 194
<211> LENGTH: 249
<212> TYPE: PRT
<213> ORGANISM: Artificial Sequence
<220> FEATURE:
<223> OTHER INFORMATION: description of the artificial sequence: the amino acid sequence of scSP34(H05_HV5LV8a)_scFv(CC)_AA

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Phe Thr Gly Leu Ile Gly Gly
            180                 185                 190

Thr Asn Lys Arg Ala Pro Gly Val Pro Ala Arg Phe Ser Gly Ser Leu
        195                 200                 205

Leu Gly Gly Lys Ala Ala Leu Thr Leu Ser Gly Ala Gln Pro Glu Asp
    210                 215                 220

Glu Ala Ile Tyr Phe Cys Ala Leu Trp Tyr Glu Asn Leu Trp Val Phe
225                 230                 235                 240

Gly Cys Gly Thr Lys Leu Thr Val Leu
                245

<210> SEQ ID NO 195
<211> LENGTH: 249
<212> TYPE: PRT
<213> ORGANISM: Artificial Sequence
<220> FEATURE:
<223> OTHER INFORMATION: description of the artificial sequence: the amino acid sequence of scSP34(H05)_scFv(SE)_AA

<400> SEQUENCE: 195

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Ser Leu Glu Trp Val
        35                  40                  45

Ala Arg Ile Arg Ser Lys Tyr Asn Asn Tyr Ala Thr Tyr Tyr Ala Asp

```
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Asp Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
        195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Glu Asn Leu Trp Val Phe
225                 230                 235                 240

Gly Glu Gly Thr Lys Leu Thr Val Leu
                245


<210> SEQ ID NO 196
<211> LENGTH: 246
<212> TYPE: PRT
<213> ORGANISM: Artificial Sequence
<220> FEATURE:
<223> OTHER INFORMATION: description of the artificial sequence: the
      amino acid sequence of scKM14(mut1-03)_scFv(CC)_AA

<400> SEQUENCE: 196

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160
```

```
Thr Cys Arg Ala Ser Gln Gly Arg Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Cys Gly
225                 230                 235                 240

Thr Lys Val Glu Ile Lys
                245
```

```
<210> SEQ ID NO 197
<211> LENGTH: 246
<212> TYPE: PRT
<213> ORGANISM: Artificial Sequence
<220> FEATURE:
<223> OTHER INFORMATION: description of the artificial sequence: the
      amino acid sequence of scKM14(mut1-04)_scFv(CC)_AA

<400> SEQUENCE: 197

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Gln Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Cys Gly
225                 230                 235                 240

Thr Lys Val Glu Ile Lys
                245
```

```
<210> SEQ ID NO 198
```

<211> LENGTH: 246
<212> TYPE: PRT
<213> ORGANISM: Artificial Sequence
<220> FEATURE:
<223> OTHER INFORMATION: description of the artificial sequence: the amino acid sequence of scKM14(mut1-18)_scFv(CC)_AA

<400> SEQUENCE: 198

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Glu Gly Ser Lys Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Cys Gly
225                 230                 235                 240

Thr Lys Val Glu Ile Lys
                245
```

<210> SEQ ID NO 199
<211> LENGTH: 246
<212> TYPE: PRT
<213> ORGANISM: Artificial Sequence
<220> FEATURE:
<223> OTHER INFORMATION: description of the artificial sequence: the amino acid sequence of scKM14(mut1-22)_scFv(CC)_AA

<400> SEQUENCE: 199

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Val Lys Tyr Tyr Ala Asp Ser Val
    50                  55                  60
```

```
Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Cys Gly
225                 230                 235                 240

Thr Lys Val Glu Ile Lys
                245


<210> SEQ ID NO 200
<211> LENGTH: 246
<212> TYPE: PRT
<213> ORGANISM: Artificial Sequence
<220> FEATURE:
<223> OTHER INFORMATION: description of the artificial sequence: the
      amino acid sequence of scKM14(mut1-25)_scFv(CC)_AA

<400> SEQUENCE: 200

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Lys Lys Asp Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
```

```
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Cys Gly
225                 230                 235                 240

Thr Lys Val Glu Ile Lys
                245


<210> SEQ ID NO 201
<211> LENGTH: 246
<212> TYPE: PRT
<213> ORGANISM: Artificial Sequence
<220> FEATURE:
<223> OTHER INFORMATION: description of the artificial sequence: the
      amino acid sequence of scKM14(mut1-26)_scFv(CC)_AA

<400> SEQUENCE: 201

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Cys Leu Glu Trp Val
        35                  40                  45

Ala Ser Ile Trp Tyr Asp Gly Ser Lys Lys Ser Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Cys Gly
225                 230                 235                 240

Thr Lys Val Glu Ile Lys
                245


<210> SEQ ID NO 202
<211> LENGTH: 246
```

<212> TYPE: PRT
<213> ORGANISM: Artificial Sequence
<220> FEATURE:
<223> OTHER INFORMATION: description of the artificial sequence: the amino acid sequence of scKM14(mut1-18)_scFv(SE)_AA

<400> SEQUENCE: 202

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Ser Leu Glu Trp Val
35 40 45

Ala Ser Ile Trp Tyr Glu Gly Ser Lys Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser Gly Gly Gly Gly
115 120 125

Ser Gly Gly Gly Gly Ser Gly Gly Gly Gly Ser Ala Ile Gln Leu Thr
130 135 140

Gln Ser Pro Ser Ser Leu Ser Ala Ser Val Gly Asp Arg Val Thr Ile
145 150 155 160

Thr Cys Arg Ala Ser Gln Gly Ile Ser Ser Ala Leu Ala Trp Tyr Gln
165 170 175

Gln Lys Pro Gly Lys Ala Pro Asn Leu Leu Ile Tyr Asp Ala Ser Ser
180 185 190

Leu Glu Ser Gly Val Pro Ser Arg Phe Ser Gly Ser Gly Ser Gly Thr
195 200 205

Asp Phe Thr Leu Thr Ile Ser Ser Leu Gln Pro Glu Asp Phe Ala Thr
210 215 220

Tyr Tyr Cys Gln Gln Phe Asn Ser Tyr Pro Arg Thr Phe Gly Glu Gly
225 230 235 240

Thr Lys Val Glu Ile Lys
245

<210> SEQ ID NO 203
<211> LENGTH: 246
<212> TYPE: PRT
<213> ORGANISM: Artificial Sequence
<220> FEATURE:
<223> OTHER INFORMATION: description of the artificial sequence: the amino acid sequence of scKM14(mut1-22)_scFv(SE)_AA

<400> SEQUENCE: 203

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Ser Leu Glu Trp Val
35 40 45

Ala Ser Ile Trp Tyr Asp Gly Ser Val Lys Tyr Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser Gly Gly Gly Gly
115 120 125

Ser Gly Gly Gly Gly Ser Gly Gly Gly Gly Ser Ala Ile Gln Leu Thr
130 135 140

Gln Ser Pro Ser Ser Leu Ser Ala Ser Val Gly Asp Arg Val Thr Ile
145 150 155 160

Thr Cys Arg Ala Ser Gln Gly Ile Ser Ser Ala Leu Ala Trp Tyr Gln
165 170 175

Gln Lys Pro Gly Lys Ala Pro Asn Leu Leu Ile Tyr Asp Ala Ser Ser
180 185 190

Leu Glu Ser Gly Val Pro Ser Arg Phe Ser Gly Ser Gly Ser Gly Thr
195 200 205

Asp Phe Thr Leu Thr Ile Ser Ser Leu Gln Pro Glu Asp Phe Ala Thr
210 215 220

Tyr Tyr Cys Gln Gln Phe Asn Ser Tyr Pro Arg Thr Phe Gly Glu Gly
225 230 235 240

Thr Lys Val Glu Ile Lys
245

<210> SEQ ID NO 204
<211> LENGTH: 246
<212> TYPE: PRT
<213> ORGANISM: Artificial Sequence
<220> FEATURE:
<223> OTHER INFORMATION: description of the artificial sequence: the amino acid sequence of scKM14(mut1-25)_scFv(SE)_AA

<400> SEQUENCE: 204

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser His
20 25 30

Gly Met His Trp Val Arg Gln Ala Pro Gly Lys Ser Leu Glu Trp Val
35 40 45

Ala Ser Ile Trp Tyr Asp Gly Ser Lys Lys Asp Tyr Ala Asp Ser Val
50 55 60

Lys Gly Arg Phe Thr Ile Ser Arg Asp Asn Ser Lys Asn Thr Leu Asp
65 70 75 80

Leu Gln Met Asn Ser Leu Arg Ala Glu Asp Thr Ala Val Tyr Tyr Cys
85 90 95

Ala Lys Thr Leu Tyr Tyr Tyr Gly Ser Glu Arg Ala His Gly Leu Asp
100 105 110

Val Trp Gly Gln Gly Thr Thr Val Thr Val Ser Ser Gly Gly Gly Gly
115 120 125

Ser Gly Gly Gly Gly Ser Gly Gly Gly Gly Ser Ala Ile Gln Leu Thr
130 135 140

Gln Ser Pro Ser Ser Leu Ser Ala Ser Val Gly Asp Arg Val Thr Ile
145 150 155 160

Thr Cys Arg Ala Ser Gln Gly Ile Ser Ser Ala Leu Ala Trp Tyr Gln
165 170 175

```
Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Glu Gly
225                 230                 235                 240

Thr Lys Val Glu Ile Lys
                245


<210> SEQ ID NO 205
<211> LENGTH: 246
<212> TYPE: PRT
<213> ORGANISM: Artificial Sequence
<220> FEATURE:
<223> OTHER INFORMATION: description of the artificial sequence: the
      amino acid sequence of scKM14(mut1-26)_scFv(SE)_AA

<400> SEQUENCE: 205

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser His
            20                  25                  30

Gly Met His Trp Val Arg Gln Ala Pro Gly Lys Ser Leu Glu Trp Val
        35                  40                  45

Ala Ser Ile Trp Tyr Asp Gly Ser Lys Lys Ser Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Thr Leu Tyr Tyr Tyr Gly Ser Glu Arg Ala His Gly Leu Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ala Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Ser Ser Ala Leu Ala Trp Tyr Gln
                165                 170                 175

Gln Lys Pro Gly Lys Ala Pro Asn Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Phe Asn Ser Tyr Pro Arg Thr Phe Gly Glu Gly
225                 230                 235                 240

Thr Lys Val Glu Ile Lys
                245


<210> SEQ ID NO 206
<211> LENGTH: 249
<212> TYPE: PRT
```

<213> ORGANISM: Artificial Sequence
<220> FEATURE:
<223> OTHER INFORMATION: description of the artificial sequence: the amino acid sequence of scSP34(H05)_scFv(LH)_AA

<400> SEQUENCE: 206

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Glu Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Lys Gly Ser Leu Lys Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Gln Ser Ile Leu Tyr Leu Gln
        195                 200                 205

Met Asn Asn Leu Lys Thr Glu Asp Thr Ala Met Tyr Tyr Cys Val Arg
    210                 215                 220

His Gly Asn Phe Gly Asn Ser Asp Val Ser Trp Phe Ala Tyr Trp Gly
225                 230                 235                 240

Gln Gly Thr Leu Val Thr Val Ser Ser
                245

<210> SEQ ID NO 207
<211> LENGTH: 249
<212> TYPE: PRT
<213> ORGANISM: Artificial Sequence
<220> FEATURE:
<223> OTHER INFORMATION: description of the artificial sequence: the amino acid sequence of scSP34(H05)_scFv(CC)(LH)_AA

<400> SEQUENCE: 207

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala

```
65                  70                  75                  80

Gln Thr Glu Asp Glu Ala Ile Tyr Phe Cys Ala Leu Trp Tyr Glu Asn
                85                  90                  95

Leu Trp Val Phe Gly Cys Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Lys Gly Ser Leu Lys Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Cys Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Gln Ser Ile Leu Tyr Leu Gln
        195                 200                 205

Met Asn Asn Leu Lys Thr Glu Asp Thr Ala Met Tyr Tyr Cys Val Arg
    210                 215                 220

His Gly Asn Phe Gly Asn Ser Asp Val Ser Trp Phe Ala Tyr Trp Gly
225                 230                 235                 240

Gln Gly Thr Leu Val Thr Val Ser Ser
                245


<210> SEQ ID NO 208
<211> LENGTH: 249
<212> TYPE: PRT
<213> ORGANISM: Artificial Sequence
<220> FEATURE:
<223> OTHER INFORMATION: description of the artificial sequence: the
      amino acid sequence of scSP34(H05_HV3LV8a)_scFv(LH)_AA

<400> SEQUENCE: 208

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Thr Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Ile Tyr Phe Cys Ala Leu Trp Tyr Glu Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175
```

```
Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Ser Leu Tyr Leu Gln
        195                 200                 205

Met Asn Ser Leu Lys Thr Glu Asp Thr Ala Val Tyr Tyr Cys Val Arg
    210                 215                 220

His Gly Asn Phe Gly Asn Ser Asp Val Ser Trp Phe Ala Tyr Trp Gly
225                 230                 235                 240

Gln Gly Thr Leu Val Thr Val Ser Ser
                245


<210> SEQ ID NO 209
<211> LENGTH: 249
<212> TYPE: PRT
<213> ORGANISM: Artificial Sequence
<220> FEATURE:
<223> OTHER INFORMATION: description of the artificial sequence: the
      amino acid sequence of scSP34(H05_HV5LV8a)_scFv(LH)_AA

<400> SEQUENCE: 209

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Thr Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Ile Tyr Phe Cys Ala Leu Trp Tyr Glu Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Ser Ser Leu Tyr Leu Gln
        195                 200                 205

Met Asn Ser Leu Lys Thr Glu Asp Thr Ala Met Tyr Tyr Cys Val Arg
    210                 215                 220

His Gly Asn Phe Gly Asn Ser Asp Val Ser Trp Phe Ala Tyr Trp Gly
225                 230                 235                 240

Gln Gly Thr Leu Val Thr Val Ser Ser
                245


<210> SEQ ID NO 210
<211> LENGTH: 249
<212> TYPE: PRT
<213> ORGANISM: Artificial Sequence
```

<220> FEATURE:
<223> OTHER INFORMATION: description of the artificial sequence: the amino acid sequence of scSP34(H05_HV3LV8a)_scFv(CC)(LH)_AA

<400> SEQUENCE: 210

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Phe Thr Gly
35 40 45

Leu Ile Gly Gly Thr Asn Lys Arg Ala Pro Gly Val Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Ile Tyr Phe Cys Ala Leu Trp Tyr Glu Asn
85 90 95

Leu Trp Val Phe Gly Cys Gly Thr Lys Leu Thr Val Leu Gly Gly Gly
100 105 110

Gly Ser Gly Gly Gly Gly Ser Gly Gly Gly Gly Ser Glu Val Gln Leu
115 120 125

Val Glu Ser Gly Gly Gly Leu Val Gln Pro Gly Gly Ser Leu Arg Leu
130 135 140

Ser Cys Ala Ala Ser Gly Phe Thr Phe Asn Thr Tyr Ala Met Asn Trp
145 150 155 160

Val Arg Gln Ala Pro Gly Lys Cys Leu Glu Trp Val Ala Arg Ile Arg
165 170 175

Ser Lys Tyr Asn Asn Tyr Ala Thr Tyr Tyr Ala Asp Ser Val Lys Asp
180 185 190

Arg Phe Thr Ile Ser Arg Asp Asp Ser Lys Asn Ser Leu Tyr Leu Gln
195 200 205

Met Asn Ser Leu Lys Thr Glu Asp Thr Ala Val Tyr Tyr Cys Val Arg
210 215 220

His Gly Asn Phe Gly Asn Ser Asp Val Ser Trp Phe Ala Tyr Trp Gly
225 230 235 240

Gln Gly Thr Leu Val Thr Val Ser Ser
245

<210> SEQ ID NO 211
<211> LENGTH: 249
<212> TYPE: PRT
<213> ORGANISM: Artificial Sequence
<220> FEATURE:
<223> OTHER INFORMATION: description of the artificial sequence: the amino acid sequence of scSP34(H05_HV5LV8a)_scFv(CC)(LH)_AA

<400> SEQUENCE: 211

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Phe Thr Gly
35 40 45

Leu Ile Gly Gly Thr Asn Lys Arg Ala Pro Gly Val Pro Ala Arg Phe
50 55 60

Ser Gly Ser Leu Leu Gly Gly Lys Ala Ala Leu Thr Leu Ser Gly Ala
65 70 75 80

```
Gln Pro Glu Asp Glu Ala Ile Tyr Phe Cys Ala Leu Trp Tyr Glu Asn
                85                  90                  95

Leu Trp Val Phe Gly Cys Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Cys Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Ser Ser Leu Tyr Leu Gln
        195                 200                 205

Met Asn Ser Leu Lys Thr Glu Asp Thr Ala Met Tyr Tyr Cys Val Arg
    210                 215                 220

His Gly Asn Phe Gly Asn Ser Asp Val Ser Trp Phe Ala Tyr Trp Gly
225                 230                 235                 240

Gln Gly Thr Leu Val Thr Val Ser Ser
                245
```

<210> SEQ ID NO 212
<211> LENGTH: 246
<212> TYPE: PRT
<213> ORGANISM: Artificial Sequence
<220> FEATURE:
<223> OTHER INFORMATION: description of the artificial sequence: the amino acid sequence of scKM14(mut1-03)_scFv(LH)_AA

<400> SEQUENCE: 212

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Arg Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gln Val Gln Leu Val Glu
        115                 120                 125

Ser Gly Gly Gly Val Val Gln Pro Gly Arg Ser Leu Arg Leu Ser Cys
    130                 135                 140

Glu Ala Ser Gly Phe Thr Phe Ser Ser His Gly Met His Trp Val Arg
145                 150                 155                 160

Gln Ala Pro Gly Lys Gly Leu Glu Trp Val Ala Ser Ile Trp Tyr Asp
                165                 170                 175

Gly Ser Lys Lys Tyr Tyr Ala Asp Ser Val Lys Gly Arg Phe Thr Ile
```

```
            180                 185                 190

Ser Arg Asp Asn Ser Lys Asn Thr Leu Asp Leu Gln Met Asn Ser Leu
        195                 200                 205

Arg Ala Glu Asp Thr Ala Val Tyr Tyr Cys Ala Lys Thr Leu Tyr Tyr
    210                 215                 220

Tyr Gly Ser Glu Arg Ala His Gly Leu Asp Val Trp Gly Gln Gly Thr
225                 230                 235                 240

Thr Val Thr Val Ser Ser
                245


<210> SEQ ID NO 213
<211> LENGTH: 246
<212> TYPE: PRT
<213> ORGANISM: Artificial Sequence
<220> FEATURE:
<223> OTHER INFORMATION: description of the artificial sequence: the
      amino acid sequence of scKM14(mut1-04)_scFv(LH)_AA

<400> SEQUENCE: 213

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Gln Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gln Val Gln Leu Val Glu
        115                 120                 125

Ser Gly Gly Gly Val Val Gln Pro Gly Arg Ser Leu Arg Leu Ser Cys
    130                 135                 140

Glu Ala Ser Gly Phe Thr Phe Ser Ser His Gly Met His Trp Val Arg
145                 150                 155                 160

Gln Ala Pro Gly Lys Gly Leu Glu Trp Val Ala Ser Ile Trp Tyr Asp
                165                 170                 175

Gly Ser Lys Lys Tyr Tyr Ala Asp Ser Val Lys Gly Arg Phe Thr Ile
            180                 185                 190

Ser Arg Asp Asn Ser Lys Asn Thr Leu Asp Leu Gln Met Asn Ser Leu
        195                 200                 205

Arg Ala Glu Asp Thr Ala Val Tyr Tyr Cys Ala Lys Thr Leu Tyr Tyr
    210                 215                 220

Tyr Gly Ser Glu Arg Ala His Gly Leu Asp Val Trp Gly Gln Gly Thr
225                 230                 235                 240

Thr Val Thr Val Ser Ser
                245


<210> SEQ ID NO 214
<211> LENGTH: 246
<212> TYPE: PRT
<213> ORGANISM: Artificial Sequence
<220> FEATURE:
```

<223> OTHER INFORMATION: description of the artificial sequence: the amino acid sequence of scKM14(mut1-18)_scFv(LH)_AA

<400> SEQUENCE: 214

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Asn Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Arg
85 90 95

Thr Phe Gly Gln Gly Thr Lys Val Glu Ile Lys Gly Gly Gly Gly Ser
100 105 110

Gly Gly Gly Gly Ser Gly Gly Gly Gly Ser Gln Val Gln Leu Val Glu
115 120 125

Ser Gly Gly Gly Val Val Gln Pro Gly Arg Ser Leu Arg Leu Ser Cys
130 135 140

Glu Ala Ser Gly Phe Thr Phe Ser Ser His Gly Met His Trp Val Arg
145 150 155 160

Gln Ala Pro Gly Lys Gly Leu Glu Trp Val Ala Ser Ile Trp Tyr Glu
165 170 175

Gly Ser Lys Lys Tyr Tyr Ala Asp Ser Val Lys Gly Arg Phe Thr Ile
180 185 190

Ser Arg Asp Asn Ser Lys Asn Thr Leu Asp Leu Gln Met Asn Ser Leu
195 200 205

Arg Ala Glu Asp Thr Ala Val Tyr Tyr Cys Ala Lys Thr Leu Tyr Tyr
210 215 220

Tyr Gly Ser Glu Arg Ala His Gly Leu Asp Val Trp Gly Gln Gly Thr
225 230 235 240

Thr Val Thr Val Ser Ser
245

<210> SEQ ID NO 215
<211> LENGTH: 246
<212> TYPE: PRT
<213> ORGANISM: Artificial Sequence
<220> FEATURE:
<223> OTHER INFORMATION: description of the artificial sequence: the amino acid sequence of scKM14(mut1-22)_scFv(LH)_AA

<400> SEQUENCE: 215

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Asn Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gln Val Gln Leu Val Glu
        115                 120                 125

Ser Gly Gly Gly Val Val Gln Pro Gly Arg Ser Leu Arg Leu Ser Cys
    130                 135                 140

Glu Ala Ser Gly Phe Thr Phe Ser Ser His Gly Met His Trp Val Arg
145                 150                 155                 160

Gln Ala Pro Gly Lys Gly Leu Glu Trp Val Ala Ser Ile Trp Tyr Asp
                165                 170                 175

Gly Ser Val Lys Tyr Tyr Ala Asp Ser Val Lys Gly Arg Phe Thr Ile
            180                 185                 190

Ser Arg Asp Asn Ser Lys Asn Thr Leu Asp Leu Gln Met Asn Ser Leu
        195                 200                 205

Arg Ala Glu Asp Thr Ala Val Tyr Tyr Cys Ala Lys Thr Leu Tyr Tyr
    210                 215                 220

Tyr Gly Ser Glu Arg Ala His Gly Leu Asp Val Trp Gly Gln Gly Thr
225                 230                 235                 240

Thr Val Thr Val Ser Ser
                245


<210> SEQ ID NO 216
<211> LENGTH: 246
<212> TYPE: PRT
<213> ORGANISM: Artificial Sequence
<220> FEATURE:
<223> OTHER INFORMATION: description of the artificial sequence: the
      amino acid sequence of scKM14(mut1-25)_scFv(LH)_AA

<400> SEQUENCE: 216

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gln Val Gln Leu Val Glu
        115                 120                 125

Ser Gly Gly Gly Val Val Gln Pro Gly Arg Ser Leu Arg Leu Ser Cys
    130                 135                 140

Glu Ala Ser Gly Phe Thr Phe Ser Ser His Gly Met His Trp Val Arg
145                 150                 155                 160

Gln Ala Pro Gly Lys Gly Leu Glu Trp Val Ala Ser Ile Trp Tyr Asp
                165                 170                 175

Gly Ser Lys Lys Asp Tyr Ala Asp Ser Val Lys Gly Arg Phe Thr Ile
            180                 185                 190
```

Ser Arg Asp Asn Ser Lys Asn Thr Leu Asp Leu Gln Met Asn Ser Leu
195 200 205

Arg Ala Glu Asp Thr Ala Val Tyr Tyr Cys Ala Lys Thr Leu Tyr Tyr
210 215 220

Tyr Gly Ser Glu Arg Ala His Gly Leu Asp Val Trp Gly Gln Gly Thr
225 230 235 240

Thr Val Thr Val Ser Ser
245

<210> SEQ ID NO 217
<211> LENGTH: 246
<212> TYPE: PRT
<213> ORGANISM: Artificial Sequence
<220> FEATURE:
<223> OTHER INFORMATION: description of the artificial sequence: the amino acid sequence of scKM14(mut1-26)_scFv(LH)_AA

<400> SEQUENCE: 217

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Asn Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Arg
85 90 95

Thr Phe Gly Gln Gly Thr Lys Val Glu Ile Lys Gly Gly Gly Gly Ser
100 105 110

Gly Gly Gly Gly Ser Gly Gly Gly Gly Ser Gln Val Gln Leu Val Glu
115 120 125

Ser Gly Gly Gly Val Val Gln Pro Gly Arg Ser Leu Arg Leu Ser Cys
130 135 140

Glu Ala Ser Gly Phe Thr Phe Ser Ser His Gly Met His Trp Val Arg
145 150 155 160

Gln Ala Pro Gly Lys Gly Leu Glu Trp Val Ala Ser Ile Trp Tyr Asp
165 170 175

Gly Ser Lys Lys Ser Tyr Ala Asp Ser Val Lys Gly Arg Phe Thr Ile
180 185 190

Ser Arg Asp Asn Ser Lys Asn Thr Leu Asp Leu Gln Met Asn Ser Leu
195 200 205

Arg Ala Glu Asp Thr Ala Val Tyr Tyr Cys Ala Lys Thr Leu Tyr Tyr
210 215 220

Tyr Gly Ser Glu Arg Ala His Gly Leu Asp Val Trp Gly Gln Gly Thr
225 230 235 240

Thr Val Thr Val Ser Ser
245

<210> SEQ ID NO 218
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (L01) CDR L1

<400> SEQUENCE: 218

Arg Ser Ser Thr Gly Ala Val Thr Thr Ser Asn Ala Ala Asn
1 5 10

<210> SEQ ID NO 219
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 scFv (L02) CDR L2

<400> SEQUENCE: 219

Pro Thr Asn Lys Arg Ala Pro
1 5

<210> SEQ ID NO 220
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 scFv (L03) CDR L2

<400> SEQUENCE: 220

Gly Thr Asn Ala Arg Ala Pro
1 5

<210> SEQ ID NO 221
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 scFv (L04) CDR L2

<400> SEQUENCE: 221

Gly Thr Asn Ile Arg Ala Pro
1 5

<210> SEQ ID NO 222
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 scFv (L05) CDR L2

<400> SEQUENCE: 222

Gly Thr Asn Ser Arg Ala Pro
1 5

<210> SEQ ID NO 223
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 scFv (L06) CDR L2

<400> SEQUENCE: 223

Gly Thr Asn Lys Arg Ala Gly
1 5

<210> SEQ ID NO 224

<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 scFv (L07) CDR L3

<400> SEQUENCE: 224

Ala Leu Trp Ala Ser Asn Leu Trp Val
1               5

<210> SEQ ID NO 225
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 scFv (L08) CDR L3

<400> SEQUENCE: 225

Ala Leu Trp Arg Ser Asn Leu Trp Val
1               5

<210> SEQ ID NO 226
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 scFv (L09) CDR L3

<400> SEQUENCE: 226

Ala Leu Trp Thr Ser Asn Leu Trp Val
1               5

<210> SEQ ID NO 227
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 scFv (L11) CDR L3

<400> SEQUENCE: 227

Ala Leu Trp Tyr Ser Asn Leu Asp Val
1               5

<210> SEQ ID NO 228
<211> LENGTH: 5
<212> TYPE: PRT
<213> ORGANISM: Artificial Sequence
<220> FEATURE:
<223> OTHER INFORMATION: description of the artificial sequence: the amino acid sequence of anti-CD3 scFv (H01) CDR H1

<400> SEQUENCE: 228

Thr Ala Ala Met Asn
1               5

<210> SEQ ID NO 229
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (H02) CDR H3

<400> SEQUENCE: 229

His Gly Asn Ala Gly Asn Ser Tyr Val Ser Trp Phe Ala Tyr
1 5 10

<210> SEQ ID NO 230
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (H03) CDR H3

<400> SEQUENCE: 230

His Gly Asn Tyr Gly Asn Ser Tyr Val Ser Trp Phe Ala Tyr
1 5 10

<210> SEQ ID NO 231
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (H04) CDR H3

<400> SEQUENCE: 231

His Gly Asn Phe Gly Asn Glu Tyr Val Ser Trp Phe Ala Tyr
1 5 10

<210> SEQ ID NO 232
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (H06) CDR H3

<400> SEQUENCE: 232

His Gly Asn Phe Gly Asn Ser Glu Val Ser Trp Phe Ala Tyr
1 5 10

<210> SEQ ID NO 233
<211> LENGTH: 14
<212> TYPE: PRT
<213> ORGANISM: Artificial Sequence
<220> FEATURE:
<223> OTHER INFORMATION: description of the artificial sequence: the amino acid sequence of anti-CD3 scFv (H07) CDR H3

<400> SEQUENCE: 233

His Gly Asn Phe Gly Asn Ser Arg Val Ser Trp Phe Ala Tyr
1 5 10

<210> SEQ ID NO 234
<211> LENGTH: 11
<212> TYPE: PRT
<213> ORGANISM: Artificial Sequence
<220> FEATURE:
<223> OTHER INFORMATION: description of the artificial sequence: the amino acid sequence of anti-CD3 antibody mut1-01 CDR L1

<400> SEQUENCE: 234

Arg Ala Ser Gln Gly Lys Ser Ser Ala Leu Ala
1 5 10

<210> SEQ ID NO 235
<211> LENGTH: 11
<212> TYPE: PRT
<213> ORGANISM: Artificial Sequence
<220> FEATURE:

<223> OTHER INFORMATION: description of the artificial sequence: the amino acid sequence of anti-CD3 antibody mut1-02 CDR L1

<400> SEQUENCE: 235

Arg Ala Ser Gln Gly Glu Ser Ser Ala Leu Ala
1               5                   10

<210> SEQ ID NO 236
<211> LENGTH: 7
<212> TYPE: PRT
<213> ORGANISM: Artificial Sequence
<220> FEATURE:
<223> OTHER INFORMATION: description of the artificial sequence: the amino acid sequence of anti-CD3 antibody mut1-05 CDR L2

<400> SEQUENCE: 236

Asp Ala Ser Ser His Glu Ser
1               5

<210> SEQ ID NO 237
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 antibody mut1-06 CDR L3

<400> SEQUENCE: 237

Gln Gln Ala Asn Ser Tyr Pro Arg Thr
1               5

<210> SEQ ID NO 238
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 antibody mut1-07 CDR L3

<400> SEQUENCE: 238

Gln Gln Asp Asn Ser Tyr Pro Arg Thr
1               5

<210> SEQ ID NO 239
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 antibody mut1-08 CDR L3

<400> SEQUENCE: 239

Gln Gln Phe Asn Ser Ala Pro Arg Thr
1               5

<210> SEQ ID NO 240
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 antibody mut1-09 CDR L3

<400> SEQUENCE: 240

Gln Gln Phe Asn Ser Asp Pro Arg Thr
1               5

<210> SEQ ID NO 241
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 antibody mut1-10 CDR L3

<400> SEQUENCE: 241

Gln Gln Phe Asn Ser Glu Pro Arg Thr
1               5

<210> SEQ ID NO 242
<211> LENGTH: 9
<212> TYPE: PRT
<213> ORGANISM: Artificial Sequence
<220> FEATURE:
<223> OTHER INFORMATION: description of the artificial sequence: the amino acid sequence of anti-CD3 antibody mut1-11 CDR L3

<400> SEQUENCE: 242

Gln Gln Phe Asn Ser Asn Pro Arg Thr
1               5

<210> SEQ ID NO 243
<211> LENGTH: 5
<212> TYPE: PRT
<213> ORGANISM: Artificial Sequence
<220> FEATURE:
<223> OTHER INFORMATION: description of the artificial sequence: the amino acid sequence of anti-CD3 antibody mut1-12 CDR H1

<400> SEQUENCE: 243

Trp His Gly Met His
1               5

<210> SEQ ID NO 244
<211> LENGTH: 5
<212> TYPE: PRT
<213> ORGANISM: Artificial Sequence
<220> FEATURE:
<223> OTHER INFORMATION: description of the artificial sequence: the amino acid sequence of anti-CD3 antibody mut1-13 CDR H1

<400> SEQUENCE: 244

Tyr His Gly Met His
1               5

<210> SEQ ID NO 245
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody mut1-14 CDR H2

<400> SEQUENCE: 245

Ser Ile Ser Tyr Asp Gly Ser Lys Lys Tyr Tyr Ala Asp Ser Val Lys
1               5                   10                  15

Gly

<210> SEQ ID NO 246
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody mut1-15 CDR H2

<400> SEQUENCE: 246

Ser Ile Asp Tyr Asp Gly Ser Lys Lys Tyr Tyr Ala Asp Ser Val Lys
1               5                   10                  15

Gly

<210> SEQ ID NO 247
<211> LENGTH: 17
<212> TYPE: PRT
<213> ORGANISM: Artificial Sequence
<220> FEATURE:
<223> OTHER INFORMATION: description of the artificial sequence: the
      amino acid sequence of anti-CD3 antibody mut1-16 CDR H2

<400> SEQUENCE: 247

Ser Ile Glu Tyr Asp Gly Ser Lys Lys Tyr Tyr Ala Asp Ser Val Lys
1               5                   10                  15

Gly

<210> SEQ ID NO 248
<211> LENGTH: 17
<212> TYPE: PRT
<213> ORGANISM: Artificial Sequence
<220> FEATURE:
<223> OTHER INFORMATION: description of the artificial sequence: the
      amino acid sequence of anti-CD3 antibody mut1-17 CDR H2

<400> SEQUENCE: 248

Ser Ile Trp Tyr Ala Gly Ser Lys Lys Tyr Tyr Ala Asp Ser Val Lys
1               5                   10                  15

Gly

<210> SEQ ID NO 249
<211> LENGTH: 17
<212> TYPE: PRT
<213> ORGANISM: Artificial Sequence
<220> FEATURE:
<223> OTHER INFORMATION: description of the artificial sequence: the
      amino acid sequence of anti-CD3 antibody mut1-19 CDR H2

<400> SEQUENCE: 249

Ser Ile Trp Tyr Asp Gly Ser Ala Lys Tyr Tyr Ala Asp Ser Val Lys
1               5                   10                  15

Gly

<210> SEQ ID NO 250
<211> LENGTH: 17
<212> TYPE: PRT
<213> ORGANISM: Artificial Sequence
<220> FEATURE:
<223> OTHER INFORMATION: description of the artificial sequence: the
      amino acid sequence of anti-CD3 antibody mut1-20 CDR H2

<400> SEQUENCE: 250

Ser Ile Trp Tyr Asp Gly Ser Asp Lys Tyr Tyr Ala Asp Ser Val Lys
1               5                   10                  15

Gly

<210> SEQ ID NO 251
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody mut1-21 CDR H2

<400> SEQUENCE: 251

Ser Ile Trp Tyr Asp Gly Ser Glu Lys Tyr Tyr Ala Asp Ser Val Lys
1 5 10 15

Gly

<210> SEQ ID NO 252
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody mut1-23 CDR H2

<400> SEQUENCE: 252

Ser Ile Trp Tyr Asp Gly Ser Trp Lys Tyr Tyr Ala Asp Ser Val Lys
1 5 10 15

Gly

<210> SEQ ID NO 253
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody mut1-24 CDR H2

<400> SEQUENCE: 253

Ser Ile Trp Tyr Asp Gly Ser Lys Lys Ala Tyr Ala Asp Ser Val Lys
1 5 10 15

Gly

<210> SEQ ID NO 254
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody mut1-27 CDR H2

<400> SEQUENCE: 254

Ser Ile Trp Tyr Asp Gly Ser Lys Lys Thr Tyr Ala Asp Ser Val Lys
1 5 10 15

Gly

<210> SEQ ID NO 255
<211> LENGTH: 17
<212> TYPE: PRT
<213> ORGANISM: Artificial Sequence
<220> FEATURE:
<223> OTHER INFORMATION: description of the artificial sequence: the amino acid sequence of anti-CD3 antibody mut1-28 CDR H2

<400> SEQUENCE: 255

Ser Ile Trp Tyr Asp Gly Ser Lys Lys Tyr Tyr Ala Ser Ser Val Lys
1 5 10 15

Gly

<210> SEQ ID NO 256
<211> LENGTH: 15
<212> TYPE: PRT
<213> ORGANISM: Artificial Sequence
<220> FEATURE:

<223> OTHER INFORMATION: description of the artificial sequence: the amino acid sequence of anti-CD3 antibody mut1-29 CDR H3

<400> SEQUENCE: 256

Thr Leu Ala Tyr Tyr Gly Ser Glu Arg Ala His Gly Leu Asp Val
1 5 10 15

<210> SEQ ID NO 257
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-30 CDR H3

<400> SEQUENCE: 257

Thr Leu Asp Tyr Tyr Gly Ser Glu Arg Ala His Gly Leu Asp Val
1 5 10 15

<210> SEQ ID NO 258
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-31 CDR H3

<400> SEQUENCE: 258

Thr Leu Glu Tyr Tyr Gly Ser Glu Arg Ala His Gly Leu Asp Val
1 5 10 15

<210> SEQ ID NO 259
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-32 CDR H3

<400> SEQUENCE: 259

Thr Leu Tyr Ala Tyr Gly Ser Glu Arg Ala His Gly Leu Asp Val
1 5 10 15

<210> SEQ ID NO 260
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-33 CDR H3

<400> SEQUENCE: 260

Thr Leu Tyr Asp Tyr Gly Ser Glu Arg Ala His Gly Leu Asp Val
1 5 10 15

<210> SEQ ID NO 261
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-34 CDR H3

<400> SEQUENCE: 261

Thr Leu Tyr Glu Tyr Gly Ser Glu Arg Ala His Gly Leu Asp Val
1 5 10 15

<210> SEQ ID NO 262
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-35 CDR H3

<400> SEQUENCE: 262

Thr Leu Tyr Tyr Ala Gly Ser Glu Arg Ala His Gly Leu Asp Val
1 5 10 15

<210> SEQ ID NO 263
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-36 CDR H3

<400> SEQUENCE: 263

Thr Leu Tyr Tyr Asp Gly Ser Glu Arg Ala His Gly Leu Asp Val
1 5 10 15

<210> SEQ ID NO 264
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-37 CDR H3

<400> SEQUENCE: 264

Thr Leu Tyr Tyr Glu Gly Ser Glu Arg Ala His Gly Leu Asp Val
1 5 10 15

<210> SEQ ID NO 265
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-38 CDR H3

<400> SEQUENCE: 265

Thr Leu Tyr Tyr Tyr Gly Ser Ala Arg Ala His Gly Leu Asp Val
1 5 10 15

<210> SEQ ID NO 266
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-39 CDR H3

<400> SEQUENCE: 266

Thr Leu Tyr Tyr Tyr Gly Ser Thr Arg Ala His Gly Leu Asp Val
1 5 10 15

<210> SEQ ID NO 267
<211> LENGTH: 15
<212> TYPE: PRT
<213> ORGANISM: Artificial Sequence
<220> FEATURE:
<223> OTHER INFORMATION: description of the artificial sequence: the amino acid sequence of anti-CD3 antibody mut1-40 CDR H3

<400> SEQUENCE: 267

-continued

```
Thr Leu Tyr Tyr Tyr Gly Ser Glu Lys Ala His Gly Leu Asp Val
1               5                   10                  15


<210> SEQ ID NO 268
<211> LENGTH: 15
<212> TYPE: PRT
<213> ORGANISM: Artificial Sequence
<220> FEATURE:
<223> OTHER INFORMATION: description of the artificial sequence: the
      amino acid sequence of anti-CD3 antibody mut1-41 CDR H3

<400> SEQUENCE: 268

Thr Leu Tyr Tyr Tyr Gly Ser Glu Ser Ala His Gly Leu Asp Val
1               5                   10                  15


<210> SEQ ID NO 269
<211> LENGTH: 15
<212> TYPE: PRT
<213> ORGANISM: Artificial Sequence
<220> FEATURE:
<223> OTHER INFORMATION: description of the artificial sequence: the
      amino acid sequence of anti-CD3 antibody mut1-42 CDR H3

<400> SEQUENCE: 269

Thr Leu Tyr Tyr Tyr Gly Ser Glu Tyr Ala His Gly Leu Asp Val
1               5                   10                  15


<210> SEQ ID NO 270
<211> LENGTH: 15
<212> TYPE: PRT
<213> ORGANISM: Artificial Sequence
<220> FEATURE:
<223> OTHER INFORMATION: description of the artificial sequence: the
      amino acid sequence of anti-CD3 antibody mut1-43 CDR H3

<400> SEQUENCE: 270

Thr Leu Tyr Tyr Tyr Gly Ser Glu Arg Ala Ala Gly Leu Asp Val
1               5                   10                  15
```